(12) United States Patent
Ito et al.

(10) Patent No.: US 9,902,687 B2
(45) Date of Patent: Feb. 27, 2018

(54) COMPOUND

(71) Applicant: IDEMITSU KOSAN CO., LTD., Tokyo (JP)

(72) Inventors: Hirokatsu Ito, Sodegaura (JP); Masahiro Kawamura, Sodegaura (JP); Yumiko Mizuki, Sodegaura (JP); Tasuku Haketa, Sodegaura (JP); Tomoharu Hayama, Sodegaura (JP); Ryota Takahashi, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 0 days.

(21) Appl. No.: 14/908,929

(22) PCT Filed: Sep. 18, 2015

(86) PCT No.: PCT/JP2015/004810
§ 371 (c)(1),
(2) Date: Jan. 29, 2016

(87) PCT Pub. No.: WO2016/042781
PCT Pub. Date: Mar. 24, 2016

(65) Prior Publication Data
US 2017/0183291 A1 Jun. 29, 2017

(30) Foreign Application Priority Data
Sep. 19, 2014 (JP) .................................. 2014-191964

(51) Int. Cl.
*C07C 211/50* (2006.01)
*H01L 51/00* (2006.01)
*C07C 255/50* (2006.01)

(52) U.S. Cl.
CPC .......... *C07C 211/50* (2013.01); *C07C 255/50* (2013.01); *H01L 51/0062* (2013.01); *H01L 51/0064* (2013.01); *H01L 51/0067* (2013.01); *H01L 2251/50* (2013.01)

(58) Field of Classification Search
None
See application file for complete search history.

(56) References Cited

U.S. PATENT DOCUMENTS

2003/0077480 A1  4/2003  Hosokawa et al.
2003/0118866 A1  6/2003  Oh et al.

| 2004/0137270 A1 | 7/2004 | Seo et al. |
| 2004/0209118 A1 | 10/2004 | Seo et al. |
| 2005/0064233 A1 | 3/2005 | Matsuura et al. |
| 2006/0134456 A1 | 6/2006 | Ikeda et al. |
| 2006/0251925 A1 | 11/2006 | Hosokawa et al. |
| 2007/0009758 A1 | 1/2007 | Funahashi |
| 2007/0060777 A1 | 3/2007 | Moriwaki et al. |
| 2007/0063638 A1 | 3/2007 | Tokairin et al. |

(Continued)

FOREIGN PATENT DOCUMENTS

JP   H08-199162 A   8/1996
JP   2002-124385 A   4/2002
(Continued)

OTHER PUBLICATIONS

Office Action dated May 11, 2017 in corresponding Chinese Patent Application No. 201580001476.X.
International Search Report for PCT/JP2015/004810 dated Dec. 15, 2015.

*Primary Examiner* — Clinton Brooks
(74) *Attorney, Agent, or Firm* — Foley & Lardner LLP

(57) ABSTRACT

A compound is represented by the following formula (1). In the formula (1), Ar is a substituted or unsubstituted aryl group including 6 to 30 ring carbon atoms, $R^a$ are independently a substituted or unsubstituted alkyl group including 1 to 15 carbon atoms, or a substituted or unsubstituted cycloalkyl group including 3 to 15 carbon atoms, $R^{b1}$ to $R^{b4}$ are independently a halogen atom, a cyano group, a substituted or unsubstituted alkyl group including 1 to 15 carbon atoms, or the like, $R^{c1}$ to $R^{c10}$ are independently a hydrogen atom, a halogen atom, a cyano group, a substituted or unsubstituted alkyl group including 1 to 15 carbon atoms, or the like, * is a bonding position at which one of $R^{c1}$ to $R^{c10}$ is bonded to either nitrogen atom, x is an integer from 0 to 3, y is an integer from 0 to 4, and z are independently an integer from 0 to 5.

(1)

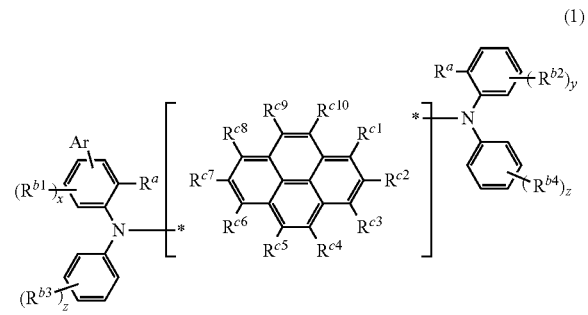

25 Claims, No Drawings

(56) References Cited

U.S. PATENT DOCUMENTS

| | | |
|---|---|---|
| 2007/0090755 A1 | 4/2007 | Eida et al. |
| 2007/0114917 A1 | 5/2007 | Funahashi et al. |
| 2007/0152565 A1 | 7/2007 | Kubota et al. |
| 2007/0202354 A1 | 8/2007 | Funahashi |
| 2007/0228368 A1 | 10/2007 | Takahashi et al. |
| 2007/0252511 A1 | 11/2007 | Funahashi |
| 2008/0001123 A1 | 1/2008 | Inoue et al. |
| 2008/0015399 A1 | 1/2008 | Funahashi |
| 2008/0100206 A1 | 5/2008 | Kondo et al. |
| 2008/0113101 A1 | 5/2008 | Inoue et al. |
| 2008/0203905 A1 | 8/2008 | Je et al. |
| 2008/0206447 A1 | 8/2008 | Inoue et al. |
| 2009/0134781 A1 | 5/2009 | Jang et al. |
| 2009/0206748 A1 | 8/2009 | Moriwaki et al. |
| 2010/0052526 A1 | 3/2010 | Je et al. |
| 2010/0109517 A1 | 5/2010 | Fukushima et al. |
| 2010/0117028 A1 | 5/2010 | Takeshima et al. |
| 2010/0141124 A1* | 6/2010 | Lee .................. C07C 211/61 313/504 |
| 2010/0171109 A1 | 7/2010 | Nishimura et al. |
| 2010/0187504 A1 | 7/2010 | Jang et al. |
| 2010/0187512 A1 | 7/2010 | Ito |
| 2010/0207110 A1 | 8/2010 | Nishimura et al. |
| 2010/0289014 A1 | 11/2010 | Ito et al. |
| 2010/0295030 A1 | 11/2010 | Kawamura |
| 2010/0301313 A1 | 12/2010 | Ito et al. |
| 2010/0320452 A1 | 12/2010 | Kawamura |
| 2011/0006289 A1 | 1/2011 | Mizuki et al. |
| 2011/0006669 A1 | 1/2011 | Lee et al. |
| 2011/0042660 A1 | 2/2011 | Kawamura et al. |
| 2011/0114934 A1 | 5/2011 | Kim et al. |
| 2011/0156011 A1 | 6/2011 | Bin et al. |
| 2011/0156016 A1 | 6/2011 | Kawamura et al. |
| 2011/0193064 A1 | 8/2011 | Funahashi |
| 2011/0220886 A1 | 9/2011 | Takeshima et al. |
| 2011/0297923 A1 | 12/2011 | Mizuki et al. |
| 2012/0056165 A1 | 3/2012 | Kawamura et al. |
| 2012/0181922 A1 | 7/2012 | Kawamura et al. |
| 2012/0248968 A1 | 10/2012 | Ogiwara et al. |
| 2013/0153867 A1 | 6/2013 | Seo et al. |
| 2013/0193382 A1 | 8/2013 | Buesing et al. |
| 2013/0228752 A1 | 9/2013 | Shin et al. |
| 2013/0234118 A1 | 9/2013 | Kwon et al. |
| 2013/0240859 A1 | 9/2013 | Arakane et al. |
| 2014/0001457 A1 | 1/2014 | Endo |
| 2014/0034943 A1 | 2/2014 | Mizuki et al. |
| 2014/0061622 A1 | 3/2014 | Ikeda et al. |
| 2014/0103329 A1 | 4/2014 | Ogiwara et al. |
| 2014/0124763 A1 | 5/2014 | Funahashi |
| 2014/0145169 A1 | 5/2014 | Lee et al. |
| 2014/0151666 A1 | 6/2014 | Miyata |
| 2014/0183468 A1 | 7/2014 | Shin et al. |
| 2014/0291646 A1 | 10/2014 | Shin et al. |
| 2014/0346406 A1 | 11/2014 | Lee et al. |
| 2014/0353646 A1 | 12/2014 | Mizuki et al. |
| 2015/0034915 A1 | 2/2015 | Kim et al. |
| 2015/0060785 A1 | 3/2015 | Kim et al. |
| 2015/0060808 A1 | 3/2015 | Kim et al. |
| 2015/0069342 A1 | 3/2015 | Lee et al. |
| 2015/0090967 A1 | 4/2015 | Lee et al. |
| 2015/0115225 A1 | 4/2015 | Kawamura et al. |
| 2015/0188070 A1 | 7/2015 | Ogiwara et al. |
| 2015/0243892 A1 | 8/2015 | Ogita et al. |
| 2015/0270502 A1 | 9/2015 | Fuchiwaki et al. |
| 2015/0280158 A1 | 10/2015 | Ogiwara et al. |
| 2015/0349265 A1 | 12/2015 | Hwang et al. |
| 2016/0172602 A1 | 6/2016 | Ogiwara et al. |
| 2016/0211462 A1 | 7/2016 | Ogiwara et al. |

FOREIGN PATENT DOCUMENTS

| | | |
|---|---|---|
| JP | 2003-142269 A | 5/2003 |
| JP | 2004-006379 A | 1/2004 |
| JP | 2004-075580 A | 3/2004 |
| JP | 2006-128715 A | 5/2006 |
| JP | 2010-053131 A | 3/2010 |
| JP | 2010-150425 A | 7/2010 |
| JP | 2011-023614 A | 2/2011 |
| JP | 2011-153201 A | 8/2011 |
| JP | 2012-104806 A | 5/2012 |
| JP | 2013-118288 A | 6/2013 |
| JP | 2013-258381 A | 12/2013 |
| JP | 2014-506232 A | 3/2014 |
| JP | 2014-075249 A | 4/2014 |
| JP | 2014-082479 A | 5/2014 |
| JP | 2014-165346 A | 9/2014 |
| JP | 2014-177441 A | 9/2014 |
| JP | 2014-205641 A | 10/2014 |
| JP | 2015-007009 A | 1/2015 |
| JP | 2015-007010 A | 1/2015 |
| JP | 2015-173263 A | 10/2015 |
| JP | 2016-027605 A | 2/2016 |
| JP | 2016-027606 A | 2/2016 |
| KR | 2007101430 A | 10/2007 |
| KR | 2008096733 A | 11/2008 |
| KR | 10-2009-0084984 A | 8/2009 |
| KR | 10-2011-0002155 A | 1/2011 |
| KR | 10-2011-0015213 A | 2/2011 |
| KR | 10-2011-0024695 A | 3/2011 |
| KR | 10-2011-0041725 A | 4/2011 |
| KR | 10-2011-0041728 A | 4/2011 |
| KR | 10-2011-0054192 A | 5/2011 |
| KR | 10-2011-0057008 A | 5/2011 |
| KR | 10-2011-0070180 A | 6/2011 |
| KR | 10-2011-0072040 A | 6/2011 |
| KR | 10-2011-0076376 A | 7/2011 |
| KR | 10-2011-0081698 A | 7/2011 |
| KR | 10-2011-0107679 A | 10/2011 |
| KR | 10-2011-0120108 A | 11/2011 |
| KR | 2012117675 A | 10/2012 |
| KR | 10-2012-0135501 A | 12/2012 |
| KR | 10-2014-0043035 A | 4/2014 |
| KR | 10-2014-0047830 A | 4/2014 |
| KR | 2014043035 A | 4/2014 |
| KR | 2014047830 A | 4/2014 |
| KR | 2014055968 A | 5/2014 |
| KR | 2014058290 A | 5/2014 |
| KR | 2014072295 A | 6/2014 |
| KR | 2014076170 A | 6/2014 |
| KR | 2014076888 A | 6/2014 |
| KR | 2014077123 A | 6/2014 |
| KR | 10-2014-0126201 A | 10/2014 |
| KR | 2014121121 A | 10/2014 |
| KR | 2014121122 A | 10/2014 |
| KR | 2014121123 A | 10/2014 |
| KR | 2014121124 A | 10/2014 |
| KR | 2014121776 A | 10/2014 |
| KR | 2014126108 A | 10/2014 |
| KR | 2014126201 A | 10/2014 |
| KR | 2014129658 A | 11/2014 |
| KR | 2014134884 A | 11/2014 |
| KR | 2014142923 A | 12/2014 |
| KR | 10-2015-0006199 A | 1/2015 |
| KR | 10-2015-0006722 A | 1/2015 |
| KR | 10-2015-0007476 A | 1/2015 |
| KR | 2015006199 A | 1/2015 |
| KR | 2015006722 A | 1/2015 |
| KR | 2015007476 A | 1/2015 |
| KR | 10-2015-0124677 A | 11/2015 |
| KR | 2015124677 A | 11/2015 |
| WO | WO-2004/083162 A1 | 9/2004 |
| WO | WO-2009/008347 A1 | 1/2009 |
| WO | WO-2009/102026 A1 | 8/2009 |
| WO | WO-2009/107596 A1 | 9/2009 |
| WO | WO-2009/133917 A1 | 11/2009 |
| WO | WO-2009/142230 A1 | 11/2009 |
| WO | WO-2010/010924 A1 | 1/2010 |
| WO | WO-2010/013675 A1 | 2/2010 |
| WO | WO-2010/013676 A1 | 2/2010 |
| WO | WO-2010/016405 A1 | 2/2010 |
| WO | WO-2014/035159 A1 | 3/2014 |
| WO | WO-2014/054452 A1 | 4/2014 |
| WO | WO 2014/069831 A1 | 5/2014 |

(56) References Cited

FOREIGN PATENT DOCUMENTS

| | | |
|---|---|---|
| WO | WO-2014/088047 A1 | 6/2014 |
| WO | WO-2014/088289 A1 | 6/2014 |
| WO | WO-2014/122933 A1 | 8/2014 |
| WO | WO-2014/166571 A1 | 10/2014 |
| WO | WO-2015/009076 A1 | 1/2015 |
| WO | WO-2015/135624 A1 | 9/2015 |
| WO | WO-2015/194839 A1 | 12/2015 |
| WO | WO-2015/198987 A1 | 12/2015 |
| WO | WO-2015/198988 A1 | 12/2015 |
| WO | WO-2016/017514 A1 | 2/2016 |
| WO | WO-2016/031785 A1 | 3/2016 |
| WO | WO-2016/042781 A1 | 3/2016 |

* cited by examiner

COMPOUND

TECHNICAL FIELD

The invention relates to a novel compound and an organic electroluminescence device using the same.

BACKGROUND ART

An organic electroluminescence (EL) device is considered to be a promising inexpensive large full-color display that utilizes solid-state emission, and has been extensively developed. The organic EL device normally includes an emitting layer, and a pair of opposing electrodes that are disposed on either side of the emitting layer. When an electric field is applied between the electrodes, electrons are injected from the cathode, and holes are injected from the anode. The electrons and the holes recombine in the emitting layer to produce an excited state, and the energy is emitted as light when the excited state returns to the ground state.

A known organic EL device has problems in that a high driving voltage is required, and only low luminance and low luminous (emission) efficiency can be achieved. It is important to improve the luminous efficiency of an organic EL device in order to reduce the power consumption of a display, and the materials used to produce an organic EL device have been gradually improved in recent years (see Patent Documents 1 and 2, for example). However, a further improvement in efficiency has been desired.

CITATION LIST

Patent Literature

Patent Document 1: JP-A-2013-118288
Patent Document 2: JP-A-2011-153201

SUMMARY OF INVENTION

An object of the invention is to provide a compound that makes it possible to produce an organic EL device that exhibits excellent luminous efficiency.

One aspect of the invention provides the following compound, for example.

A compound represented by the following formula (1), wherein Ar is a substituted or unsubstituted aryl group including 6 to 30 carbon atoms that form a ring (hereinafter referred to as "ring carbon atoms"), $R^a$ are independently a substituted or unsubstituted alkyl group including 1 to 15 carbon atoms, or a substituted or unsubstituted cycloalkyl group including 3 to 15 carbon atoms, $R^{b1}$ to $R^{b4}$ are independently a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 atoms that form a ring (hereinafter referred to as "ring atoms"), $R^{c1}$ to $R^{c10}$ are independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, a substituted

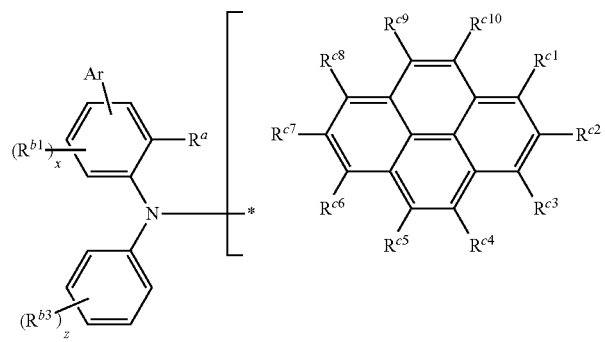
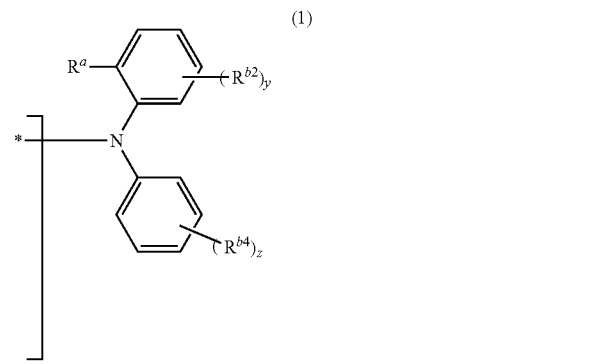

(1)

or unsubstituted heteroaryl group including 3 to 30 ring atoms, or a single bond that is bonded to either nitrogen atom,

* is a bonding position at which one of $R^{c1}$ to $R^{c10}$ is bonded to either nitrogen atom, x is an integer from 0 to 3, y is an integer from 0 to 4, z are independently an integer from 0 to 5, a plurality of $R^{b1}$ are either identical or different when x is an integer equal to or larger than 2, a plurality of $R^{b2}$ are either identical or different when y is an integer equal to or larger than 2, and a plurality of $R^{b3}$ or $R^{b4}$ are either identical or different when z is an integer equal to or larger than 2.

The invention thus provides a compound that makes it possible to produce an organic EL device that exhibits excellent luminous efficiency.

DESCRIPTION OF EMBODIMENTS

The compound according to one aspect of the invention is represented by the following formula (1).

substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 ring atoms.

$R^{c1}$ to $R^{c10}$ are independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon

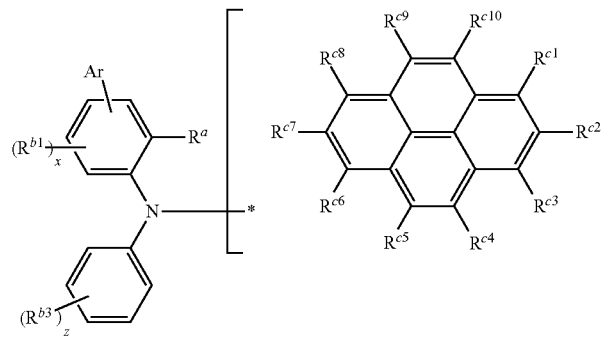
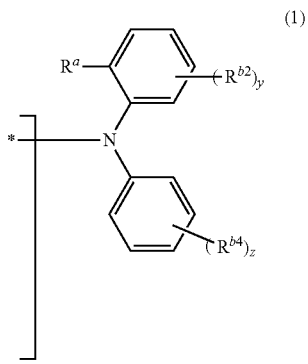

(1)

Ar in the formula (1) is a substituted or unsubstituted aryl group including 6 to 30 ring carbon atoms.

$R^a$ are independently a substituted or unsubstituted alkyl group including 1 to 15 carbon atoms, or a substituted or unsubstituted cycloalkyl group including 3 to 15 carbon atoms.

$R^{b1}$ to $R^{b4}$ are independently a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a atoms, a substituted or unsubstituted heteroaryl group including 3 to 30 ring atoms, or a single bond that is bonded to either nitrogen atom.

* is a bonding position at which any of $R^{c1}$ to $R^{c10}$ is bonded to either nitrogen atom.

x is an integer from 0 to 3, y is an integer from 0 to 4, and z are independently an integer from 0 to 5. A plurality of $R^{b1}$ are either identical or different when x is an integer equal to or larger than 2, a plurality of $R^{b2}$ are either identical or different when y is an integer equal to or larger than 2, and a plurality of $R^{b3}$ or $R^{b4}$ are either identical or different when z is an integer equal to or larger than 2.

The compound according to one aspect of the invention exhibits excellent luminous efficiency when used for an organic EL device due to the above specific structure.

The compound is preferably represented by the following formula (2).

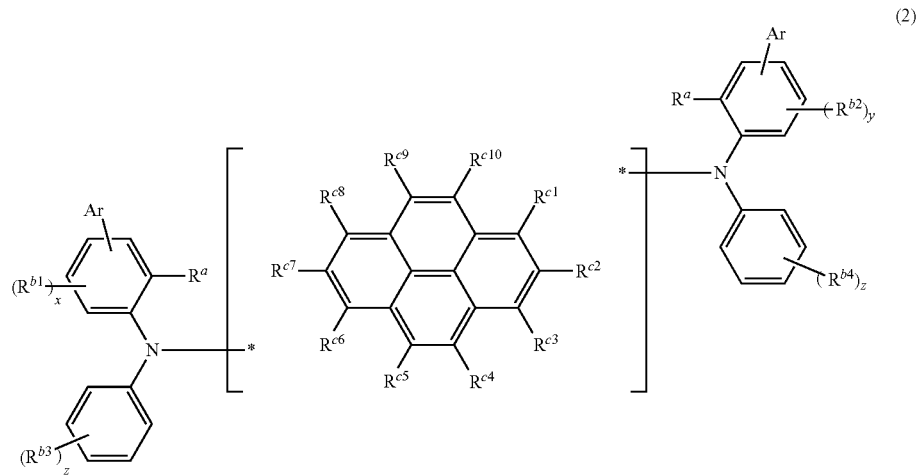

(2)

Ar, $R^a$, $R^{b1}$ to $R^{b4}$, $R^{c1}$ to $R^{c10}$, x, z, and * in the formula (2) are the same as defined for the formula (1).

It is preferable that $R^{c1}$ to $R^{c10}$ be independently a group other than an arylamino group. Specifically, it is preferable that $R^{c1}$ to $R^{c10}$ be independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted aryl group including 6 to 30 ring carbon atoms, a substituted or unsubstituted heteroaryl group including 3 to 30 ring atoms, or a single bond that is bonded to either nitrogen atom.

In this case, the compound is an arylamino group-disubstitution product.

The compound is preferably represented by the following formula (3), and more preferably represented by the following formula (4).

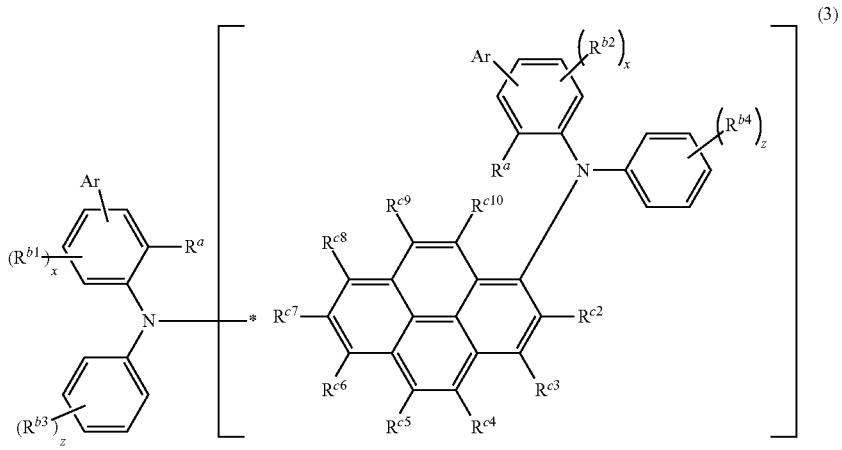

(3)

Ar, $R^a$, $R^{b1}$ to $R^{b4}$, $R^{c2}$ to $R^{c10}$, x, z, and * in the formula (3) are the same as defined for the formula (1).

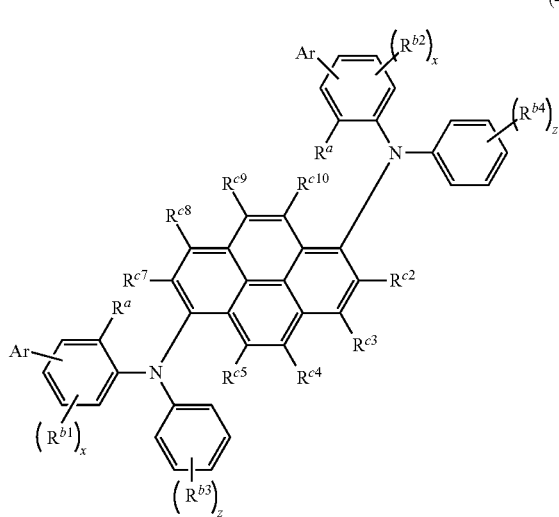

(4)

Ar, $R^a$, $R^{b1}$ to $R^{b4}$, x, and z in the formula (4) are the same as defined for the formula (1).

$R^{c2}$ to $R^{c5}$ and $R^{c7}$ to $R^{c10}$ are independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 ring atoms.

When the compound is represented by the formula (4), the compound is more preferably represented by the following formula (4-1).

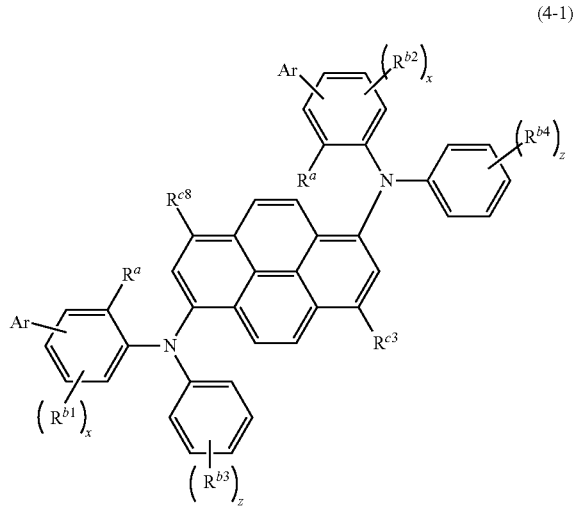

(4-1)

Ar, $R^a$, $R^{b1}$ to $R^{b4}$, $R^{c3}$, $R^{c8}$, x, and z in the formula (4-1) are the same as defined for the formula (4).

It is preferable that $R^{c3}$ and $R^{c8}$ be independently a hydrogen atom, an alkyl group including 1 to 6 carbon atoms, or a cycloalkyl group including 1 to 6 carbon atoms.

The compound is preferably represented by the following formula (5).

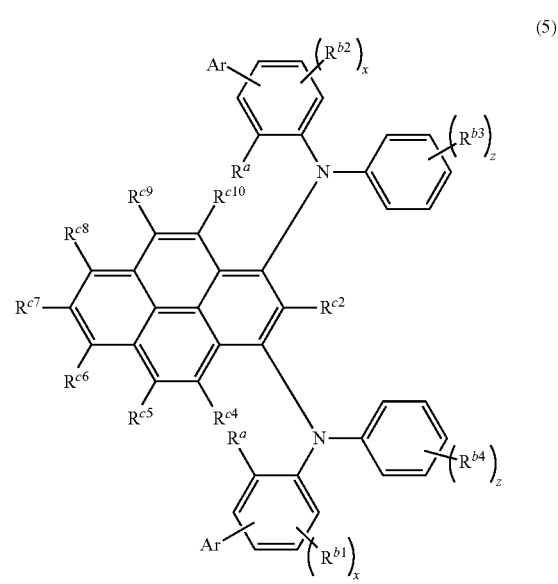

(5)

Ar, $R^a$, $R^{b1}$ to $R^{b4}$, x, and z in the formula (5) are the same as defined for the formula (1).

$R^{c2}$ and $R^{c4}$ to $R^{c10}$ are independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 ring atoms.

When the compound is represented by the formula (5), the compound is more preferably represented by the following formula (5-1).

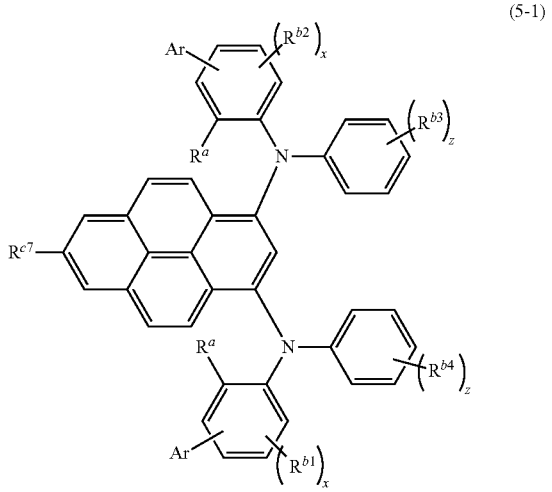

(5-1)

Ar, $R^a$, $R^{b1}$ to $R^{b4}$, $R^{c7}$, x, and z in the formula (5-1) are the same as defined for the formula (5).

It is preferable that $R^{c7}$ be a substituted or unsubstituted alkyl group including 1 to 15 carbon atoms, or a substituted or unsubstituted cycloalkyl group including 3 to 15 carbon atoms.

It is preferable that the benzene ring-containing group in the formula (1) to which $R^{b1}$ is bonded, and the benzene ring-containing group in the formula (1) to which $R^{b2}$ is bonded, have a structure in which the benzene ring-containing group is not substituted with a substituent (i.e., a hydrogen atom is bonded) at the para position with respect to the bonding position at which the N atom is bonded. Specifically, it is preferable that the benzene ring-containing group to which $R^{b1}$ is bonded have a structure in which $R^{b1}$ and Ar are not bonded at the para position with respect to the bonding position at which the N atom is bonded, and the benzene ring-containing group to which $R^{b2}$ is bonded have a structure in which $R^{b2}$ is not bonded at the para position with respect to the bonding position at which the N atom is bonded. Likewise, it is preferable that the benzene ring-containing group in the formula (2) and the like to which $R^{b1}$ is bonded have a structure in which $R^{b1}$ and Ar are not bonded at the para position with respect to the bonding position at which the N atom is bonded, and the benzene ring-containing group to which $R^{b2}$ is bonded have a structure in which $R^{b2}$ and Ar are not bonded at the para position with respect to the bonding position at which the N atom is bonded.

When the compound according to one aspect of the invention is used as a dopant material for an emitting layer that forms an organic EL device, the emission wavelength may increase, and the blue chromaticity of the resulting light may decrease if an alkyl group or an aryl group is bonded at the para position with respect to the bonding position at which the N atom is bonded. Since deep (short-wavelength) blue light is suitable for various applications that utilize an organic EL device, it is preferable that an alkyl group, an aryl group, or the like is absent at the para position with respect to the bonding position at which the N atom is bonded.

Note that the benzene ring-containing group may be substituted with $R^{b1}$ and Ar at para positions.

In the formula (1), it is preferable that Ar be bonded at the para position with respect to $R^a$. Specifically, it is preferable that the benzene ring-containing group to which $R^{b1}$ is bonded be represented by the following formula (10), and the benzene ring-containing group to which $R^{b2}$ is bonded be represented by the following formula (11). In this case, it is considered that the molecular arrangement of the compound according to one aspect of the invention in an organic film is optimized or nearly optimized, and an energy transfer from an emitting layer and the like are optimized or nearly optimized when the compound according to one aspect of the invention is used as a dopant material for an emitting layer that forms an organic EL device, so that the luminous efficiency is improved.

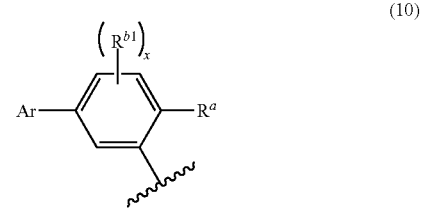

(10)

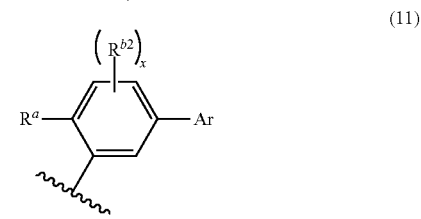

(11)

Ar, $R^a$, $R^{b1}$, $R^{b2}$, and x in the formulas (10) and (11) are the same as defined for the formula (1).

It is preferable that $R^{b3}$ and $R^{b4}$ in the formula (1) not be bonded at the para position with respect to the bonding position at which the N atom is bonded. Specifically, it is preferable that $R^{b3}$ and $R^{b4}$ be bonded at the meta position or the ortho position with respect to the bonding position at which the N atom is bonded, and it is preferable that $R^{b3}$ and $R^{b4}$ be bonded at the ortho position with respect to the bonding position at which the N atom is bonded. Specifically, it is preferable that the benzene ring-containing group to which $R^{b3}$ is bonded be represented by the following formula (12), and the benzene ring-containing group to which $R^{b4}$ is bonded be represented by the following formula (13).

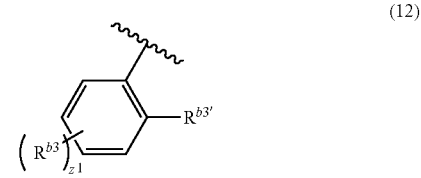

(12)

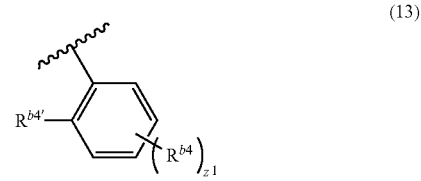

(13)

$R^{b3}$ and $R^{b4}$ in the formulas (12) and (13) are the same as defined for the formula (1).

$R^{b3'}$ and $R^{b4'}$ are independently a substituted or unsubstituted alkyl group including 1 to 15 carbon atoms, or a substituted or unsubstituted cycloalkyl group including 3 to 15 carbon atoms, and z1 are independently an integer from 0 to 4.

It is preferable that $R^a$ be independently a substituted or unsubstituted alkyl group including 1 to 6 carbon atoms.

It is preferable that $R^{b1}$ to $R^{b4}$ be independently a group other than an electron-withdrawing group. Specifically, it is preferable that $R^{b1}$ to $R^{b4}$ be independently a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 ring atoms.

It is more preferable that $R^{b1}$ to $R^{b4}$ be independently a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, or a substituted or unsubstituted aryl group including 6 to 30 ring carbon atoms.

It is preferable that $R^{c1}$ to $R^{c10}$ be a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, or a substituted or unsubstituted arylsilyl group including 6 to 50 carbon atoms, and more preferably a substituted or unsubstituted alkyl group including 1 to 15 carbon atoms, or a substituted or unsubstituted cycloalkyl group including 3 to 15 carbon atoms.

It is preferable that the compound according to one aspect of the invention be a compound represented by the following formula (4-2) or (5-2).

(4-2)

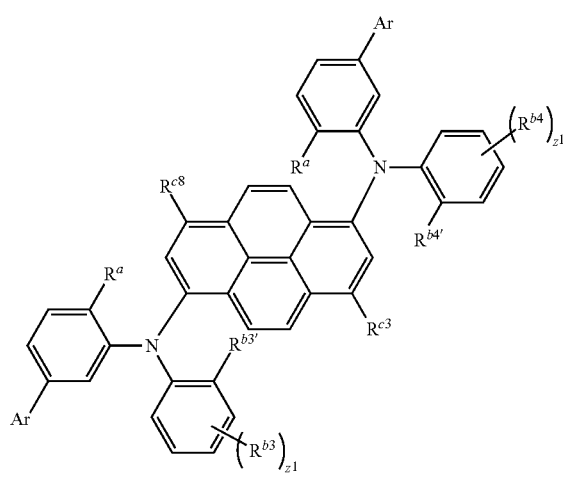

(5-2)

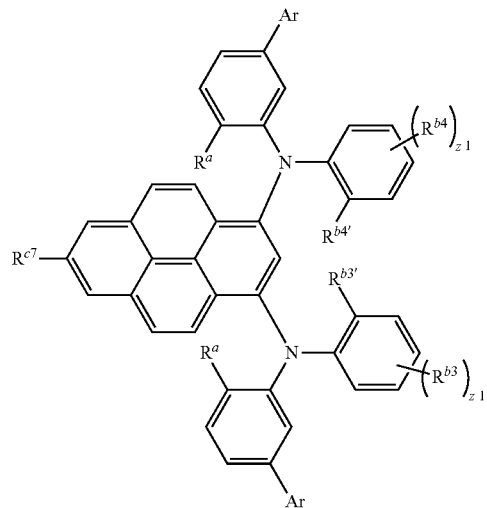

Each group in the formulas (4-2) and (5-2) is the same as defined above.

The compound may be produced using the method described in the examples. The compound according to the invention may be synthesized in accordance with the reaction described in the examples using an appropriate known alternative reaction or raw material taking account of the target product.

The term "hydrogen atom" used herein includes isotopes of hydrogen that differ in the number of neutrons (i.e., protium, deuterium, and tritium).

The term "number of ring carbon atoms" used herein refers to the number of carbon atoms among the atoms that form the ring of a compound including a structure in which atoms are bonded in a ring-like manner (e.g., monocyclic compound, fused ring compound, bridged compound, carbocyclic compound, and heterocyclic compound). When the ring is substituted with a substituent, the number of ring carbon atoms excludes the number of carbon atoms included in the substituent. The above definition is applied to the term "number of ring carbon atoms" unless otherwise specified. For example, the number of ring carbon atoms of a benzene ring is 6, the number of ring carbon atoms of a naphthalene ring is 10, the number of ring carbon atoms of a pyridinyl group is 5, and the number of ring carbon atoms of a furanyl group is 4. For example, when a benzene ring or a naphthalene ring is substituted with an alkyl group, the number of ring carbon atoms excludes the number of carbon atoms of the alkyl group. For example, when a fluorene ring is substituted with a fluorene ring (including a spirofluorene ring), the number of ring carbon atoms excludes the number of carbon atoms of the fluorene ring that is bonded as a substituent.

The term "number of ring atoms" used herein refers to the number of atoms that form the ring of a compound including a structure (e.g., monocyclic ring, fused ring, and ring assembly) in which atoms are bonded in a ring-like manner (e.g., monocyclic compound, fused ring compound, bridged compound, carbocyclic compound, and heterocyclic compound). The number of ring atoms excludes the number of atoms that do not form the ring (e.g., a hydrogen atom that is bonded to (terminates) an atom that forms the ring), and the number of atoms included in a substituent when the ring is substituted. The above definition is applied to the term "number of ring atoms" unless otherwise specified. For example, the number of ring atoms of a pyridine ring is 6, the number of ring atoms of a quinazoline ring is 10, and the number of ring atoms of a furan ring is 5. The number of ring atoms excludes the number of hydrogen atoms that are bonded to the carbon atoms of a pyridine ring or a quinazoline ring, and the number of atoms that are included in a substituent. For example, when a fluorene ring is substituted with a fluorene ring (including a spirofluorene ring), the number of ring atoms excludes the number of atoms of the fluorene ring that is bonded as a substituent.

The expression "XX to YY carbon atoms" used in connection with the expression "substituted or unsubstituted ZZ group including XX to YY carbon atoms" refers to the number of carbon atoms when the ZZ group is unsubstituted, and excludes the number of carbon atoms included in a substituent when the ZZ group is substituted. Note that "YY" is larger than "XX", and "XX" and "YY" are independently an integer equal to or larger than 1.

The expression "XX to YY atoms" used in connection with the expression "substituted or unsubstituted ZZ group including XX to YY atoms" refers to the number of atoms when the ZZ group is unsubstituted, and excludes the number of atoms included in a substituent when the ZZ group is substituted. Note that "YY" is larger than "XX", and "XX" and "YY" are independently an integer equal to or larger than 1.

The term "unsubstituted" used in connection with the expression "substituted or unsubstituted" means that the group is not substituted with a substituent (i.e., a hydrogen atom is bonded).

Each group that is or may be included in each formula is described in detail below.

Examples of the alkyl group include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, and the like.

The number of carbon atoms of the alkyl group is preferably 1 to 10, and more preferably 1 to 6. A methyl group, an ethyl group, a propyl group, an isopropyl group, an n-butyl group, an s-butyl group, an isobutyl group, a t-butyl group, an n-pentyl group, and an n-hexyl group are preferable as the alkyl group.

Examples of the cycloalkyl group include a cyclopropyl group, a cyclobutyl group, a cyclopentyl group, a cyclohexyl group, a 4-methylcyclohexyl group, an adamantyl group, a norbornyl group, and the like. The number of ring carbon atoms of the cycloalkyl group is preferably 3 to 10, more preferably 3 to 8, and still more preferably 5 to 8. The number of ring carbon atoms of the cycloalkyl group may be 3 to 6.

Examples of the aryl group include a phenyl group, a naphthyl group, an anthryl group, a phenanthryl group, a naphthacenyl group, a pyrenyl group, a chrysenyl group, a benzo[c]phenanthryl group, a benzo[g]chrysenyl group, a triphenylenyl group, a fluorenyl group, a benzofluorenyl group, a dibenzofluorenyl group, a biphenylyl group, an o-terphenyl group, an m-terphenyl group, a p-terphenyl group, a fluoranthenyl group, and the like.

The number of ring carbon atoms of the aryl group is preferably 6 to 20, and more preferably 6 to 12. A phenyl group and a biphenyl group are particularly preferable as the aryl group.

The alkylsilyl group is represented by —$SiY_3$. Examples of Y include the groups mentioned above in connection with the alkyl group. Examples of the alkylsilyl group include a trimethylsilyl group, a triethylsilyl group, a t-butyldimethylsilyl group, a vinyldimethylsilyl group, a propyldimethylsilyl group, a triisopropylsilyl group, and the like.

The arylsilyl group is a silyl group that is substituted with one to three aryl groups. Examples of the aryl group include the groups mentioned above in connection with the aryl group. The arylsilyl group may be further substituted with an alkyl group mentioned above. Examples of the arylsilyl group include a triphenylsilyl group, a phenyldimethylsilyl group, and the like.

The alkoxy group is represented by —OY. Examples of Y include the groups mentioned above in connection with the alkyl group. Examples of the alkoxy group include a methoxy group and an ethoxy group.

The aryloxy group is represented by —OZ. Examples of Z include the groups mentioned above in connection with the aryl group. Examples of the aryloxy group include a phenoxy group.

The alkylthio group is represented by —SY. Examples of Y include the groups mentioned above in connection with the alkyl group.

The arylthio group is represented by —SZ. Examples of Z include the groups mentioned above in connection with the aryl group.

The arylamino group is represented by —$NZ_2$. Examples of Z include the groups mentioned above in connection with the aryl group.

Examples of the heteroaryl group include a pyrrolyl group, a triazinyl group, a pyrazinyl group, a pyrimidinyl group, a pyridinyl group, an indolyl group, an isoindolyl group, an imidazolyl group, a furyl group, a benzofuranyl group, an isobenzofuranyl group, a dibenzofuranyl group, a dibenzothiophenyl group, a quinolyl group, an isoquinolyl group, a quinoxalinyl group, a carbazolyl group, a phenanthridinyl group, an acridinyl group, a phenanthrolinyl group, a phenazinyl group, a phenothiazinyl group, a phenoxadinyl group, an oxazolyl group, an oxadiazolyl group, a furazanyl group, a thienyl group, a benzothiophenyl group, and the like.

The number of ring atoms of the heteroaryl group is preferably 5 to 20, and more preferably 5 to 14.

A dibenzofuranyl group, a dibenzothiophenyl group, and a carbazolyl group are preferable as the heteroaryl group, and a 1-dibenzofuranyl group, a 2-dibenzofuranyl group, a 3-dibenzofuranyl group, a 4-dibenzofuranyl group, a 1-dibenzothiophenyl group, a 2-dibenzothiophenyl group, a 3-dibenzothiophenyl group, and a 4-dibenzothiophenyl group are more preferable as the heteroaryl group.

The term "carbazolyl group" used herein also includes the groups respectively having the following structures.

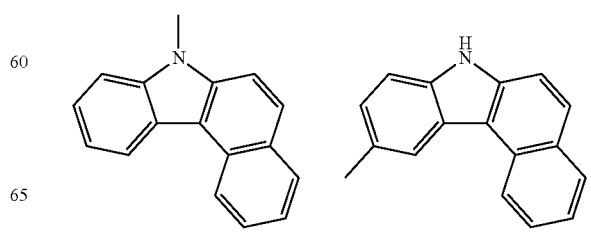

-continued

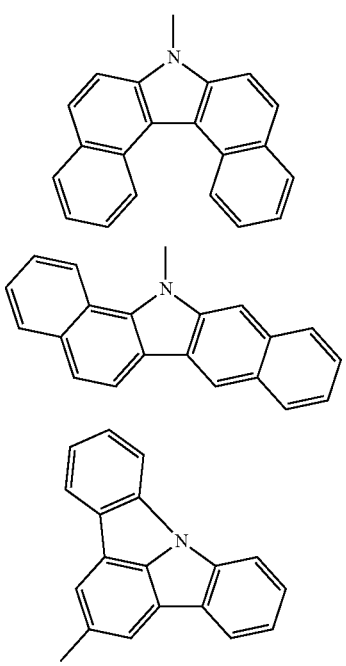

The term "heteroaryl group" used herein also includes the groups respectively having the following structures.

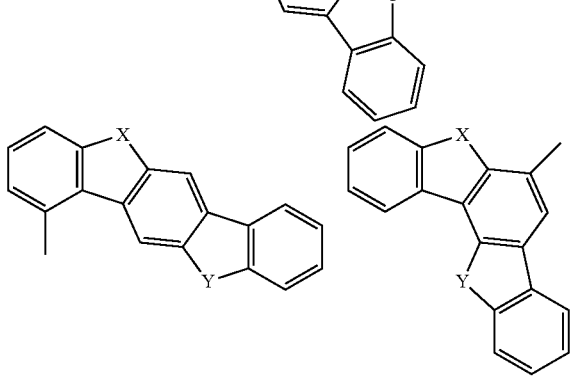

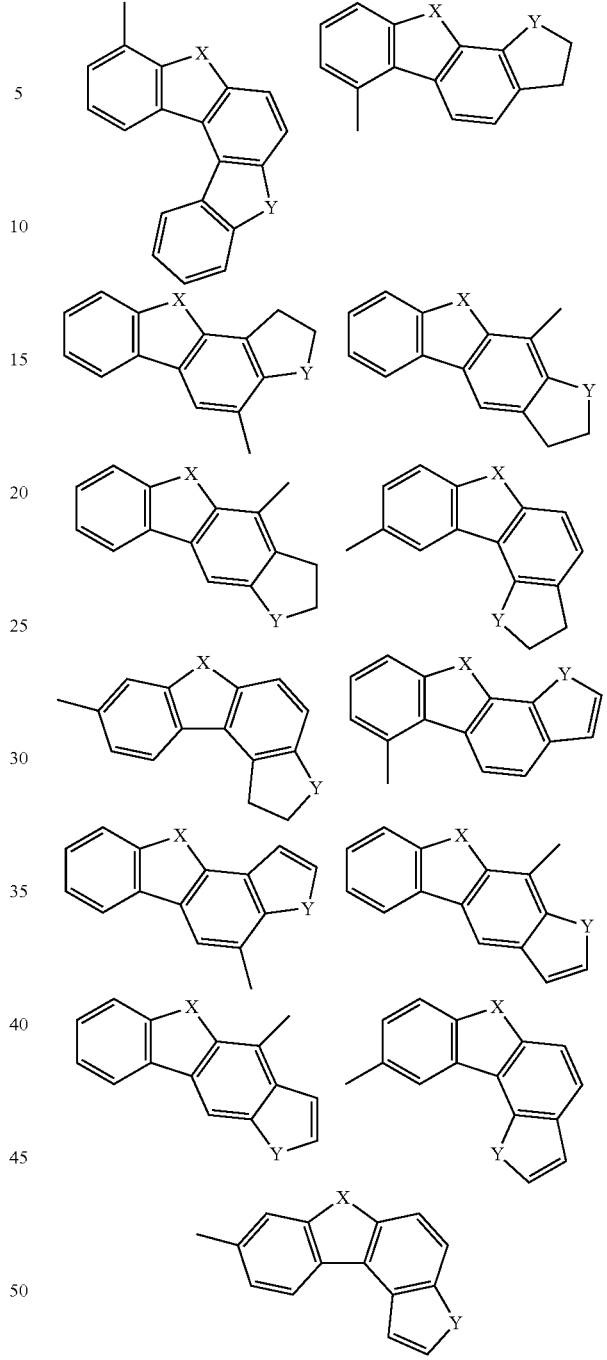

wherein X and Y are independently an oxygen atom, a sulfur atom, a nitrogen atom, or an —NH— group.

Examples of the halogen atom include a fluorine atom, a chlorine atom, a bromine atom, an iodine atom, and the like. Among these, a fluorine atom is preferable.

Examples of a substituent when the expression "substituted or unsubstituted" is used include those mentioned above.

The substituent may be further substituted with another substituent mentioned above. A plurality of substituents may be bonded to form a ring.

Examples of the compound according to one aspect of the invention include the following compounds.

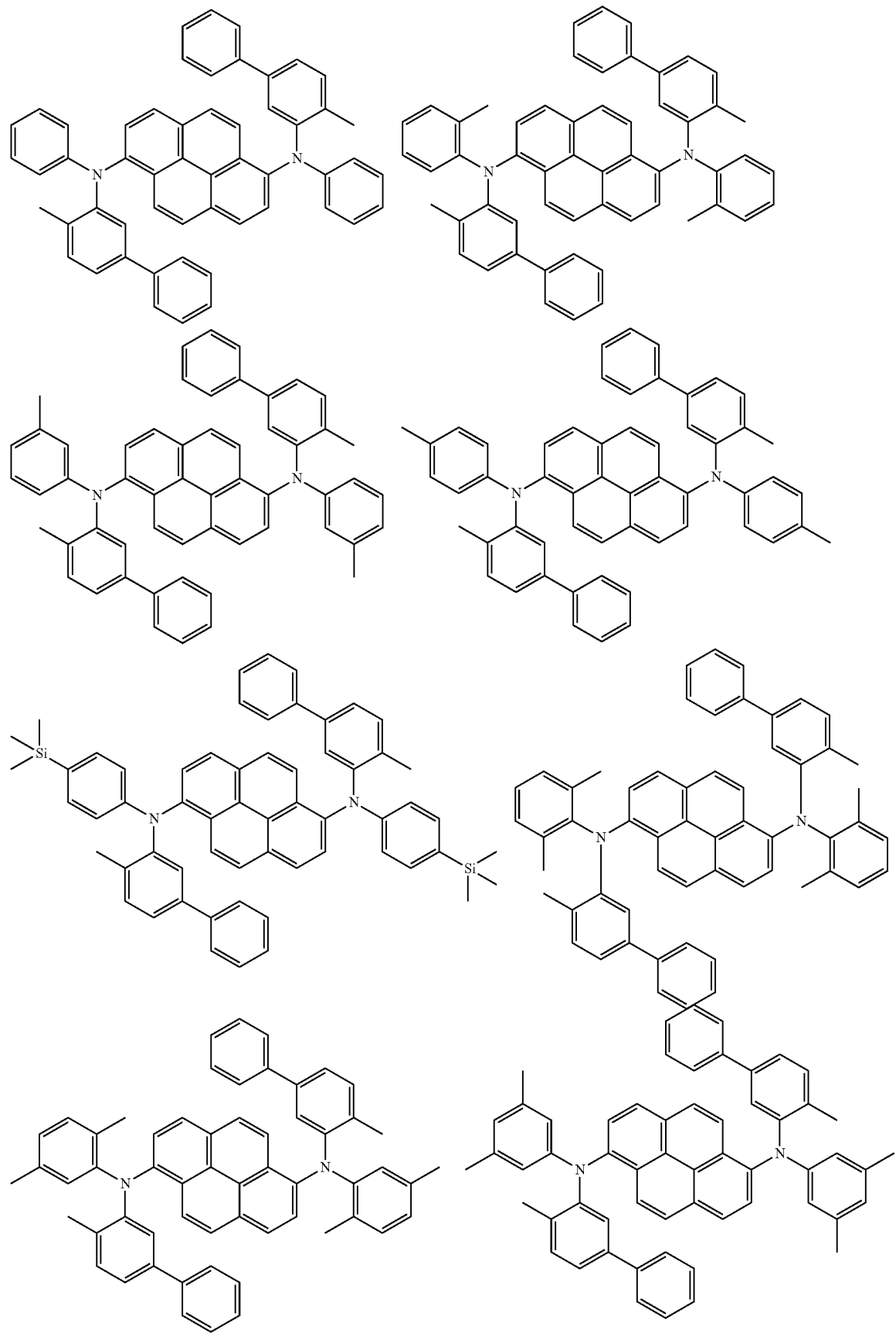

-continued
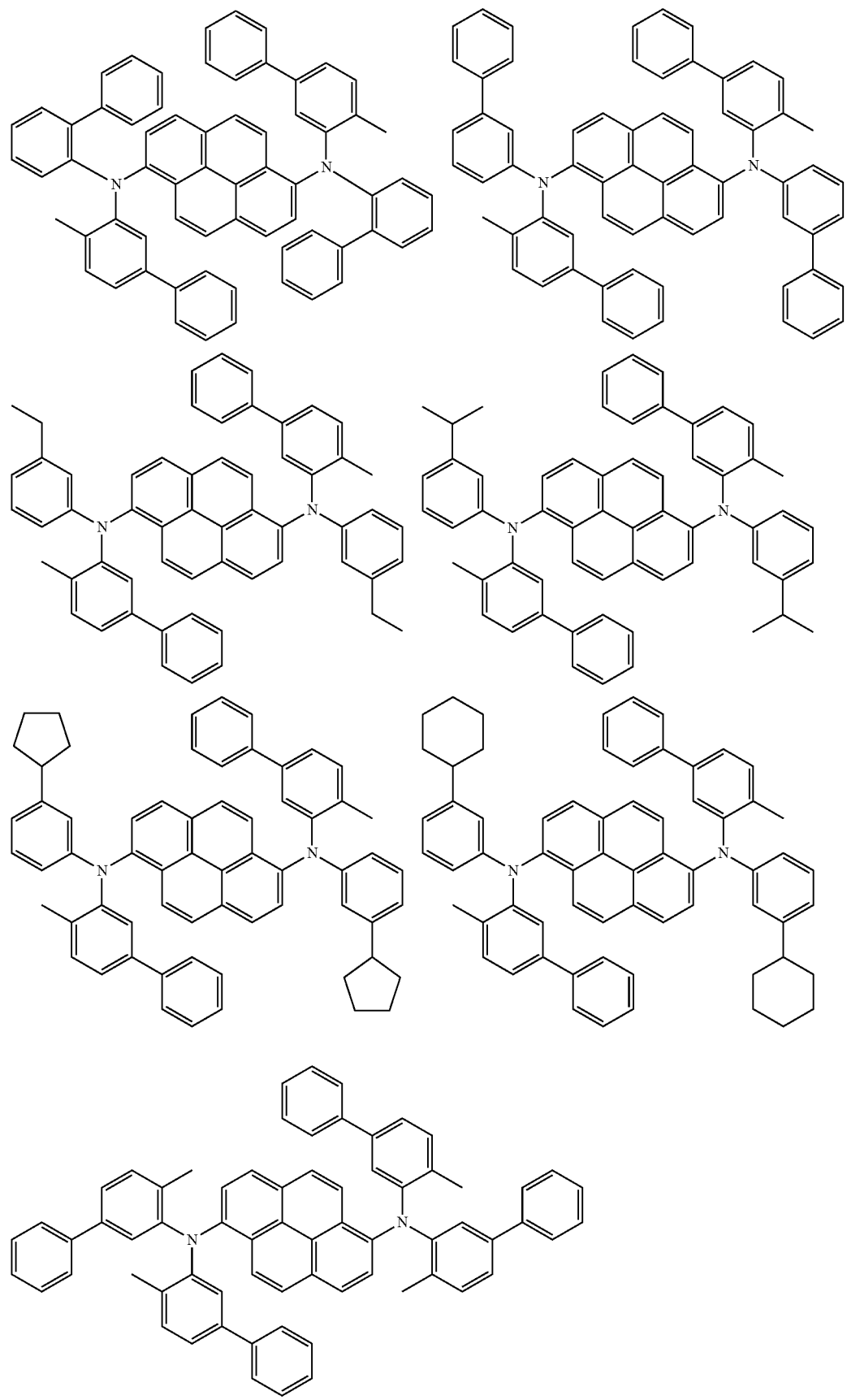

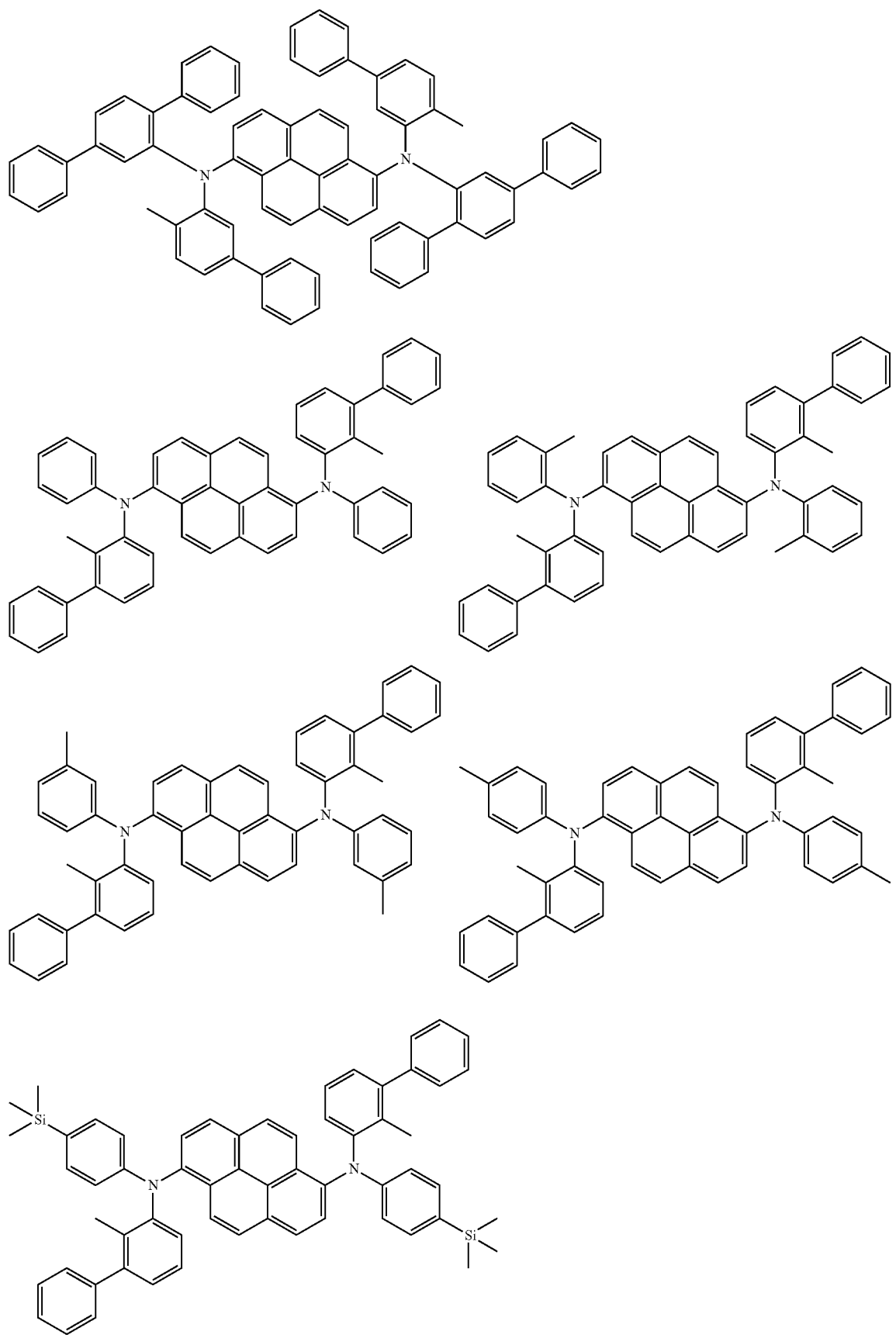

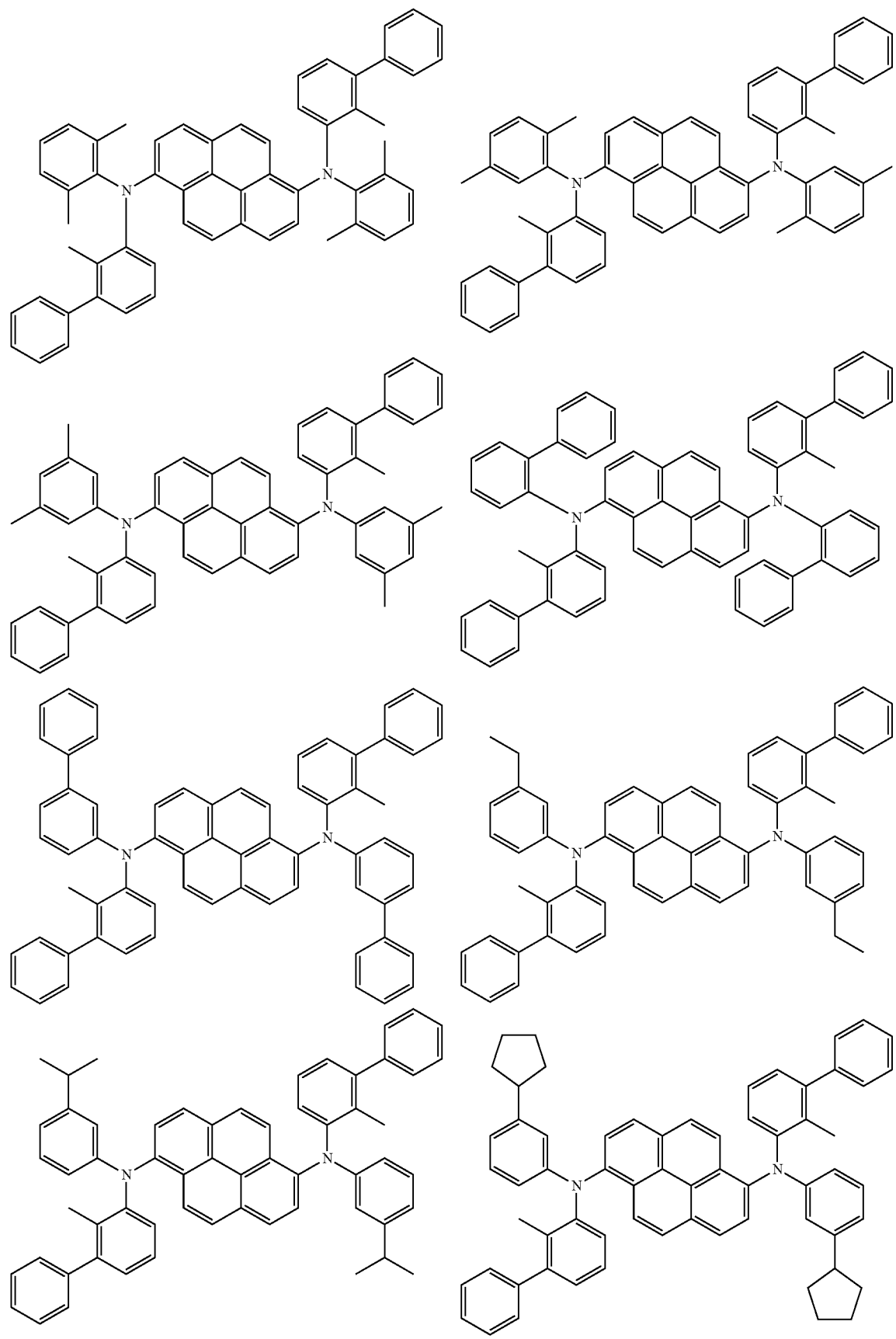

-continued
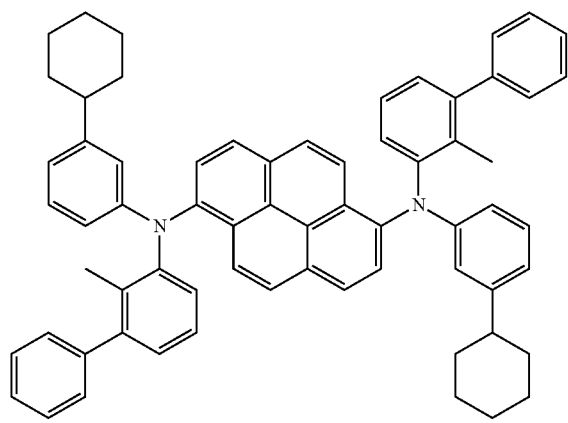
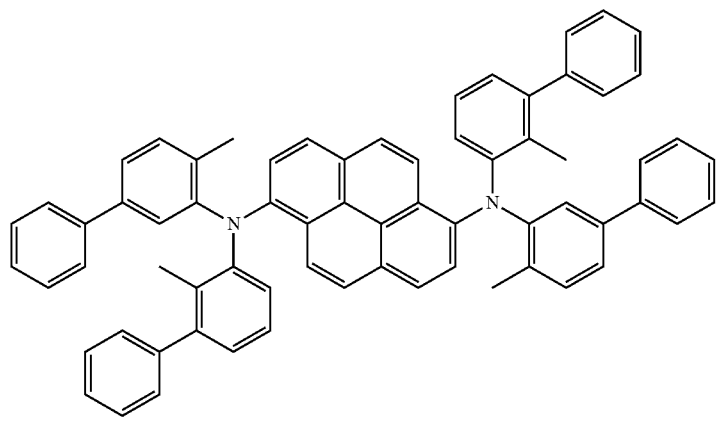
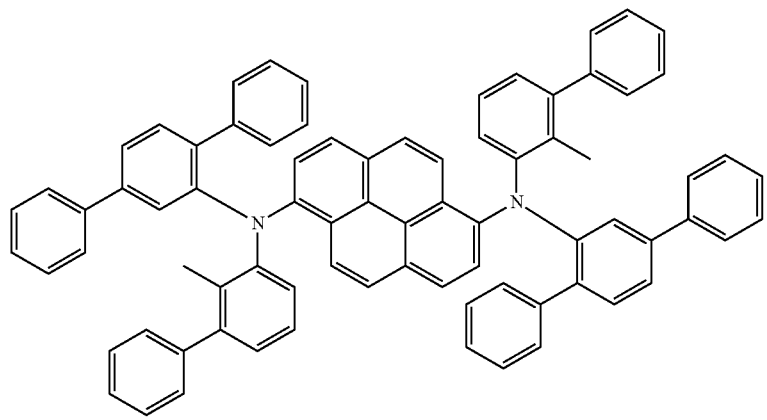
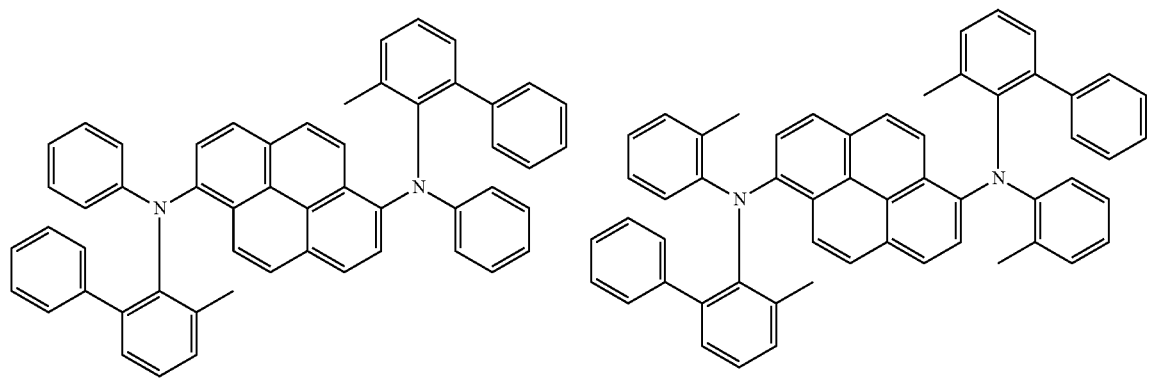

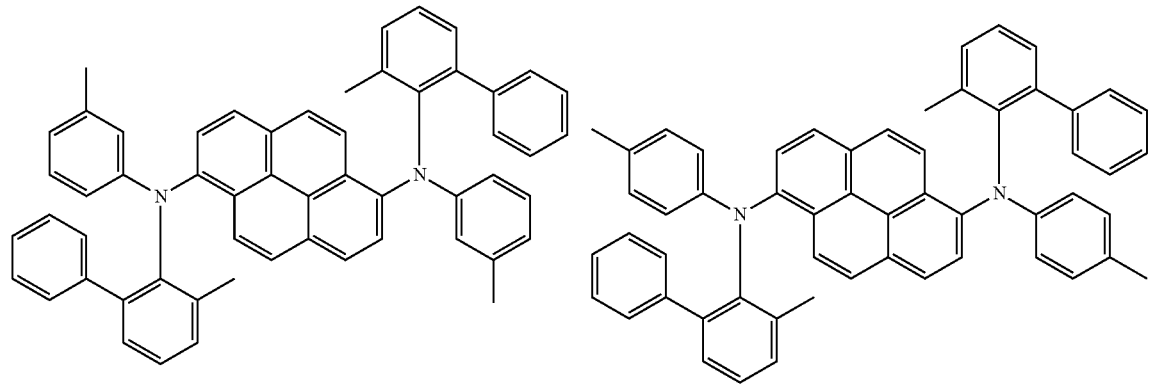
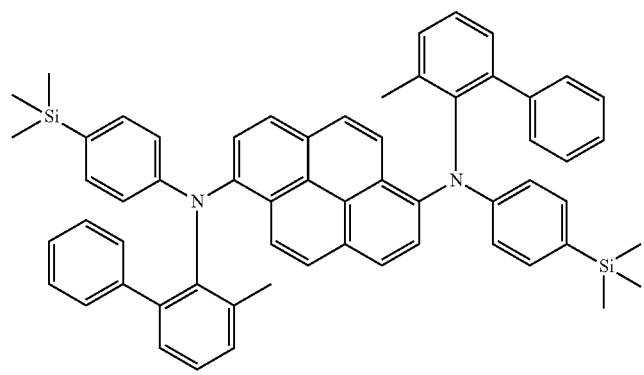
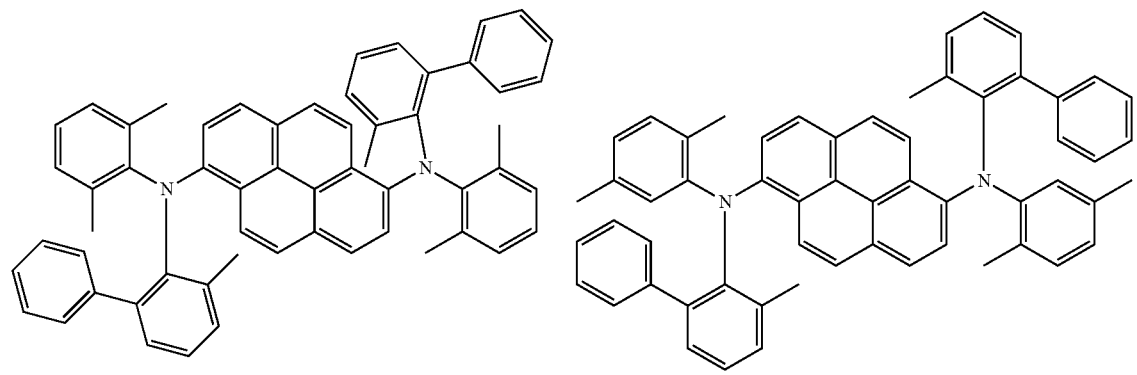
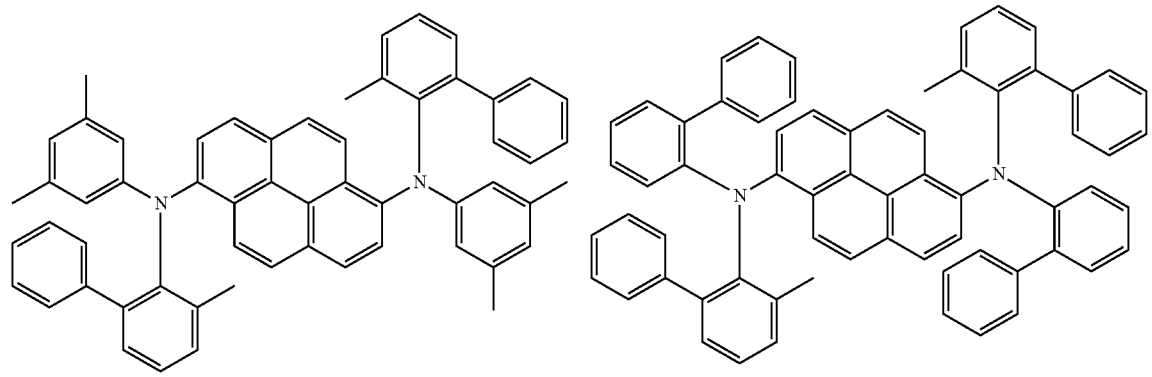

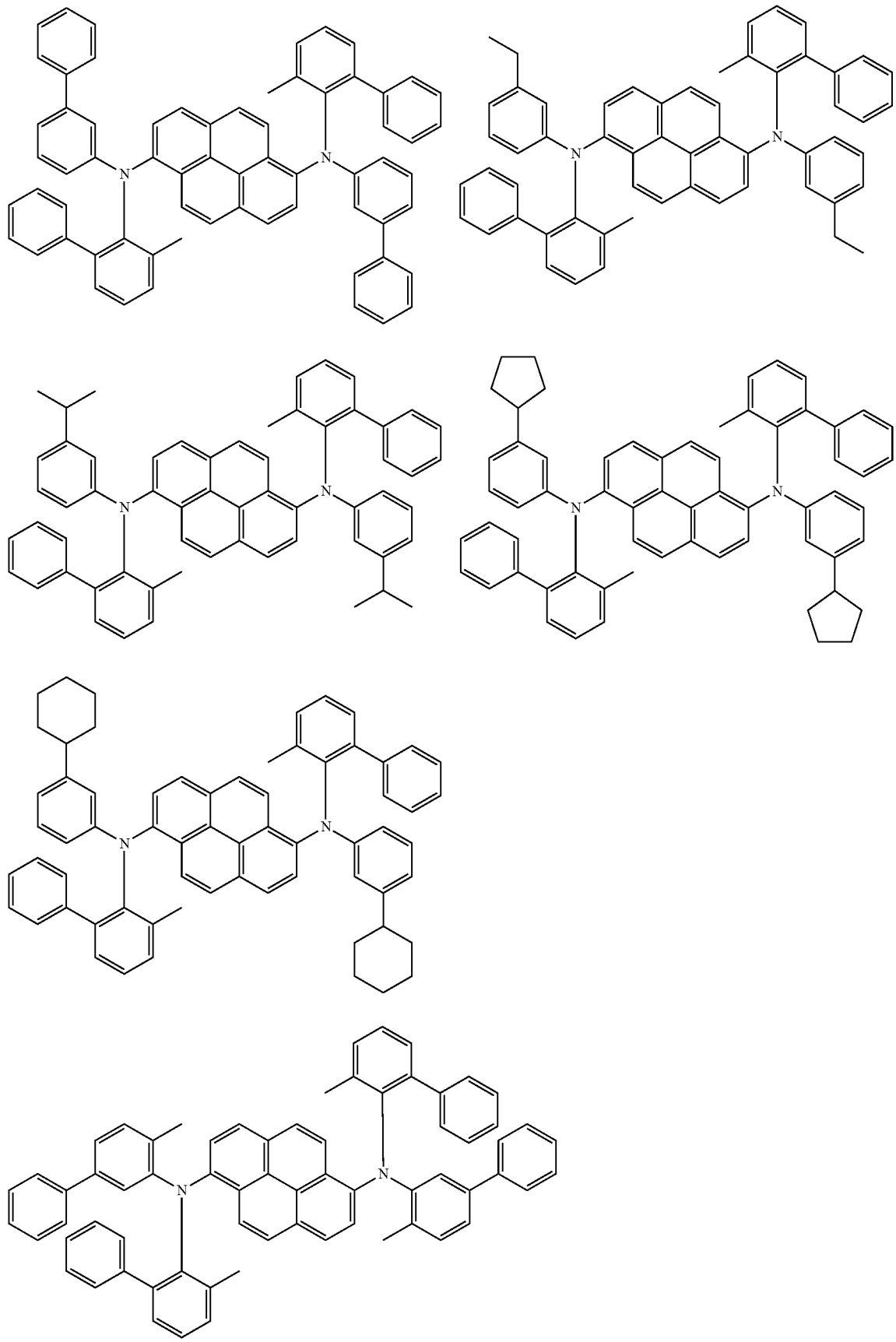

-continued
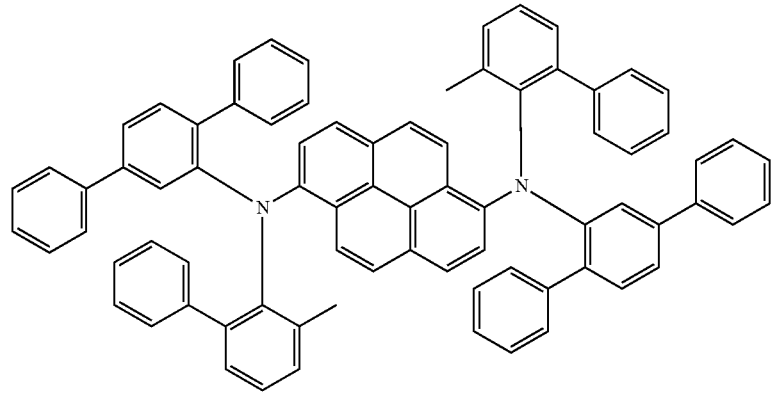
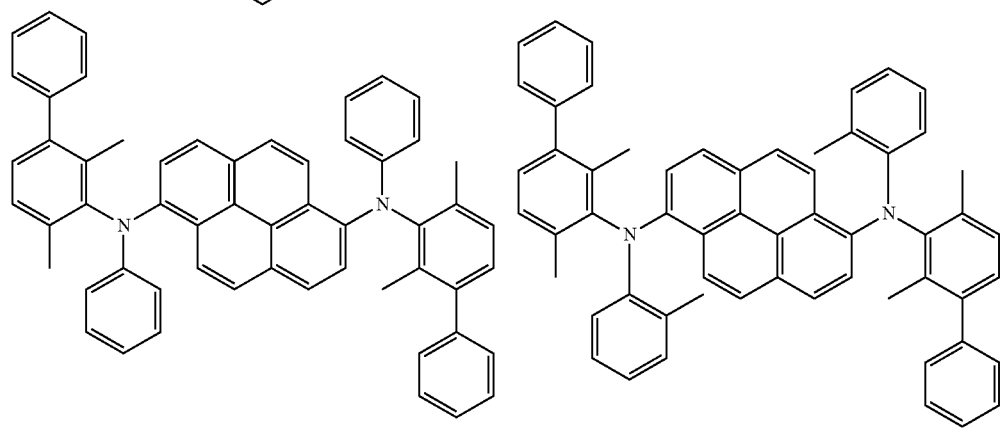
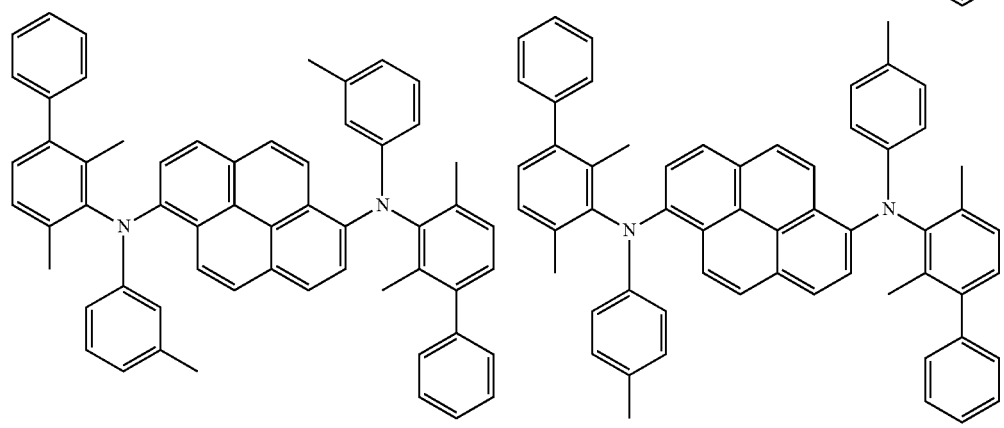
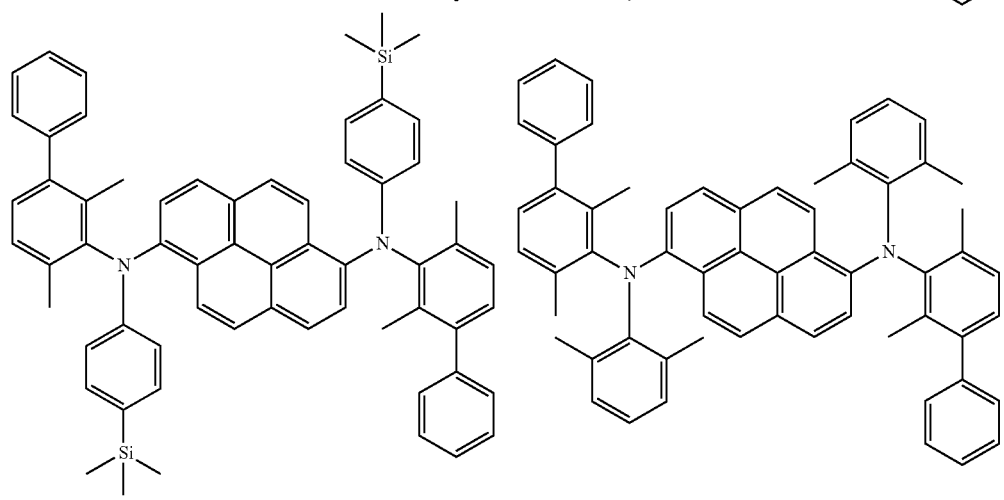

-continued
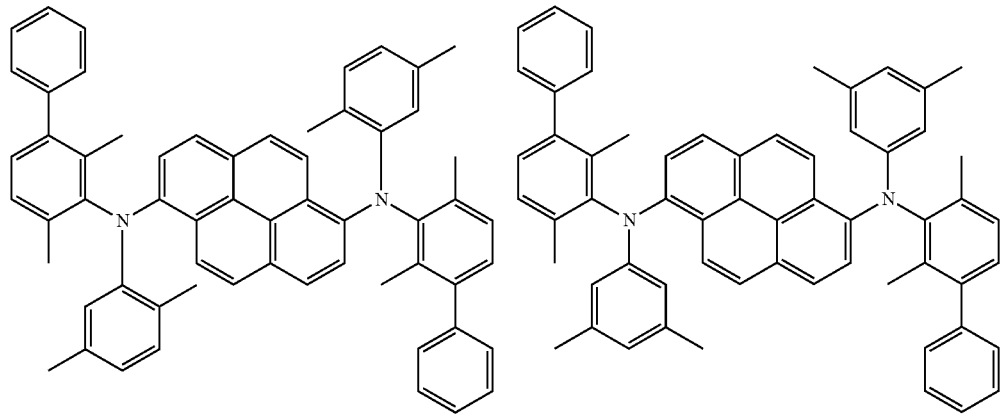
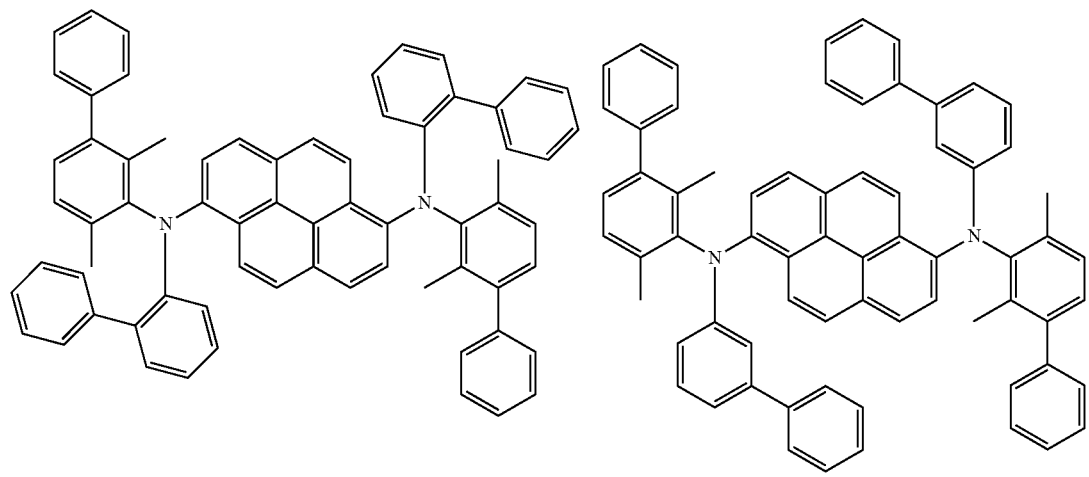
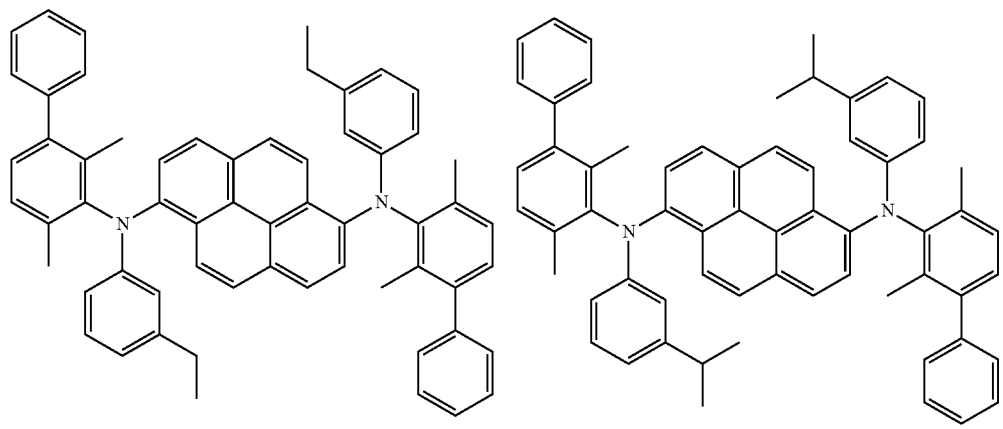

-continued
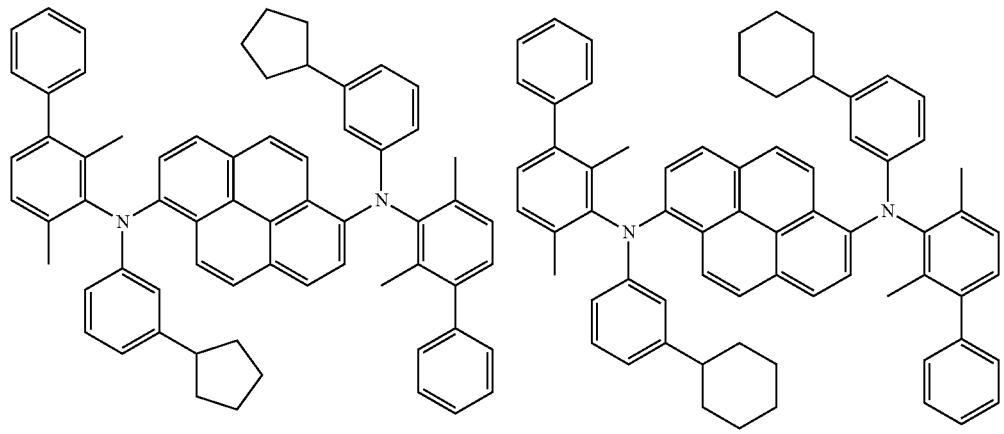
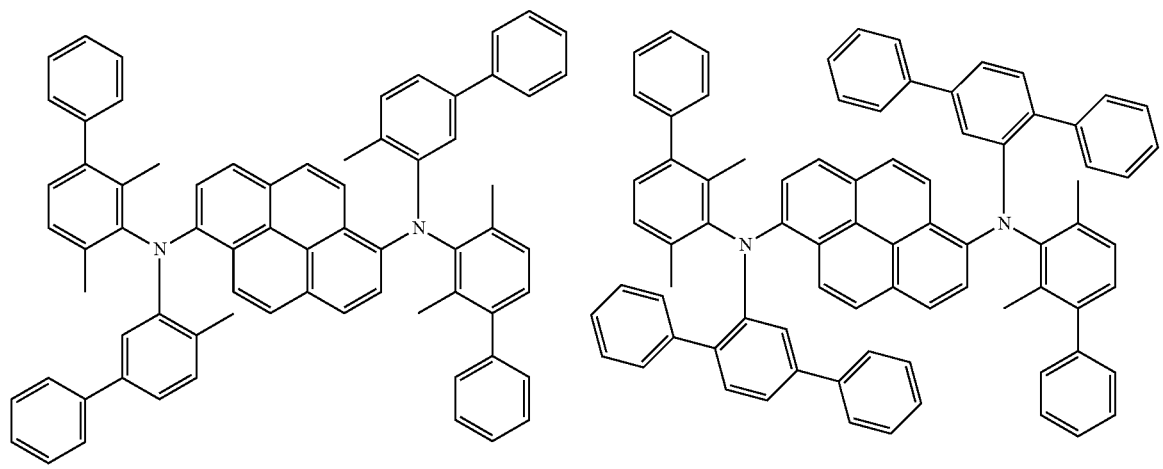
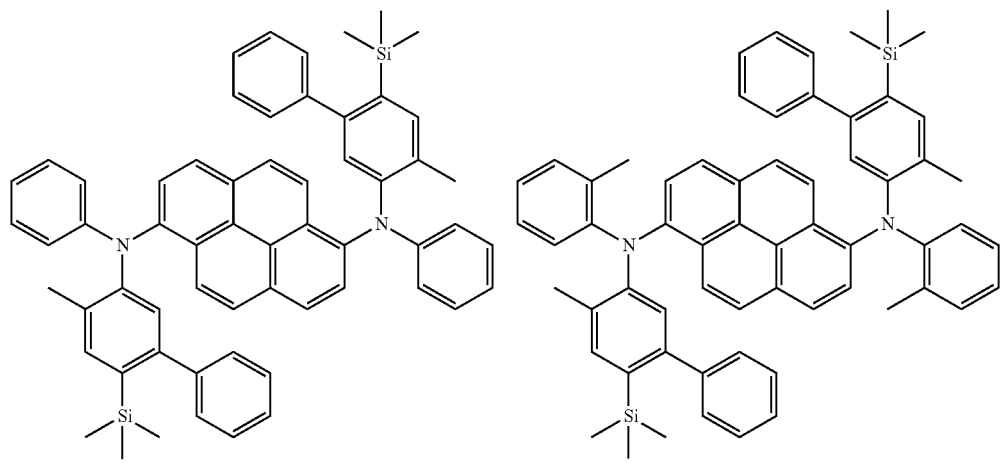

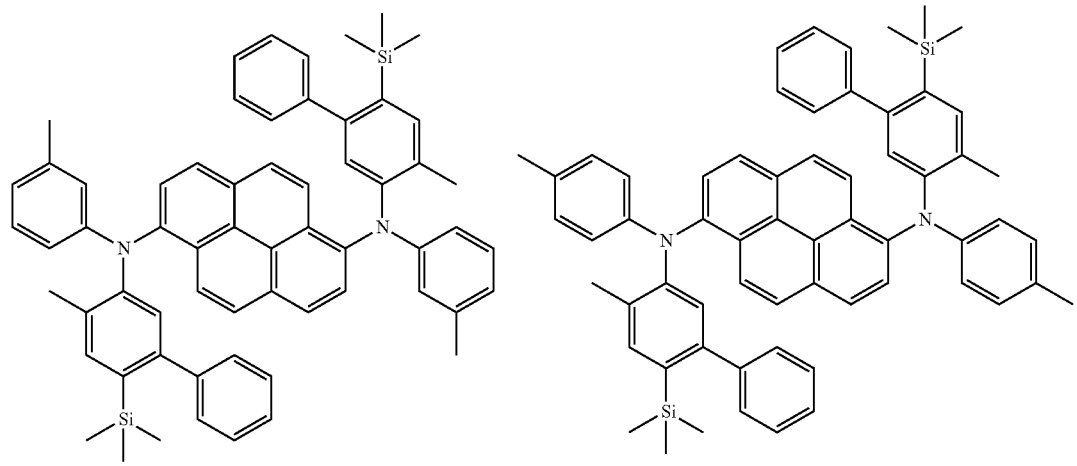
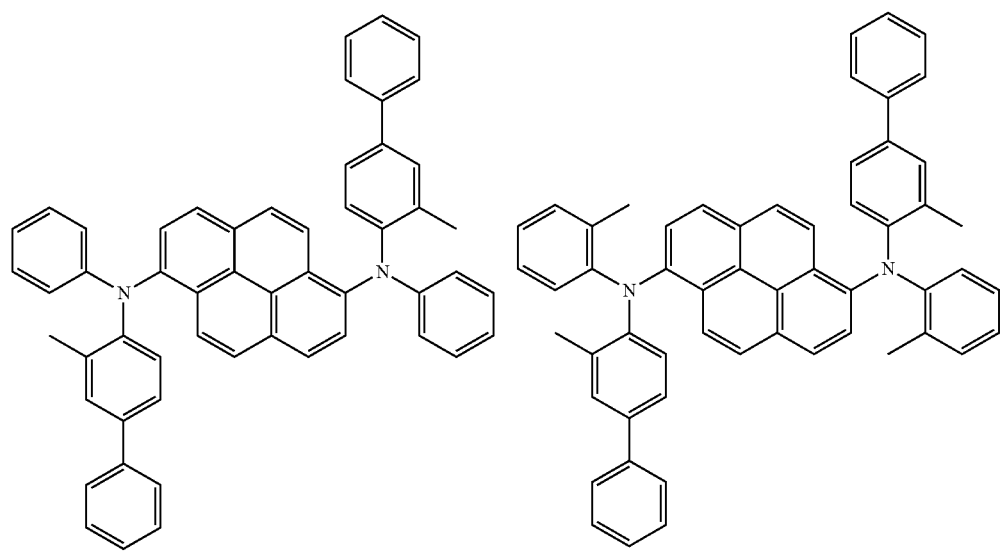
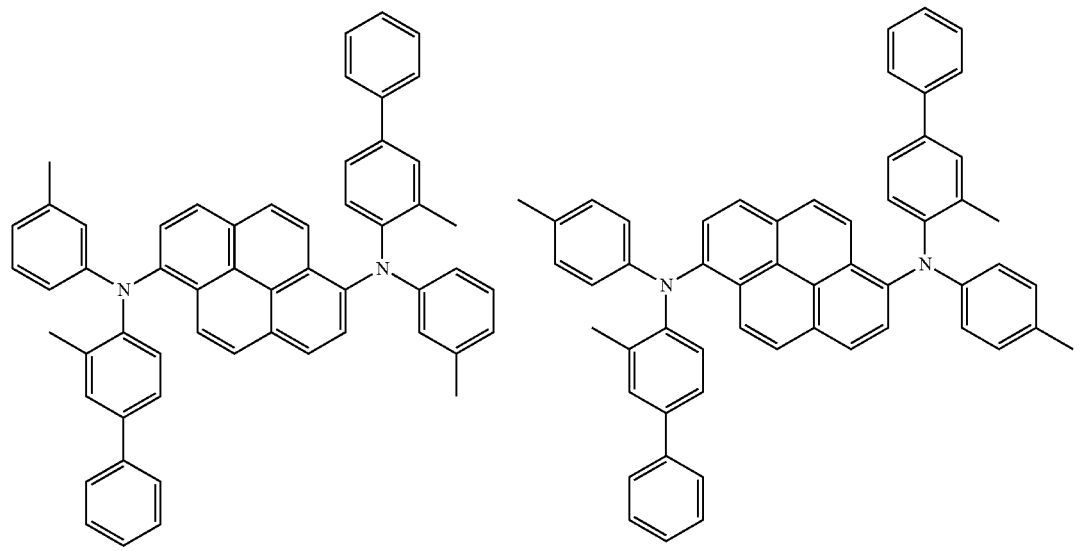

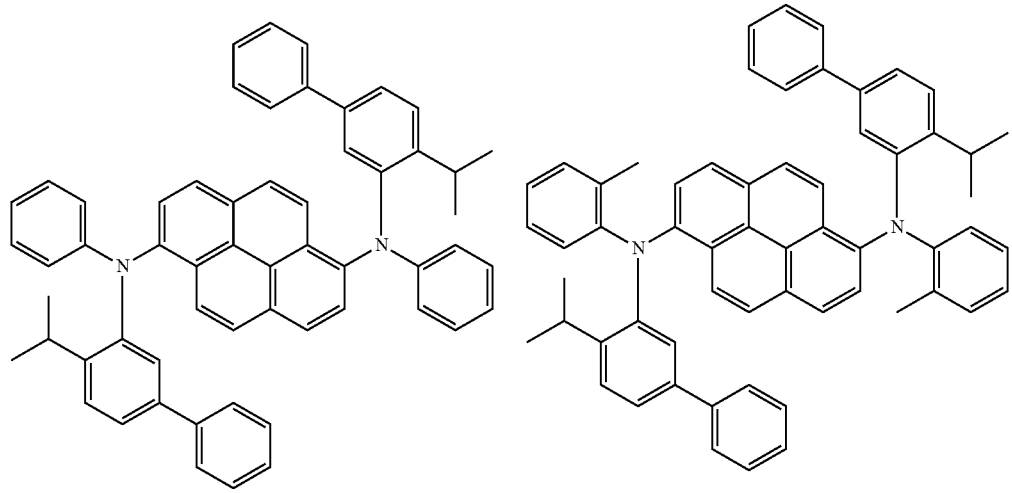
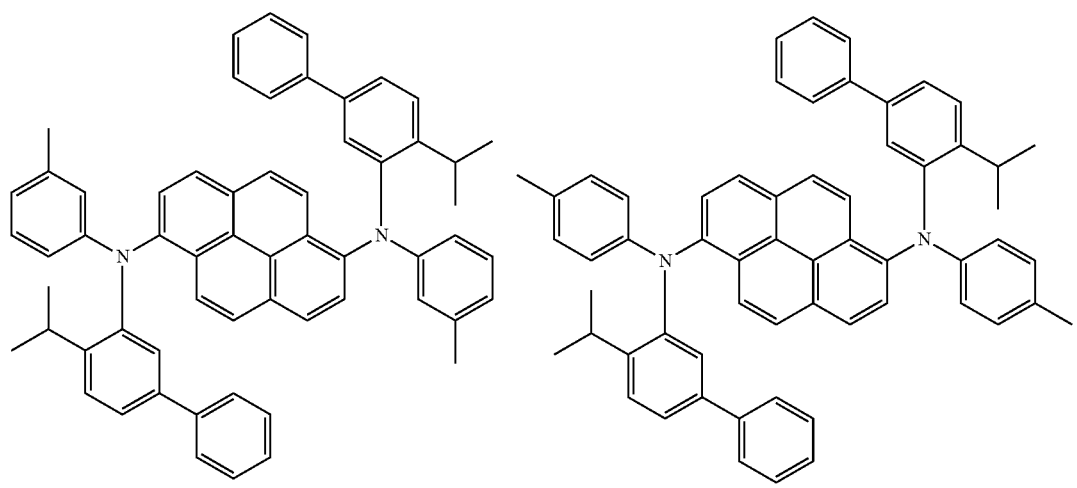
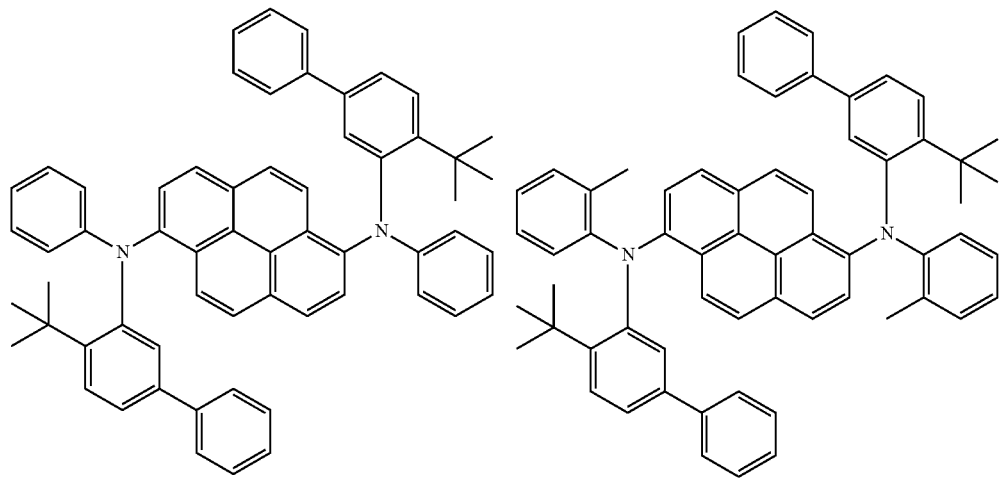

-continued
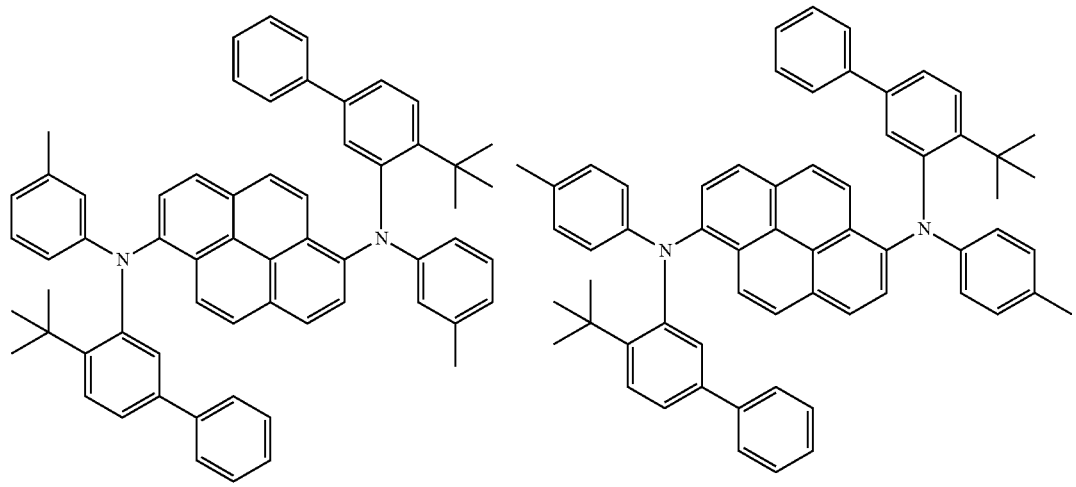
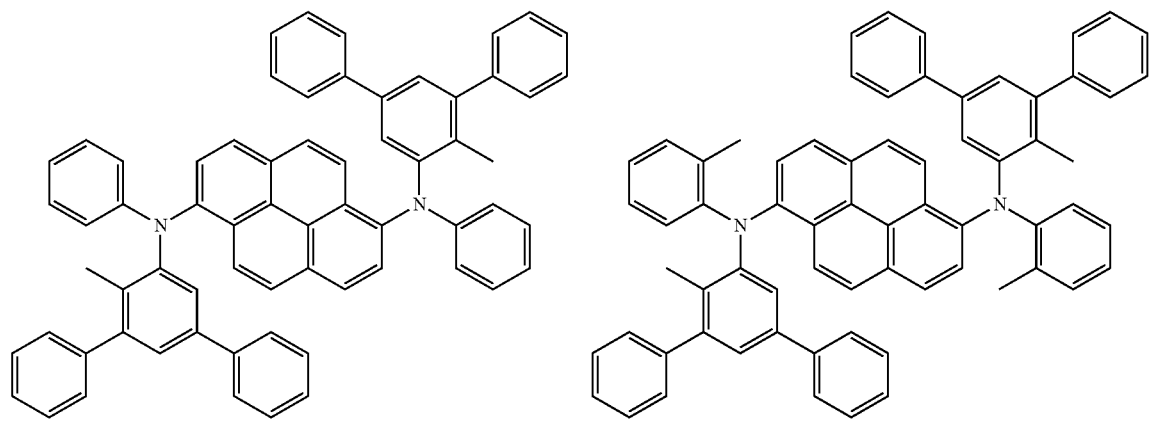
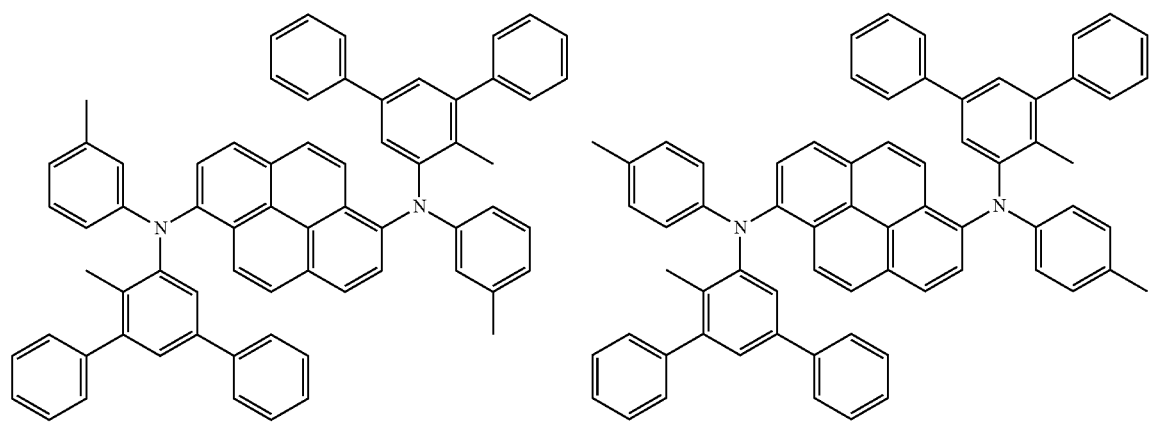

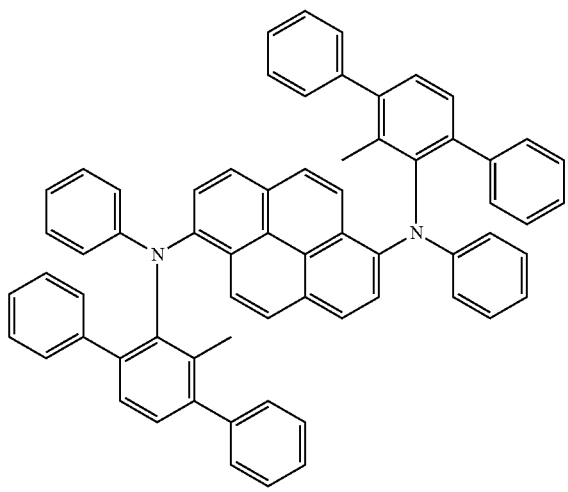
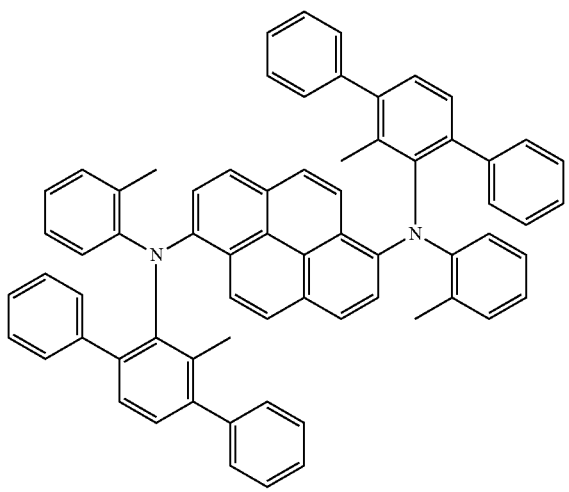
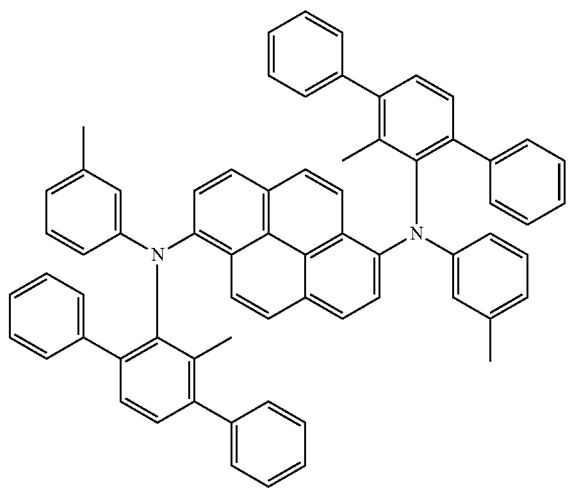
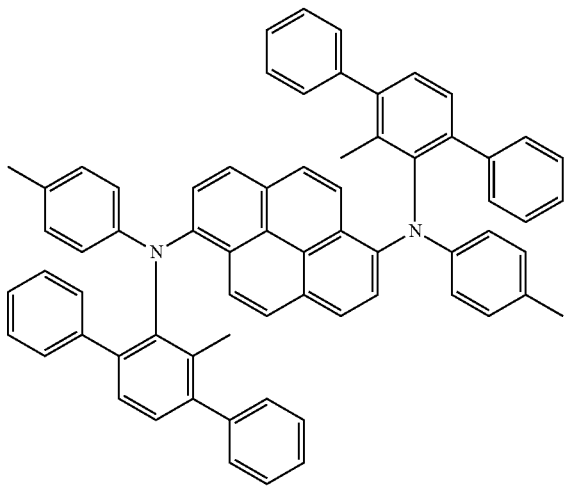
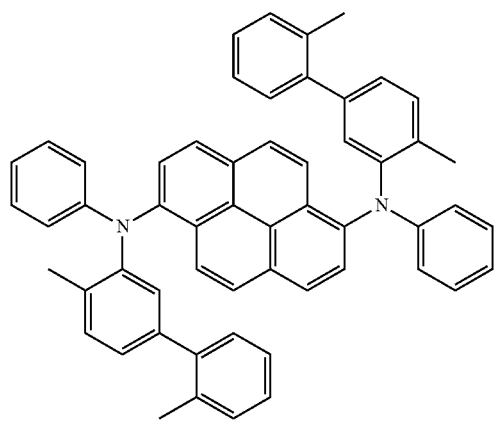
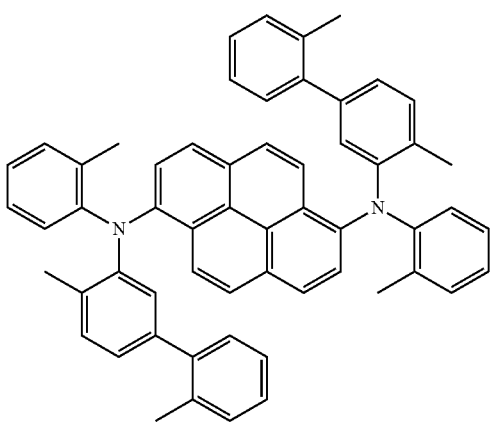

-continued
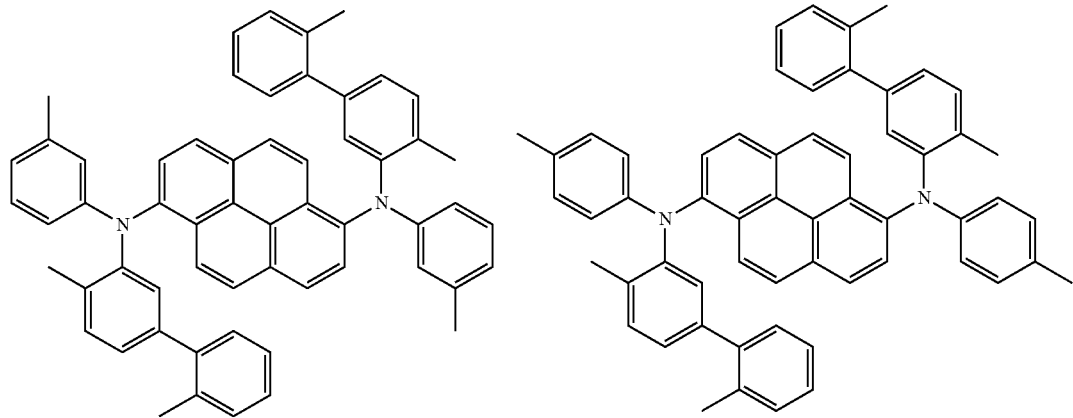
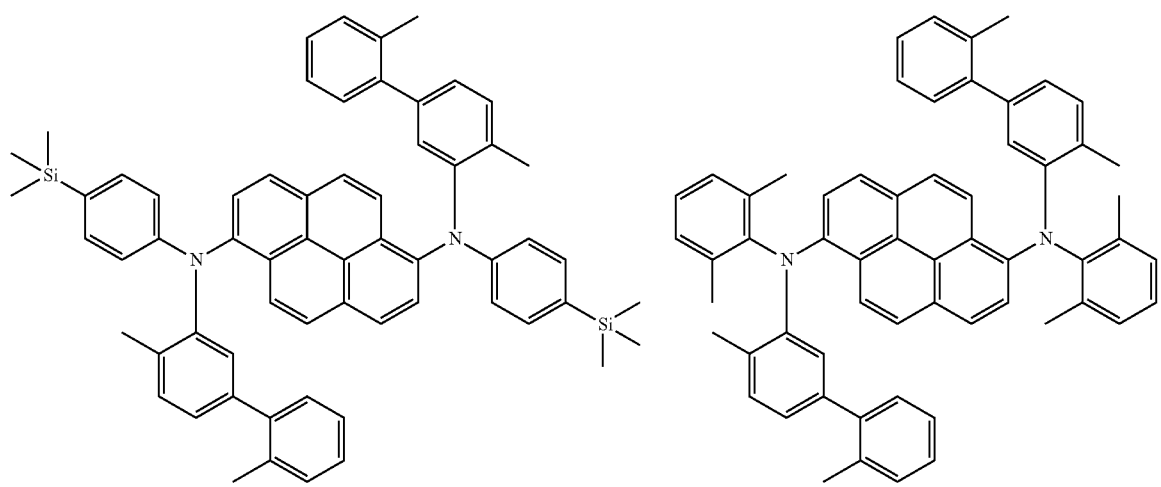
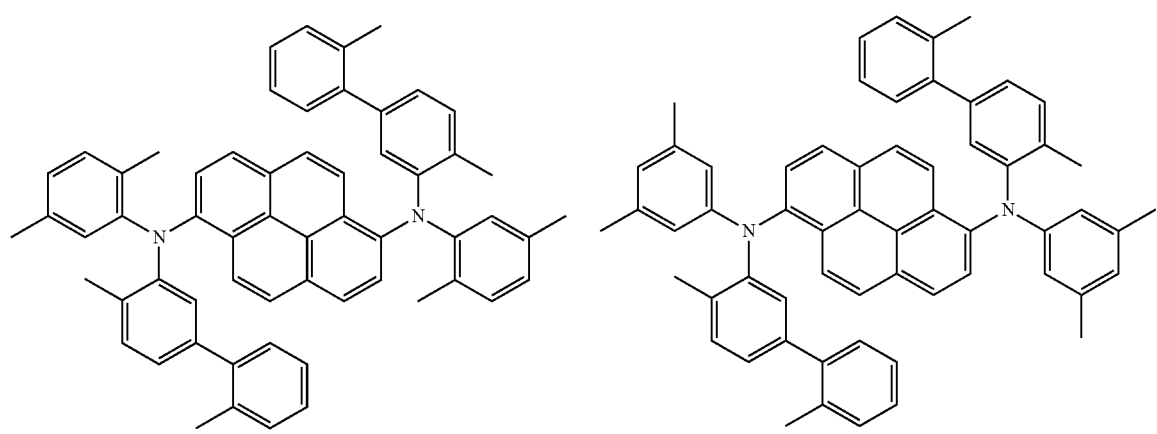

-continued
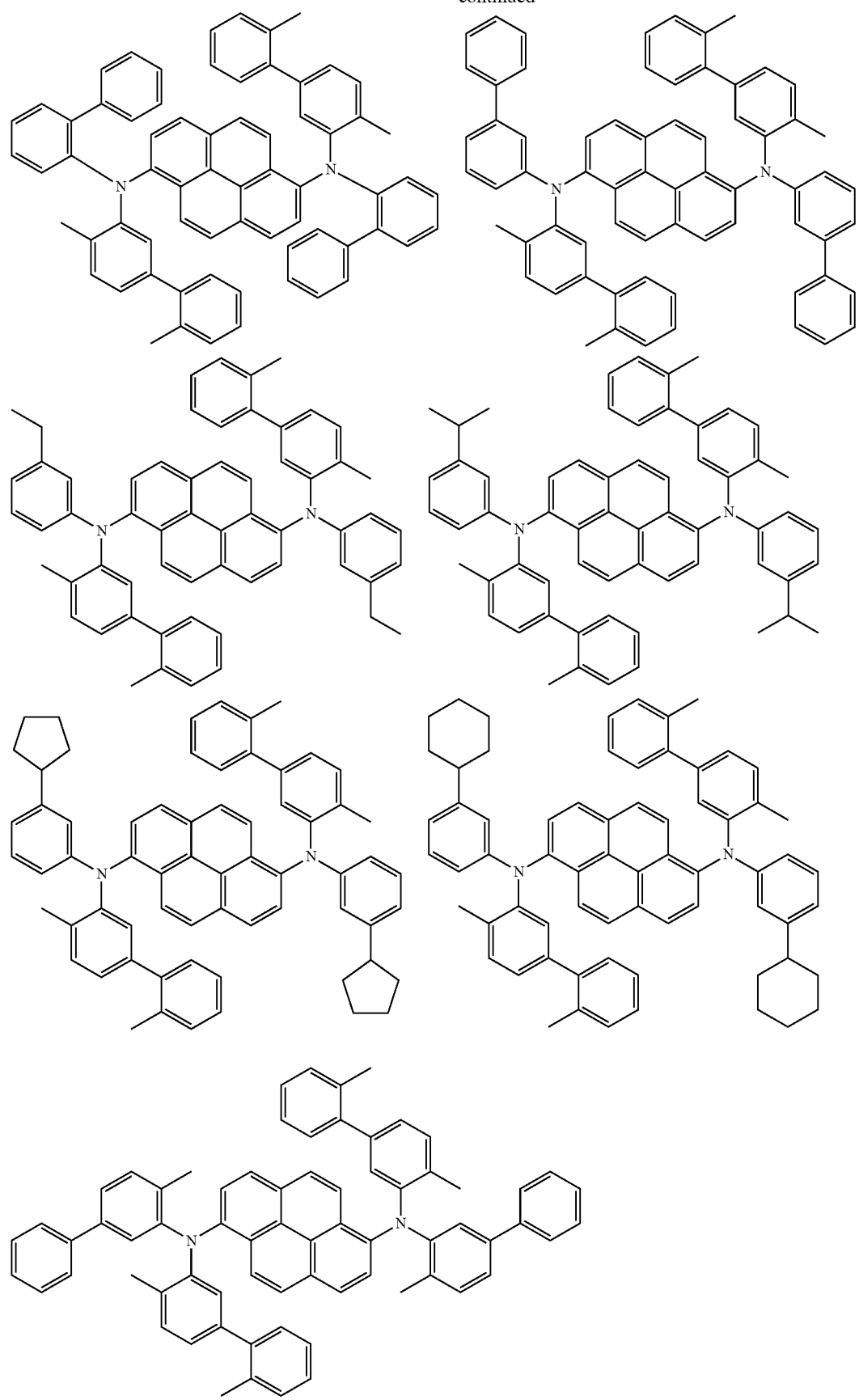

-continued
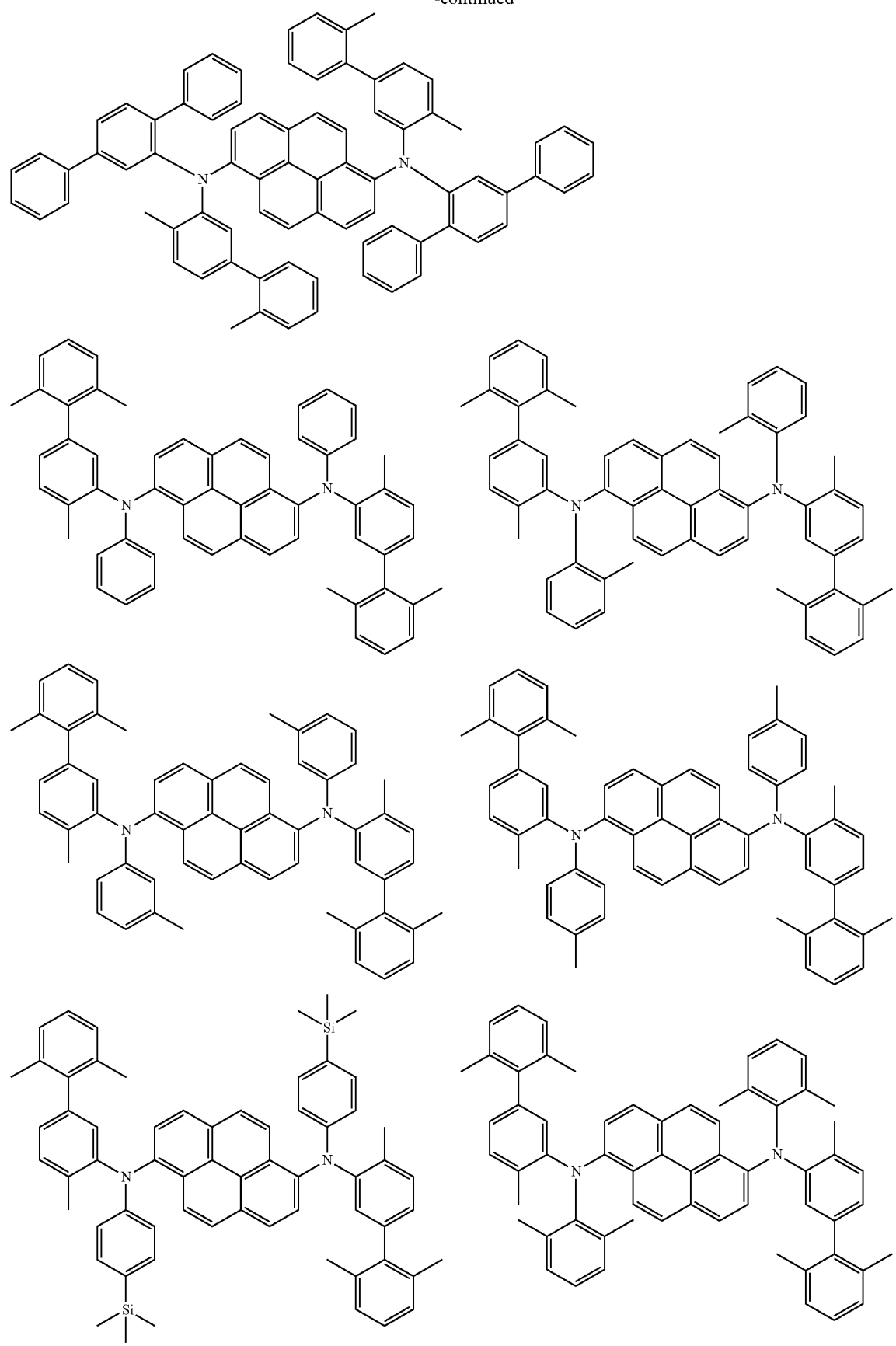

-continued
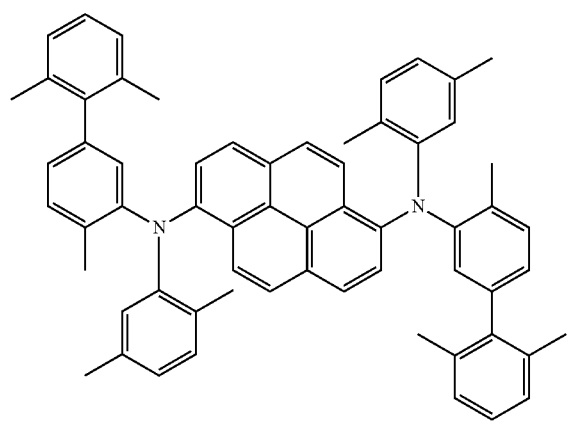
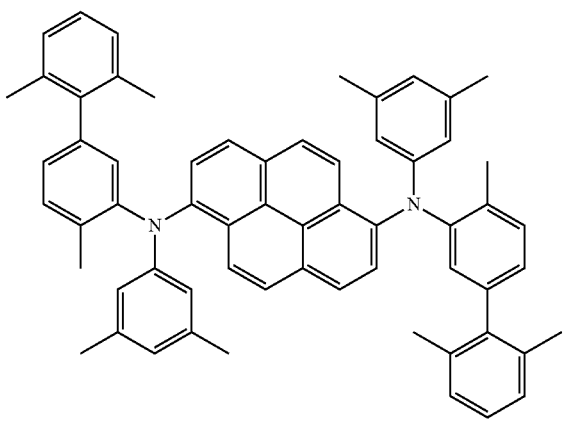
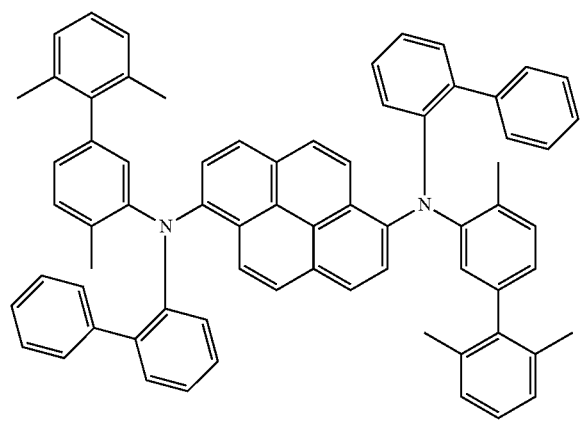
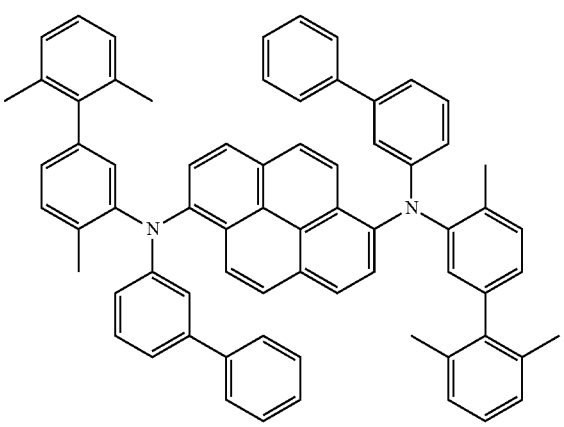
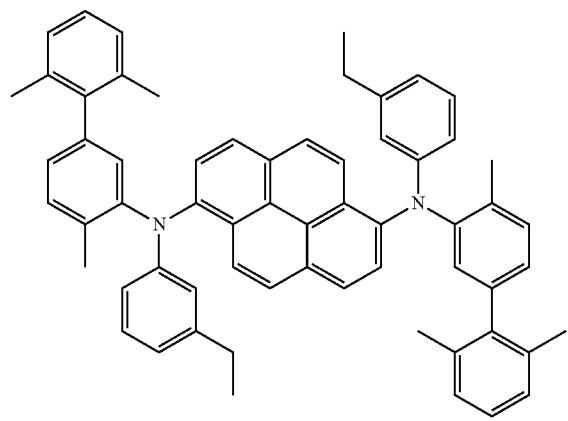
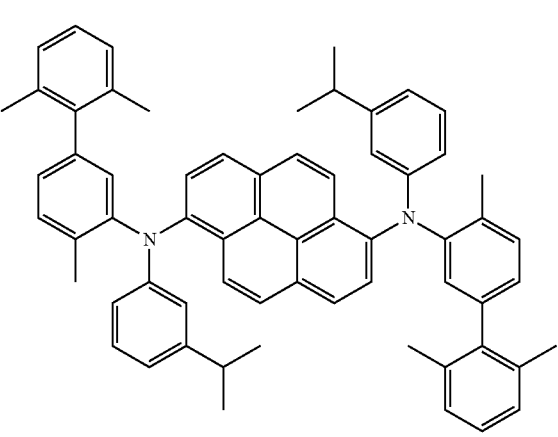
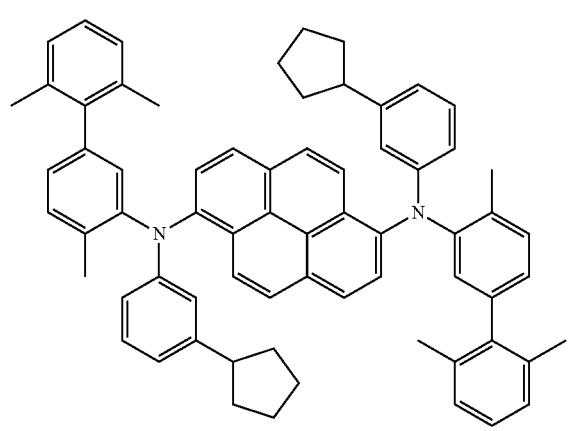
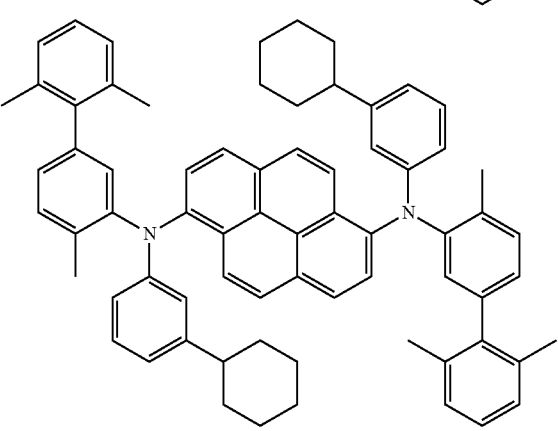

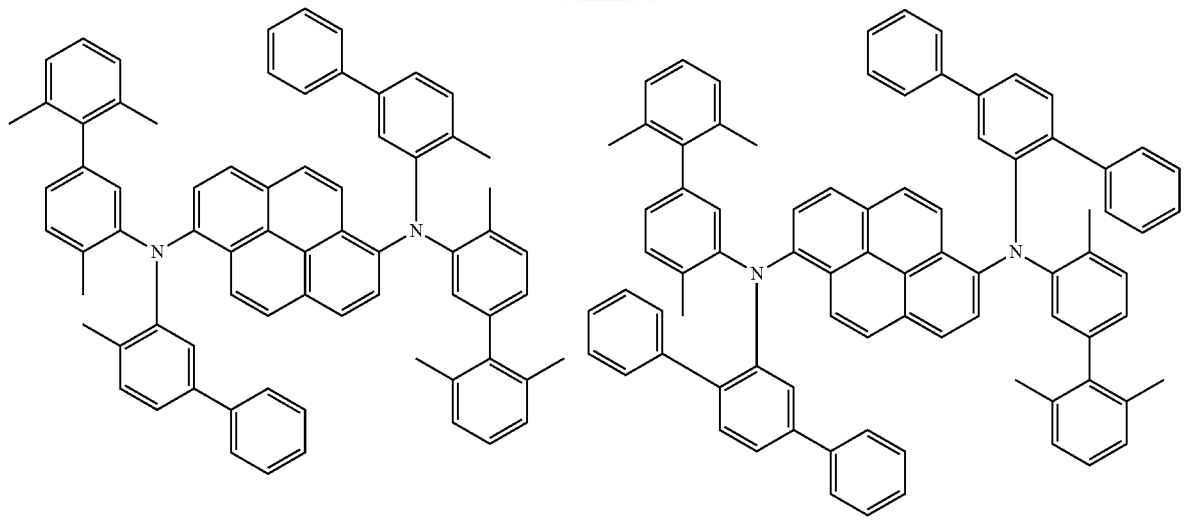
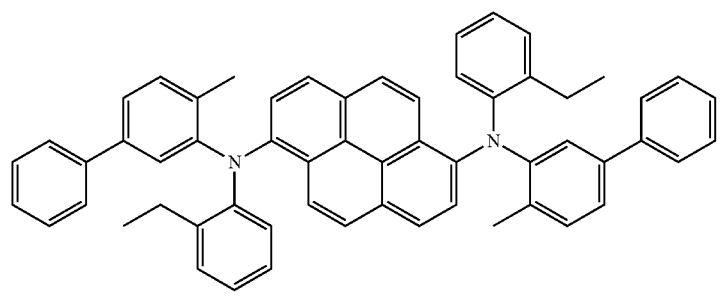
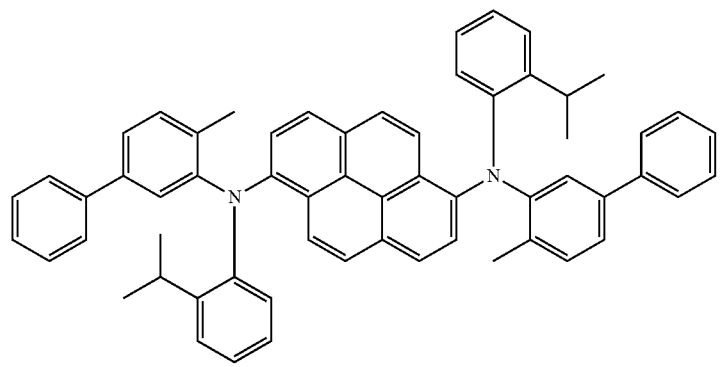
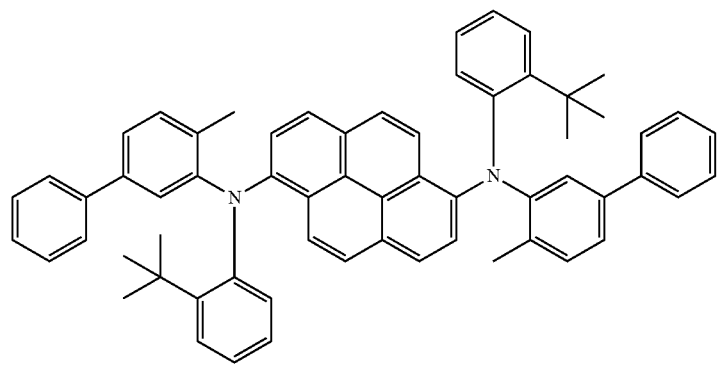

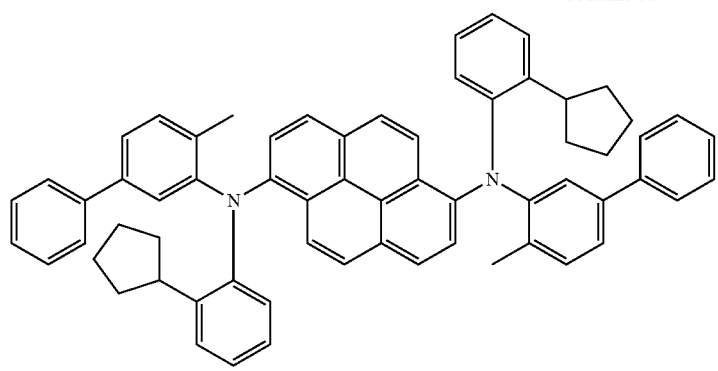
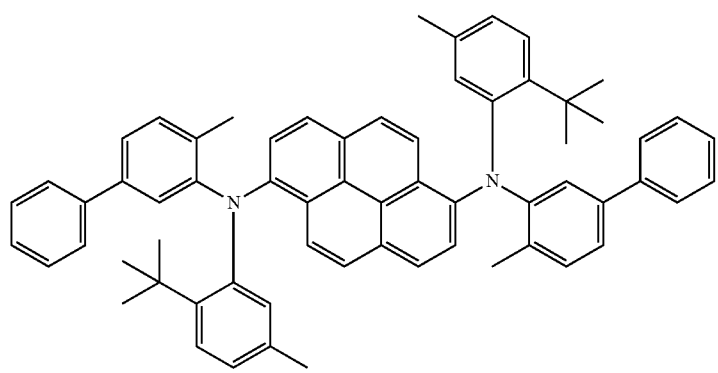
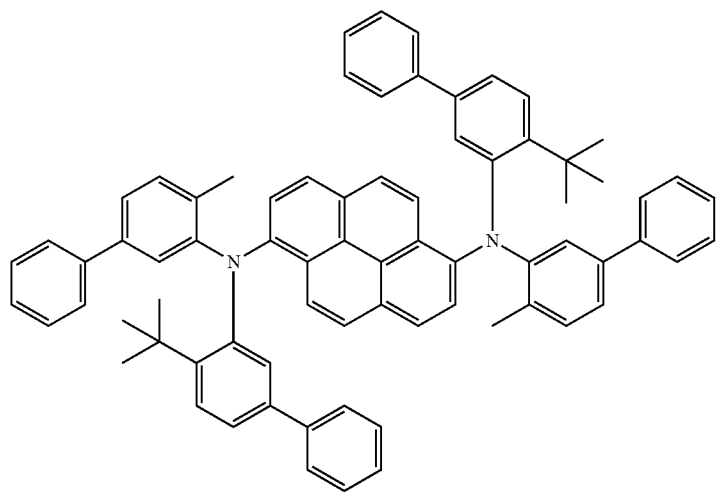
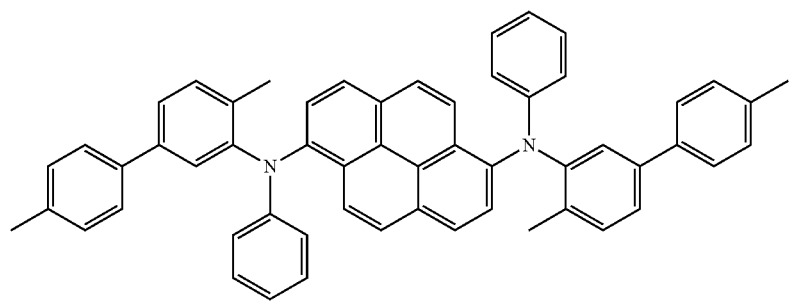

-continued
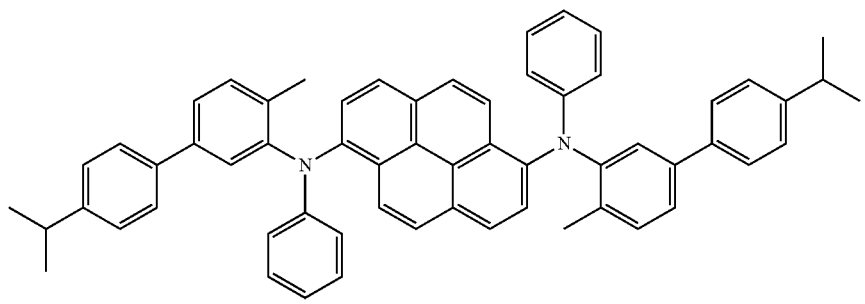
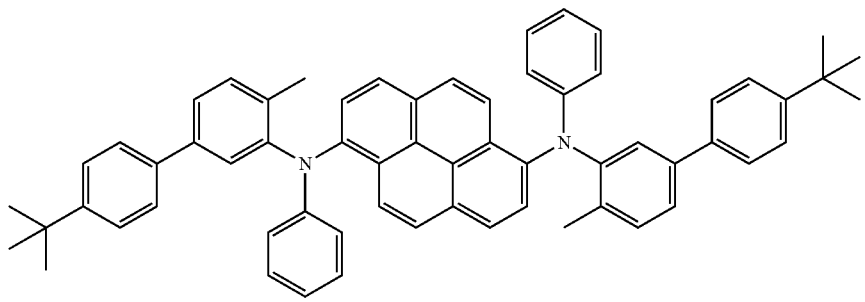
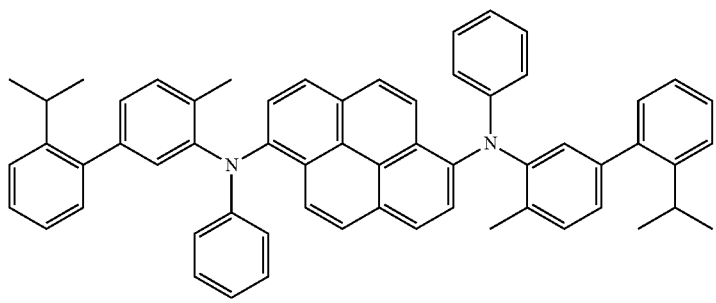
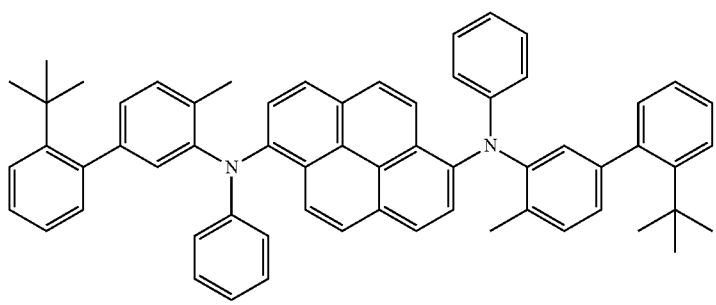
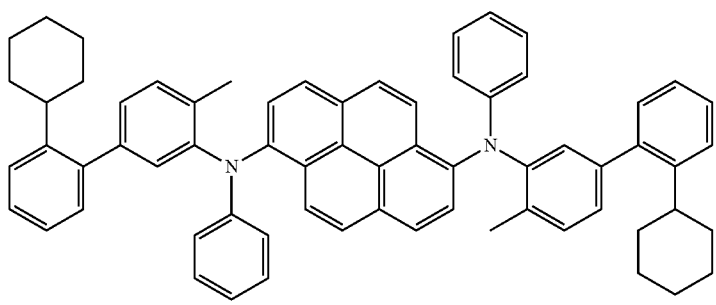

-continued
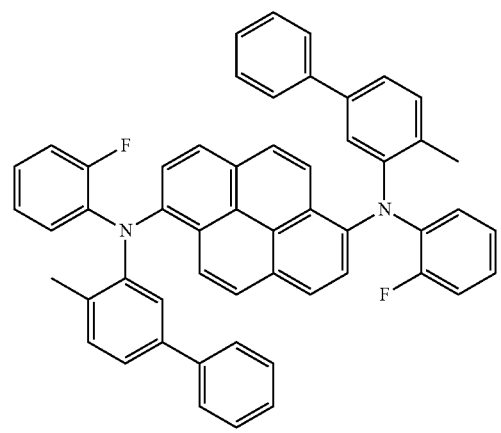
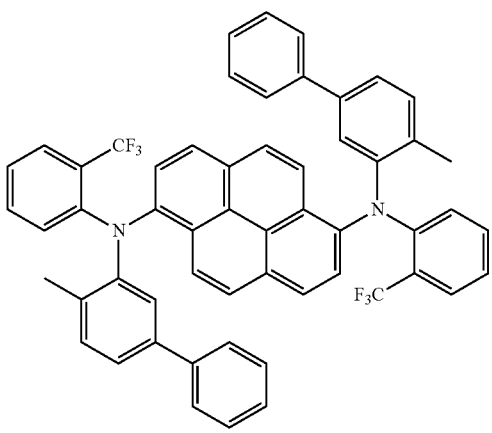
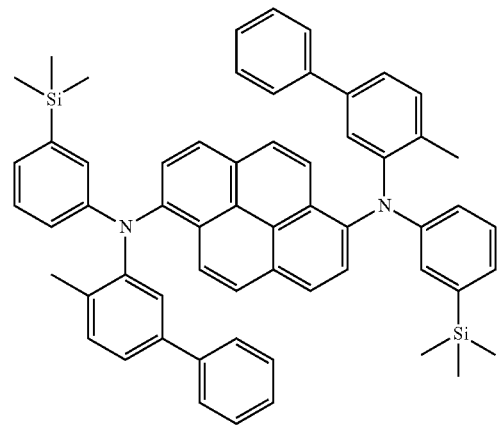
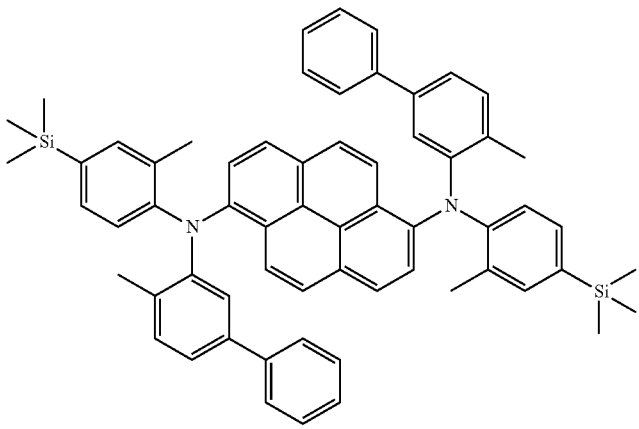
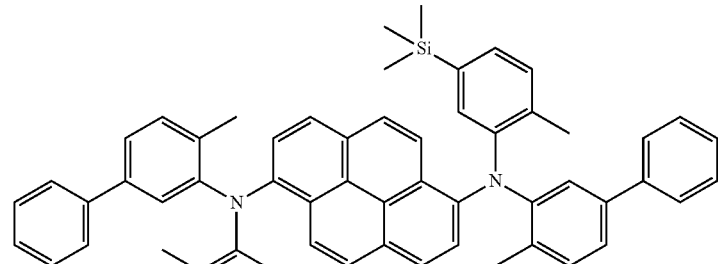
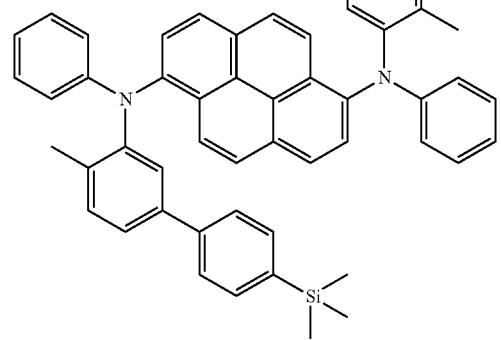
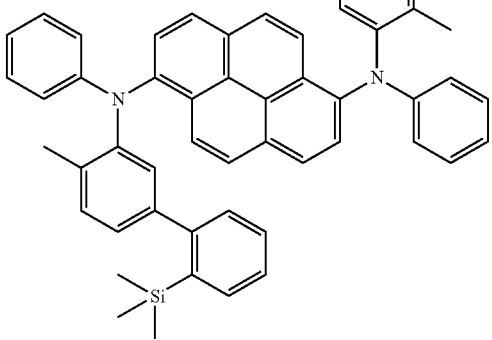

-continued
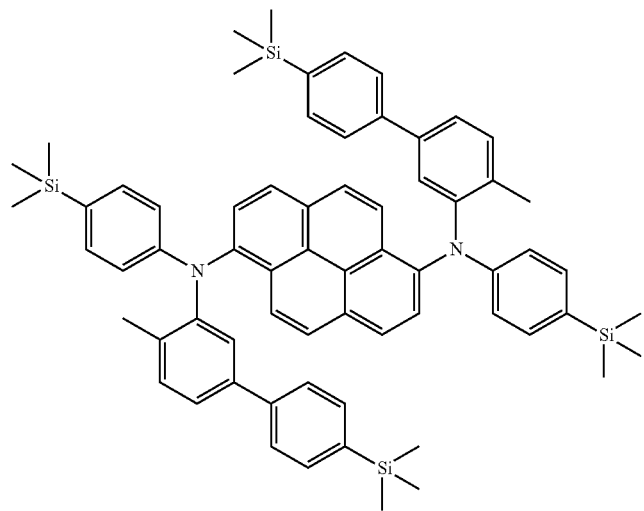
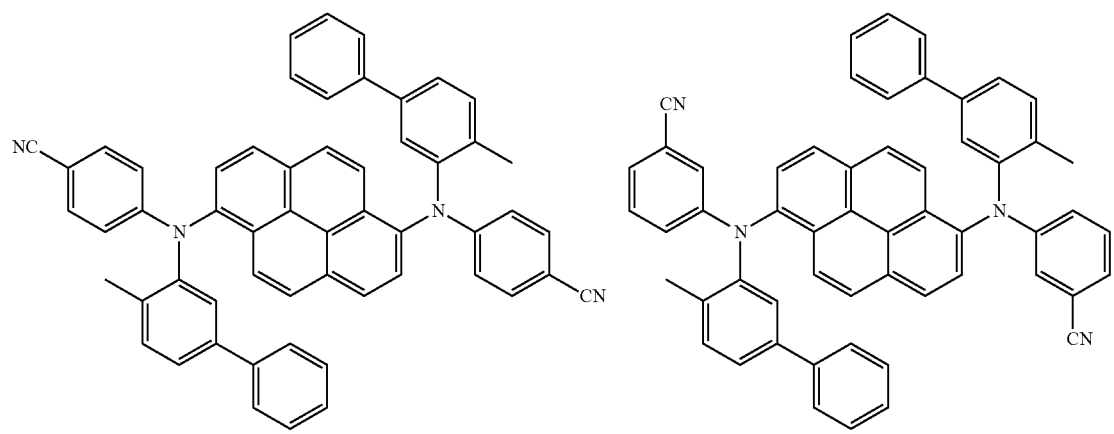
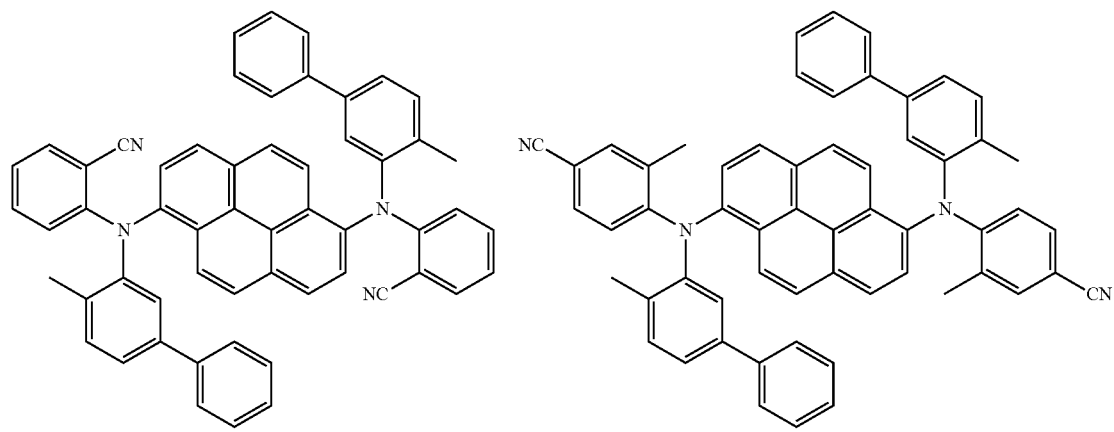

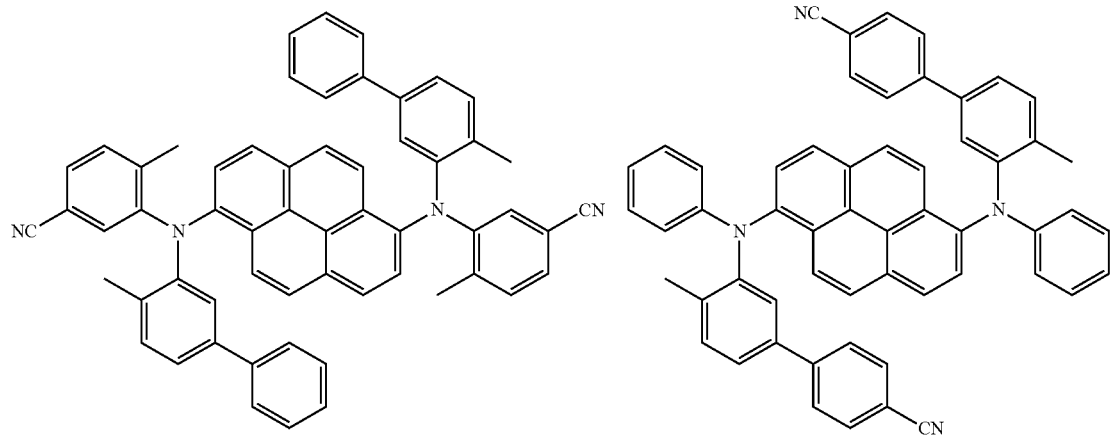
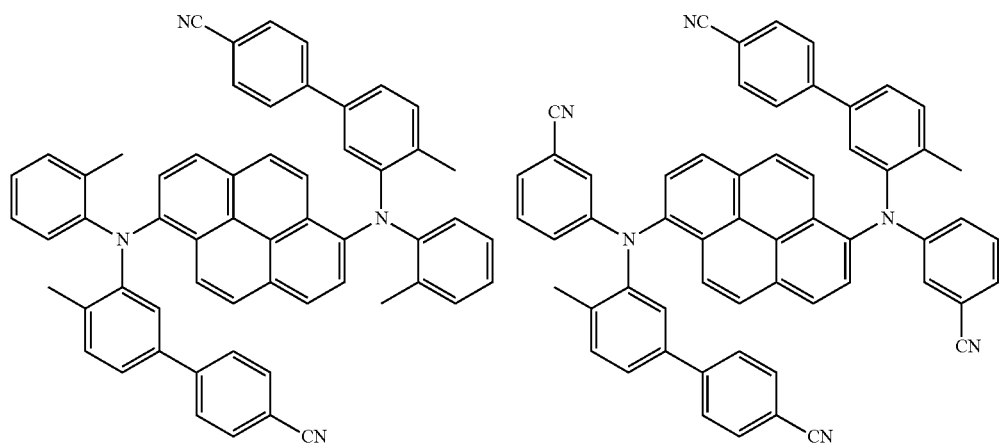
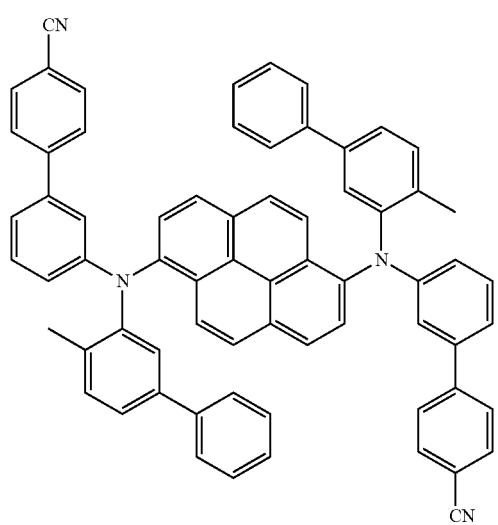

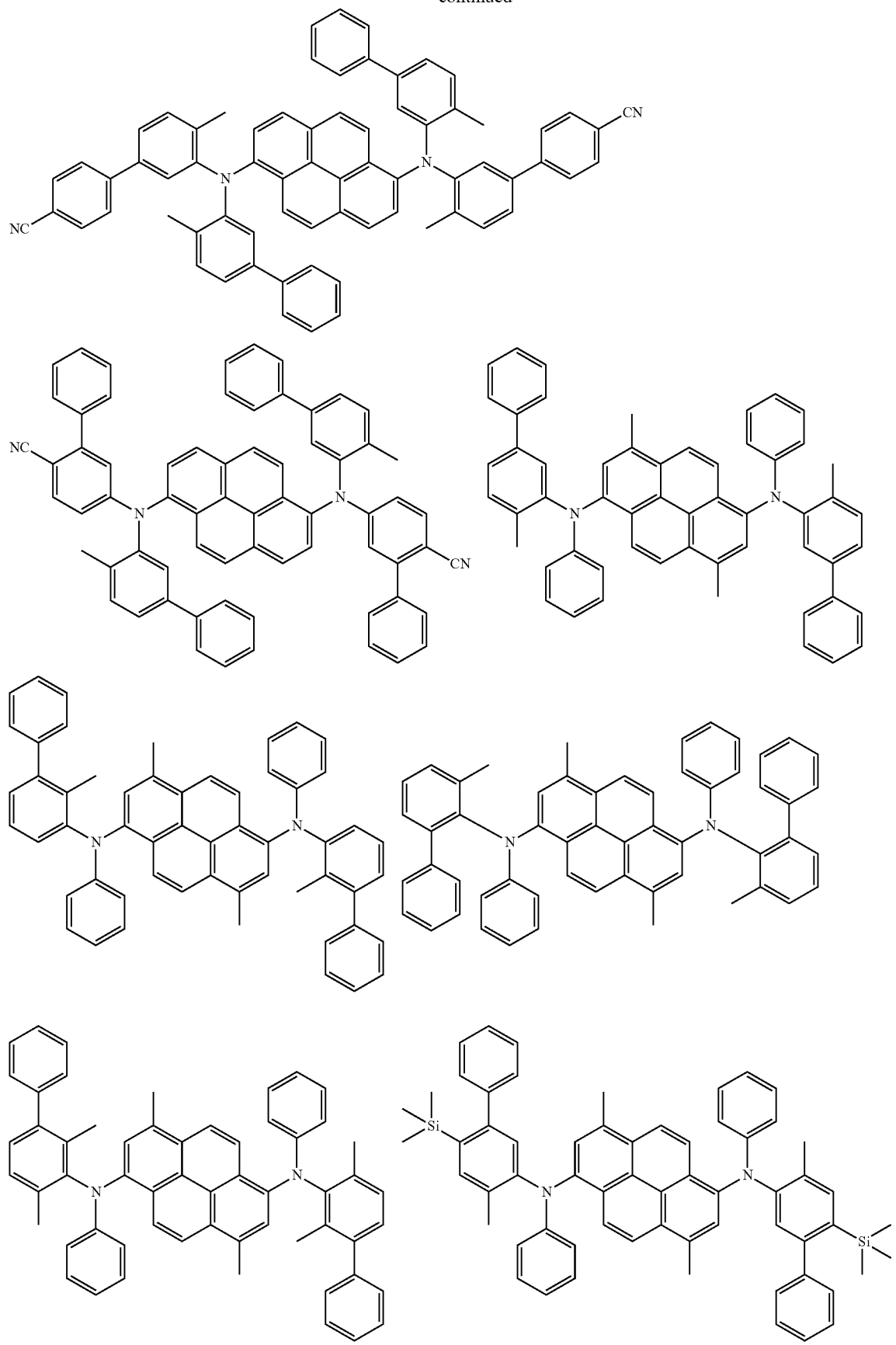

-continued
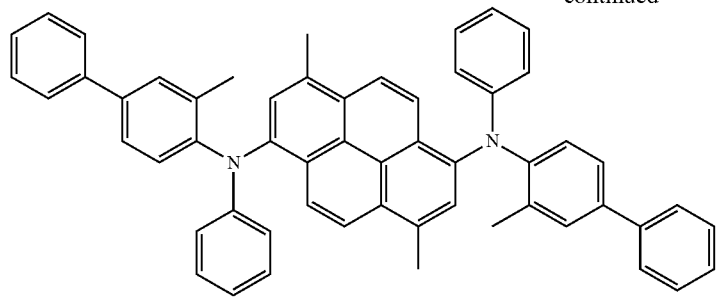
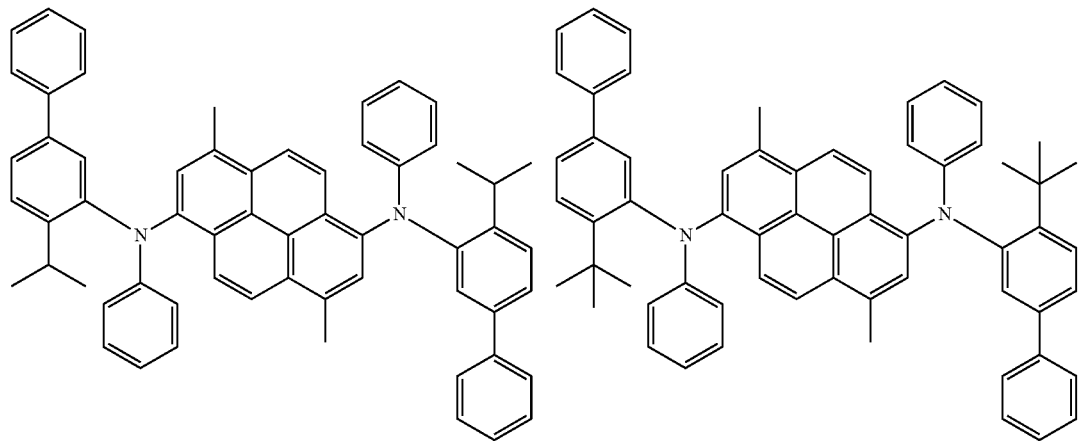
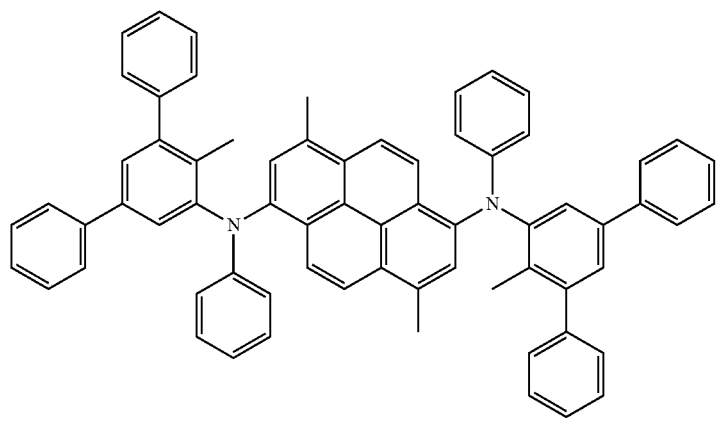
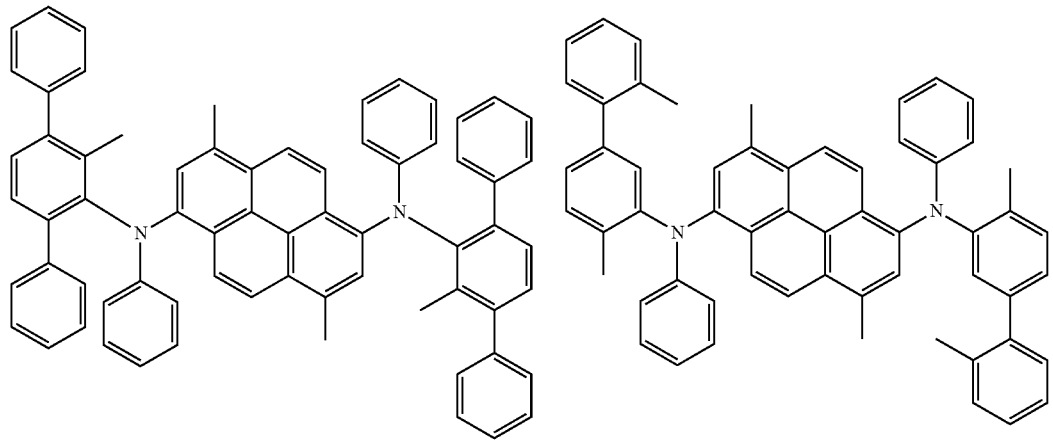

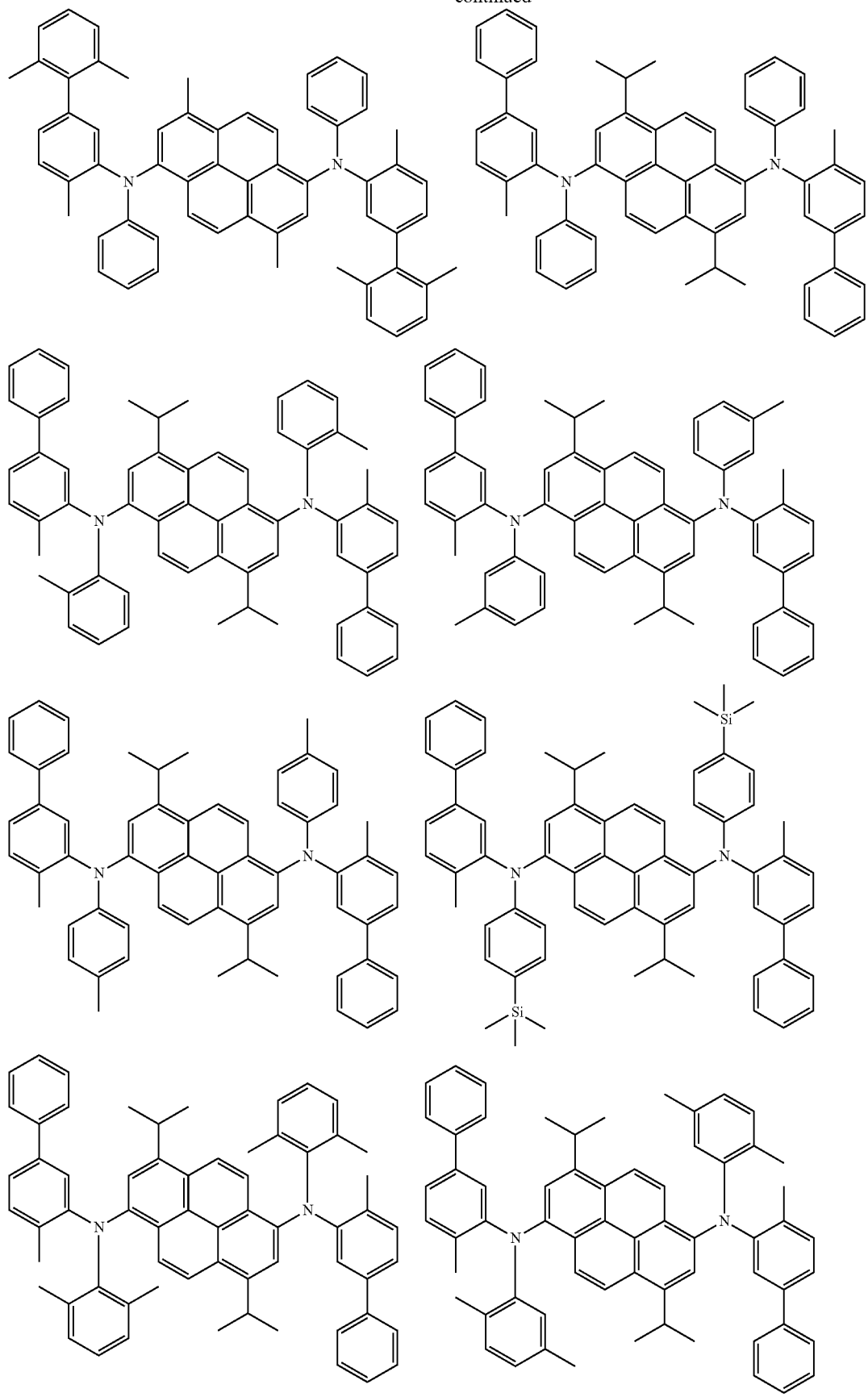

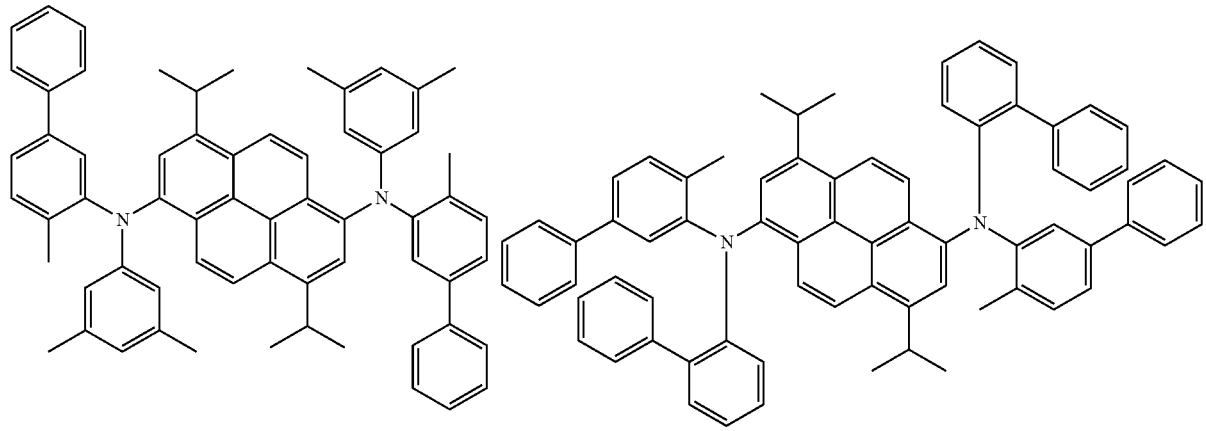
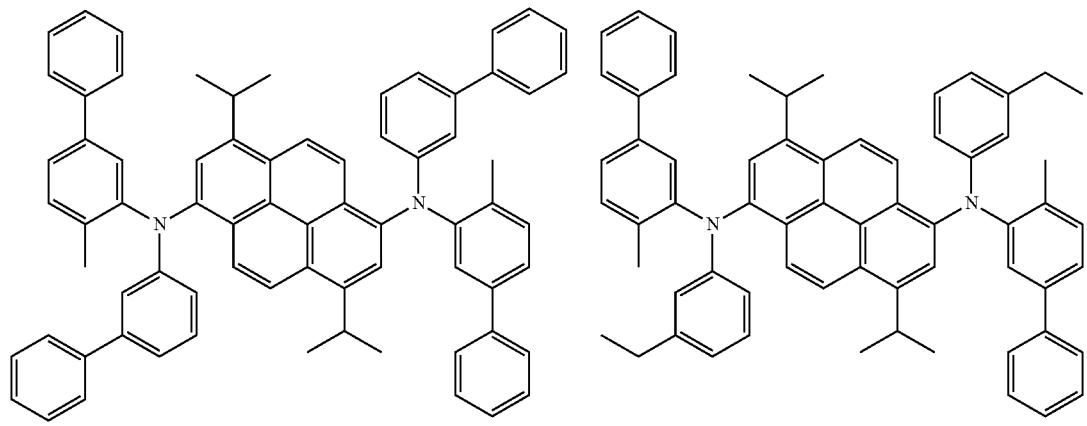
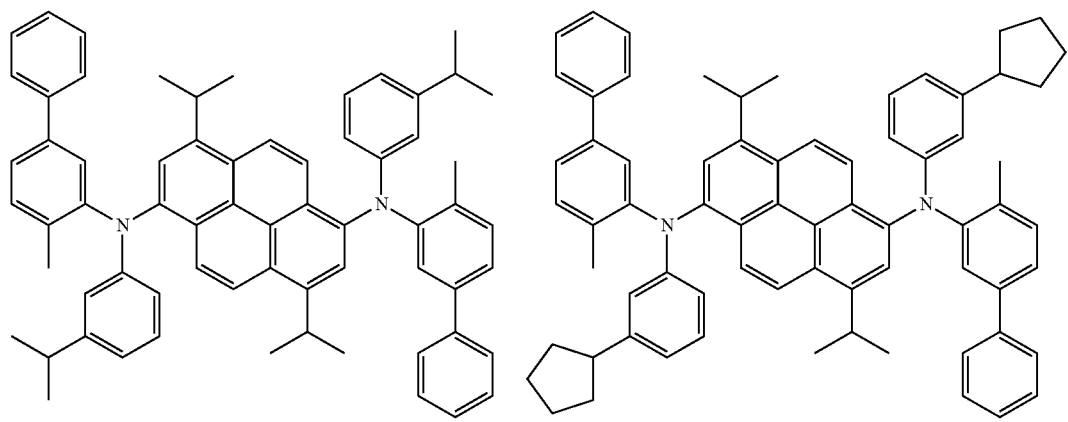

-continued
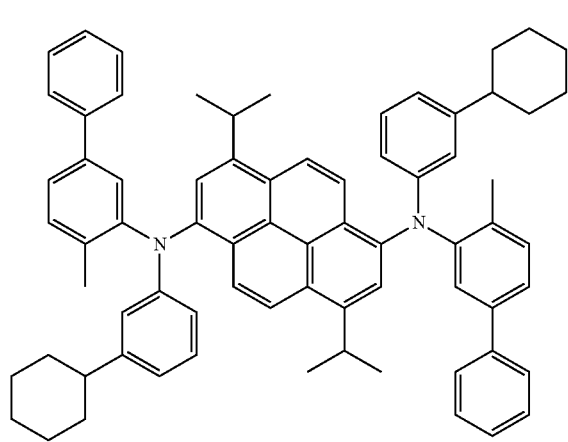
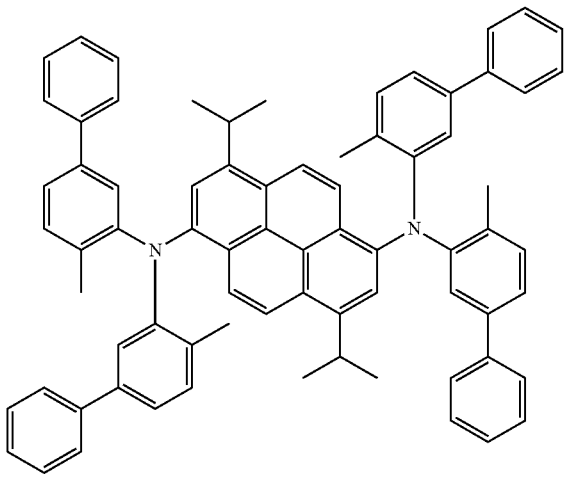
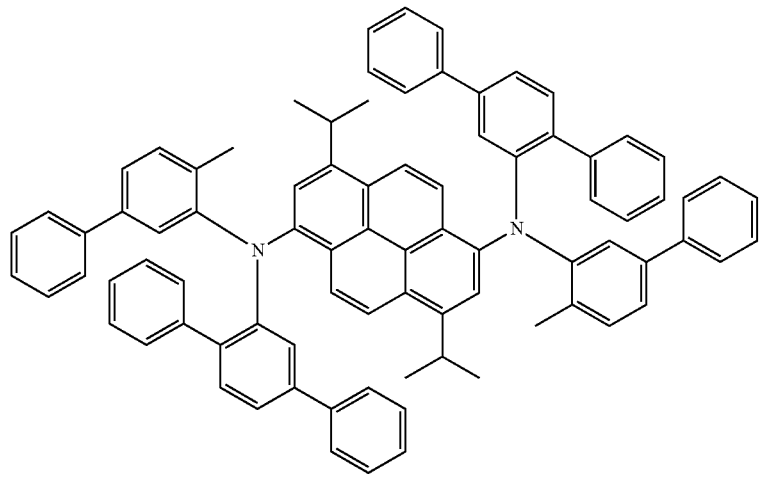
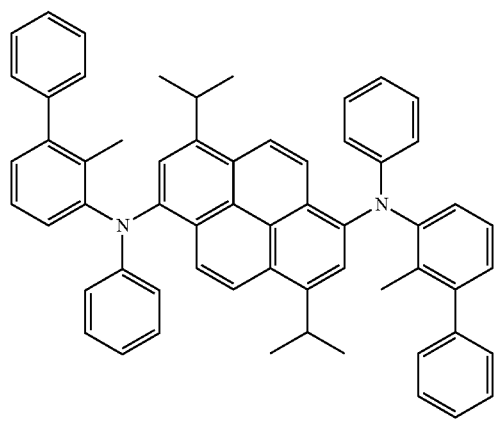
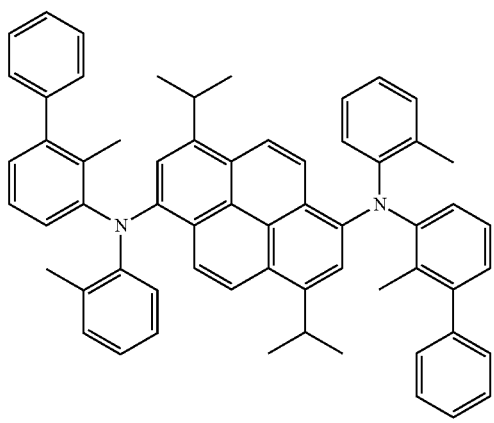

-continued
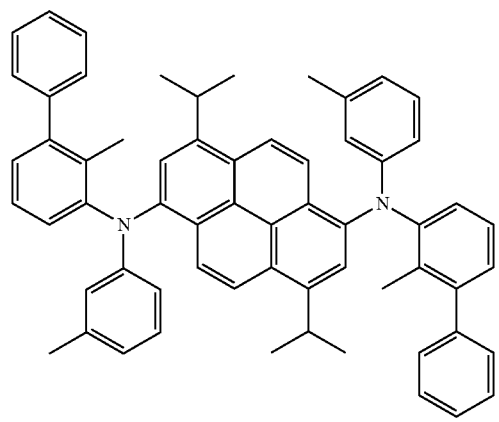
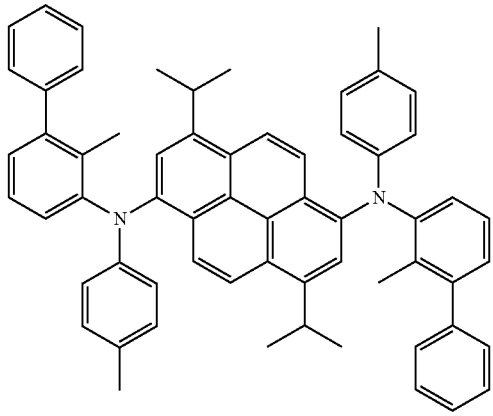
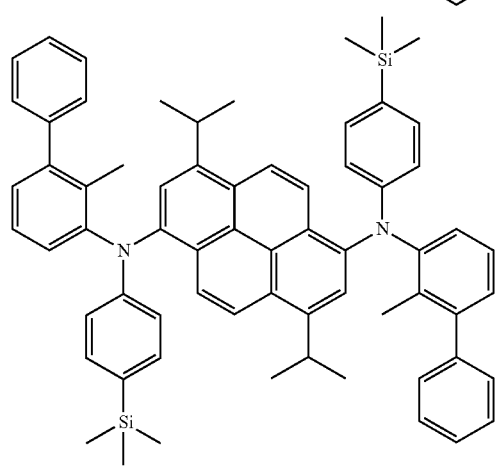
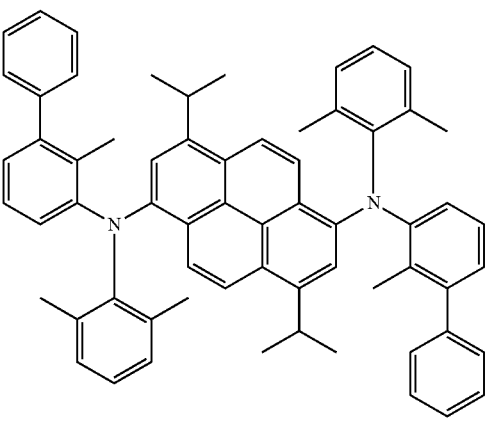
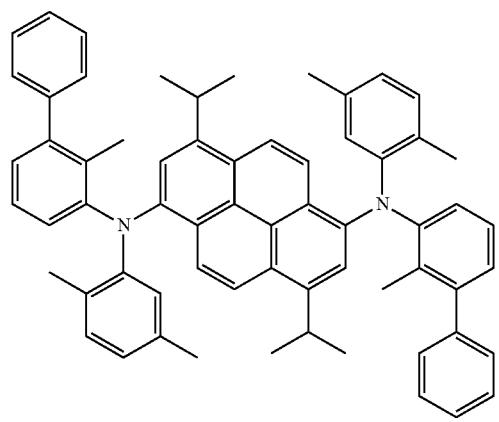
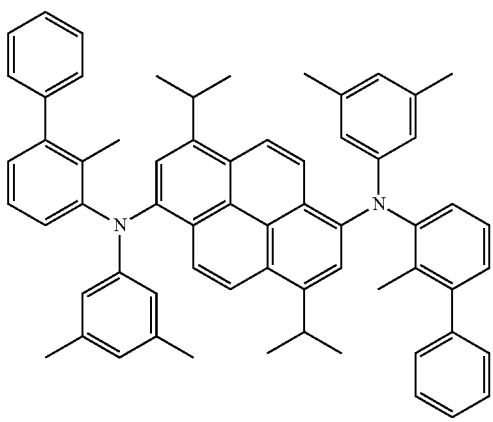
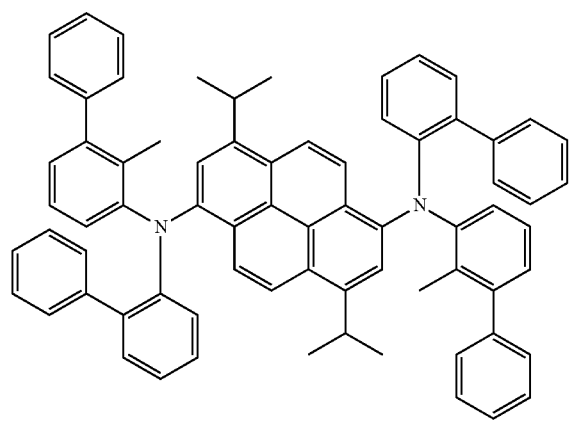
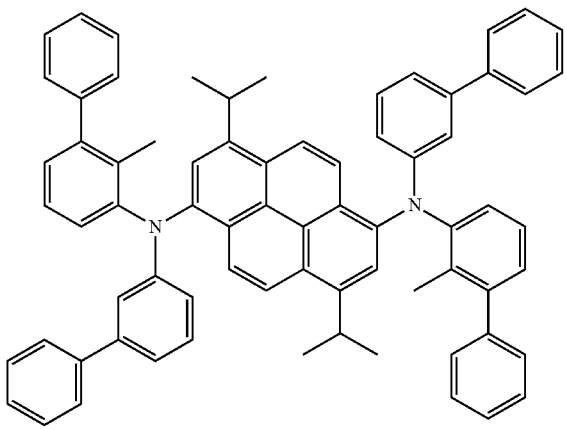

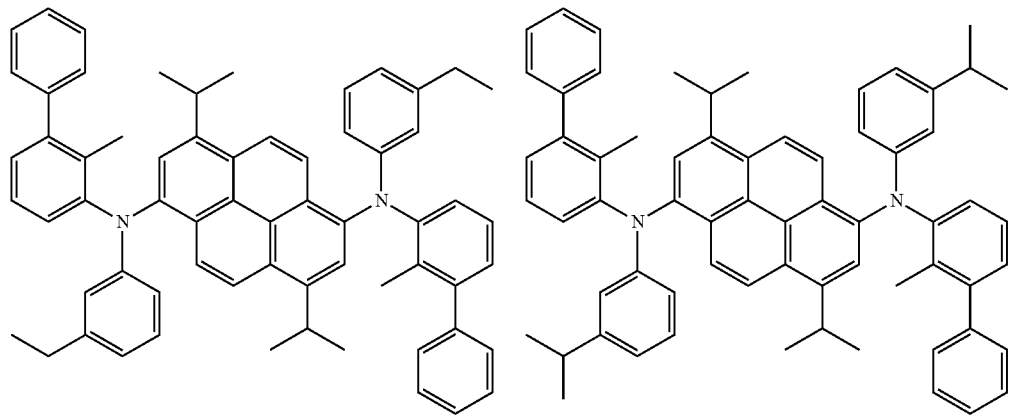
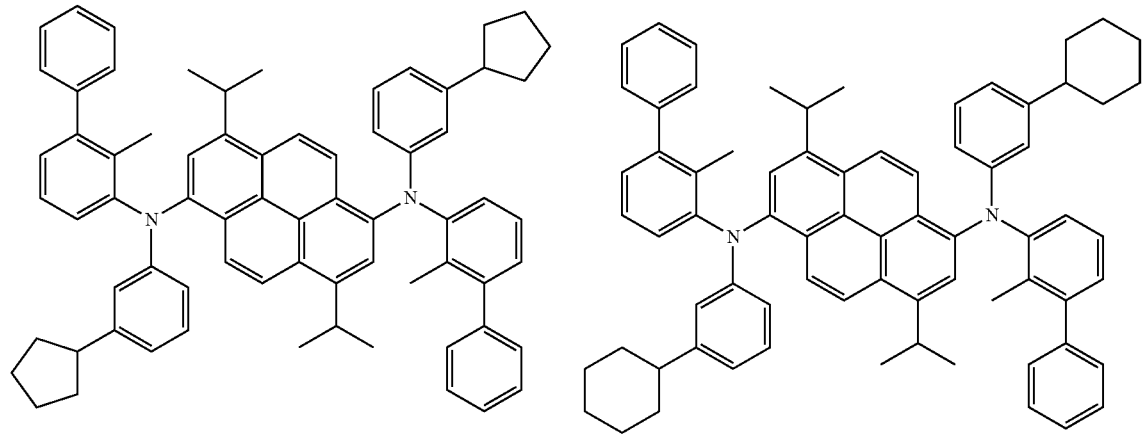
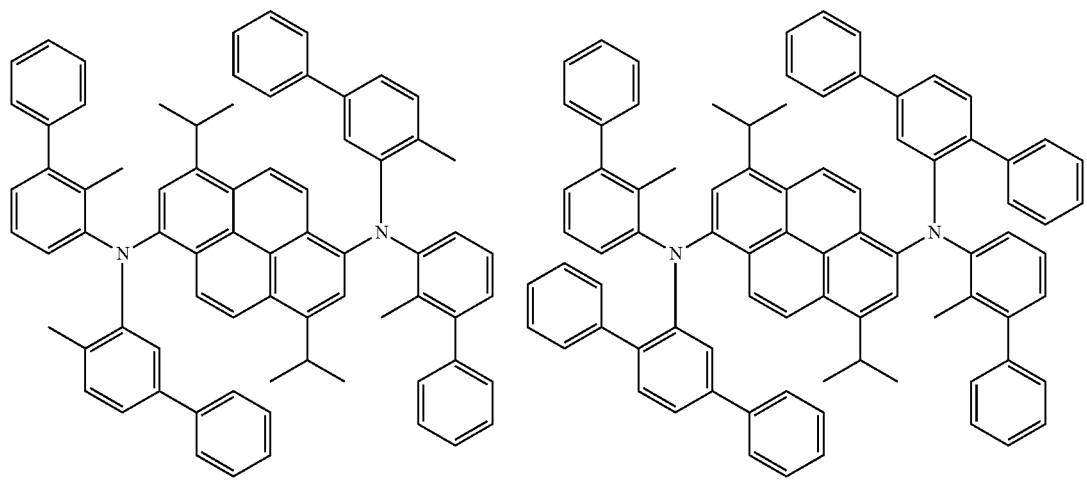
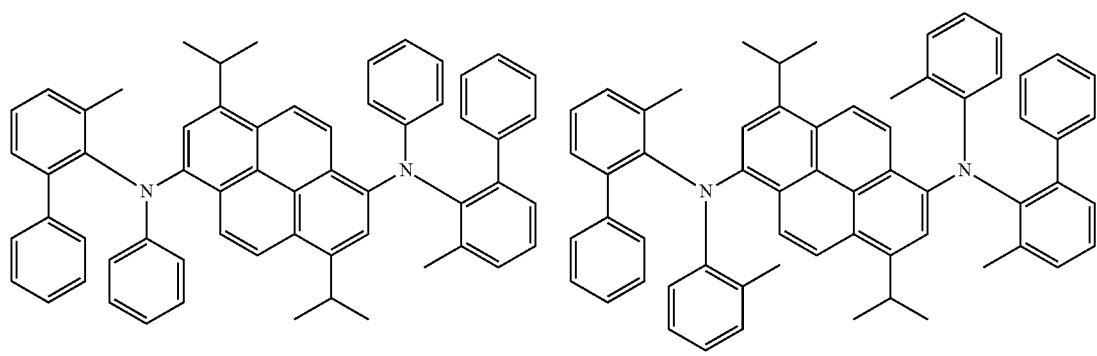

-continued
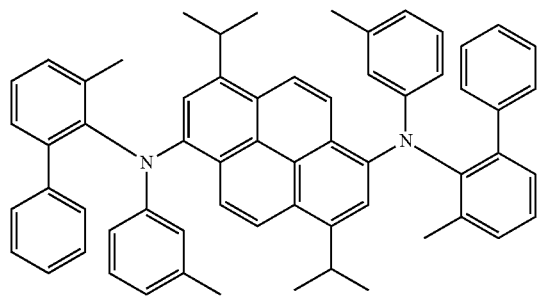
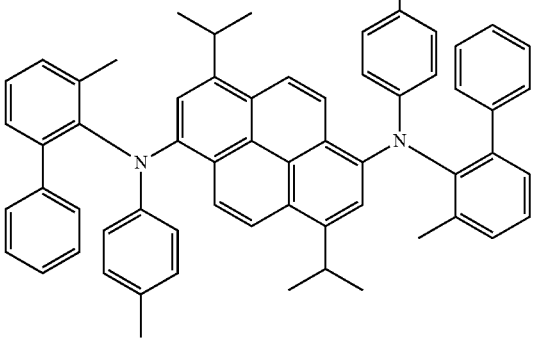
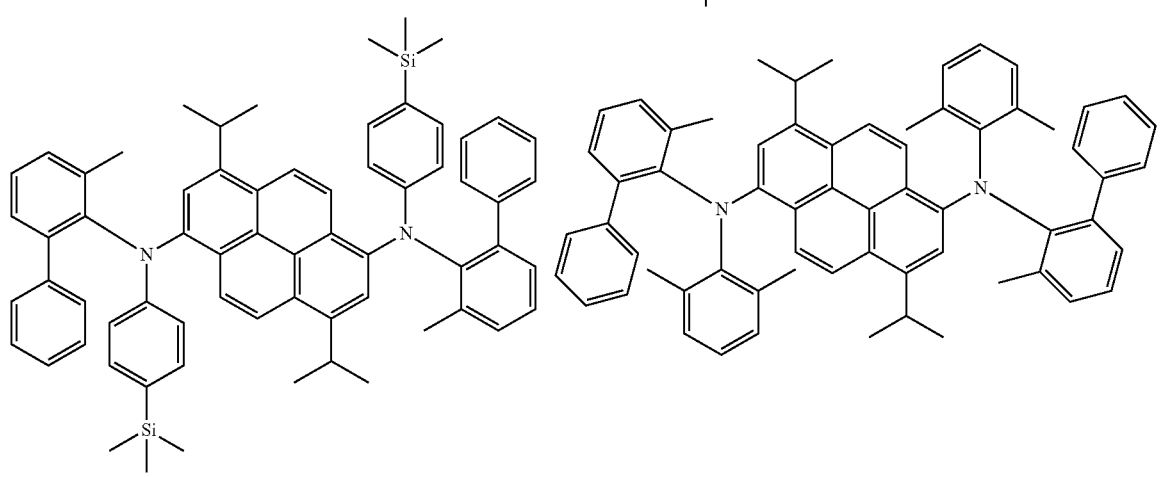
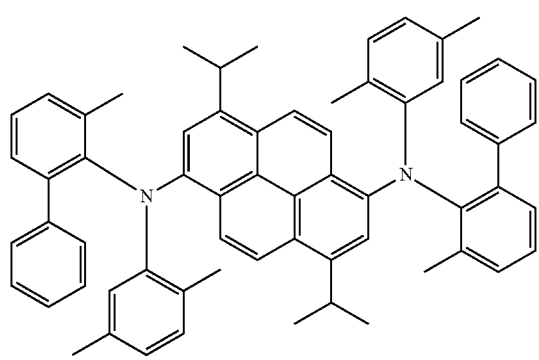
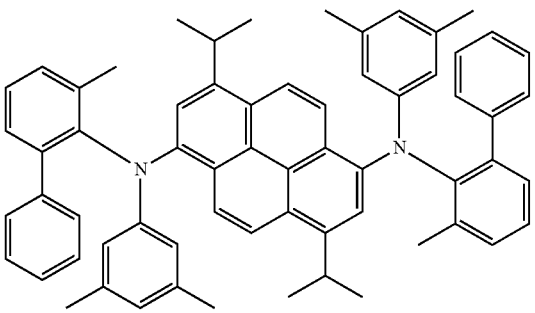
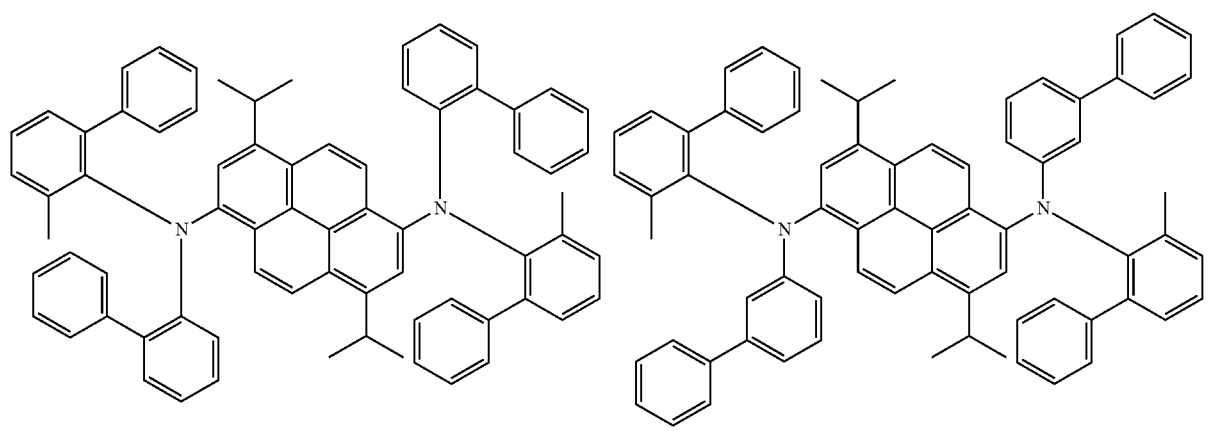

| 81 | 82 |
|---|---|
| 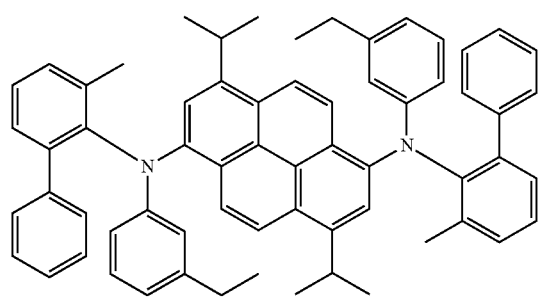 | 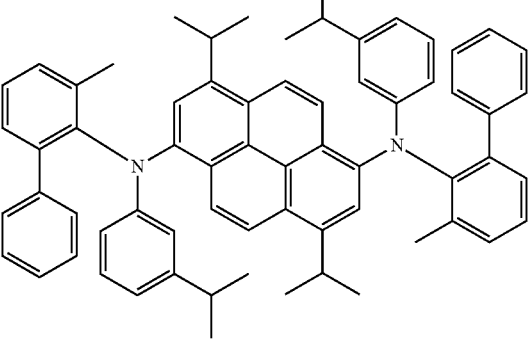 |
| 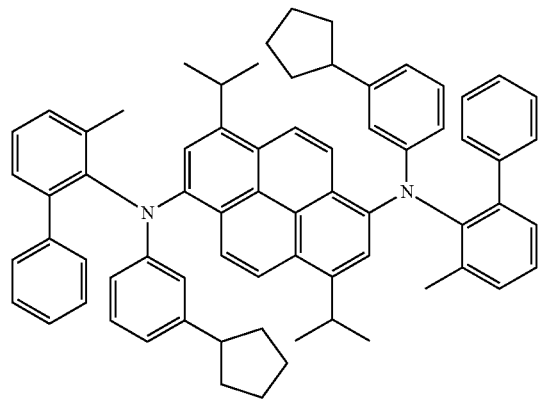 | 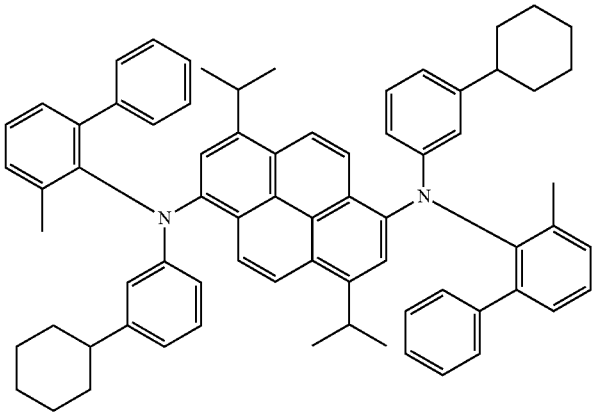 |
| 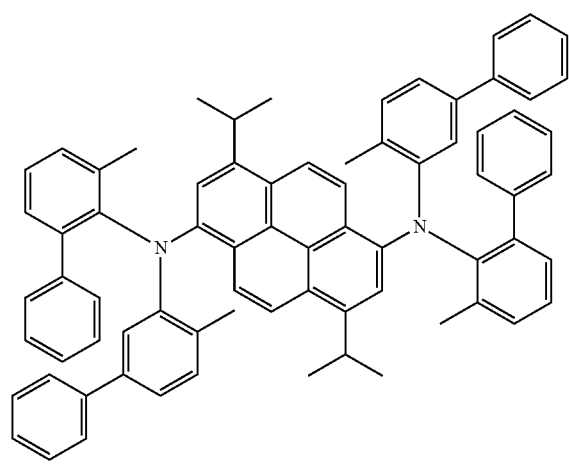 | 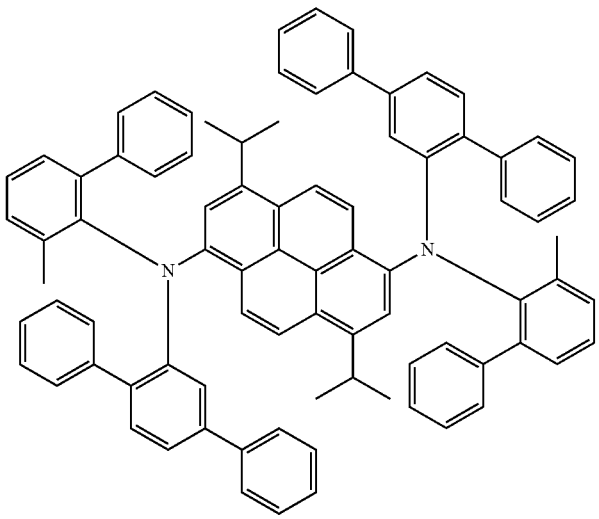 |
| 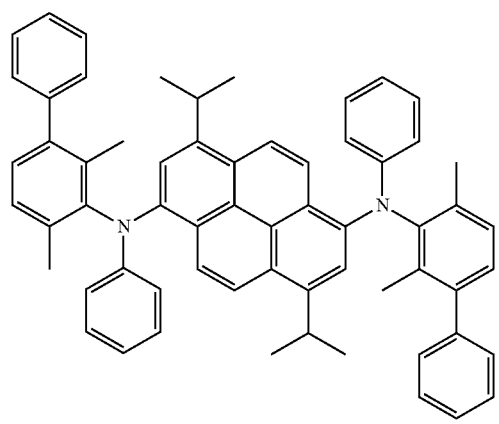 | 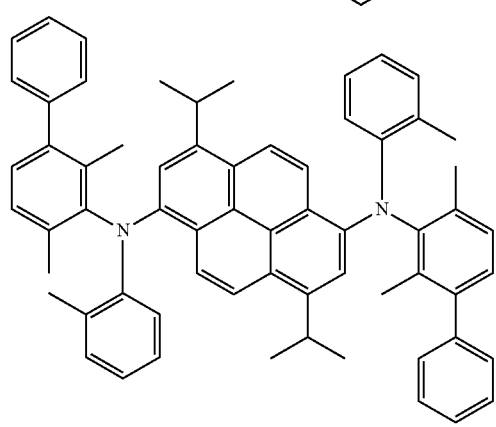 |

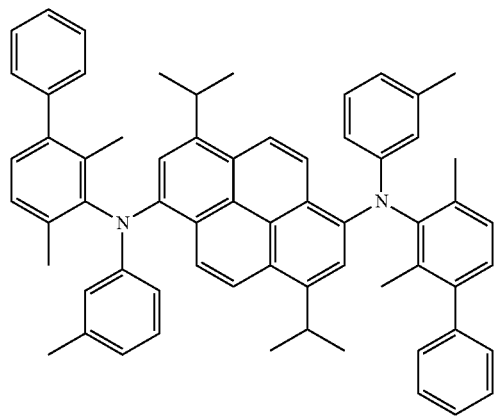
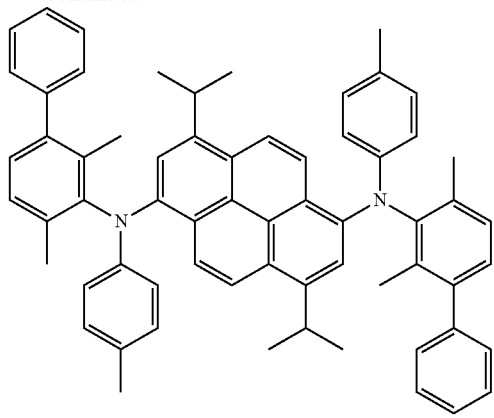
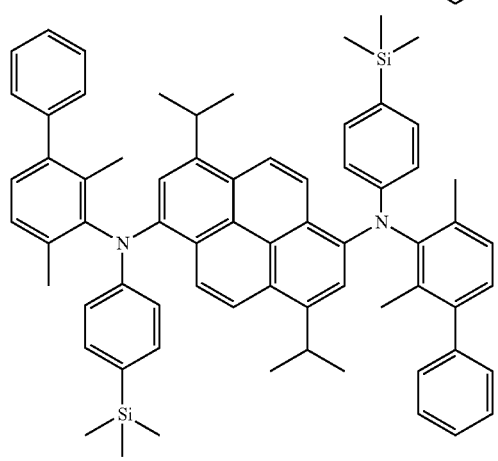
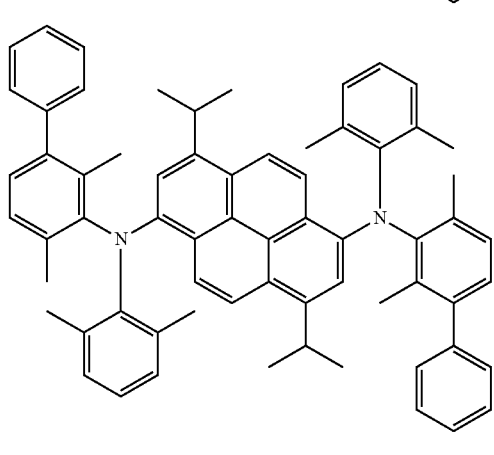
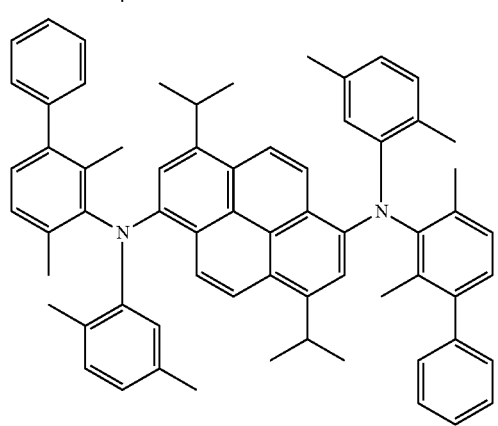
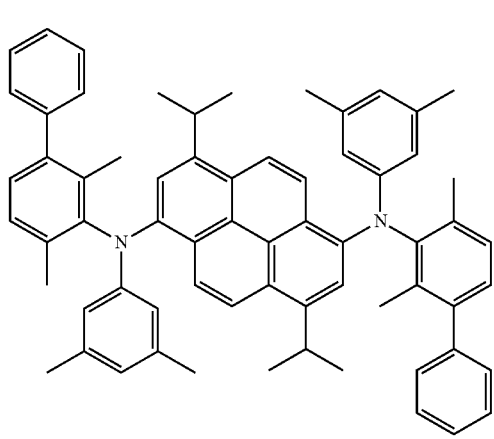
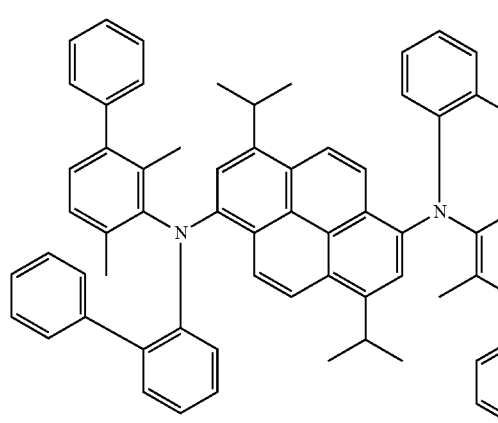
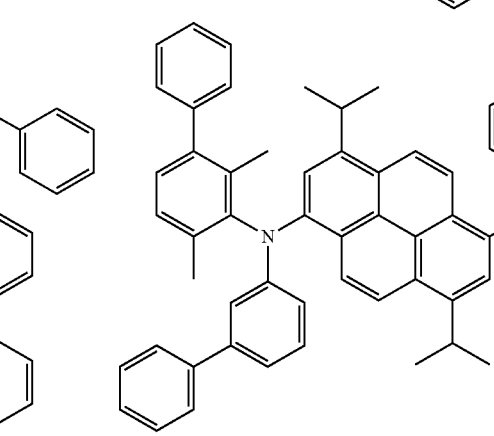

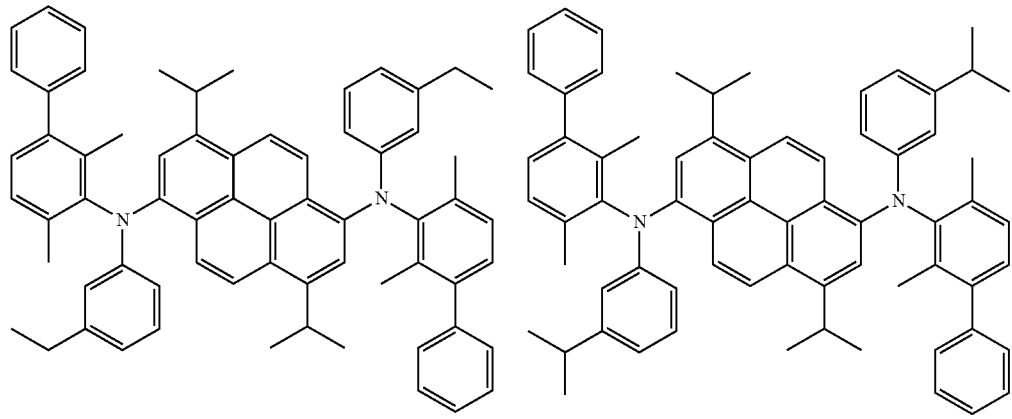
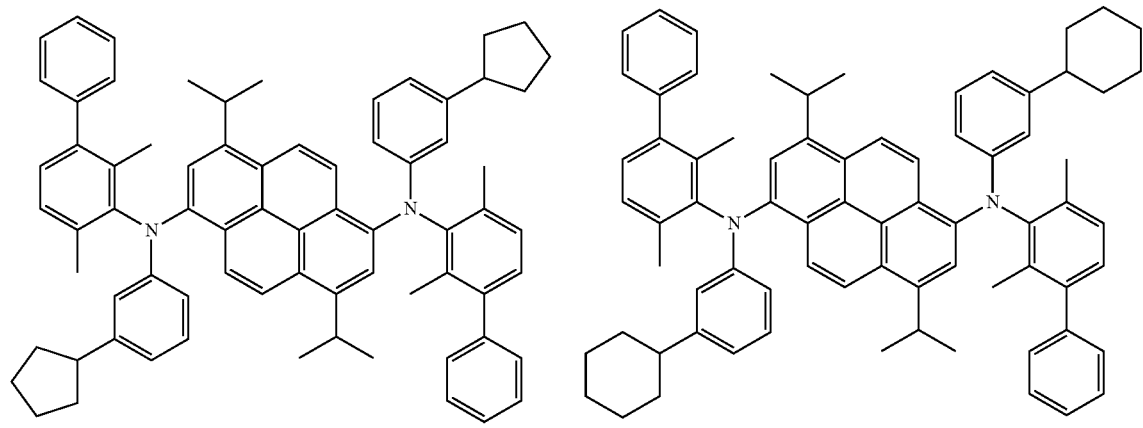
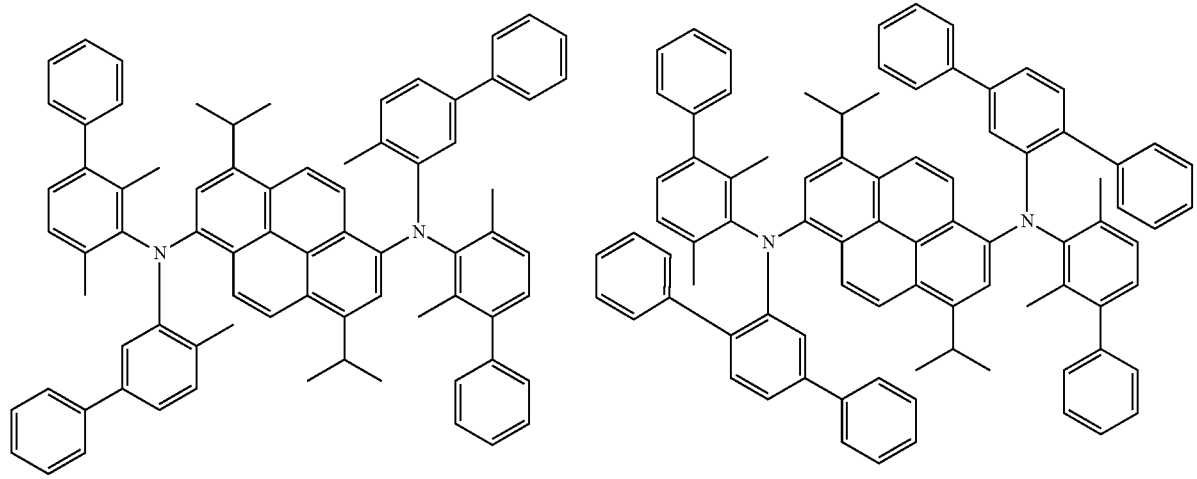

-continued
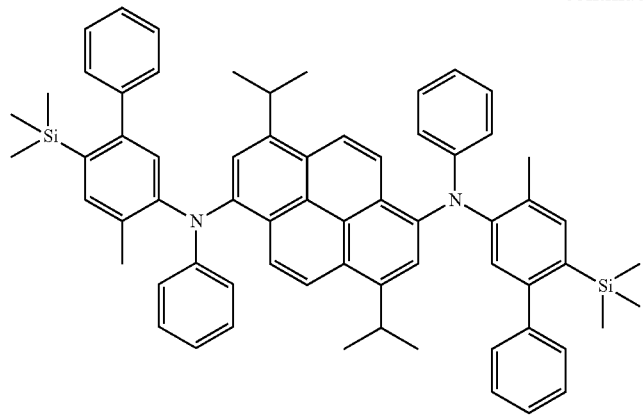
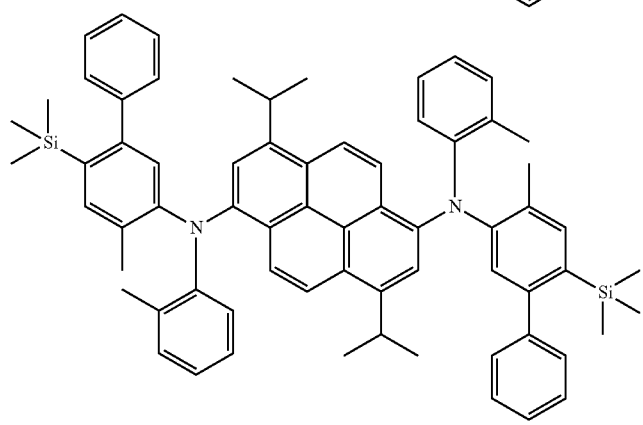
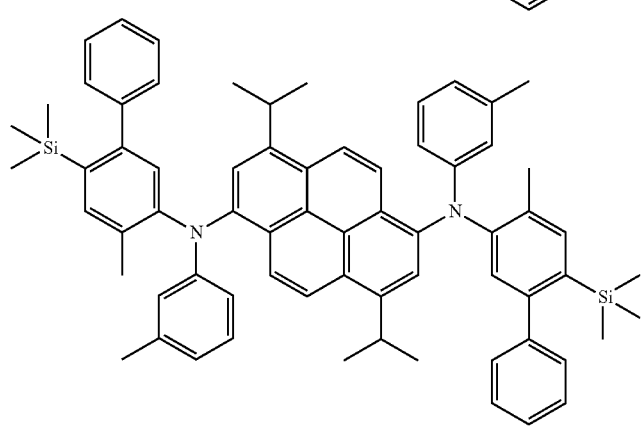
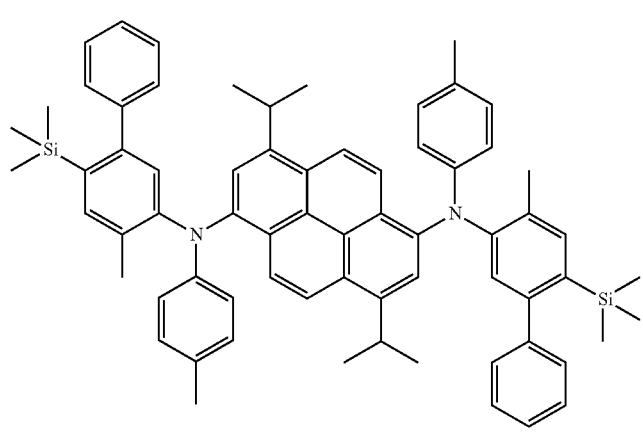

-continued
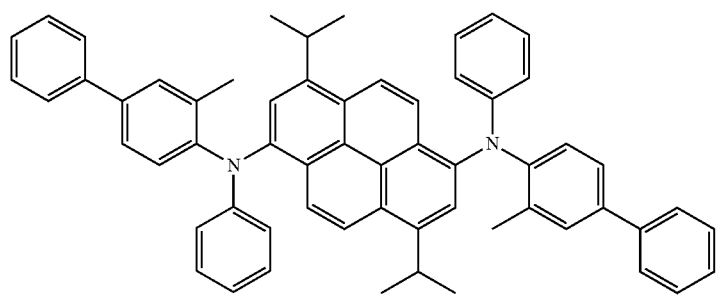
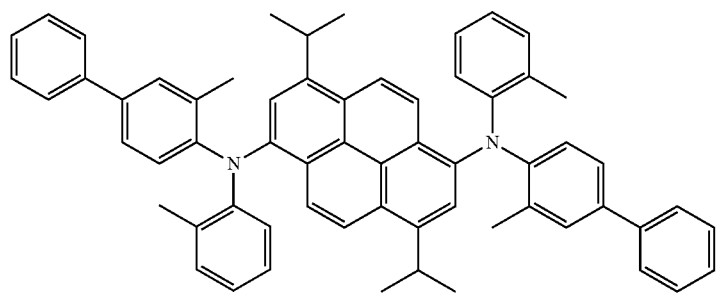
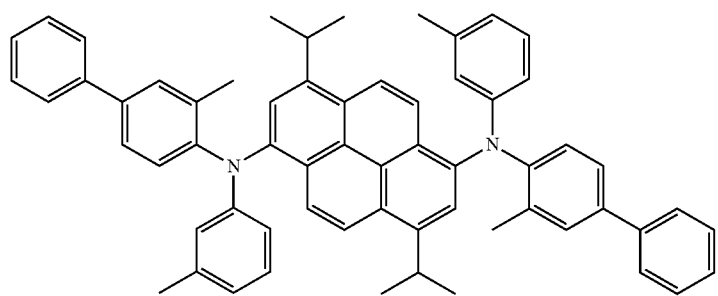
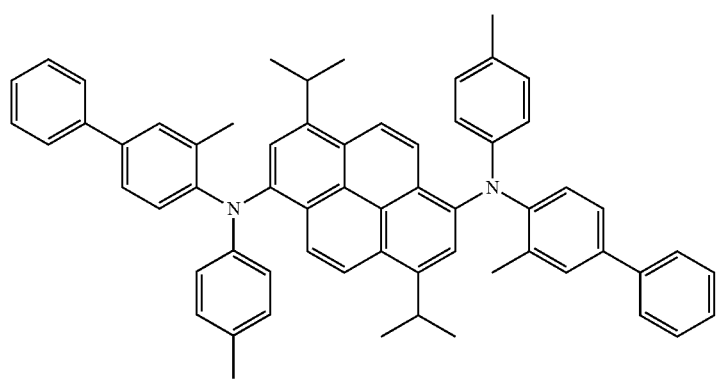
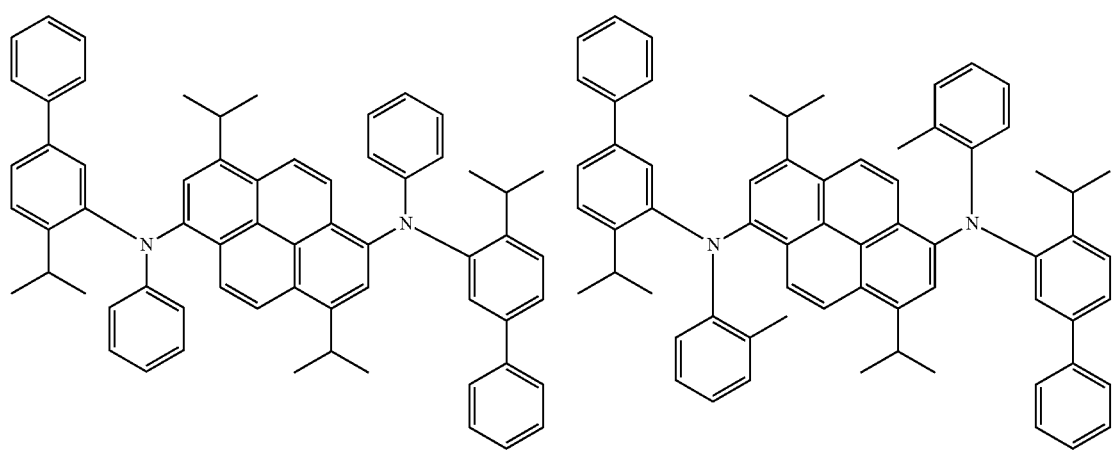

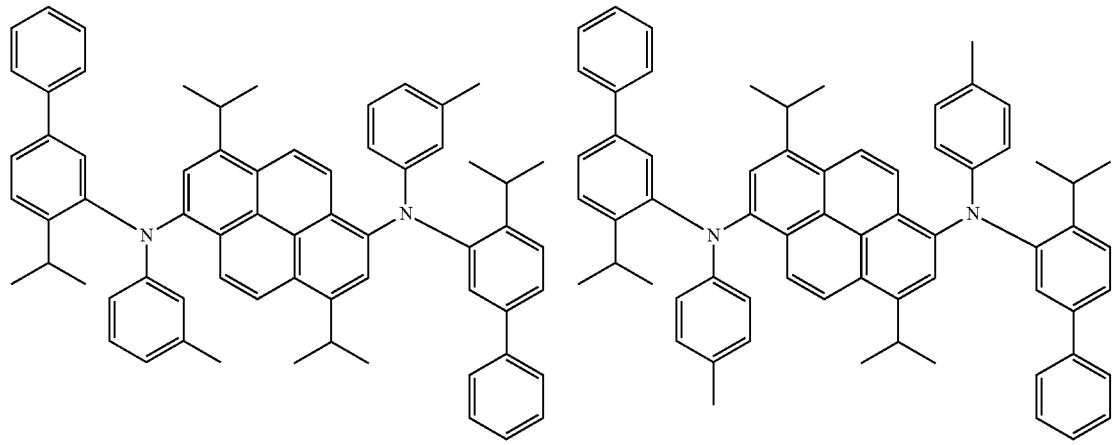
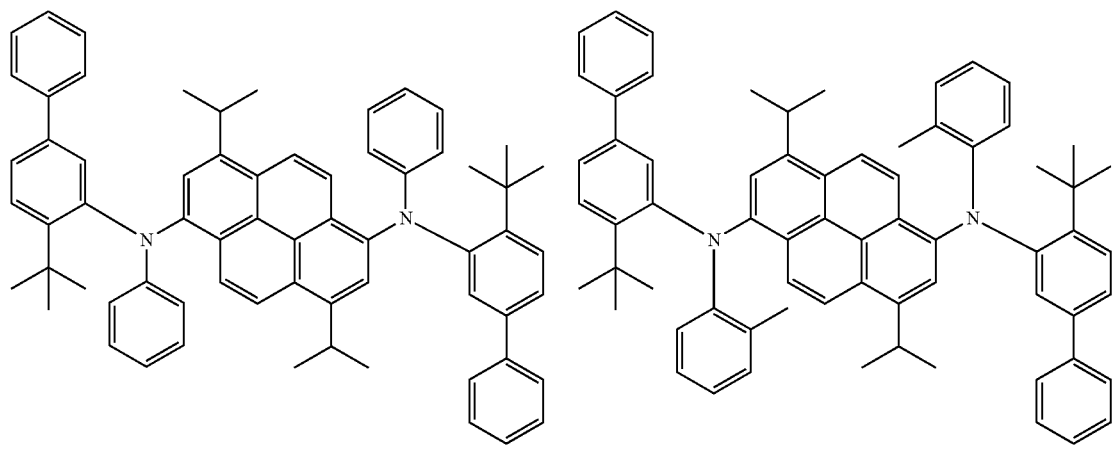
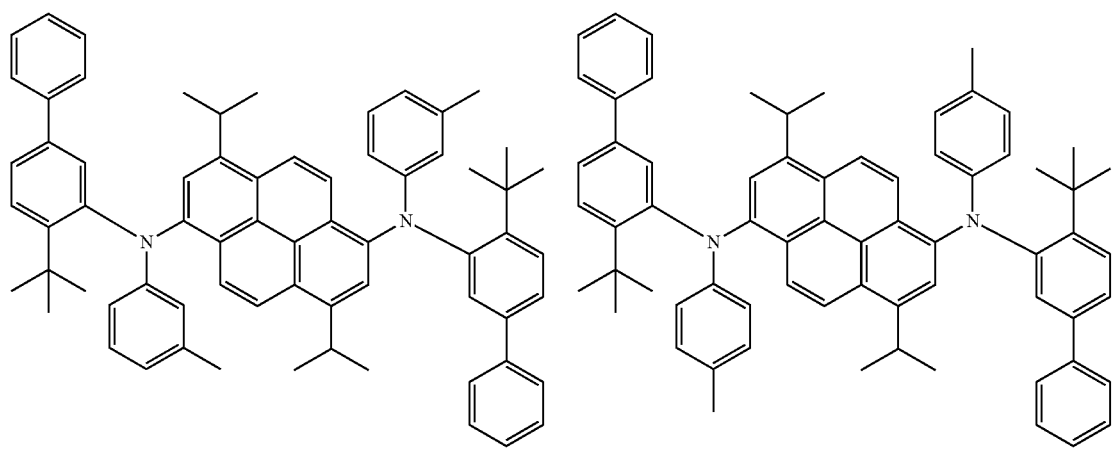

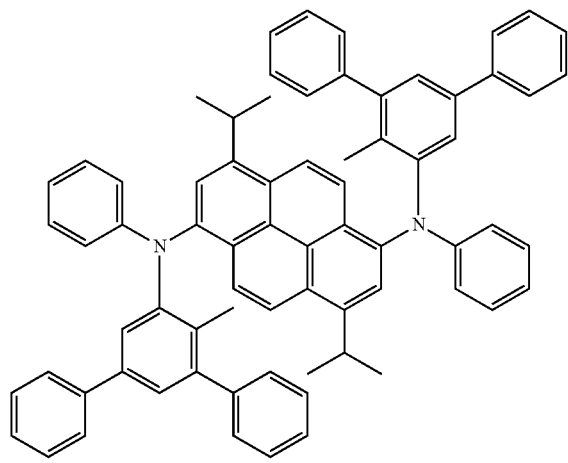
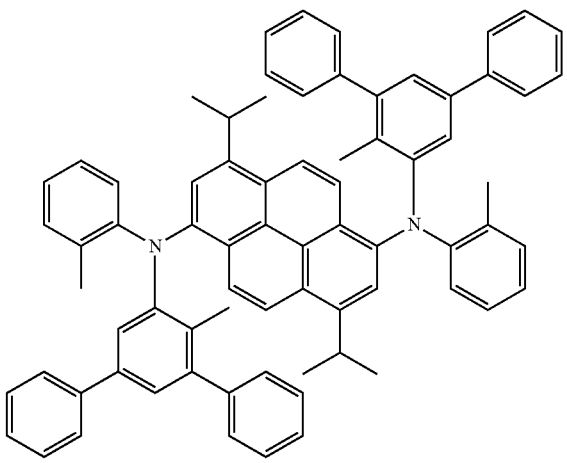
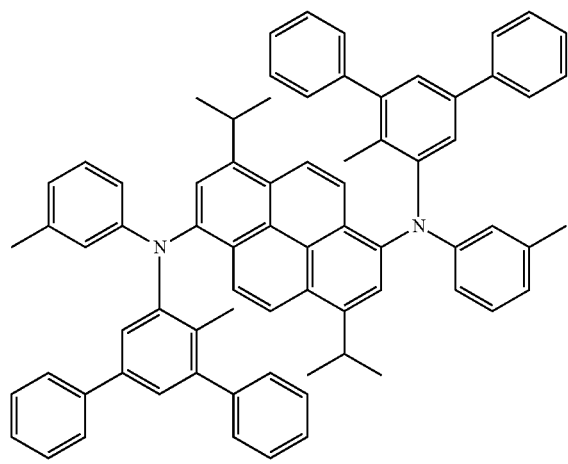
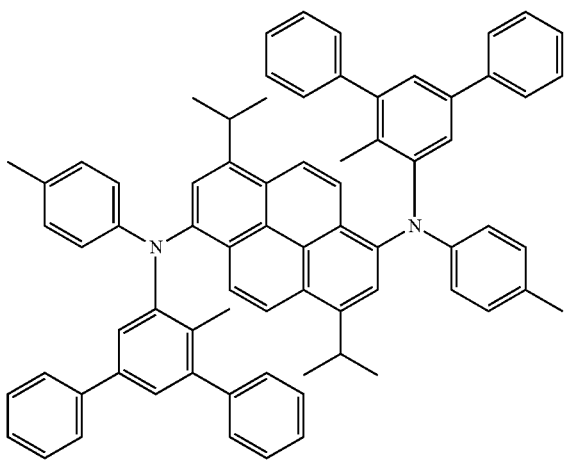
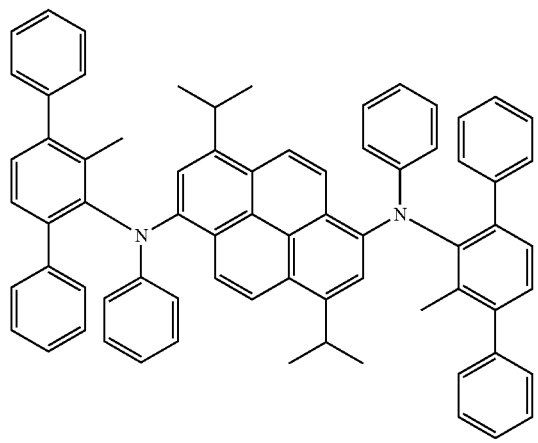
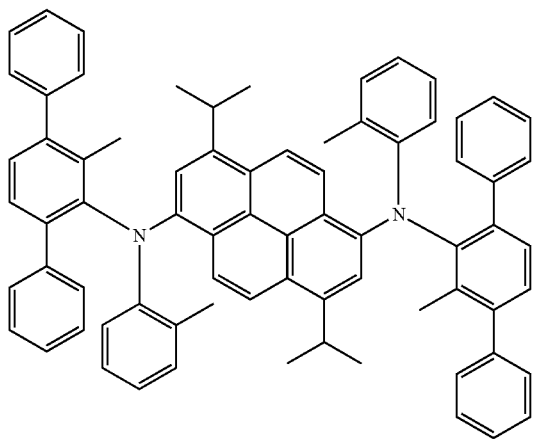

-continued
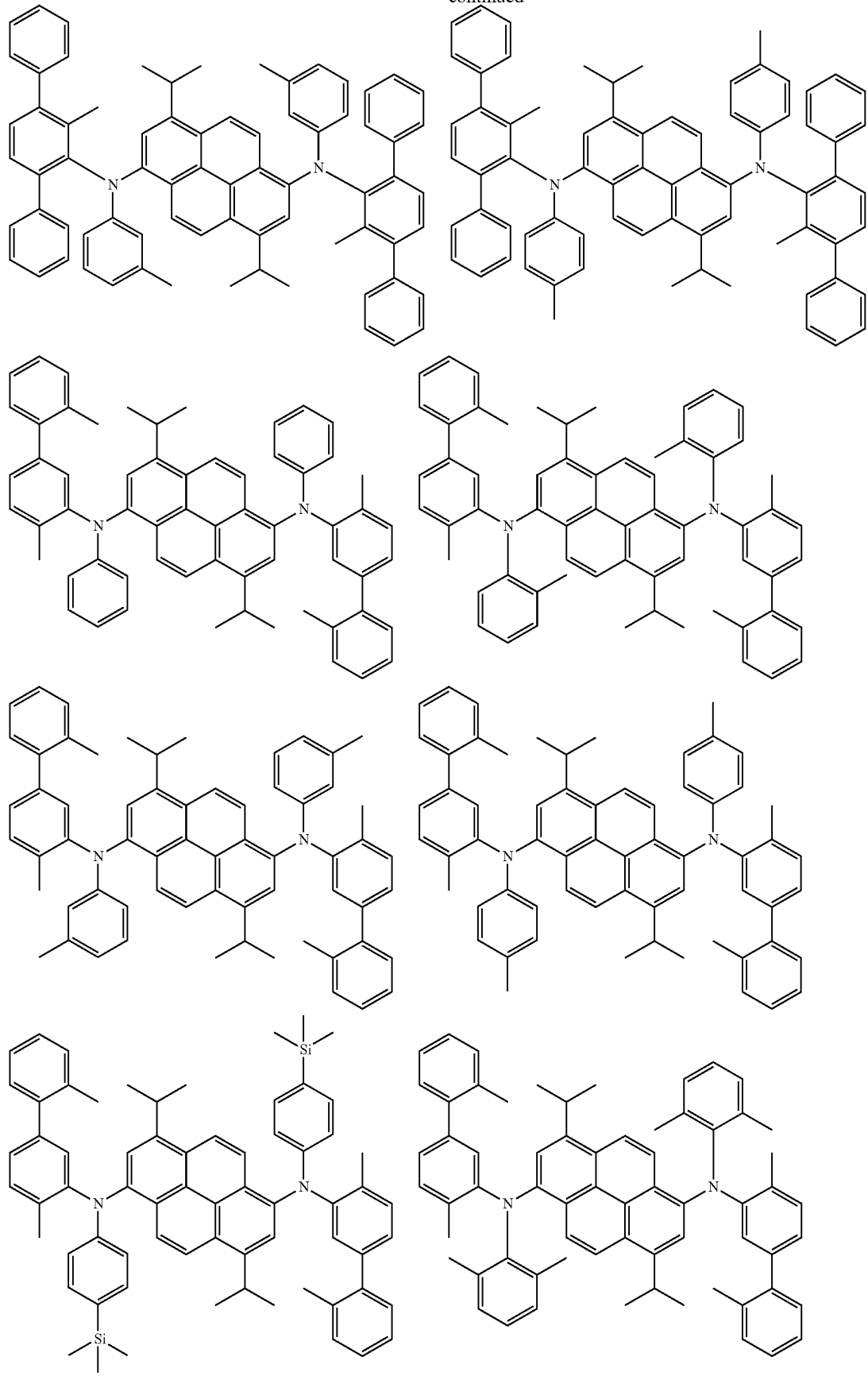

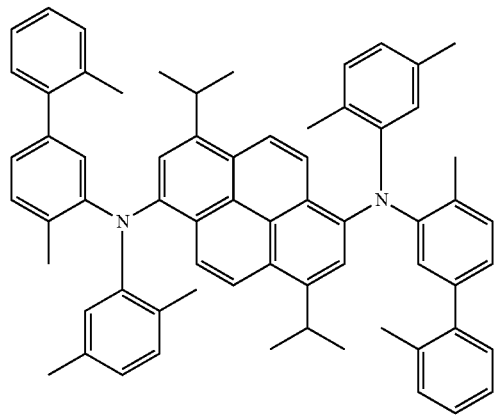
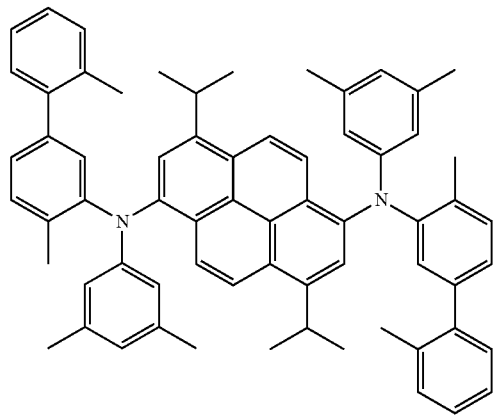
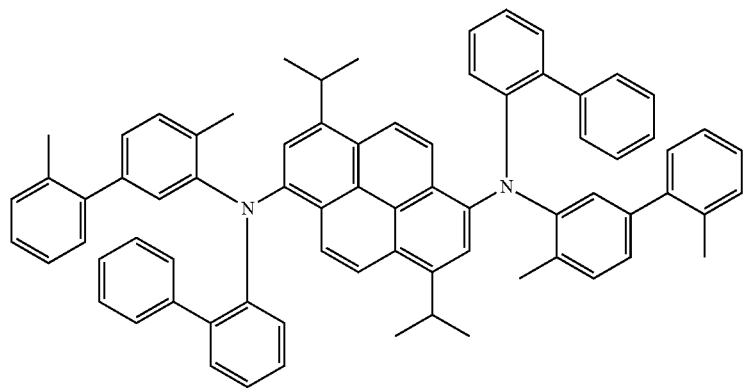
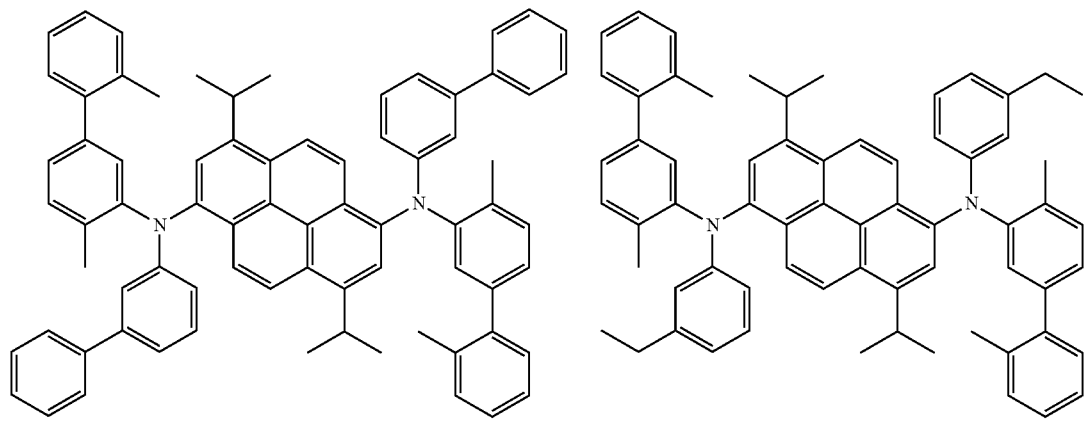
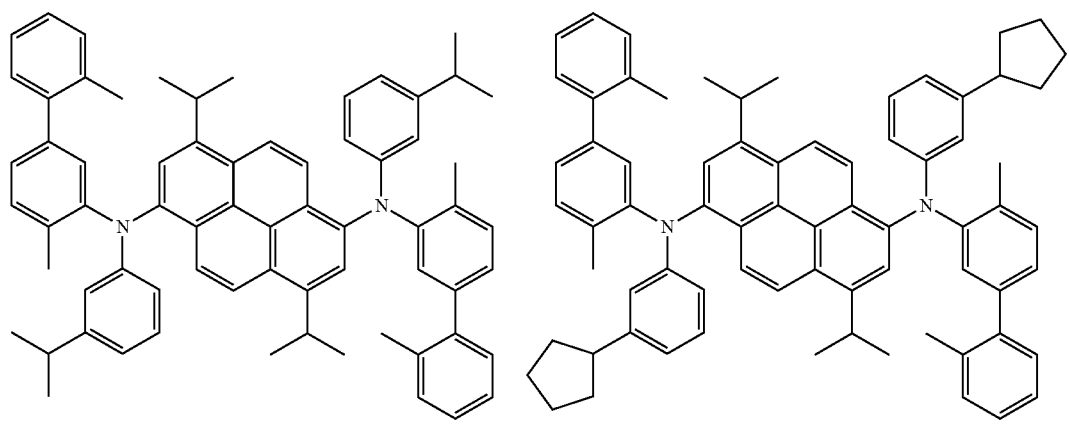

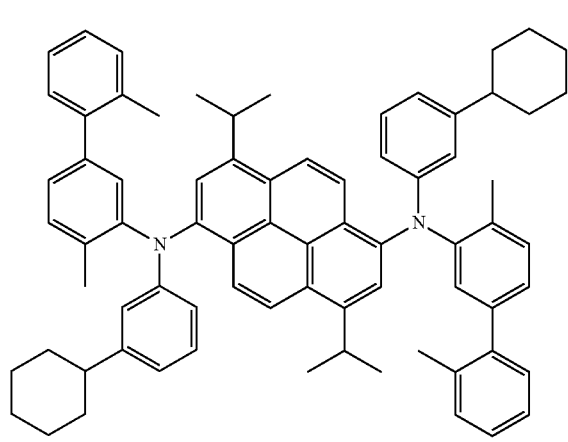
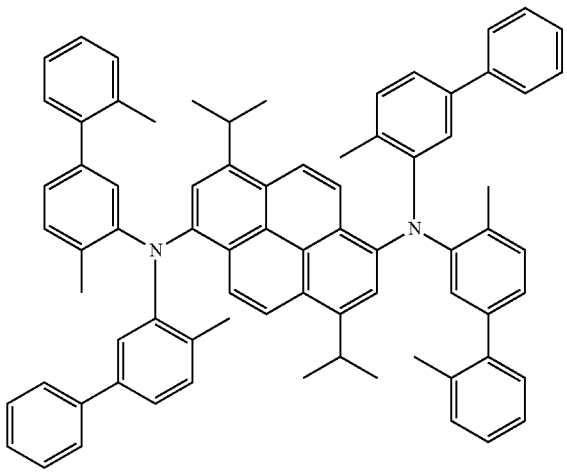
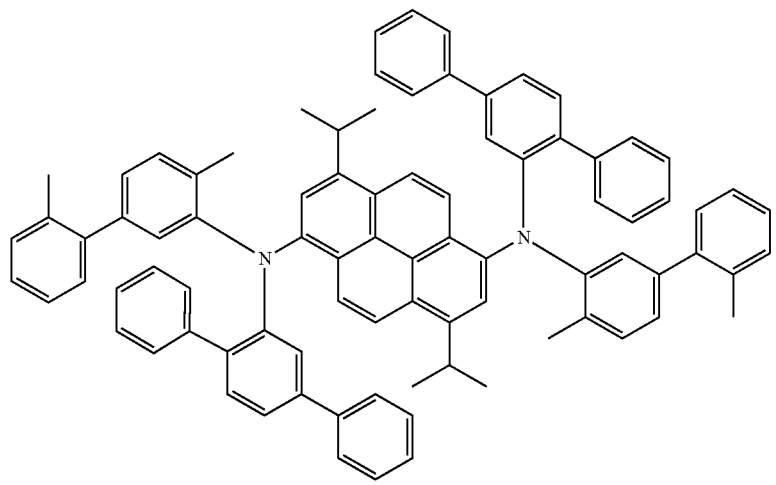
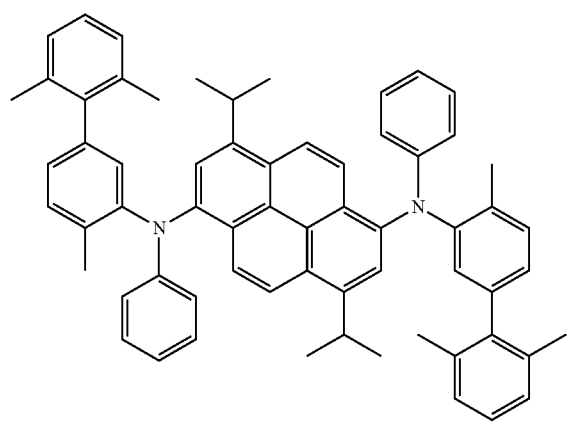
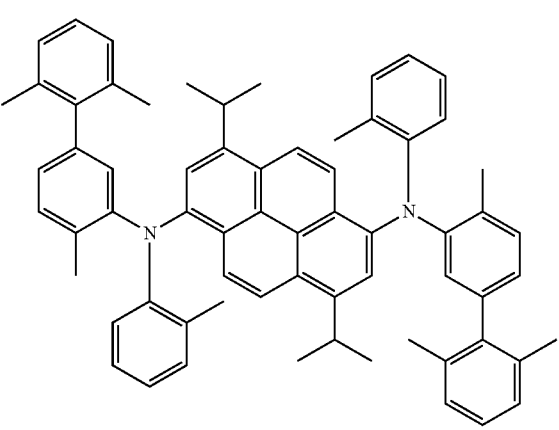

-continued
101
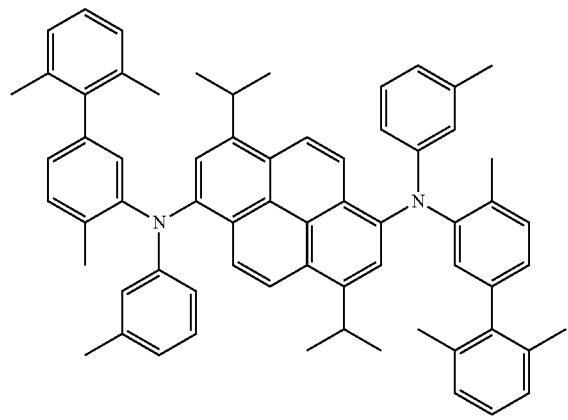
102
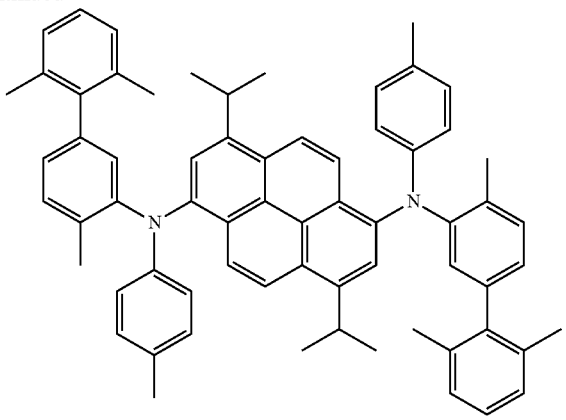
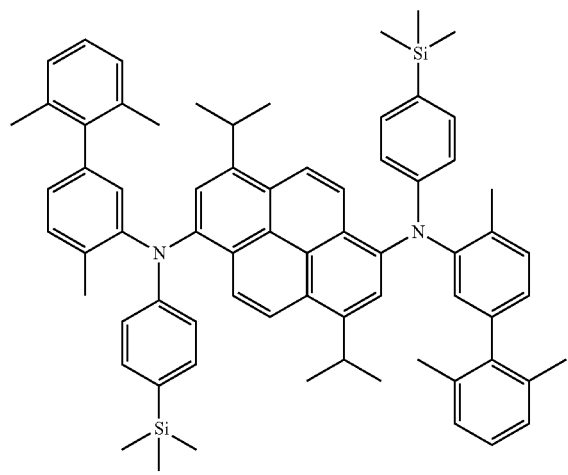
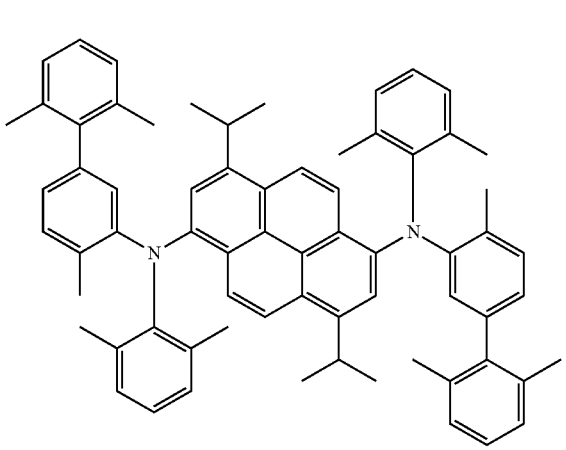
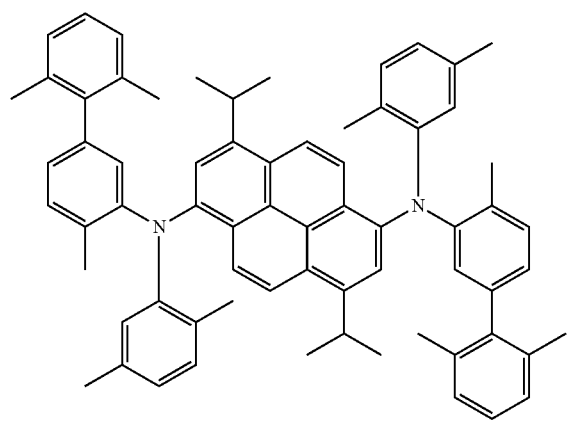
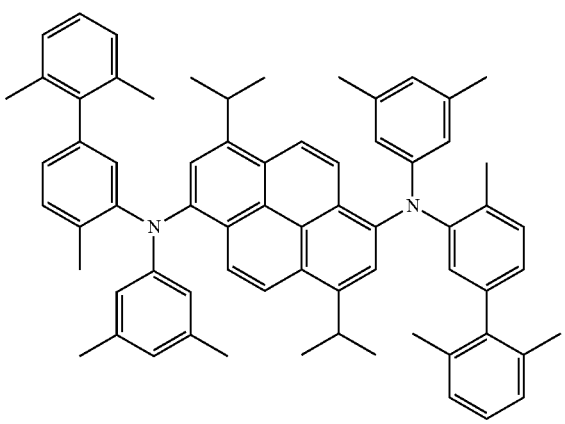
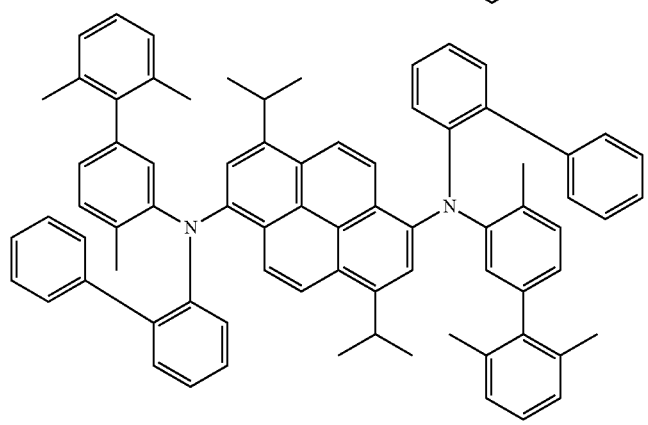

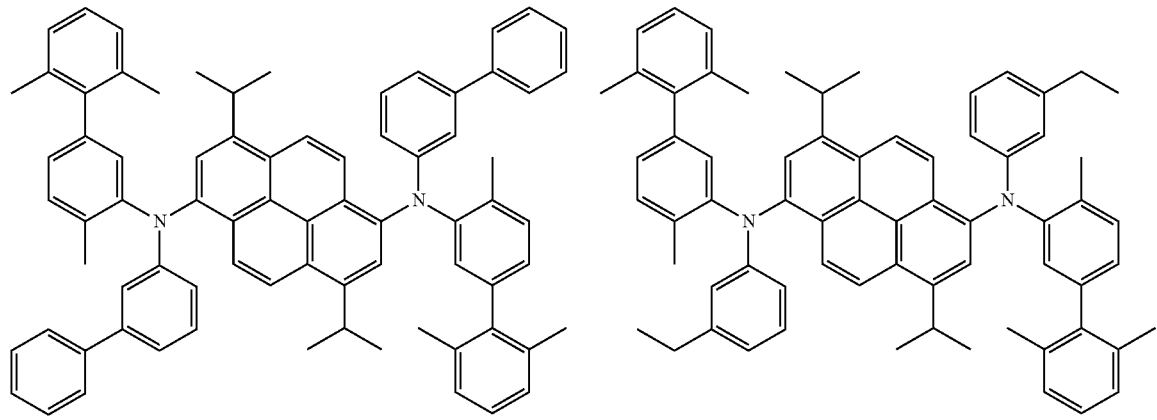
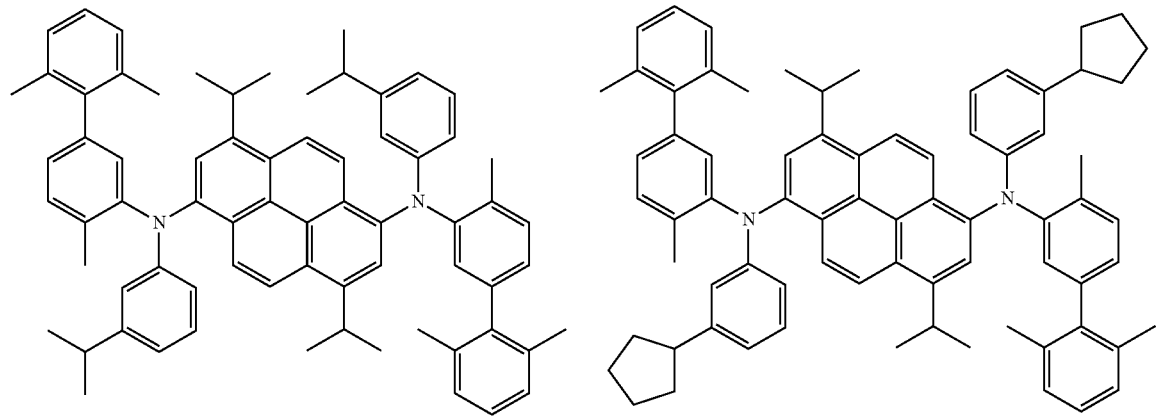
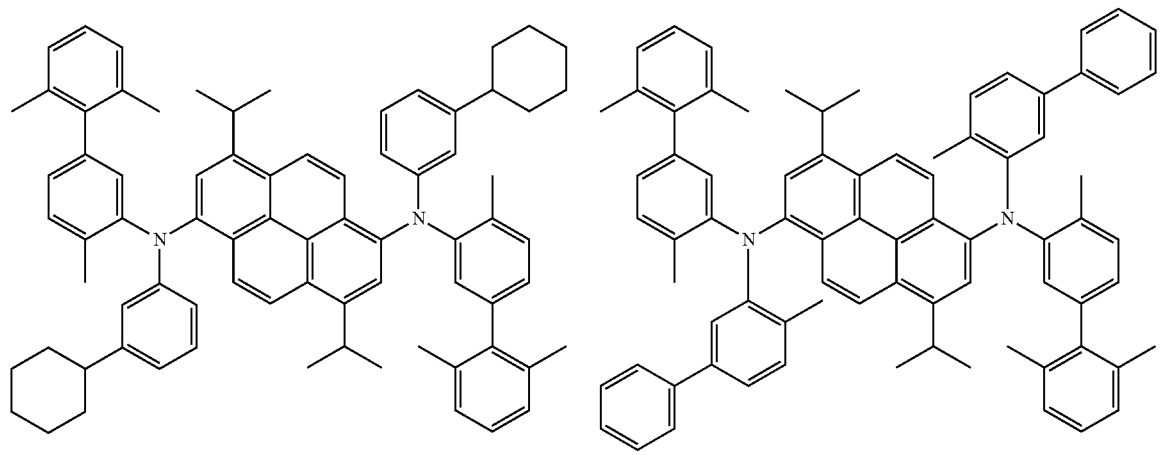

-continued
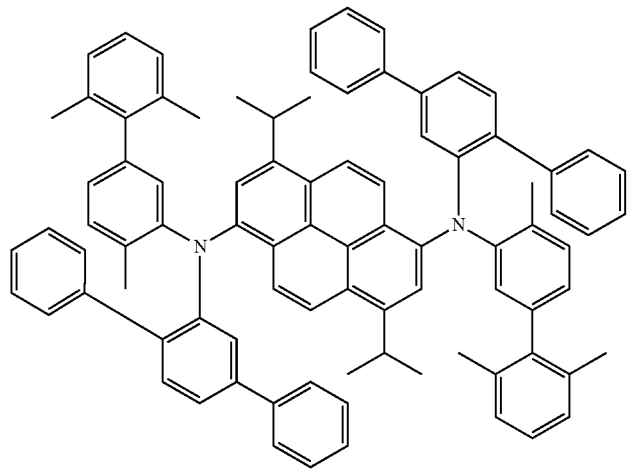
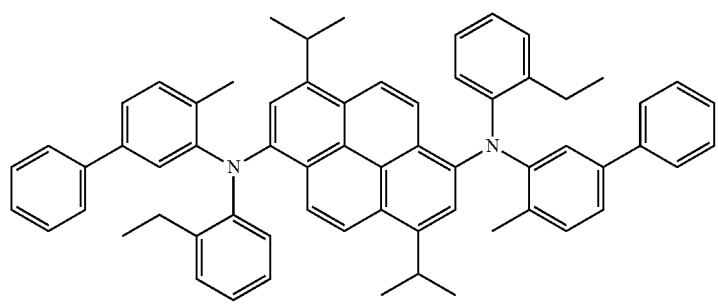
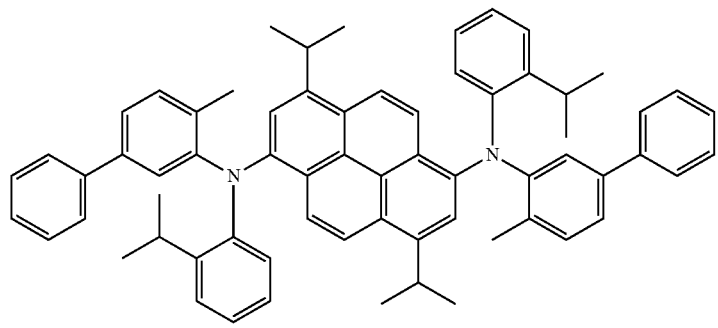
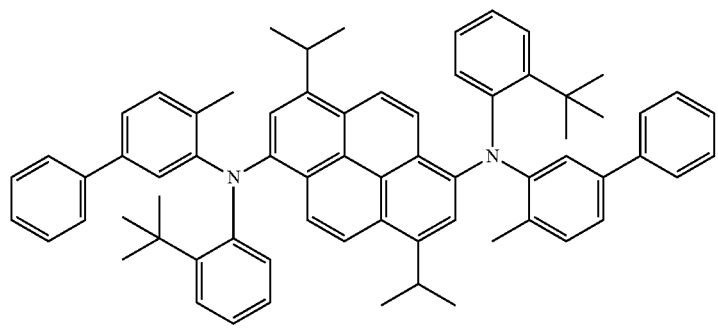

-continued
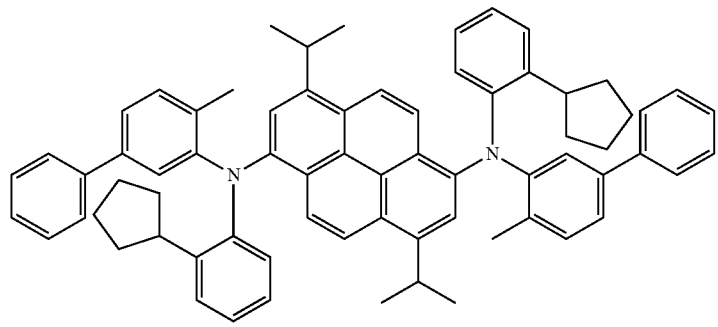
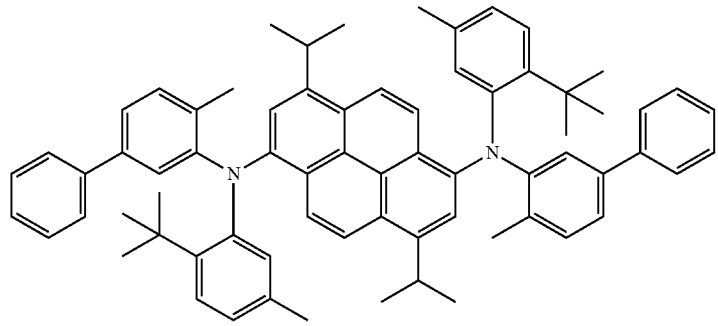
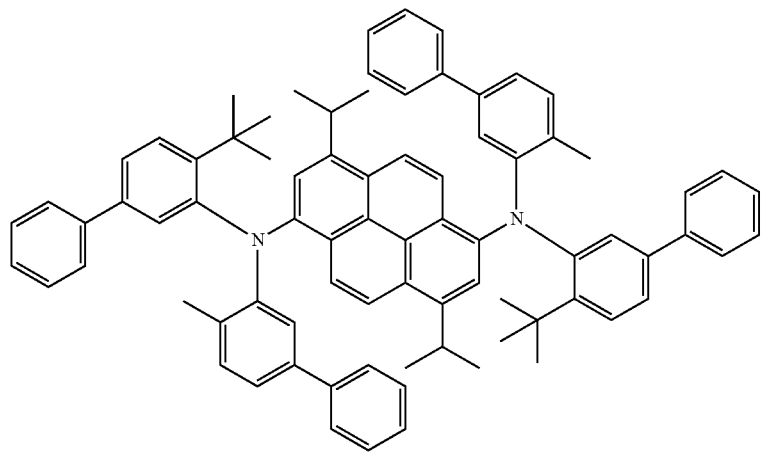
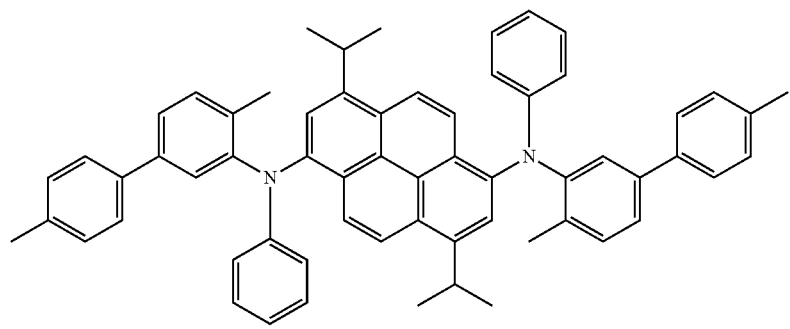
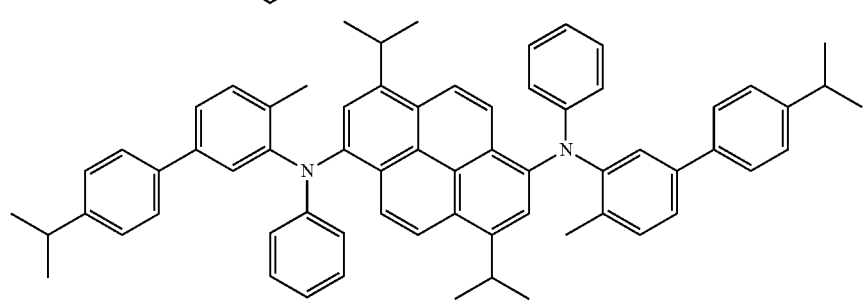

-continued
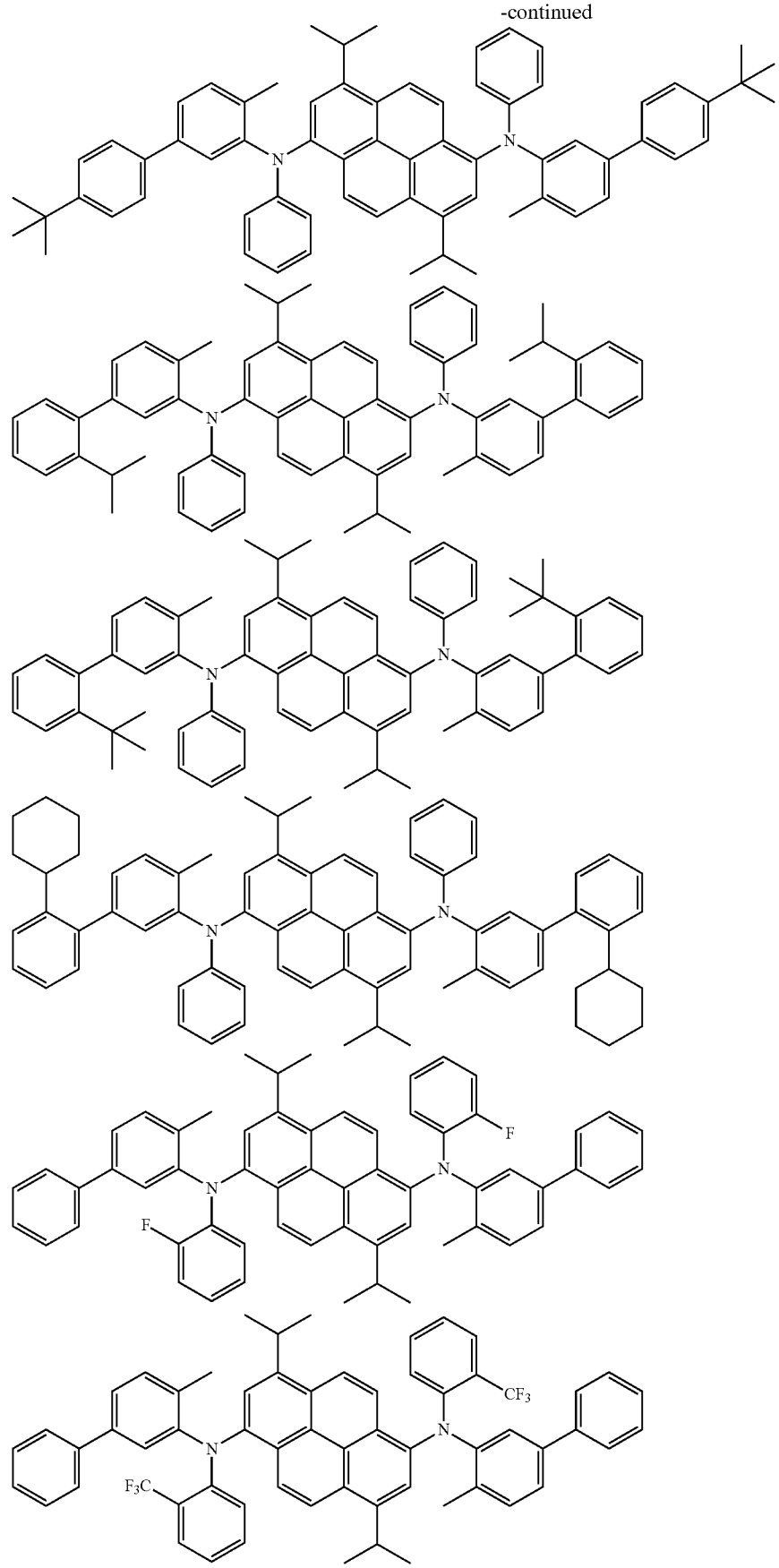

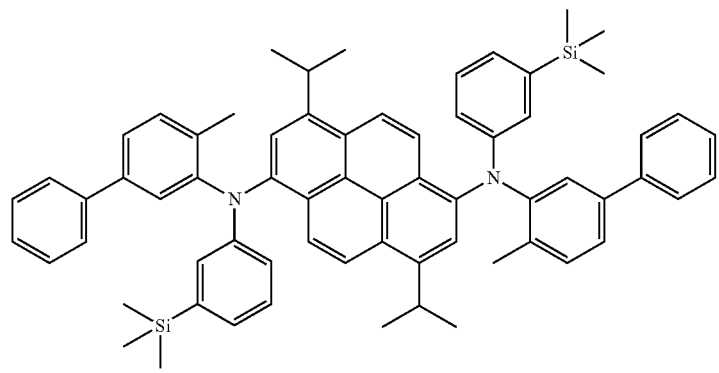
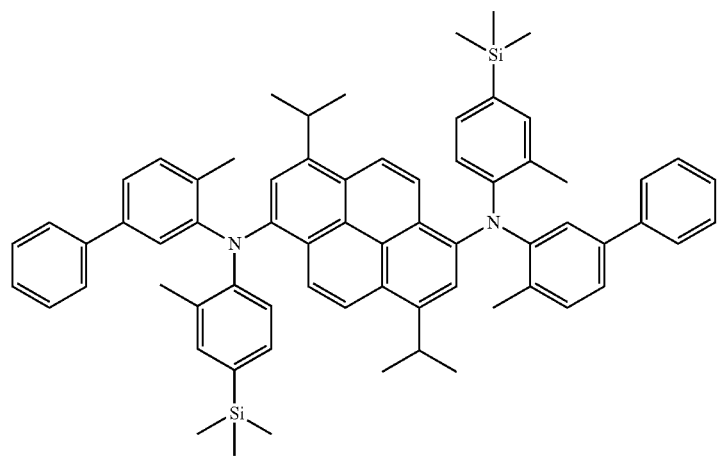
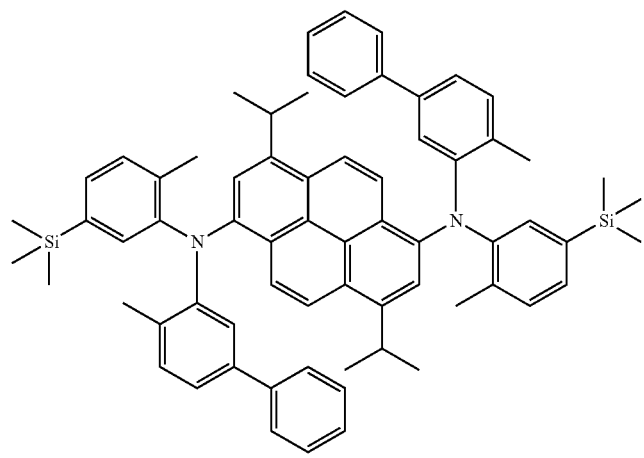
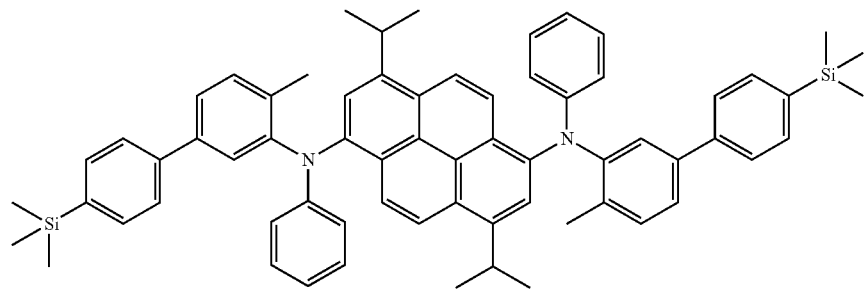

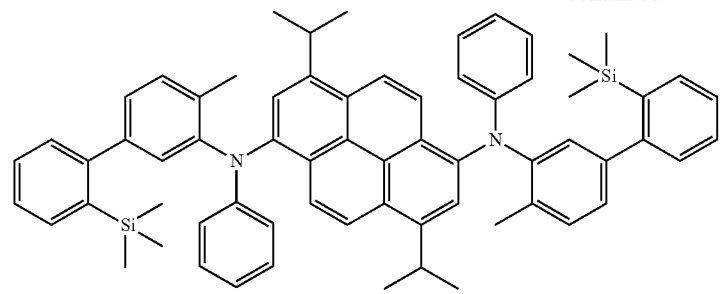
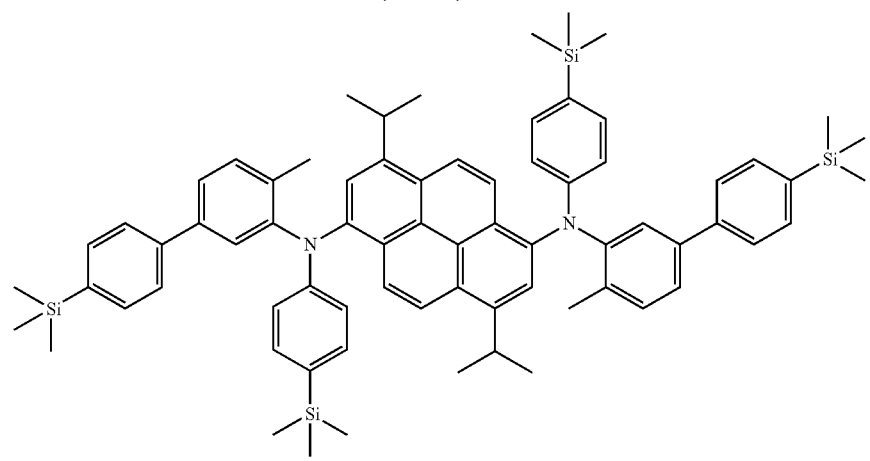
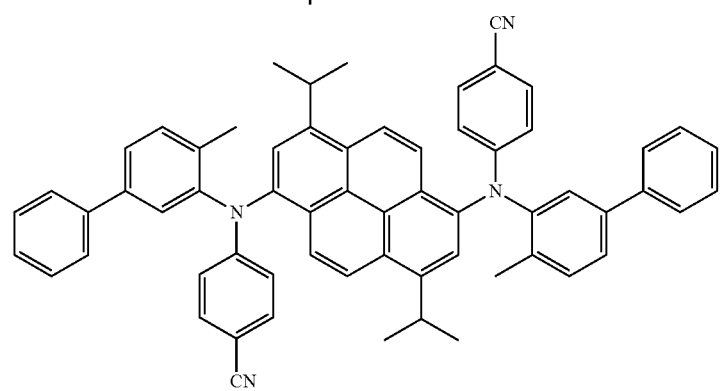
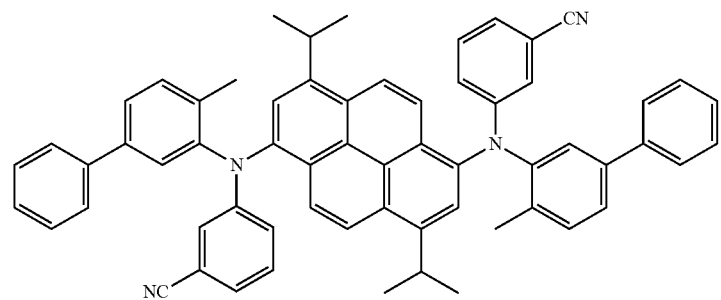
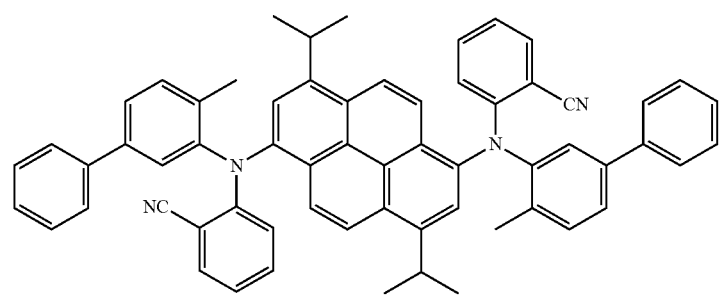

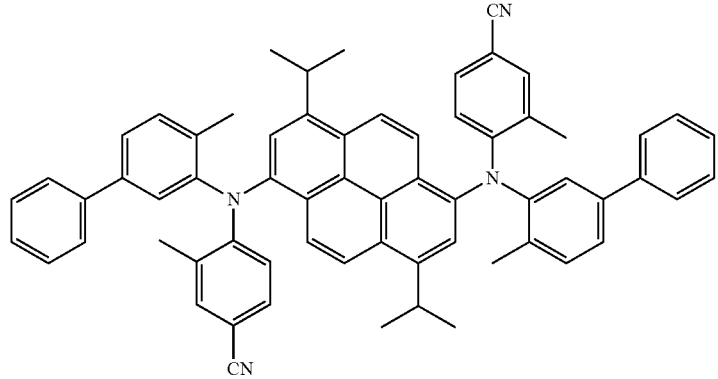
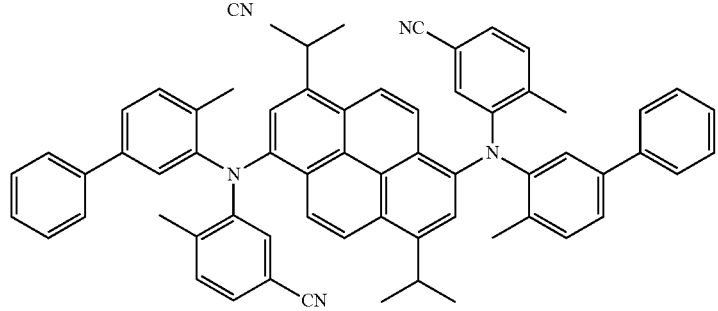
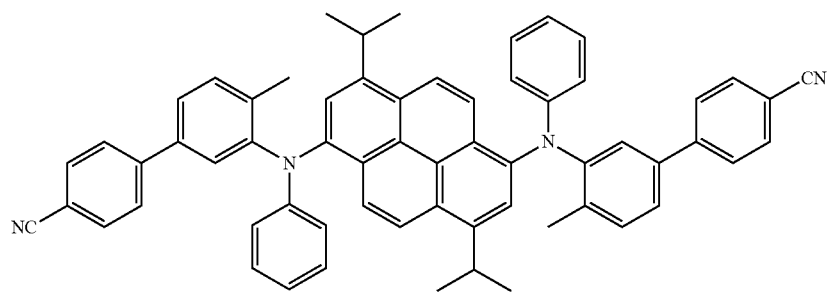
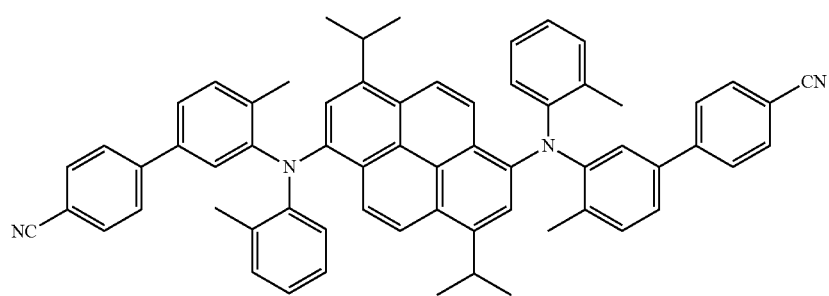
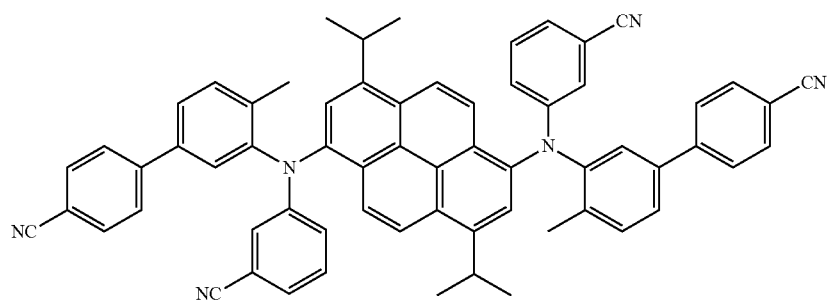

-continued
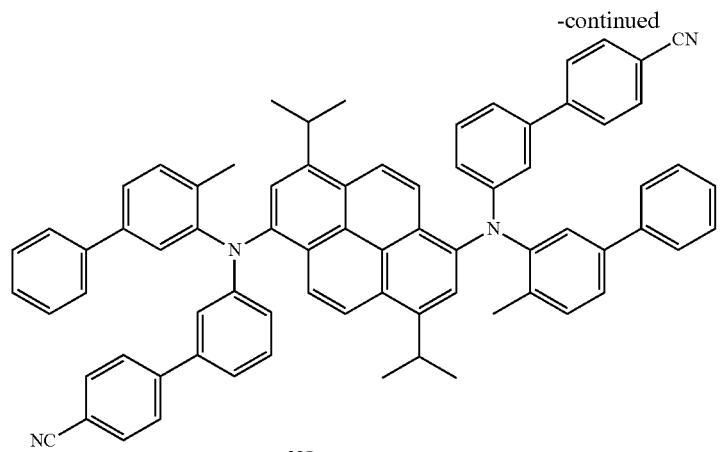
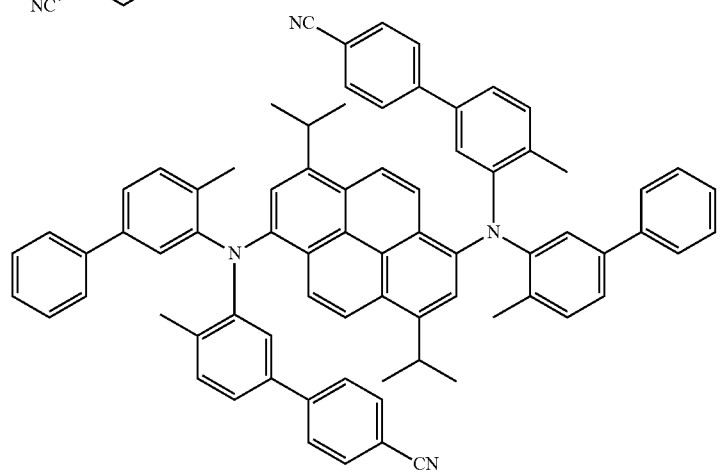
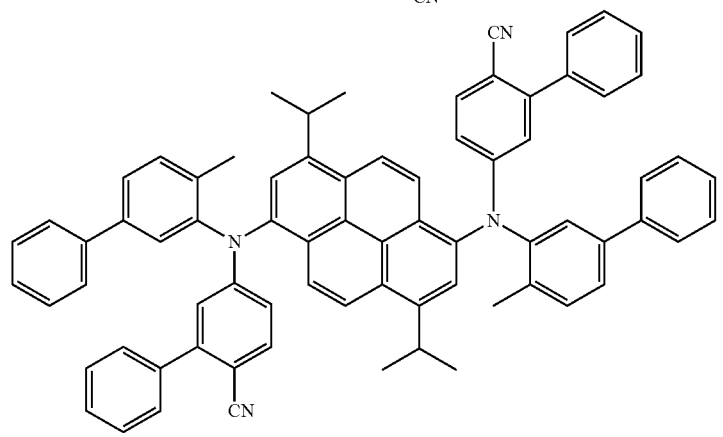
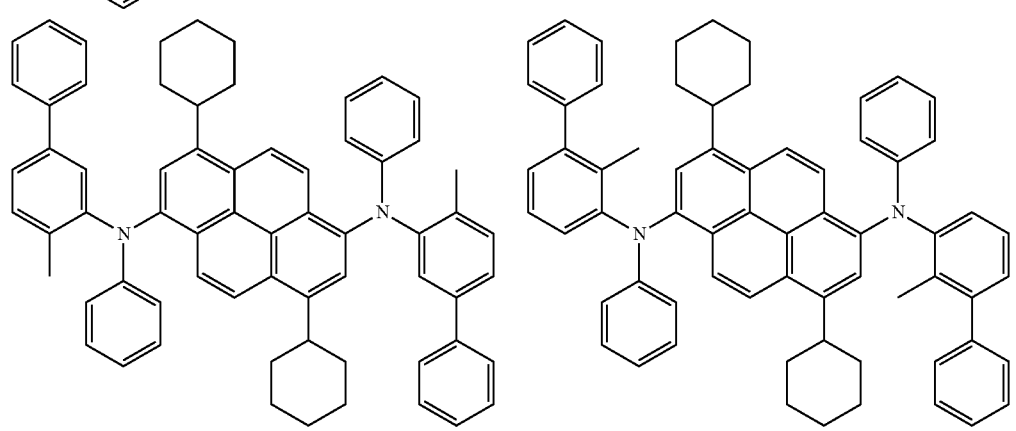

-continued
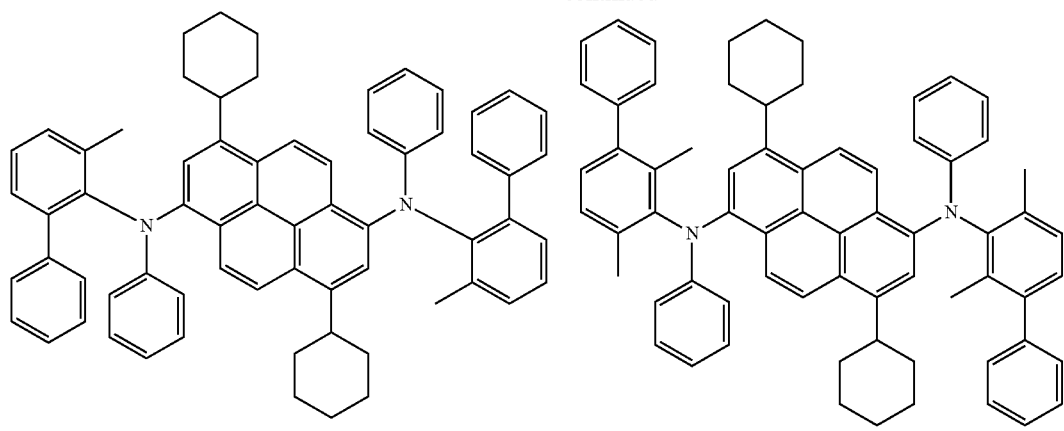
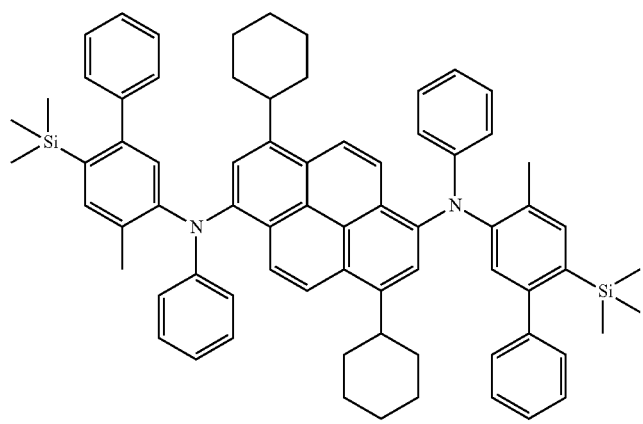
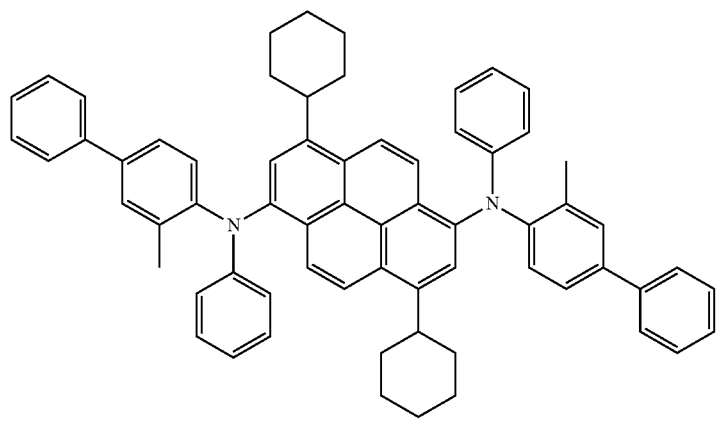
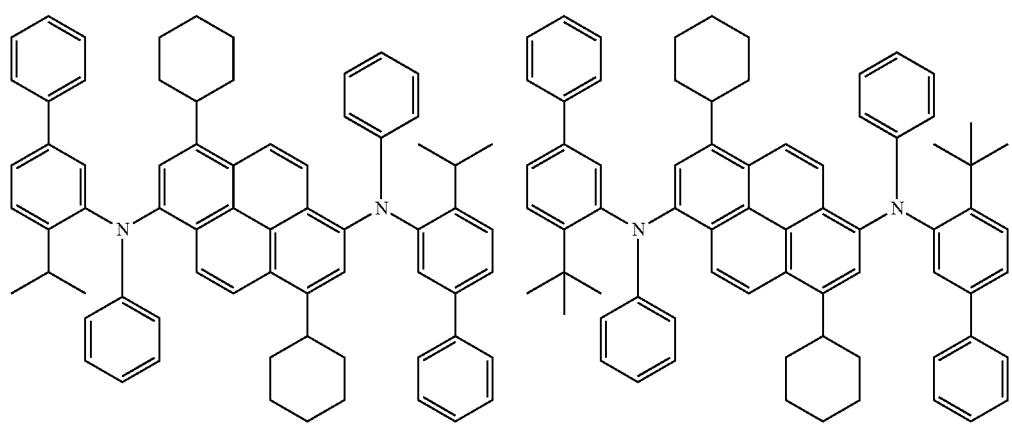

-continued
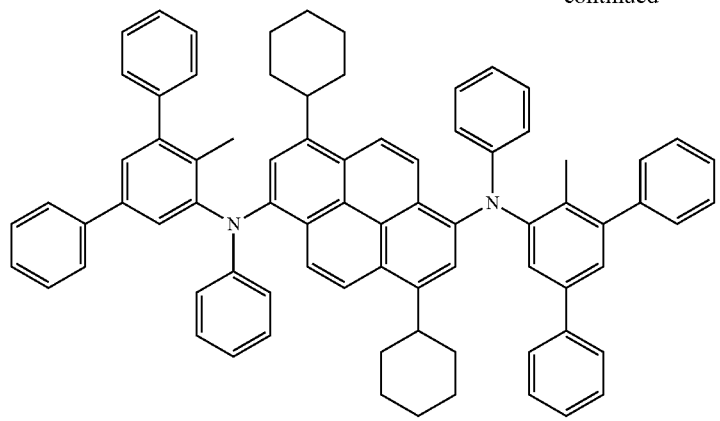
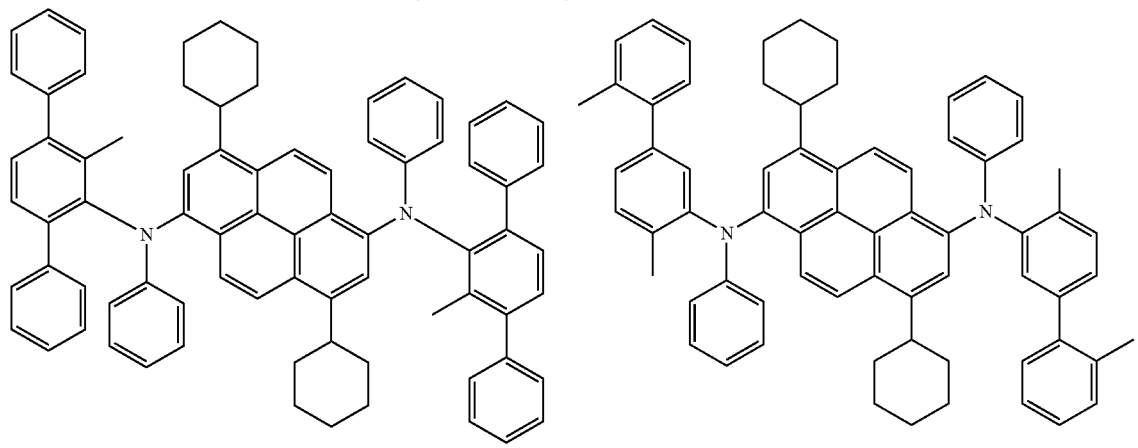
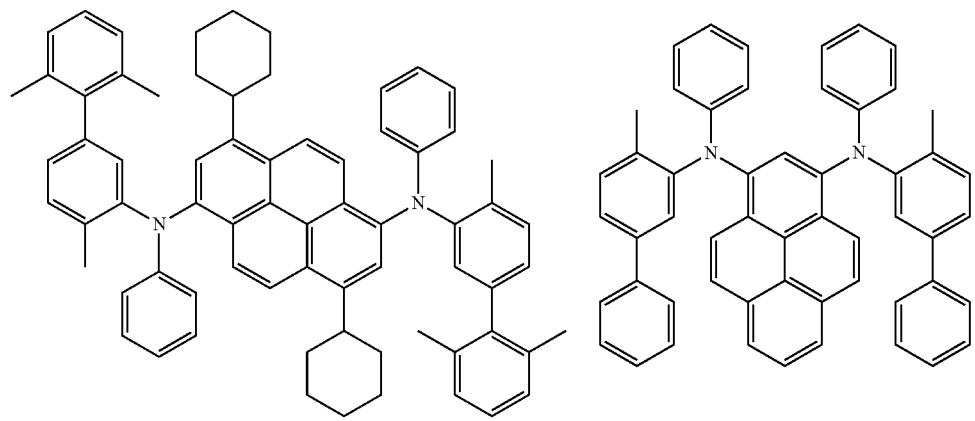
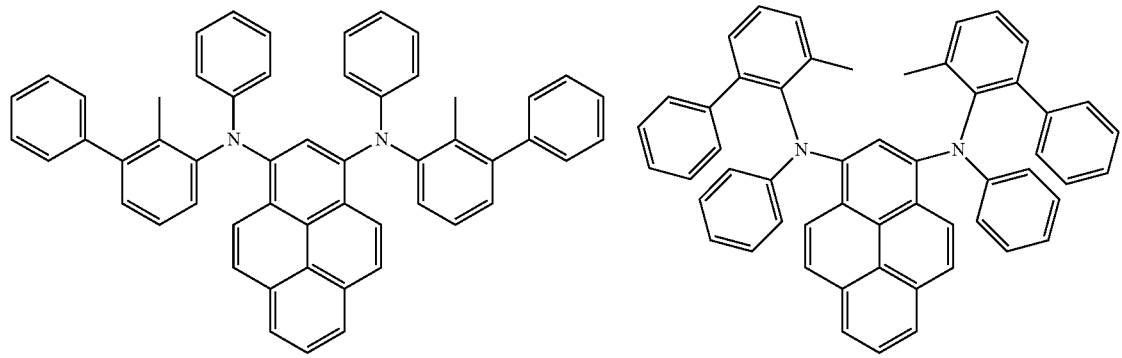

-continued
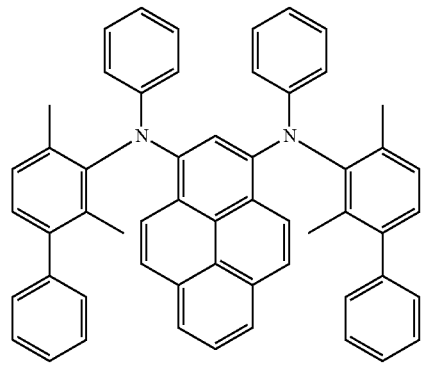
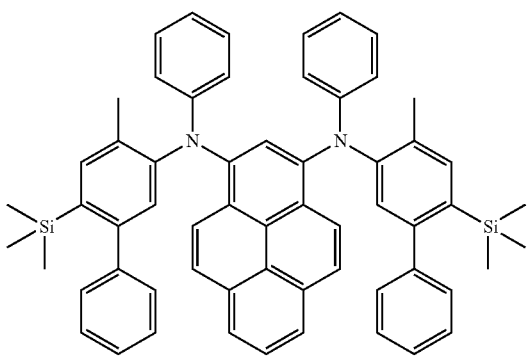
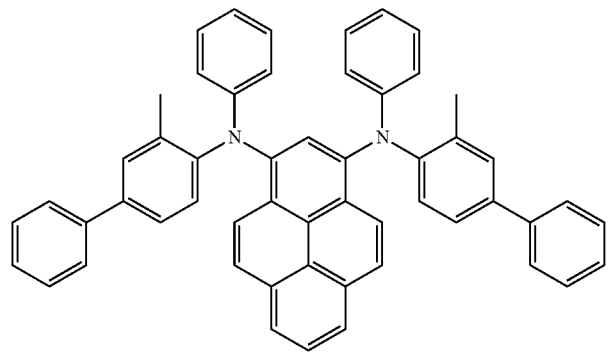
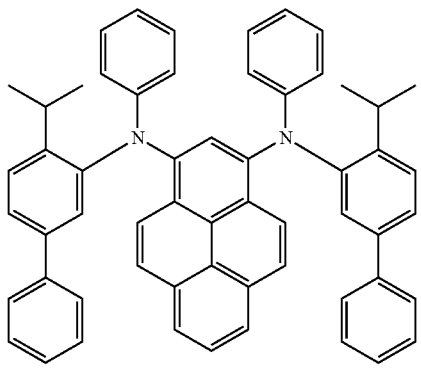
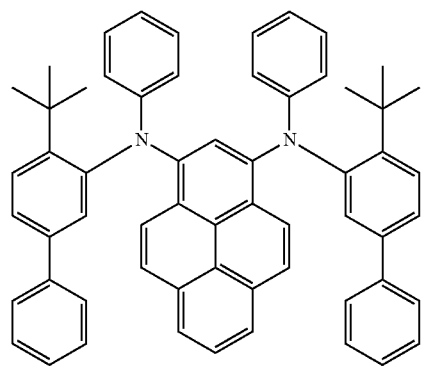
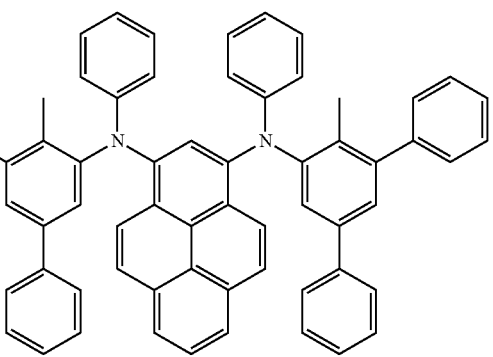
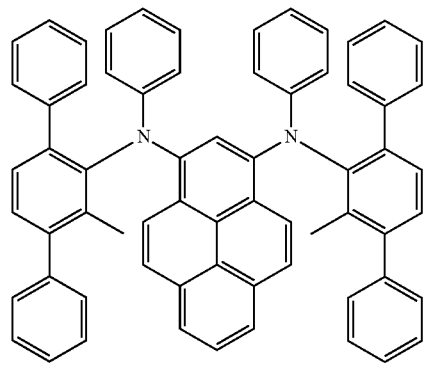
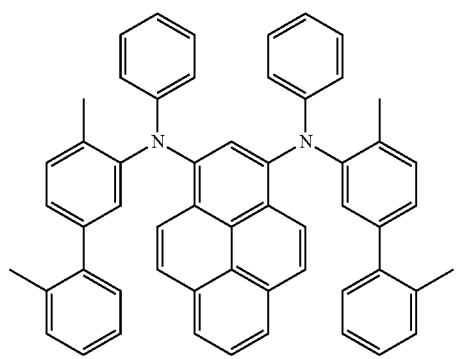

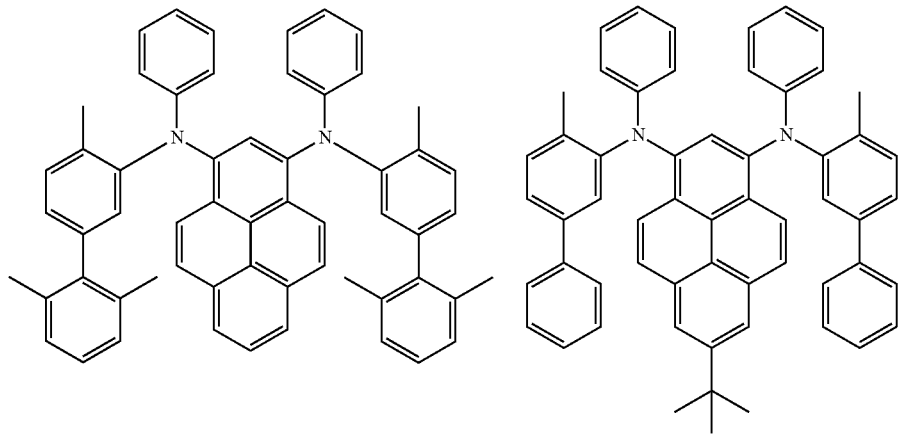
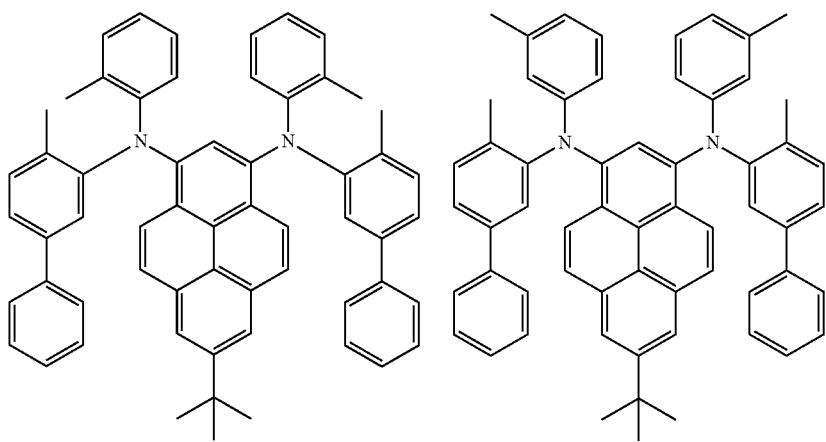
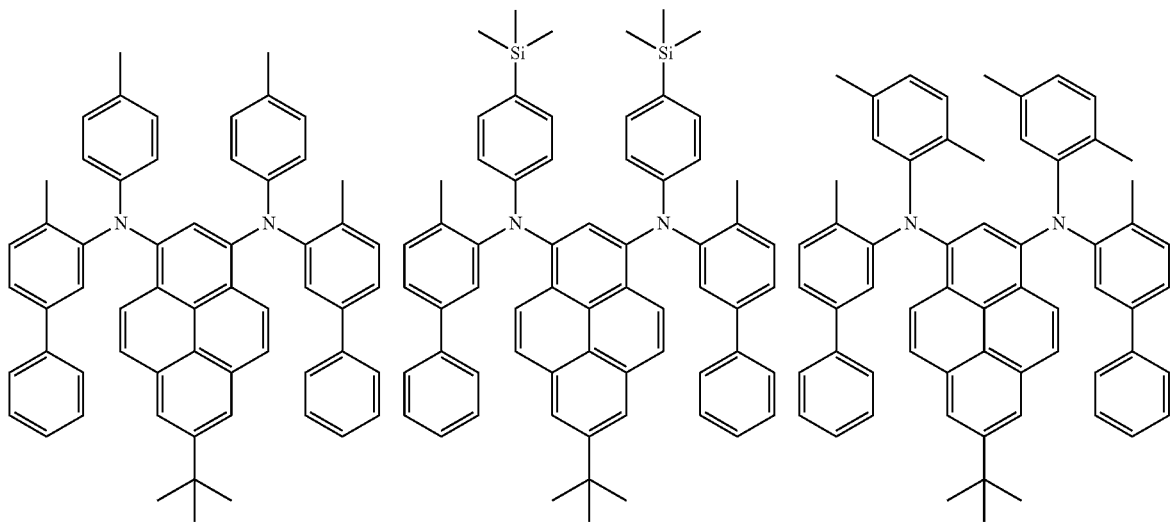

-continued
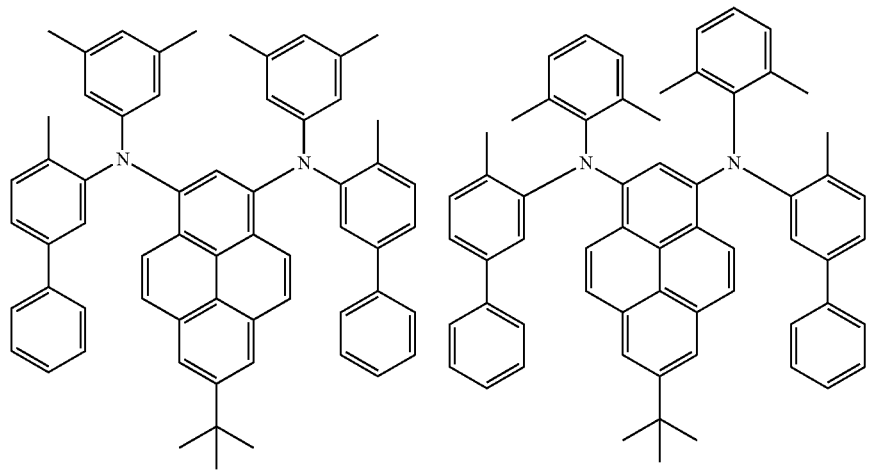
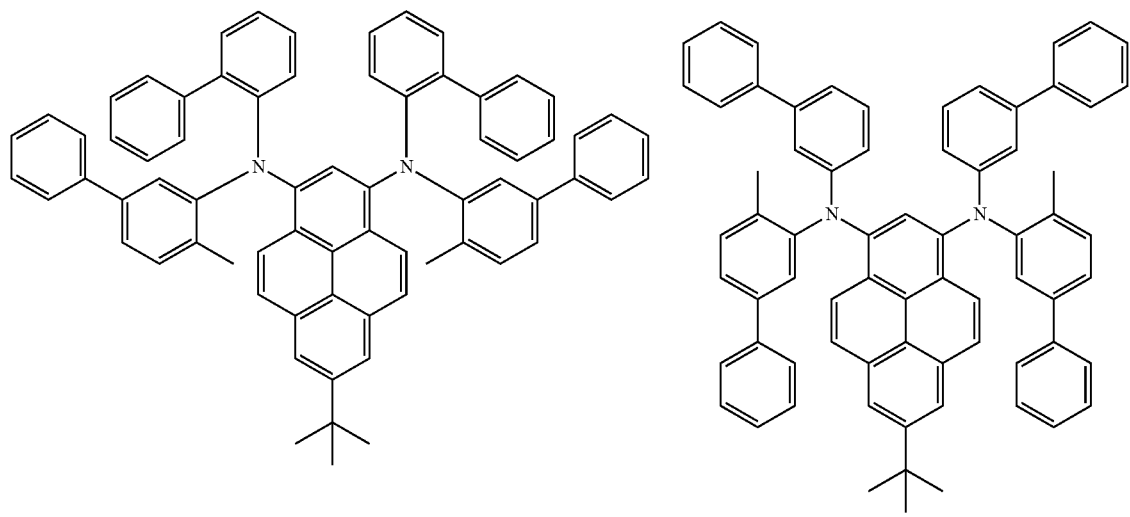
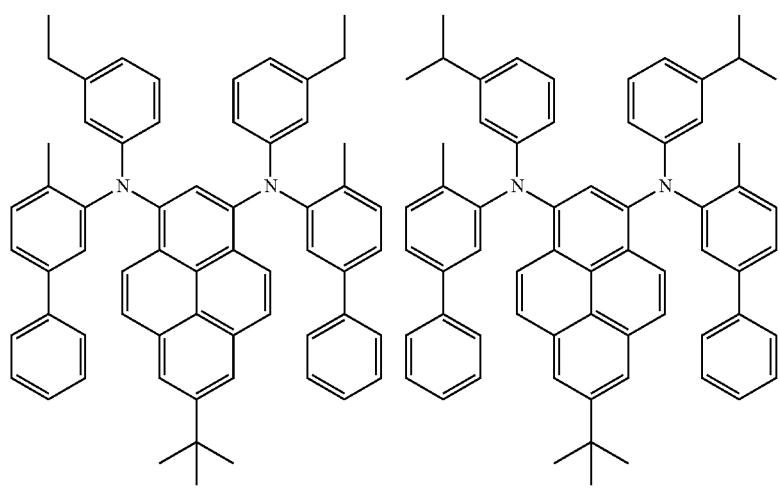

-continued
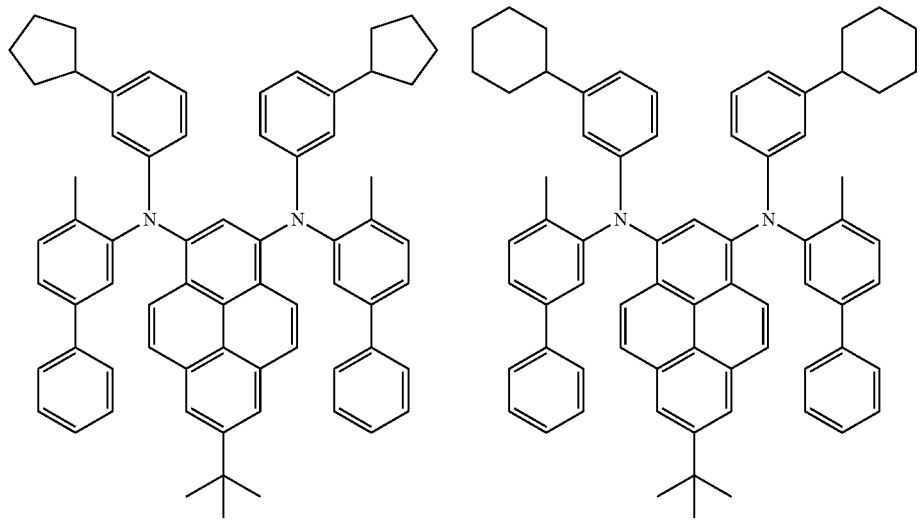
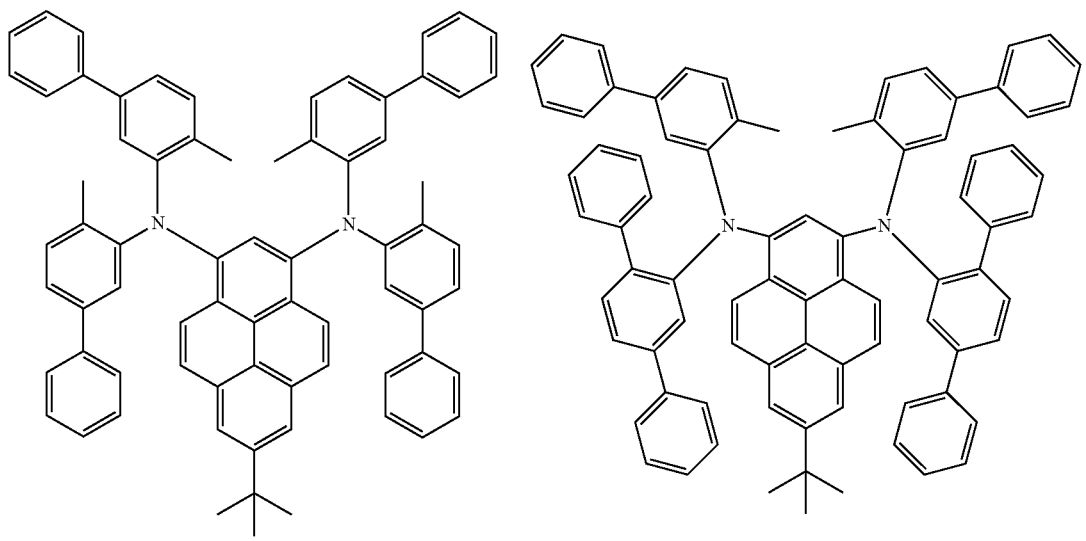
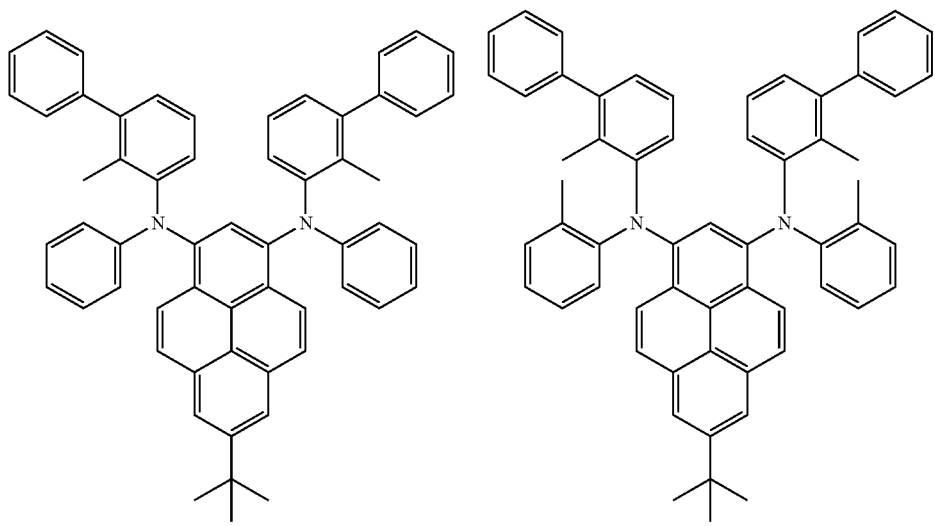

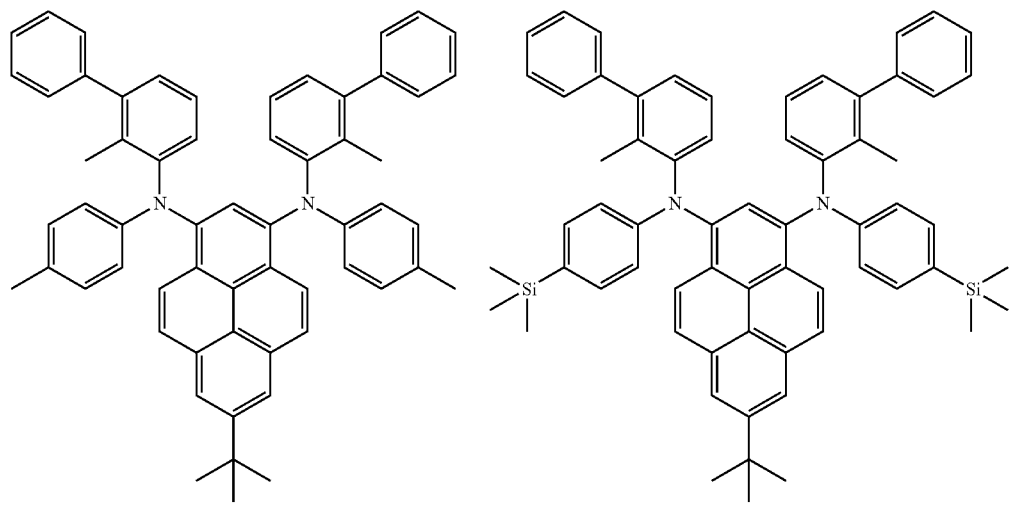
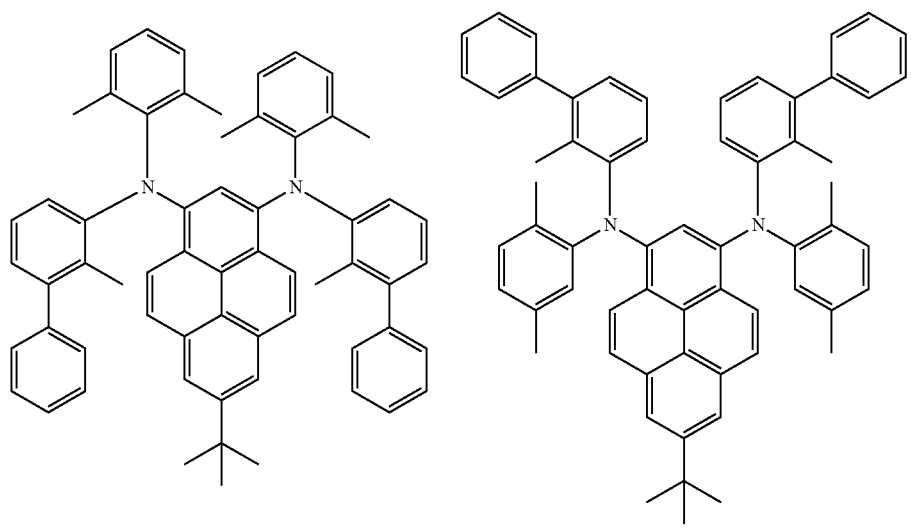
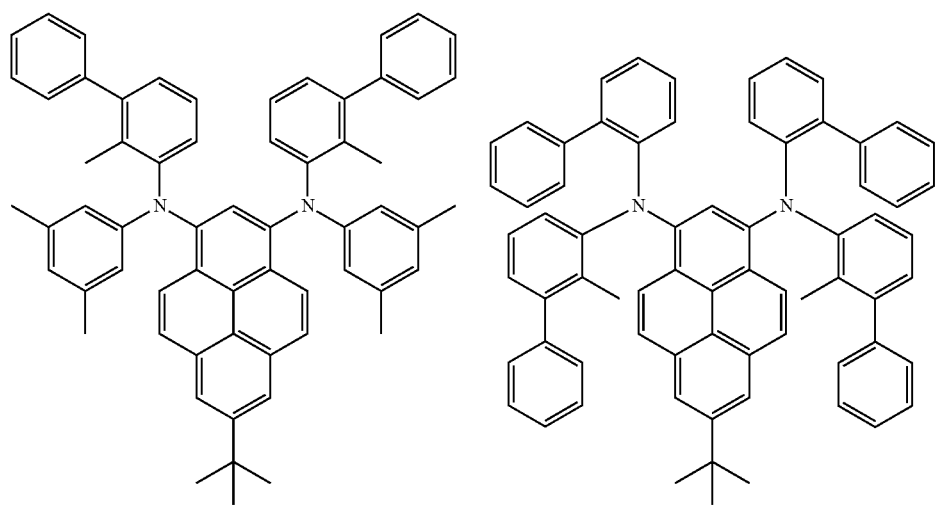

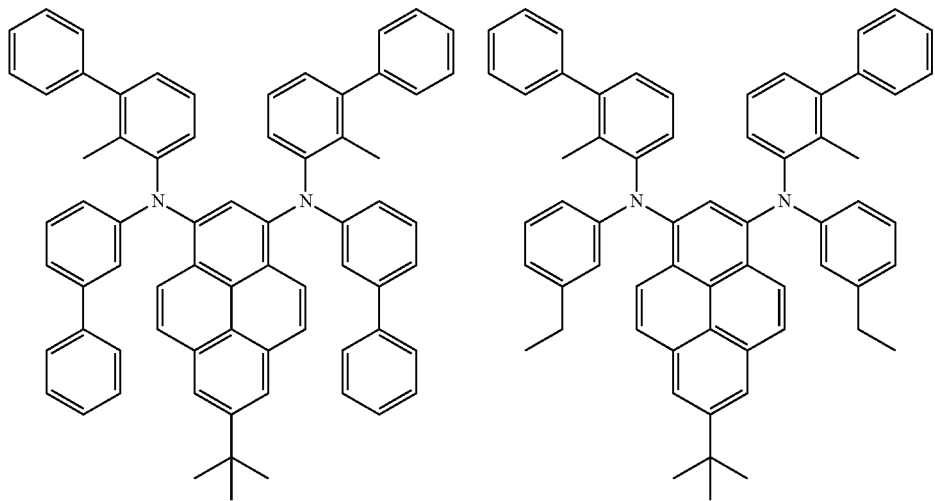
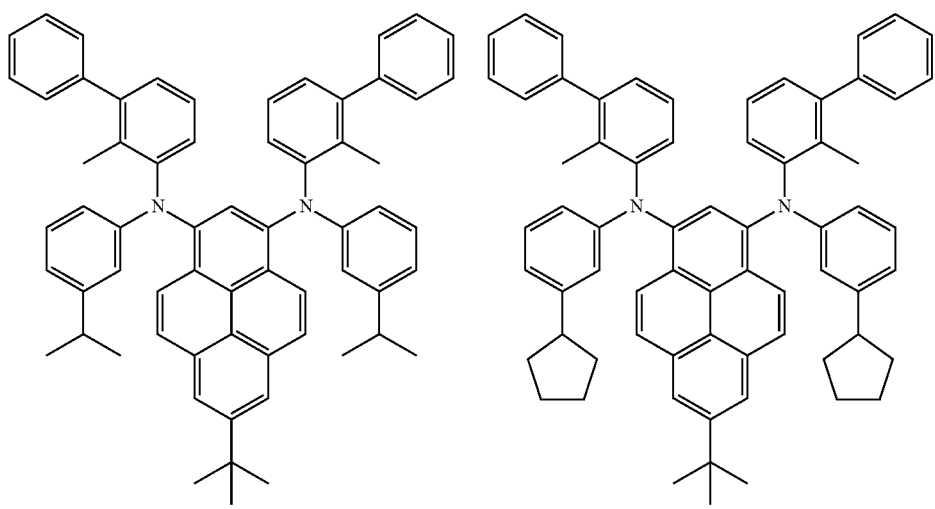
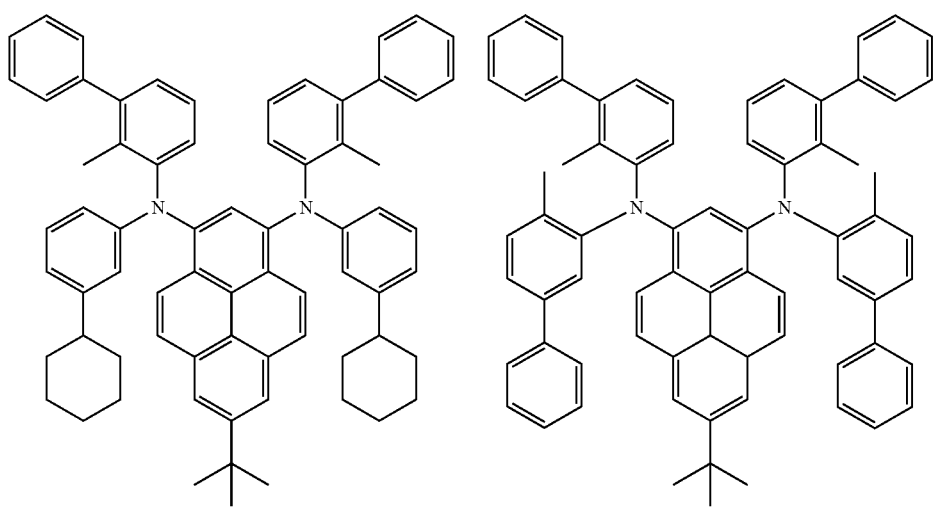

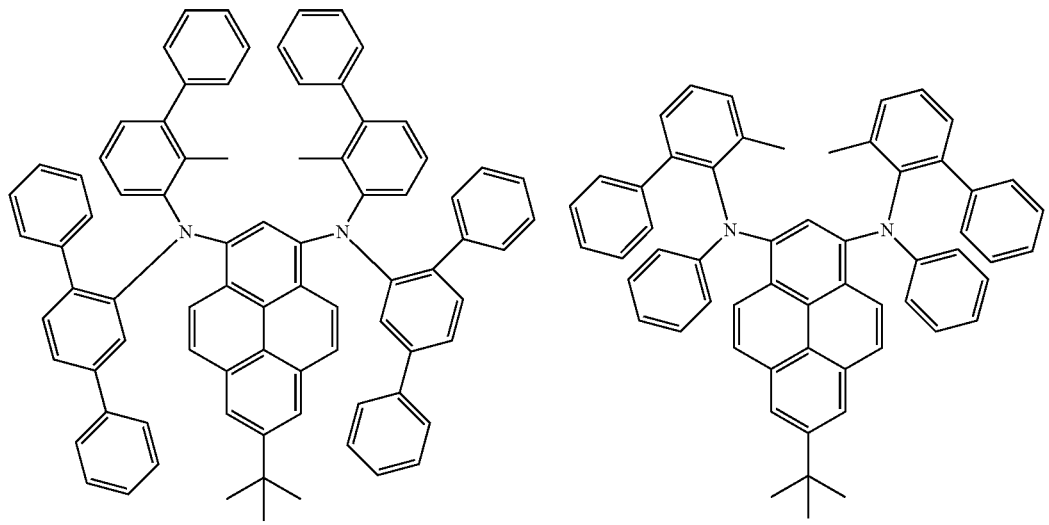
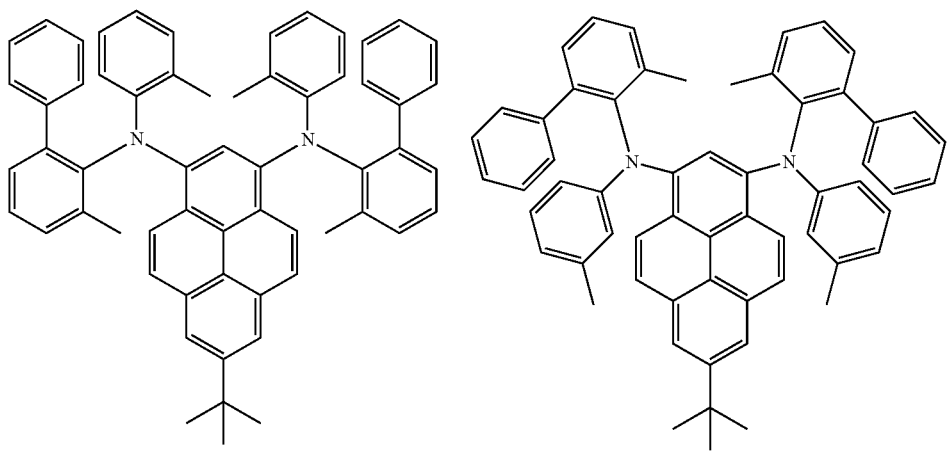
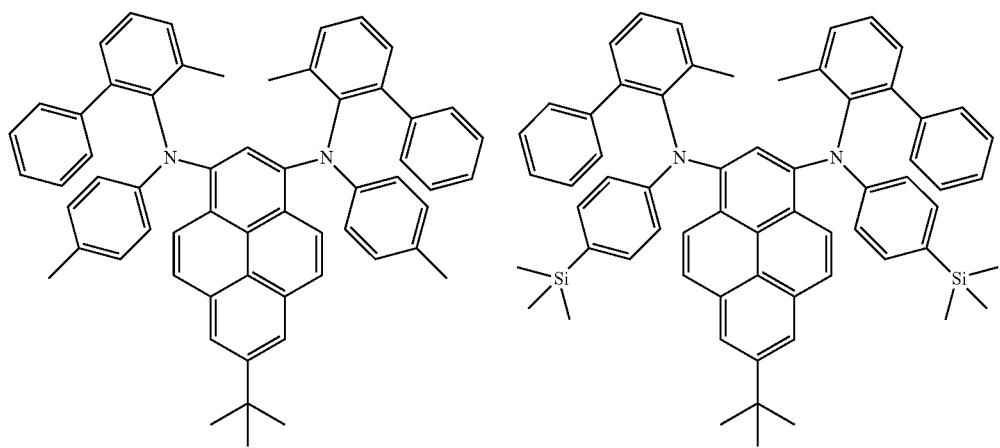

-continued
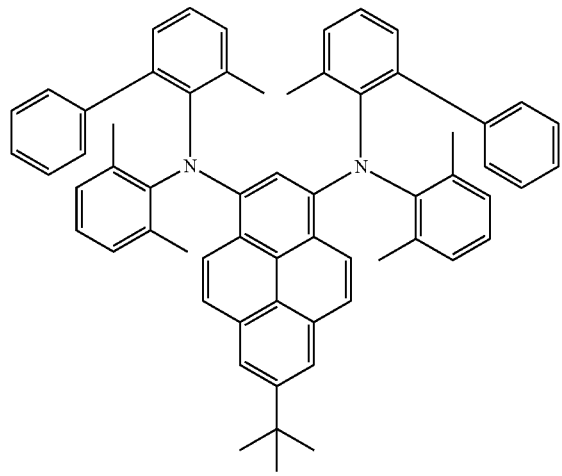
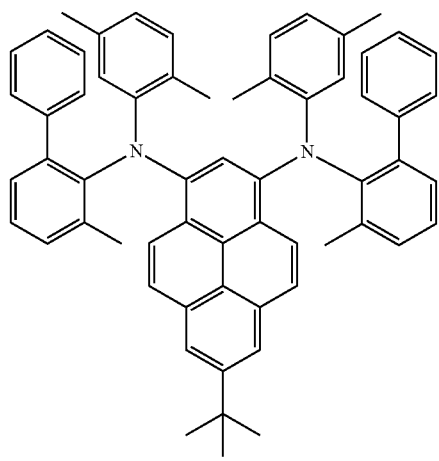
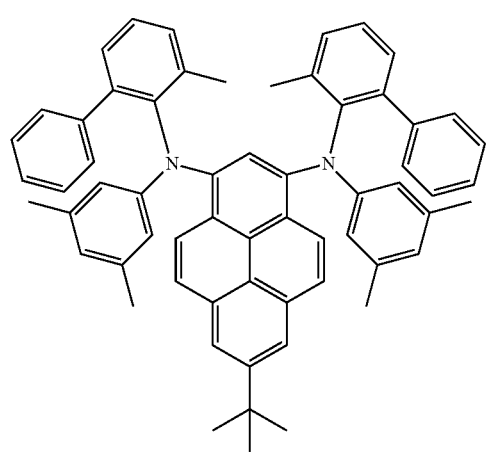
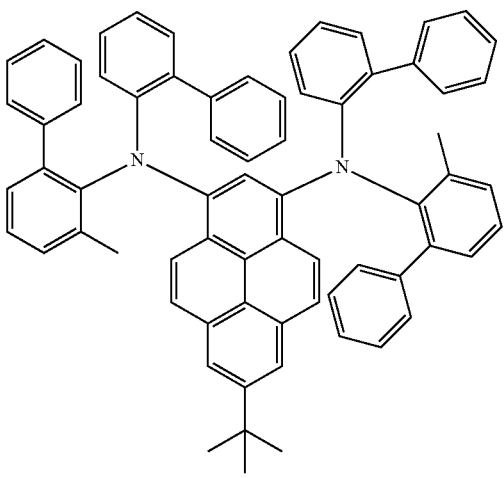
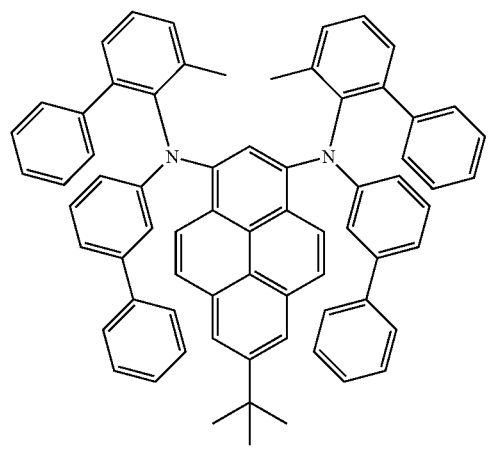
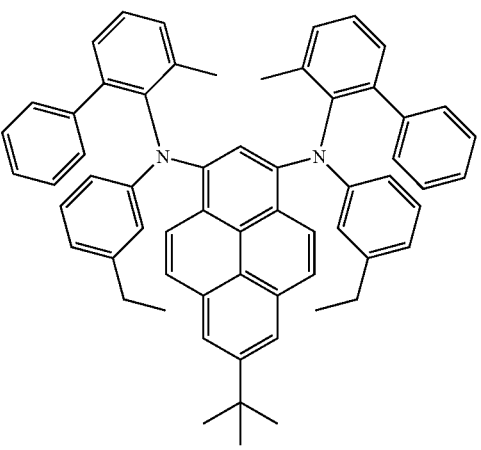

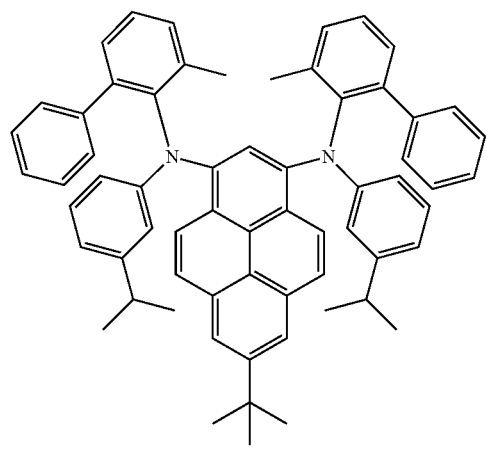
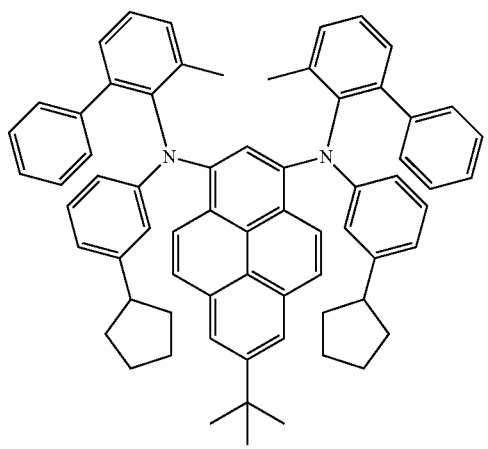
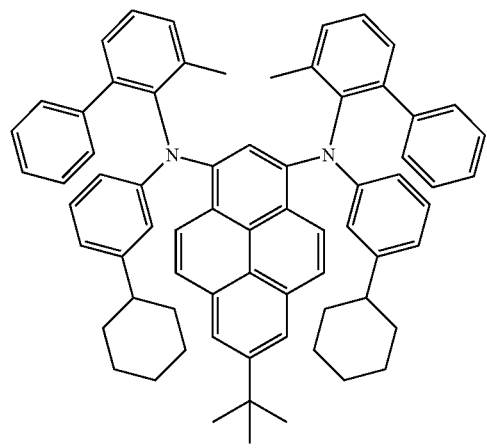
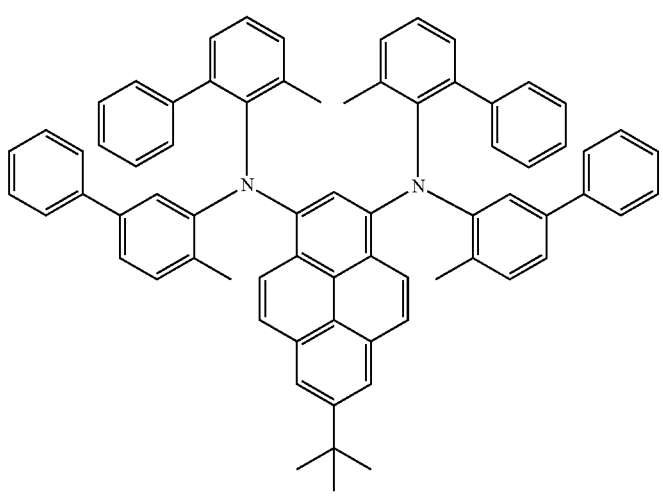
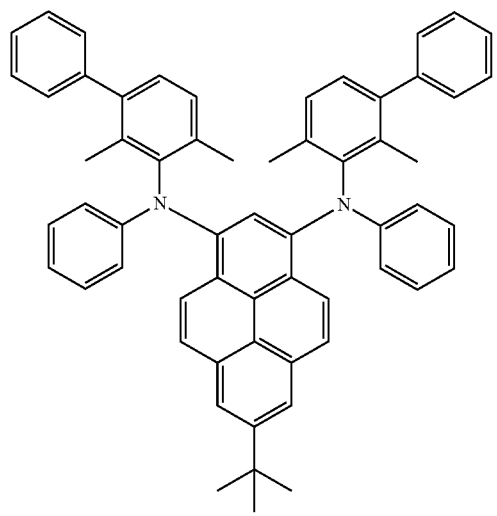
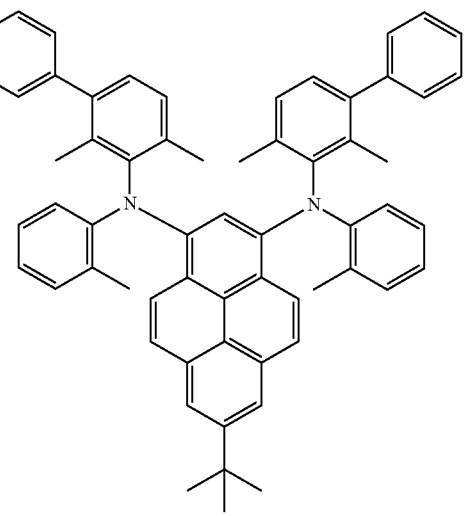

-continued
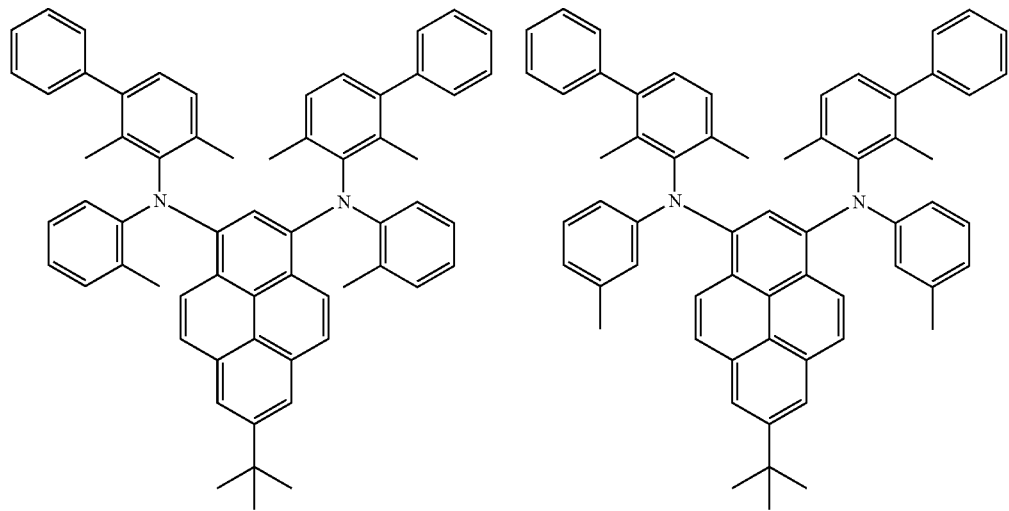
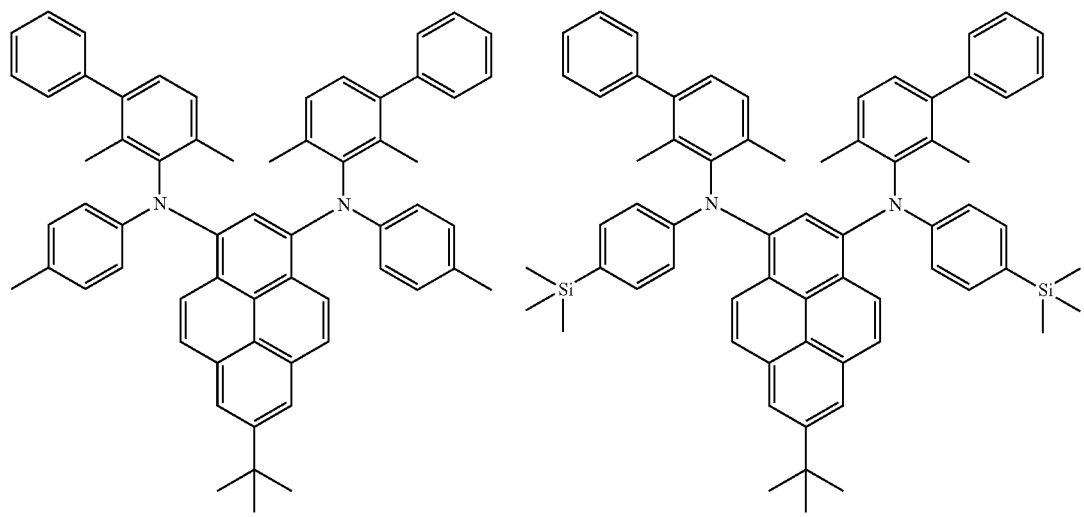
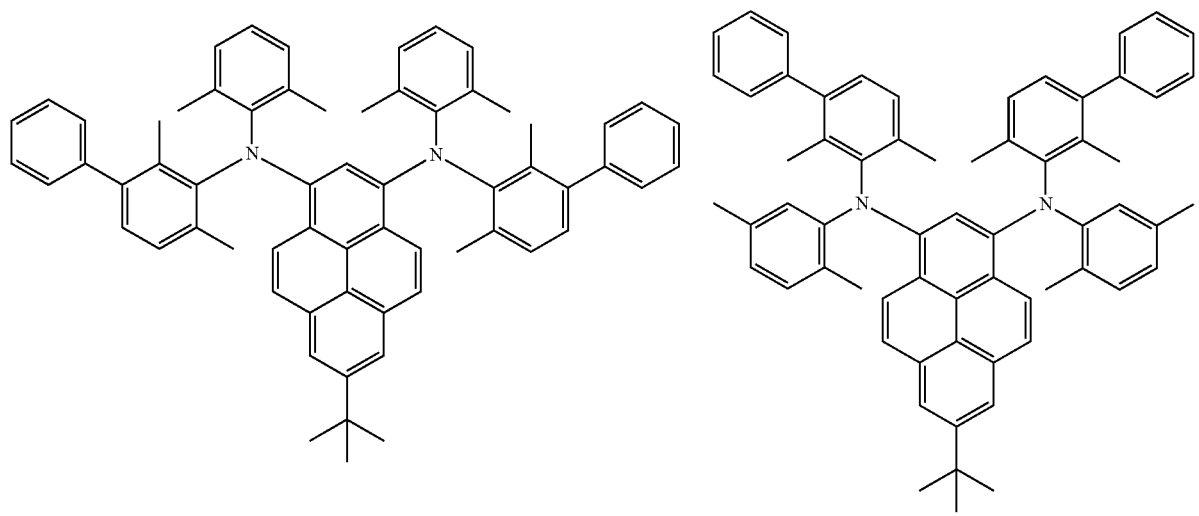

-continued
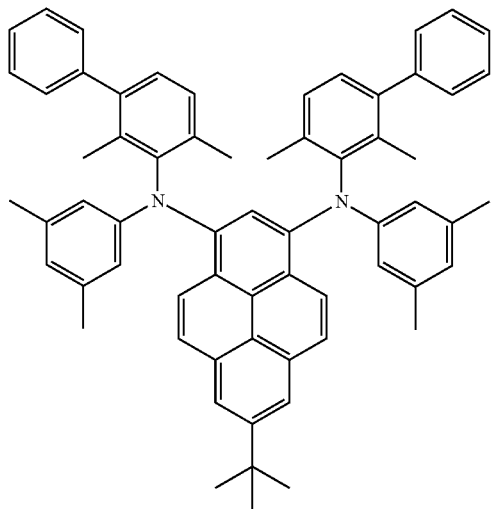
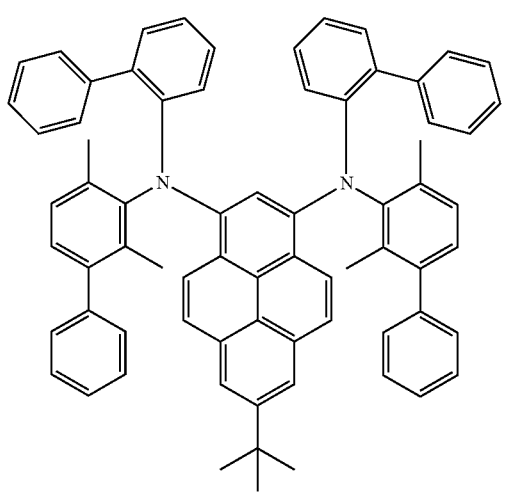
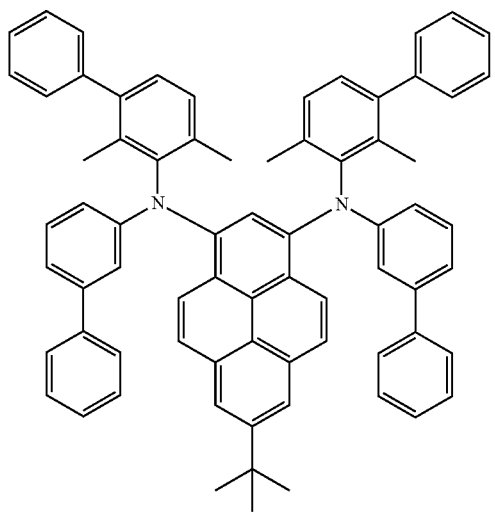
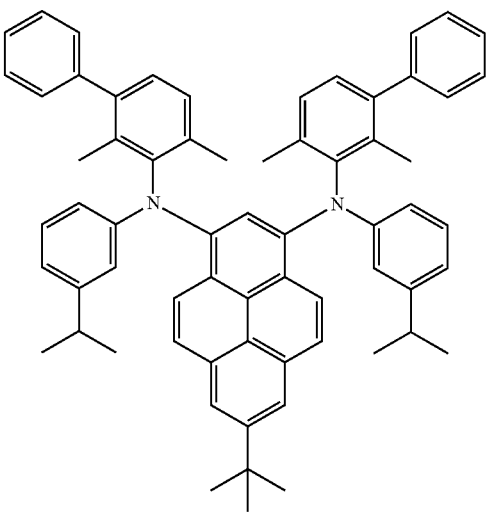
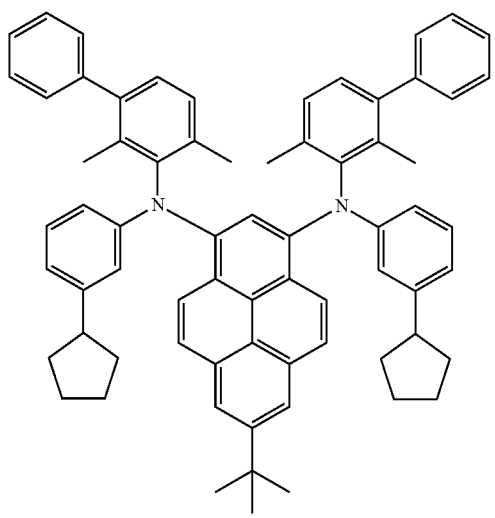
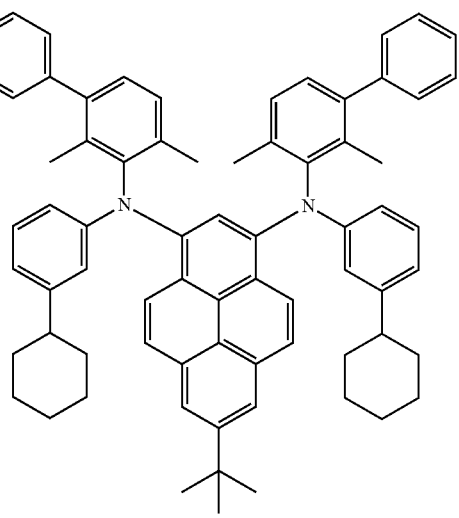

-continued
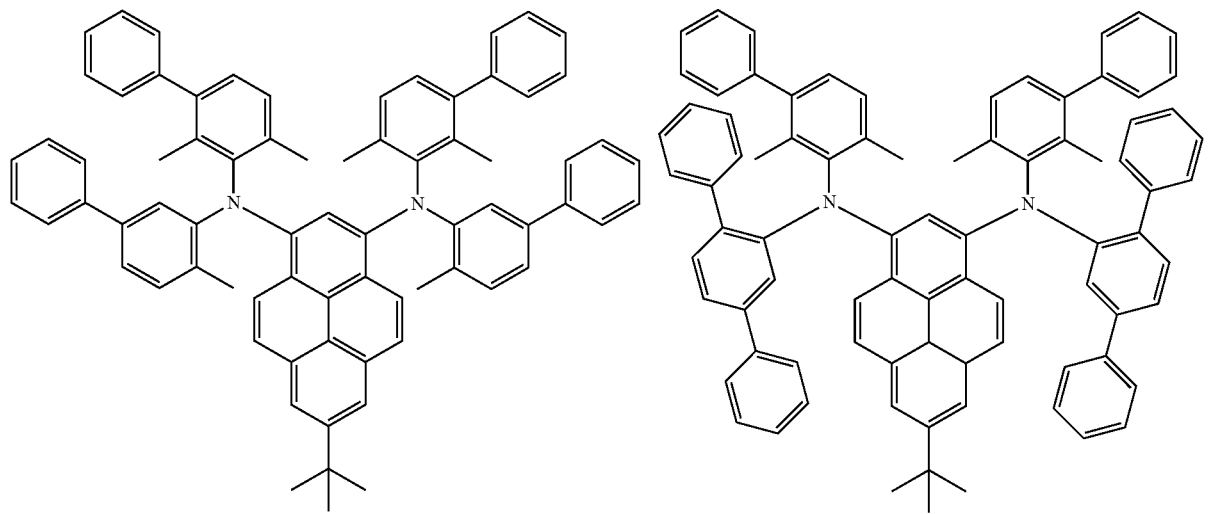
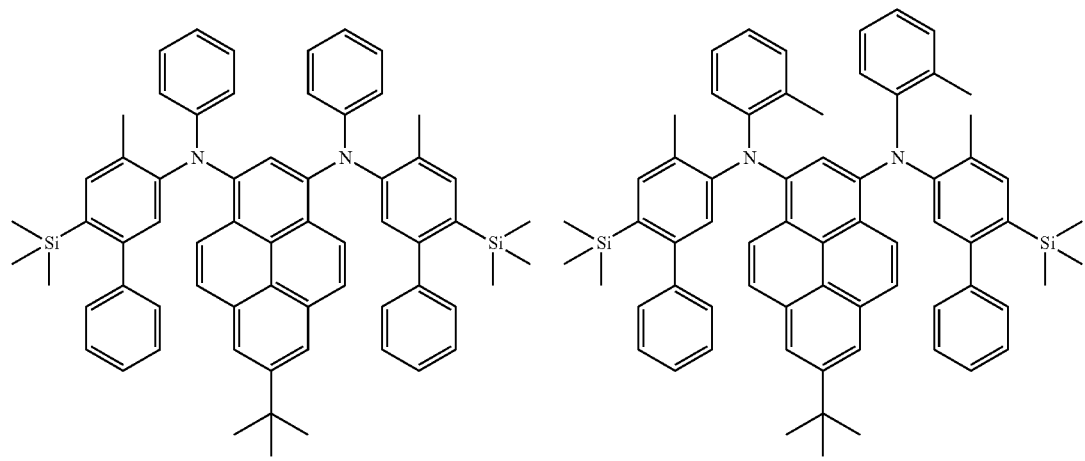
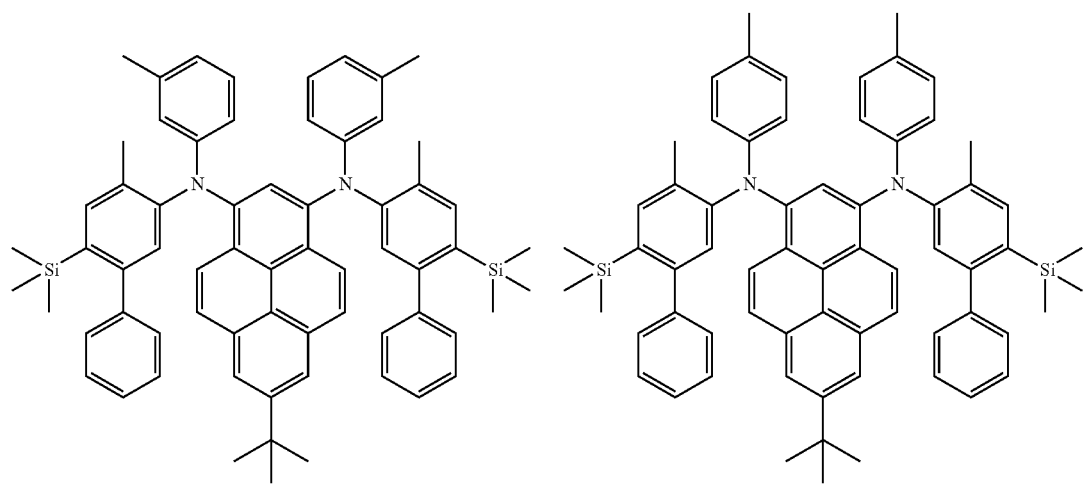

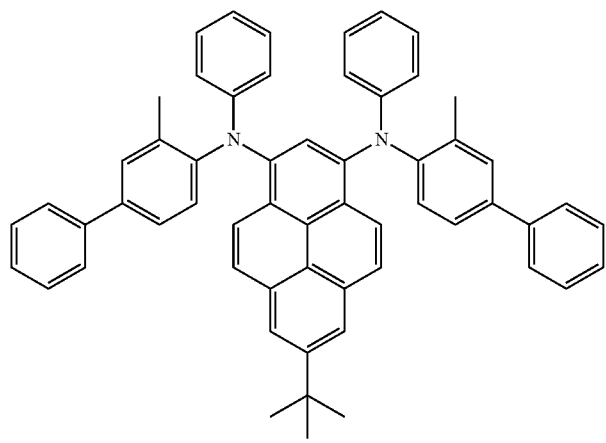

-continued
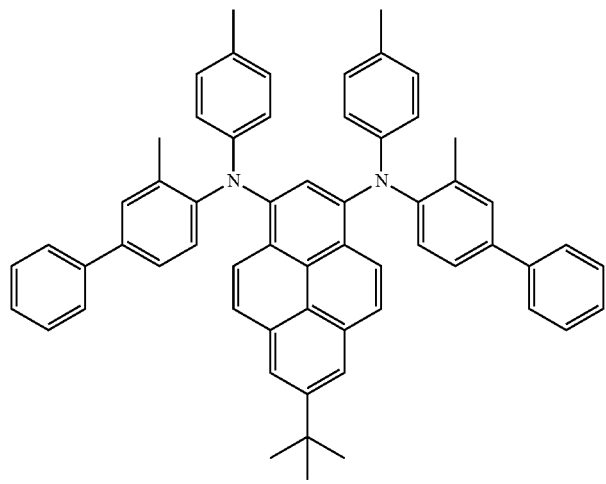
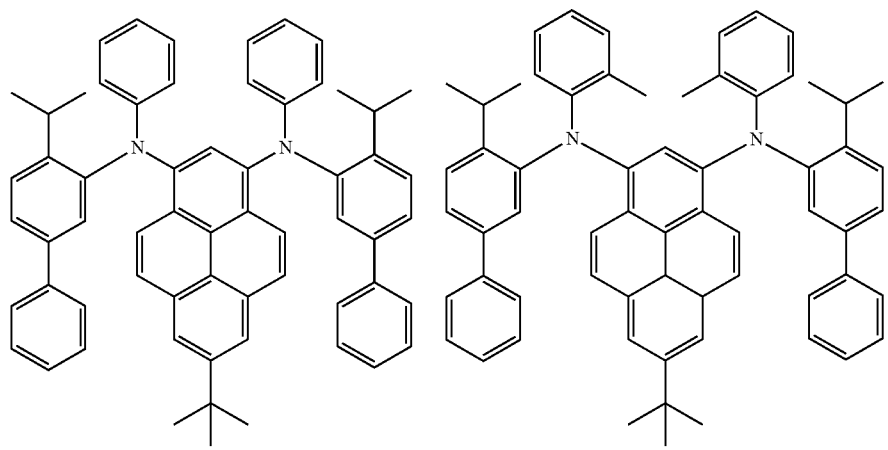
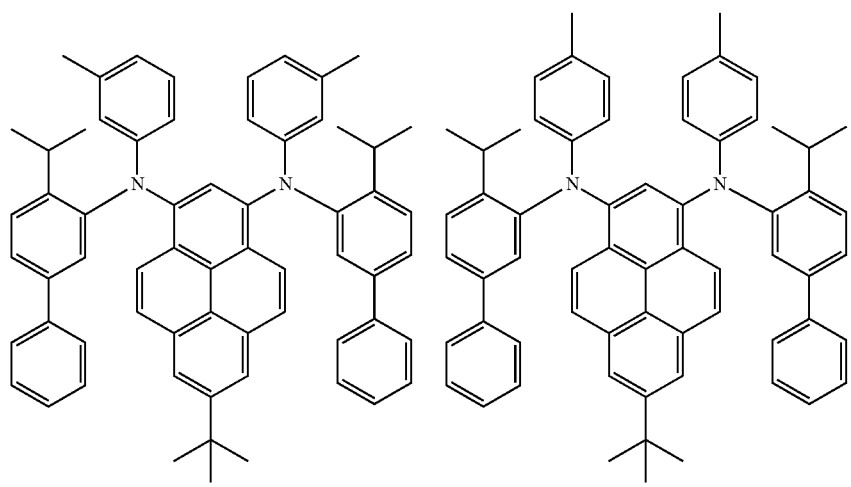

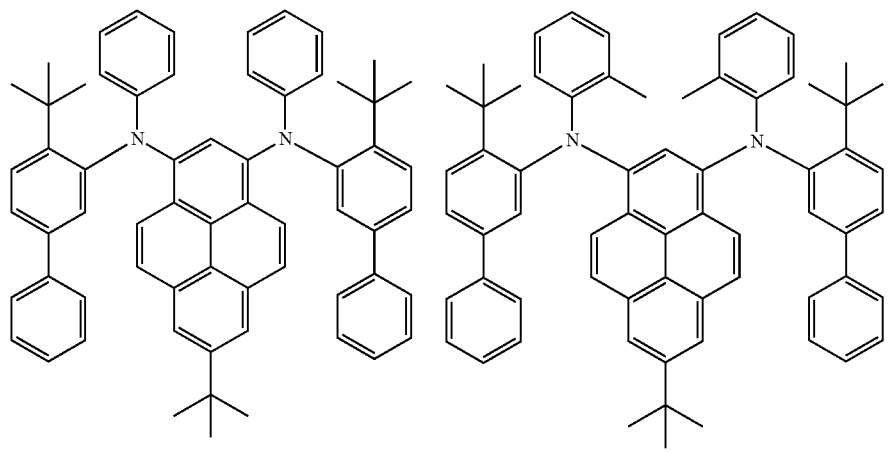
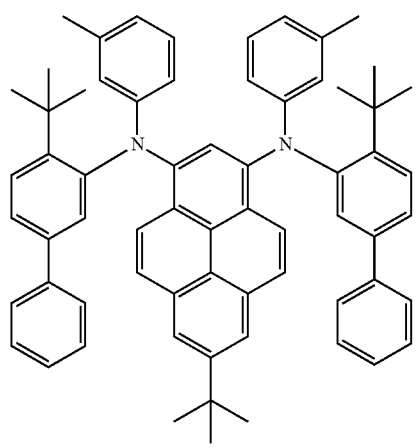
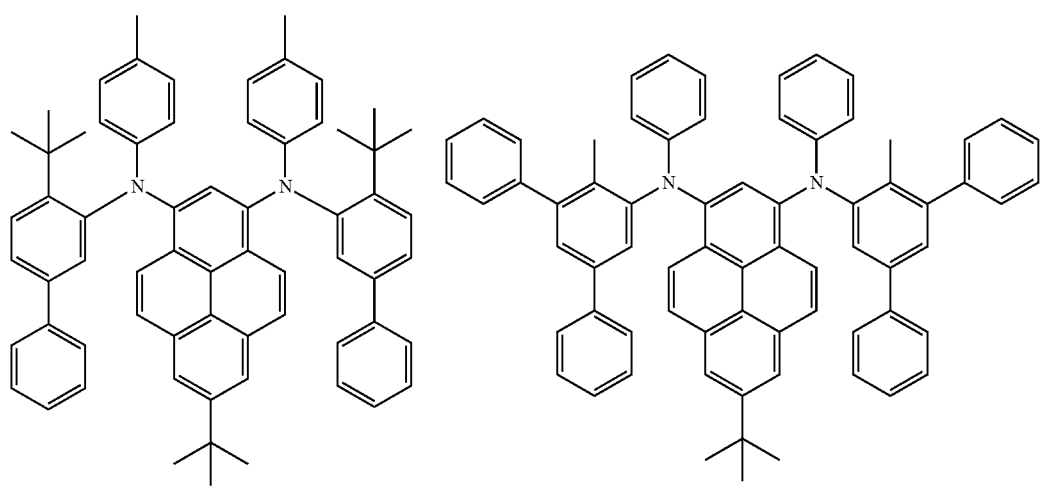

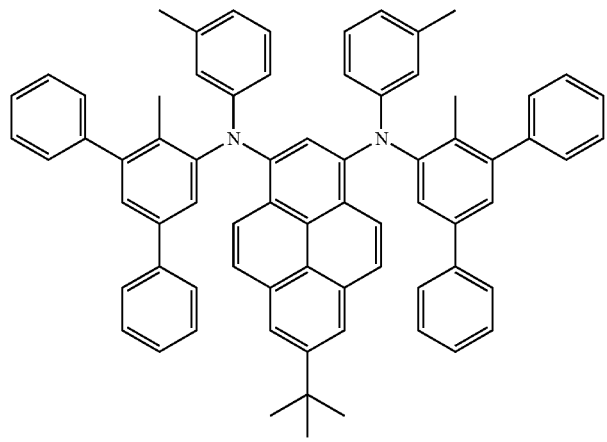
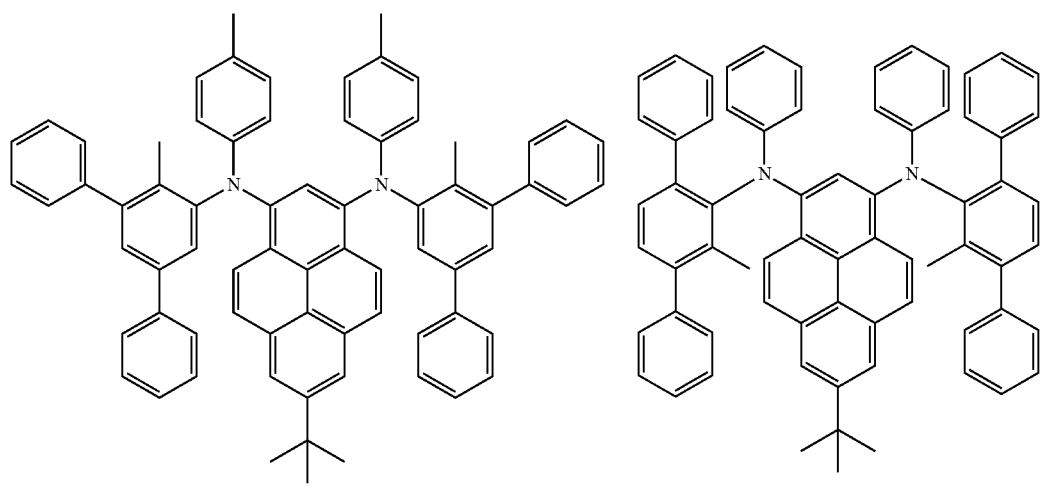
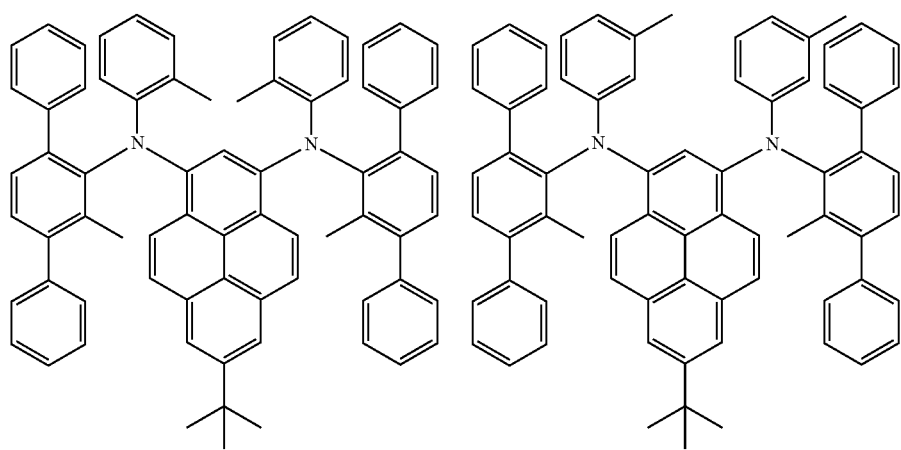

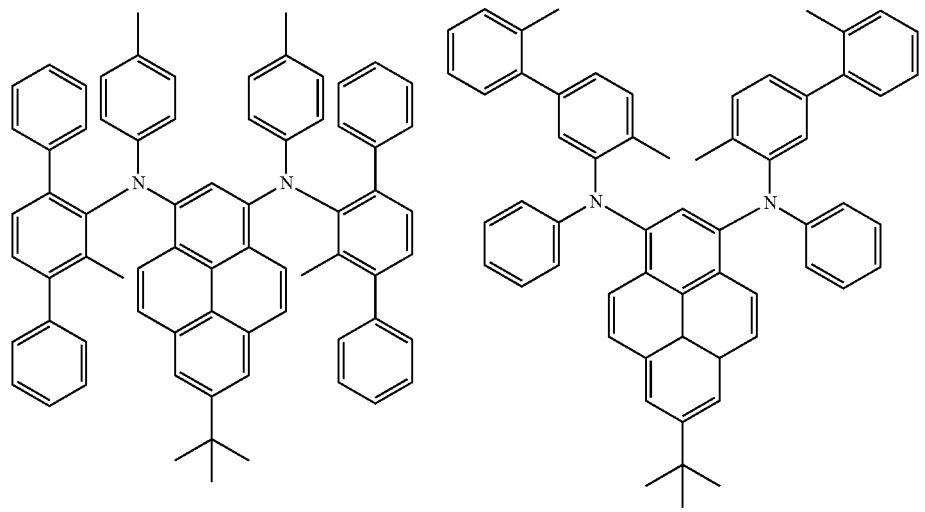
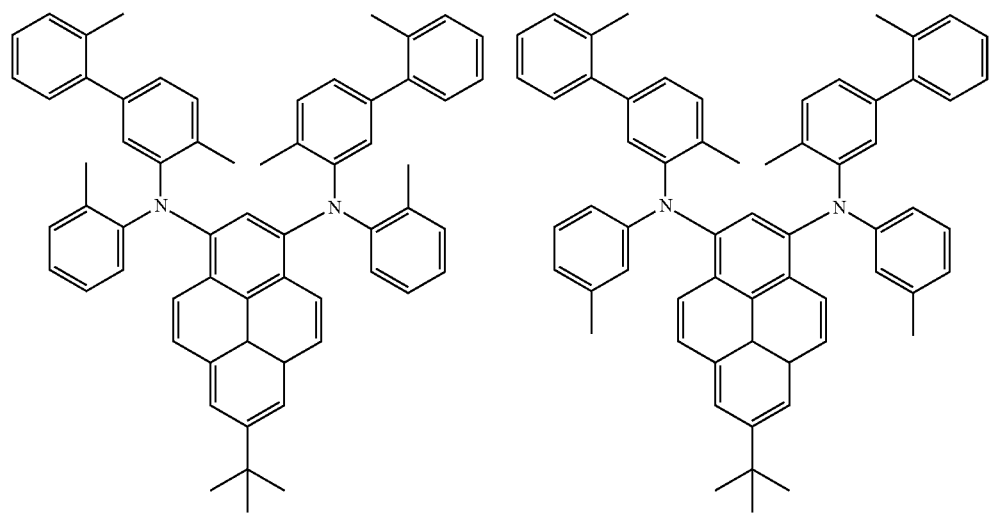
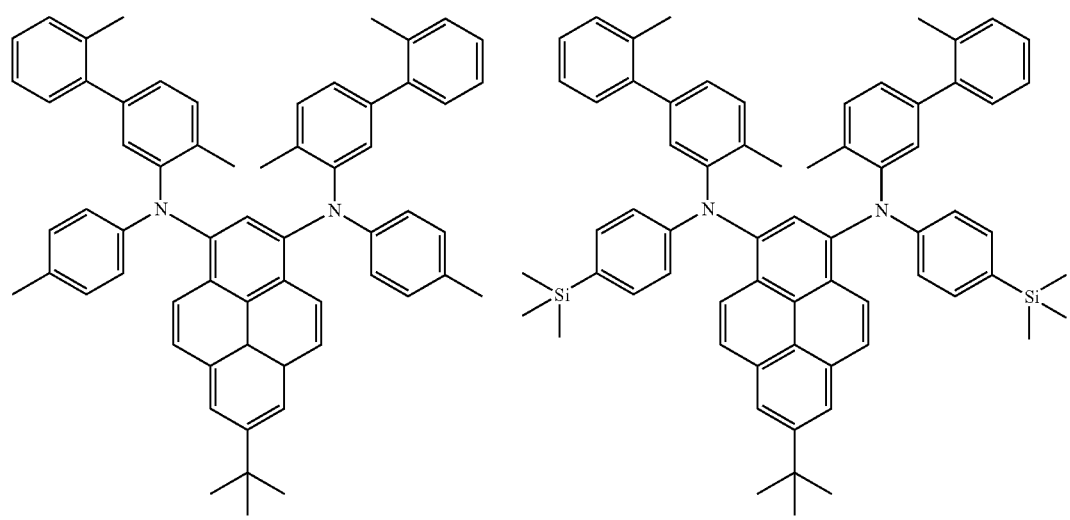

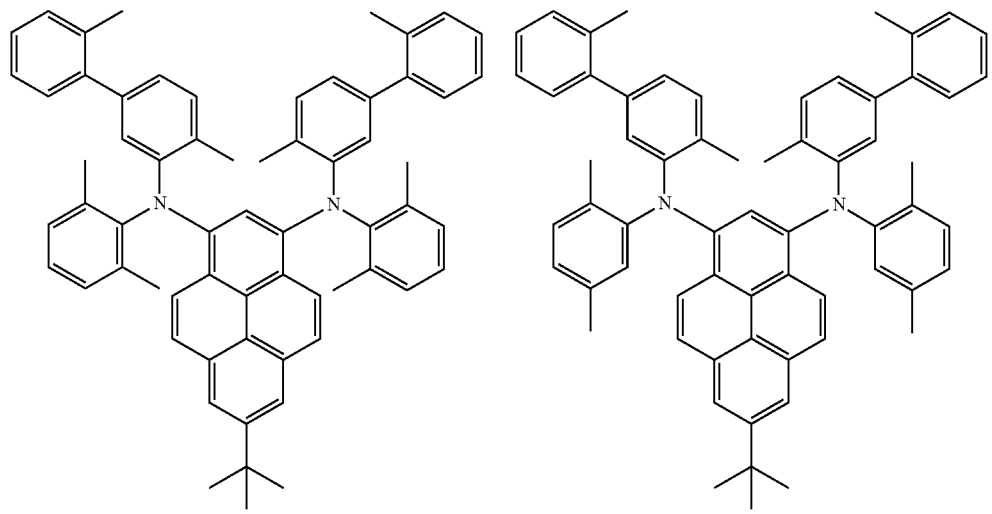
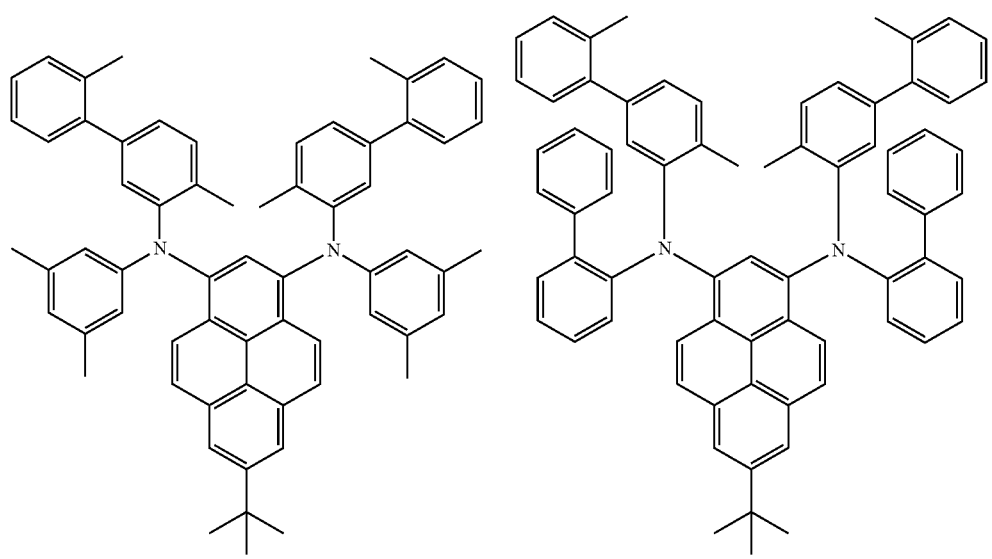
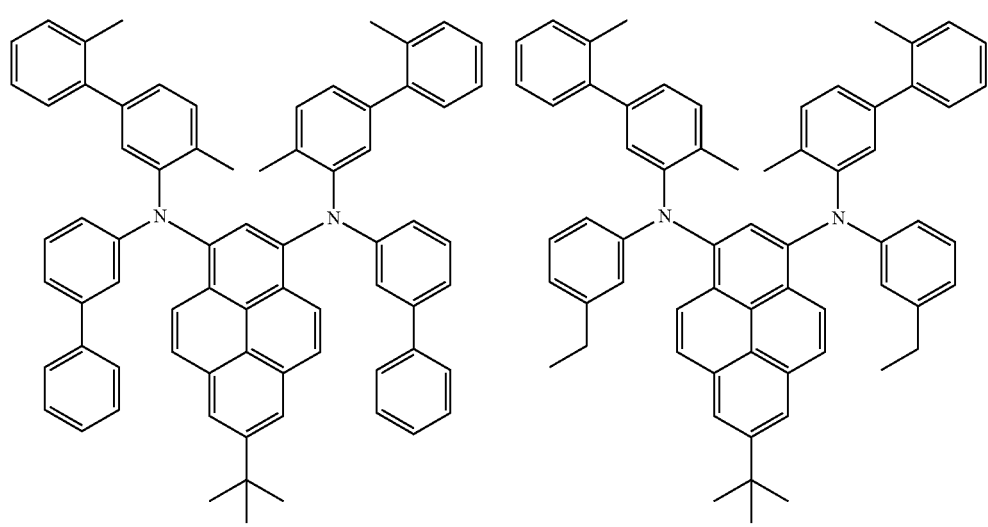

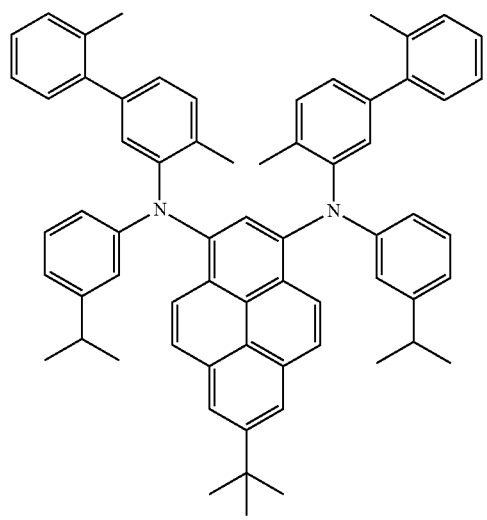
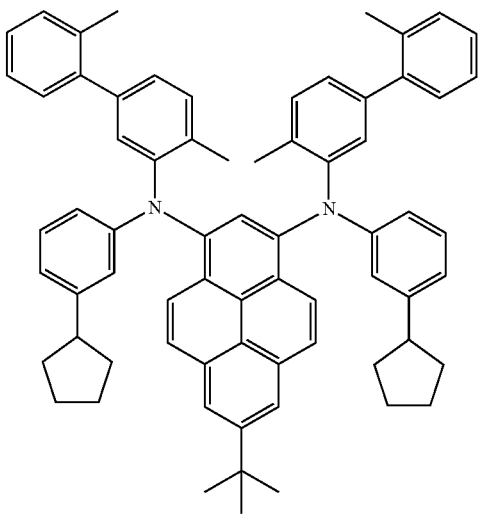
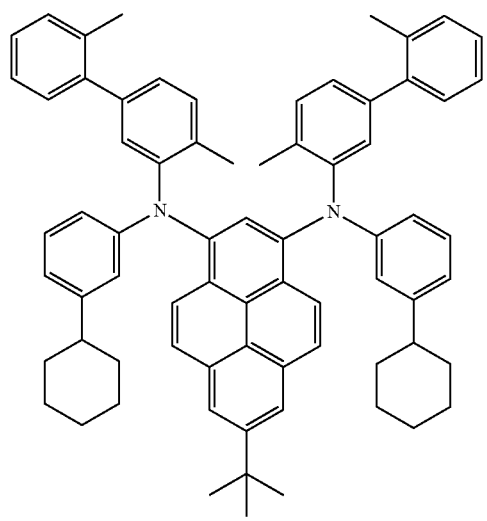
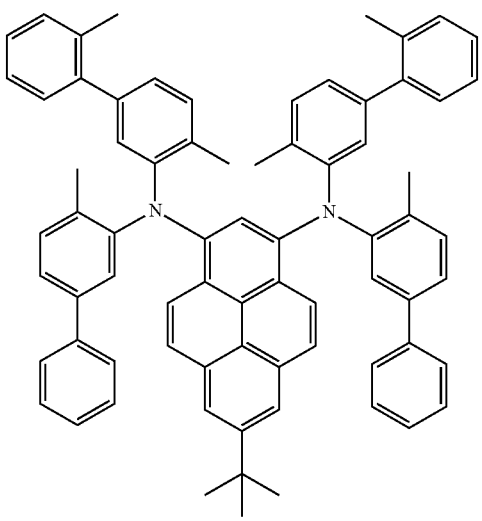
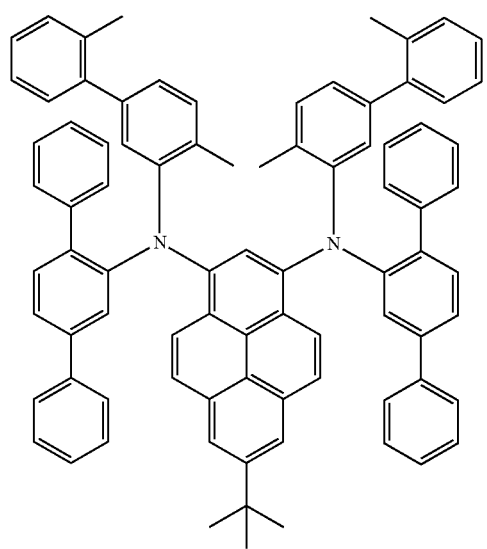
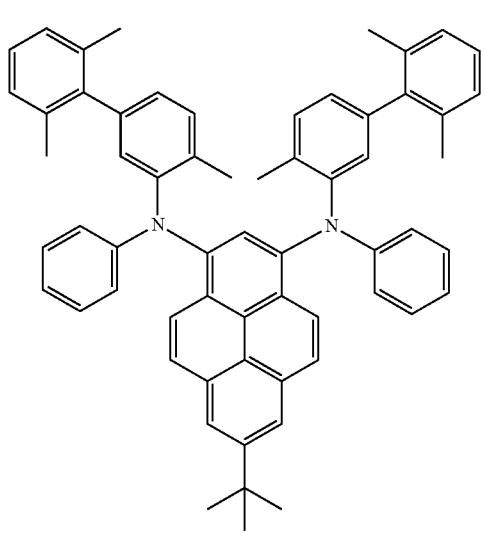

161
162
-continued
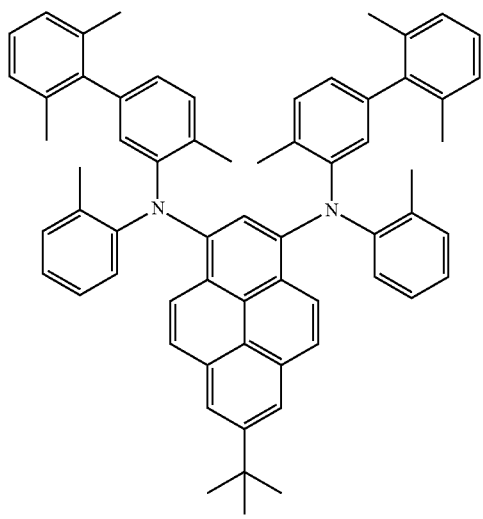
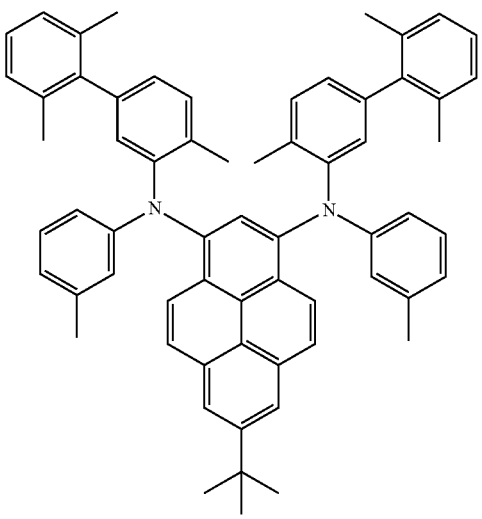
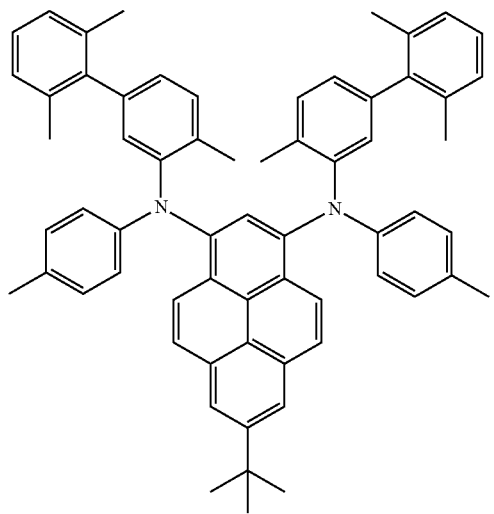
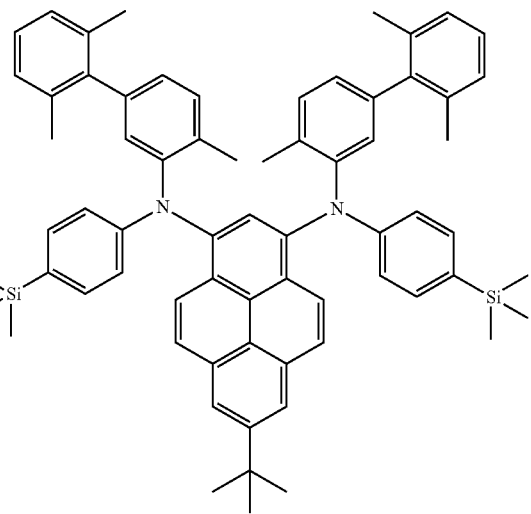
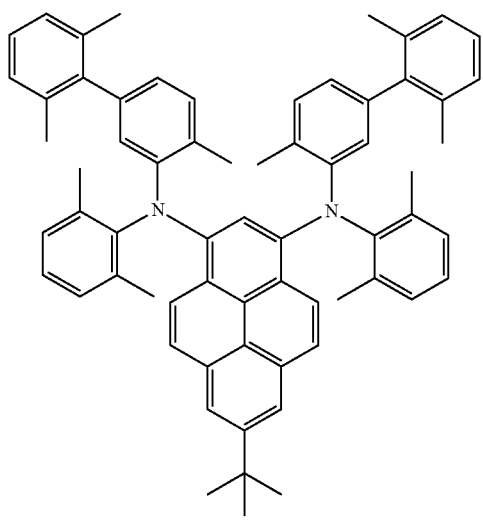
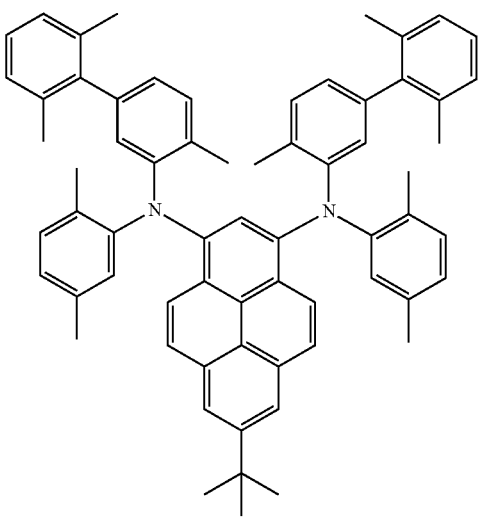

-continued
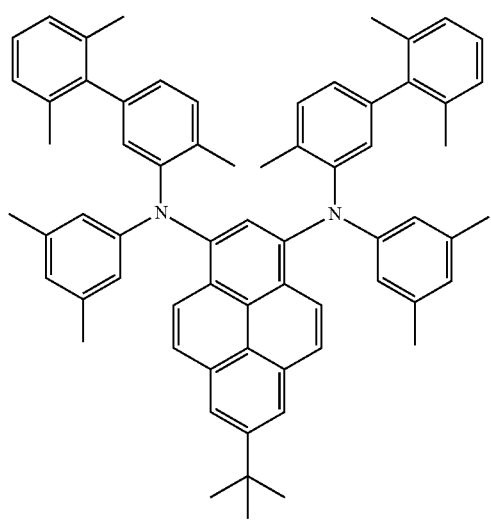
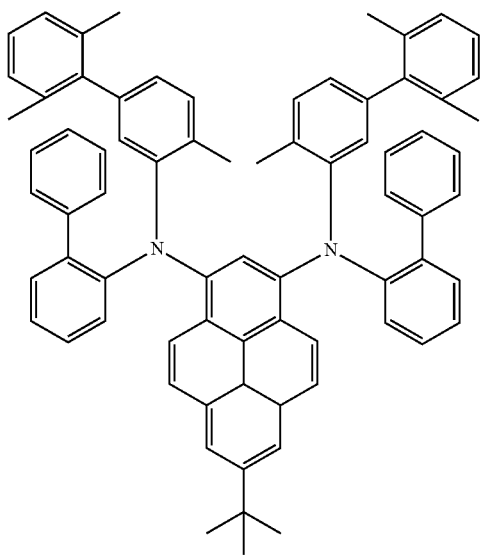
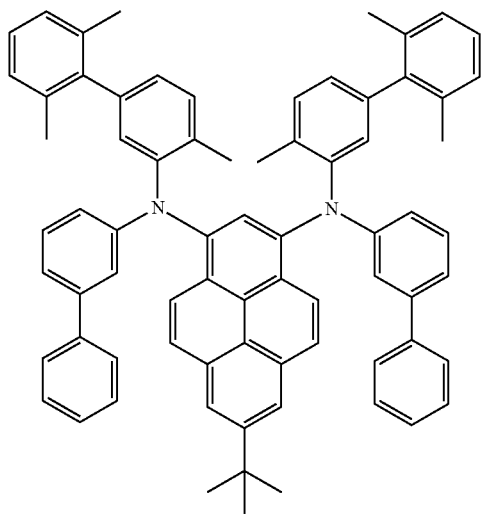
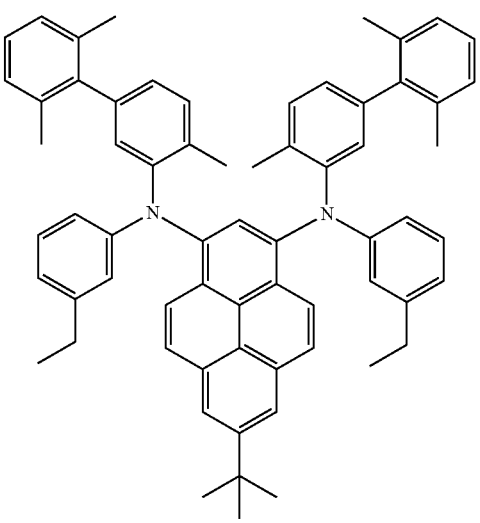
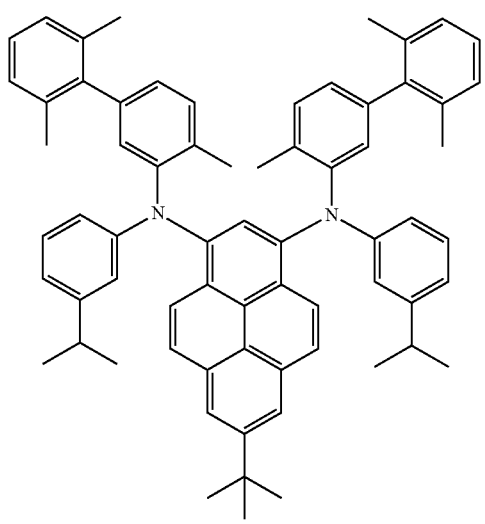
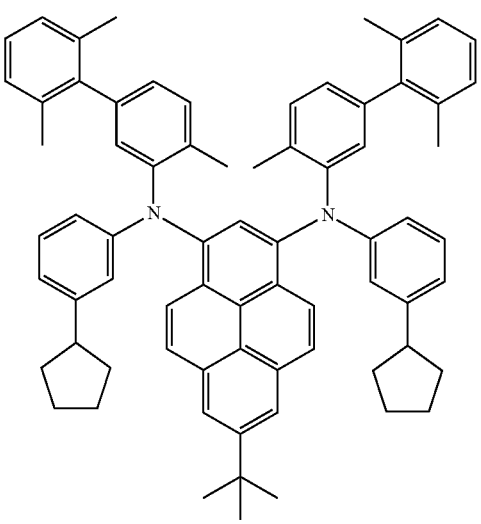

-continued
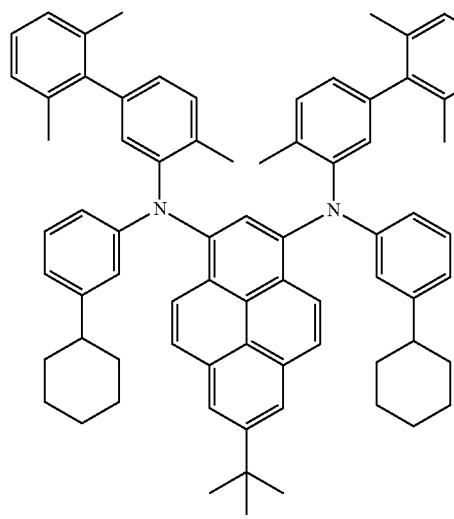
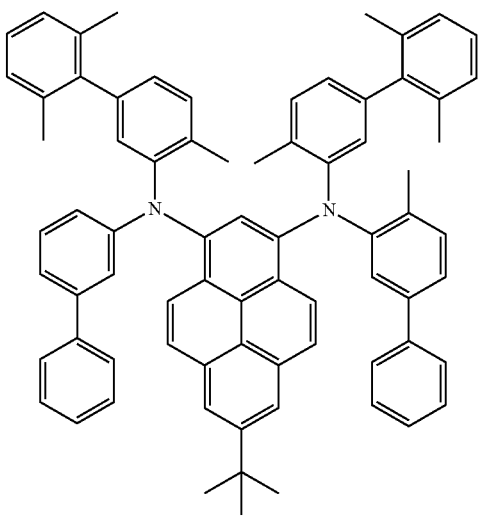
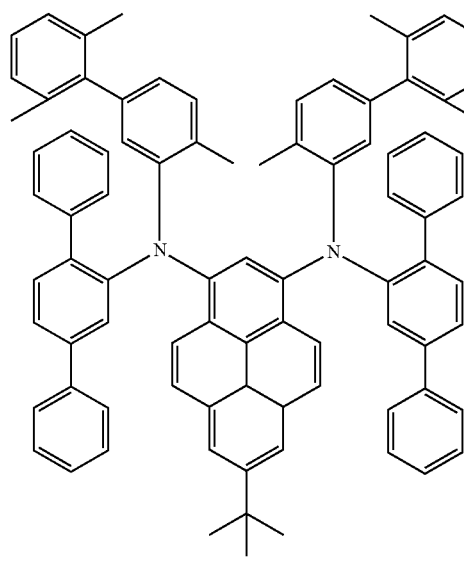
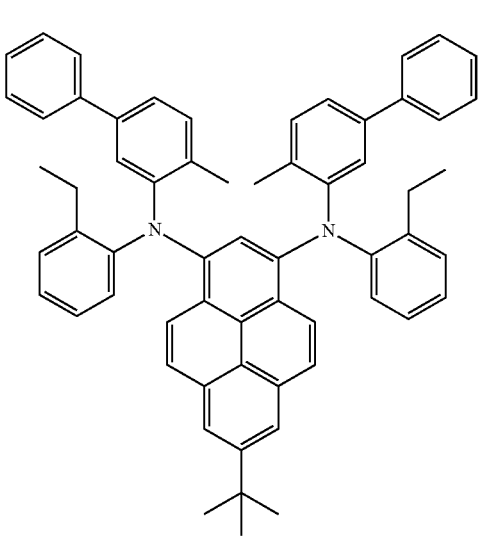
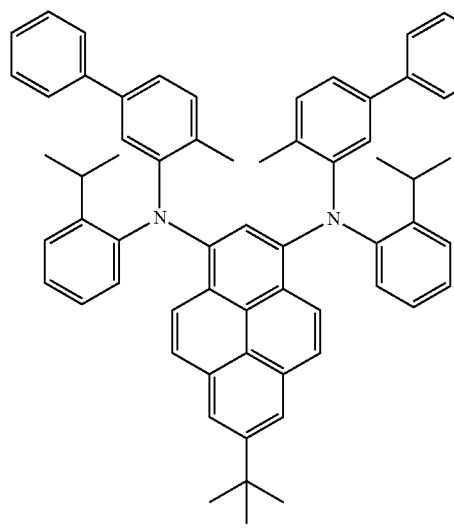
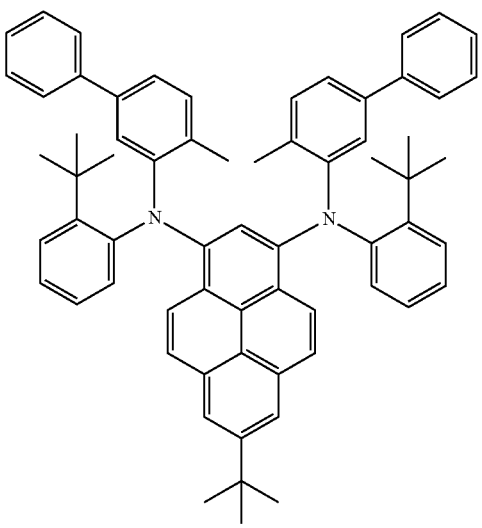

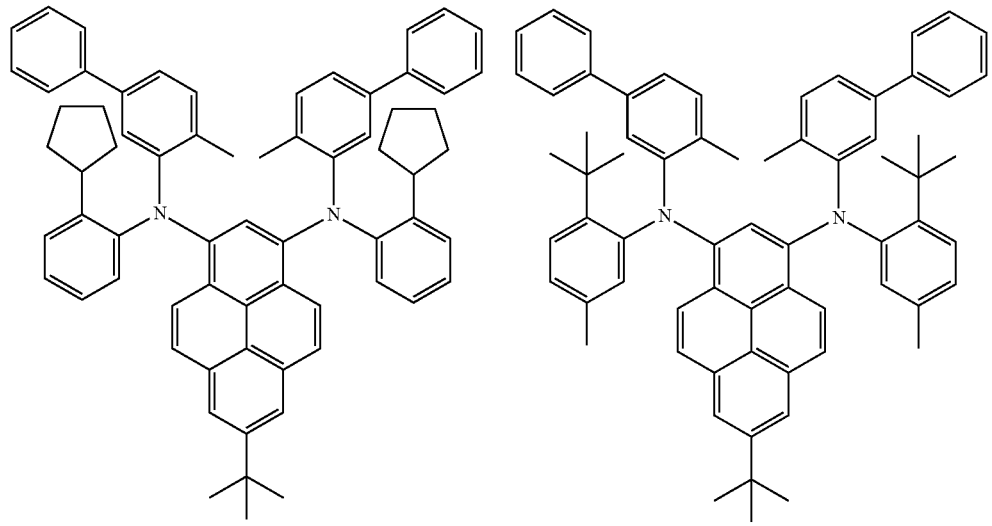
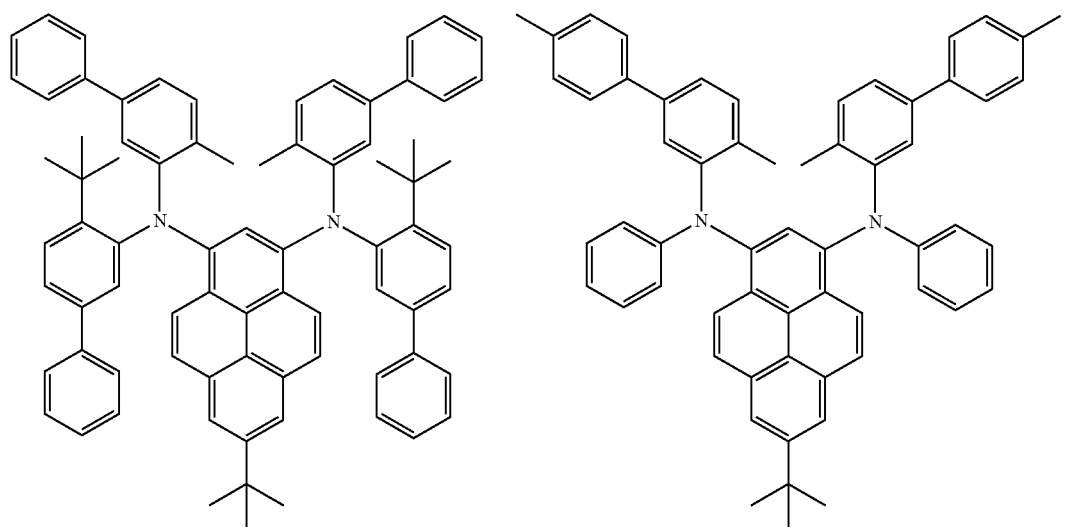
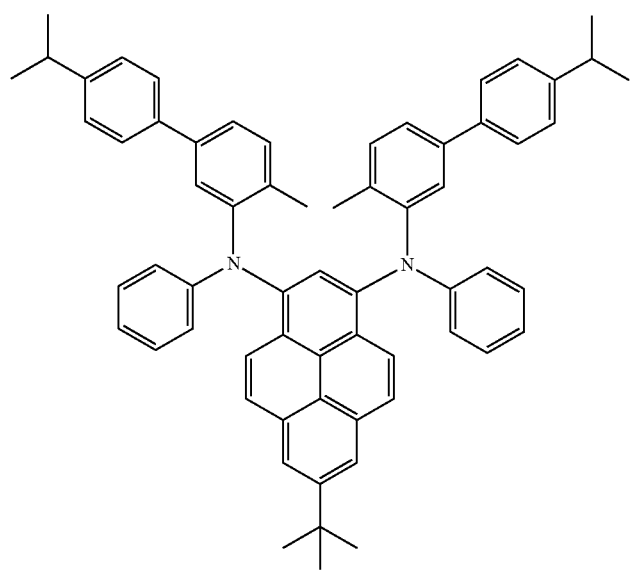

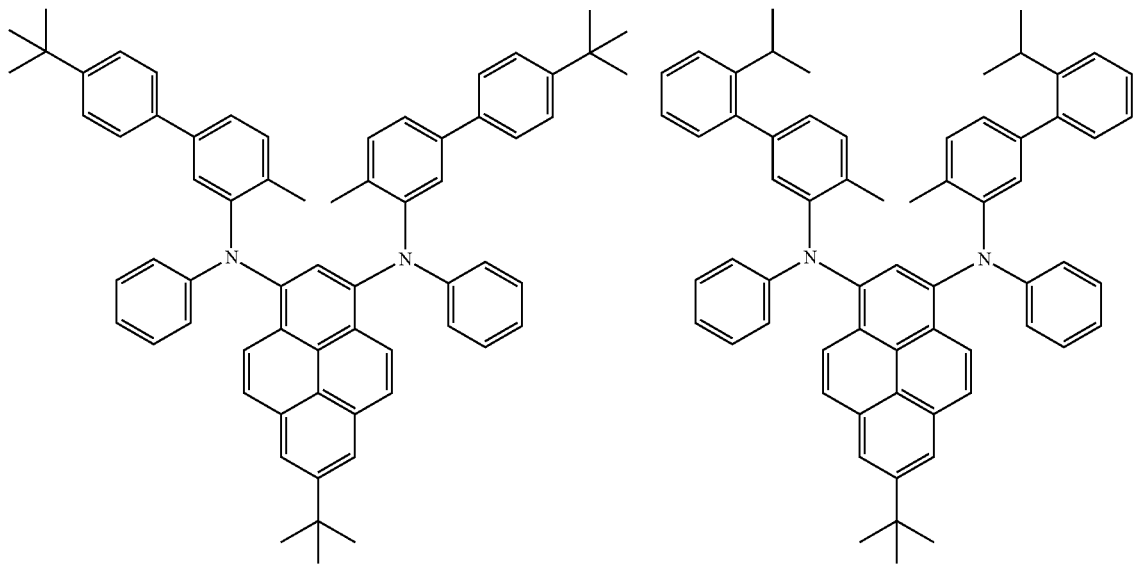
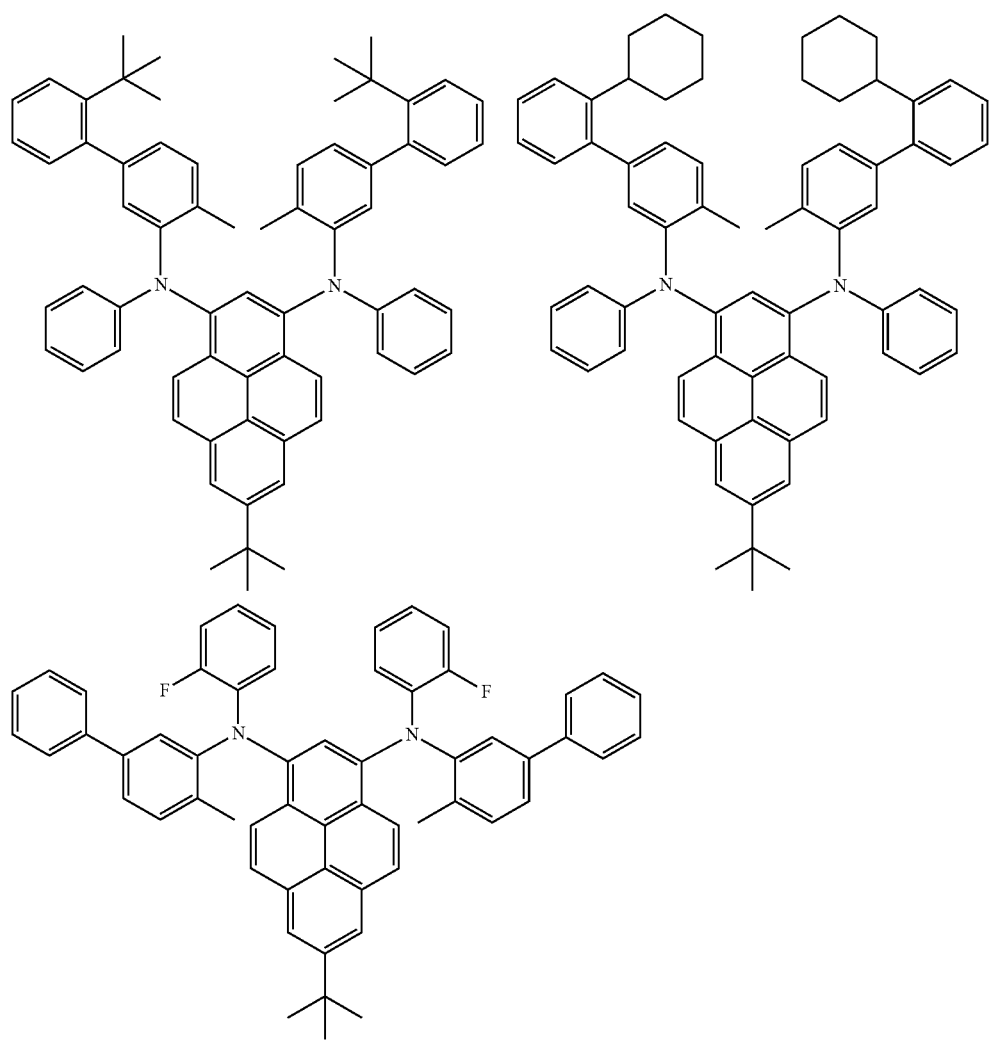

-continued
171
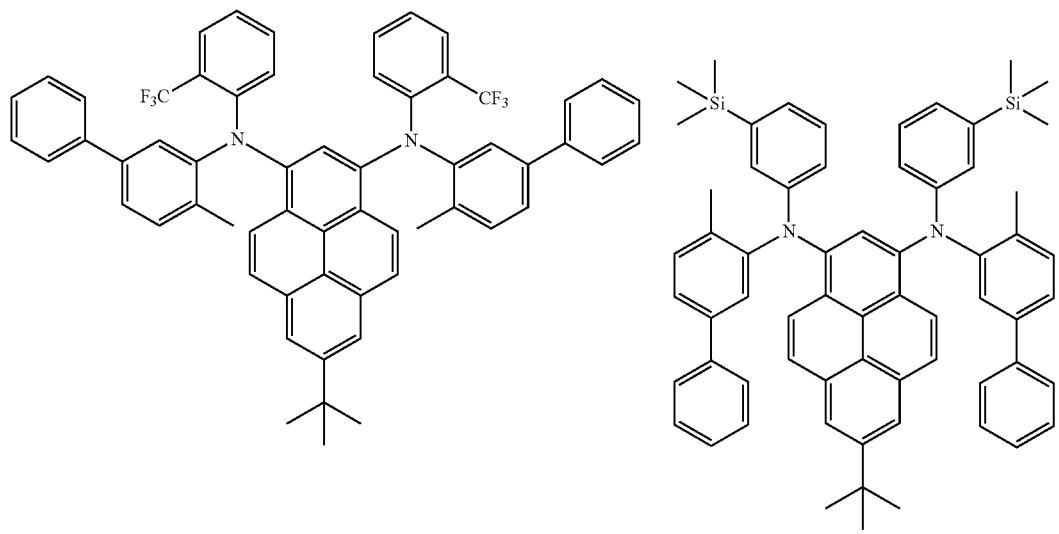
172
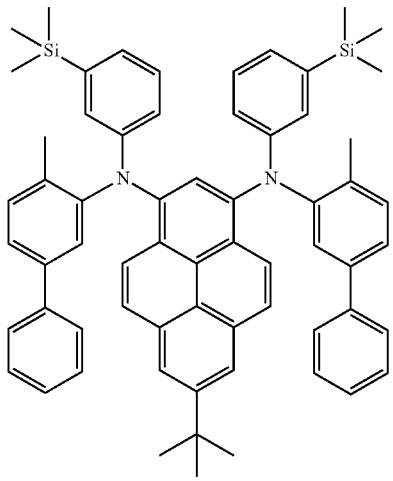
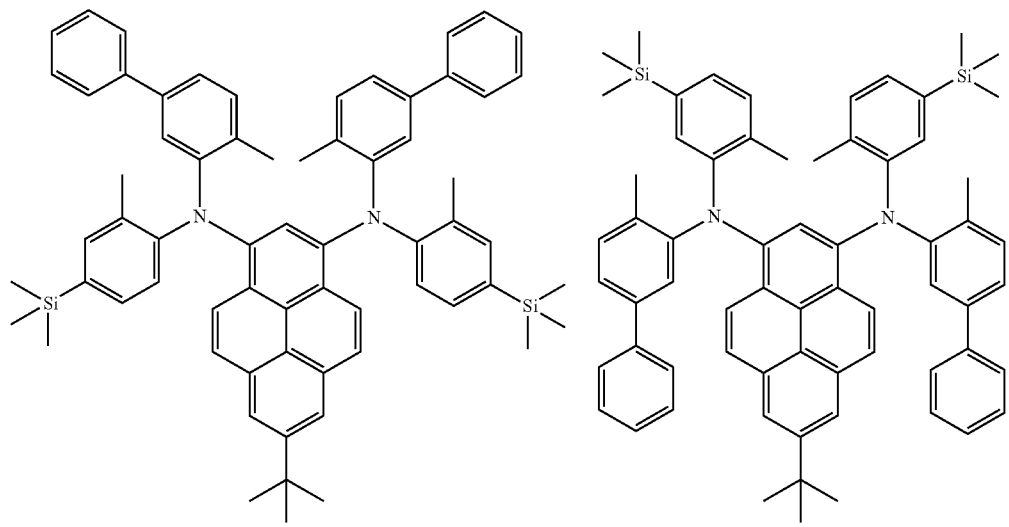
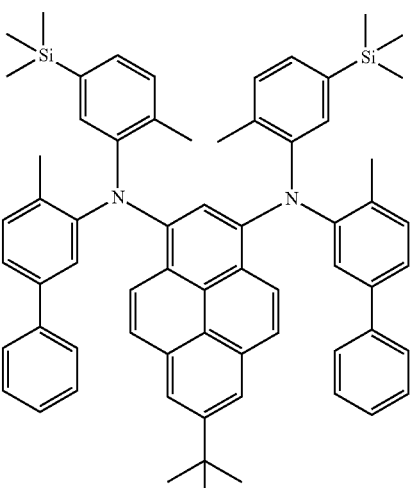
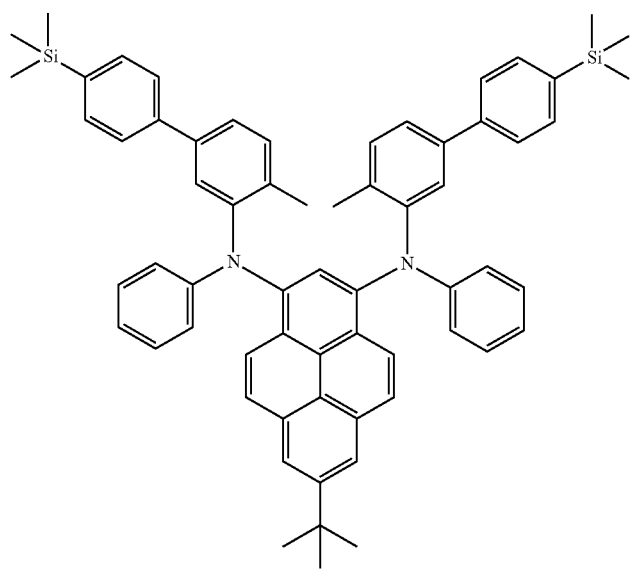
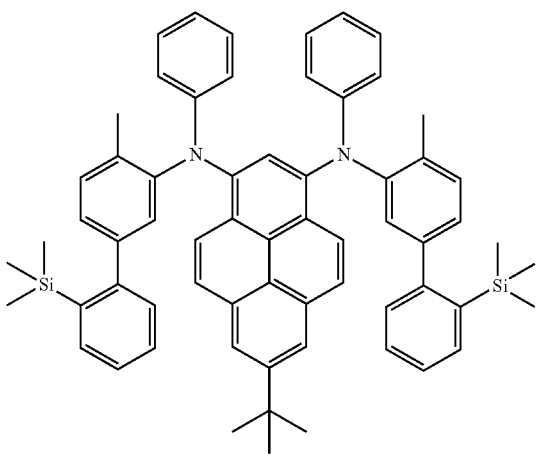

-continued
173
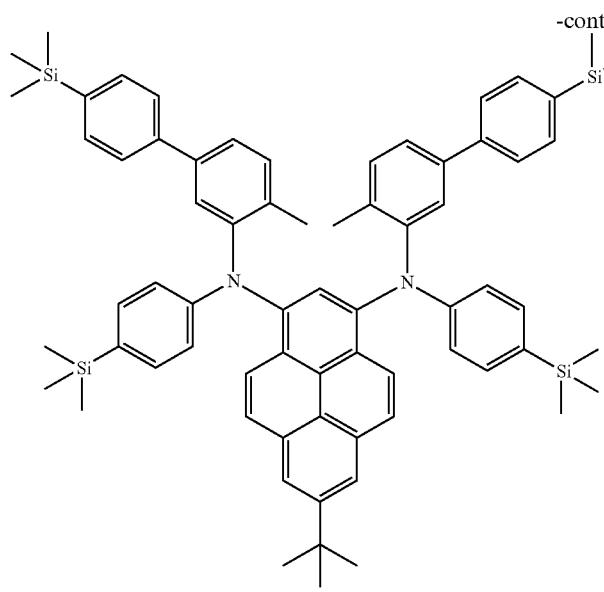
174
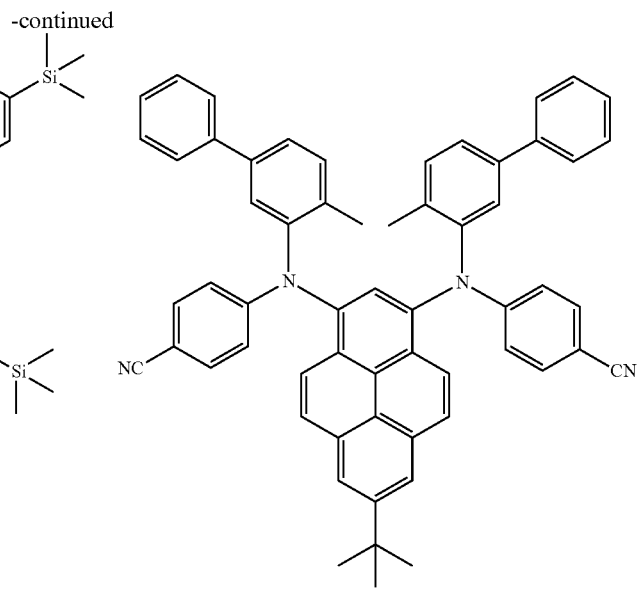
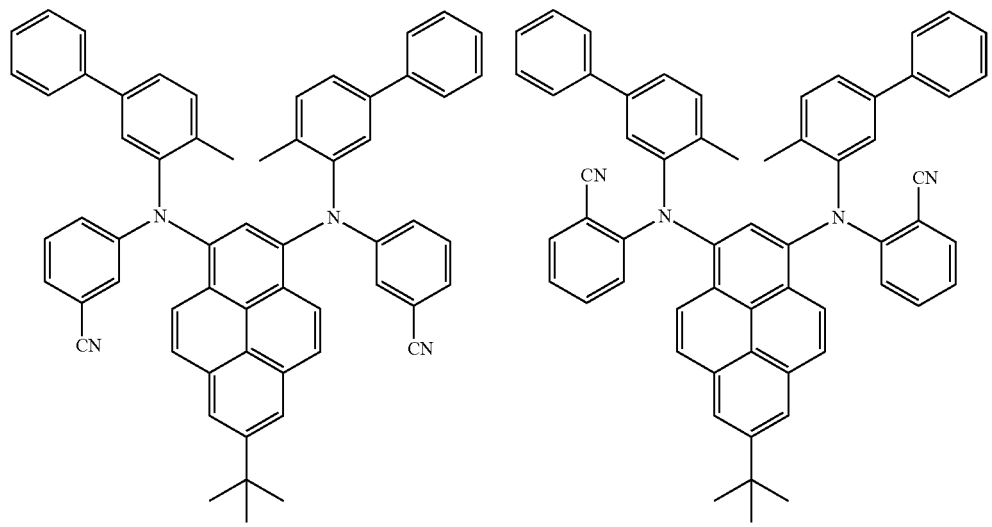
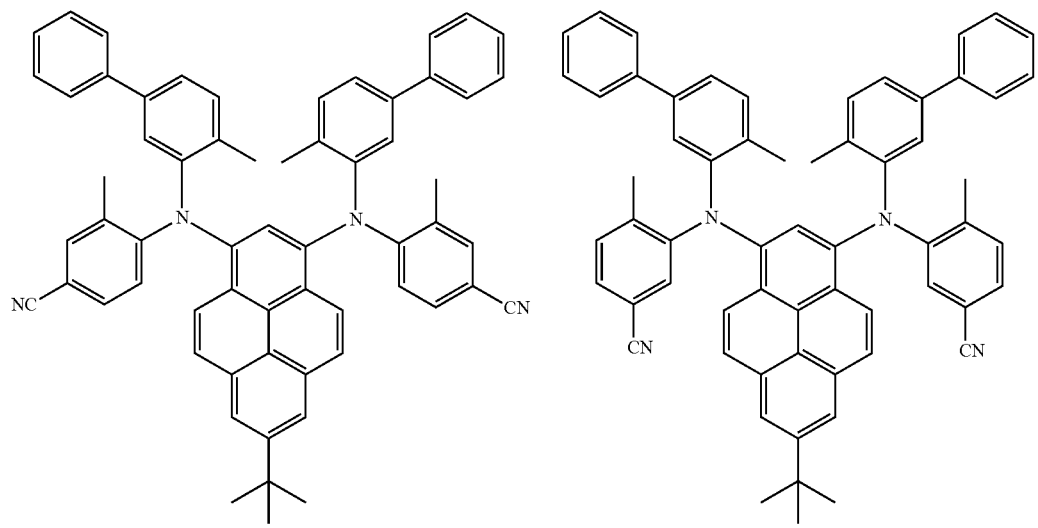

175 176
-continued
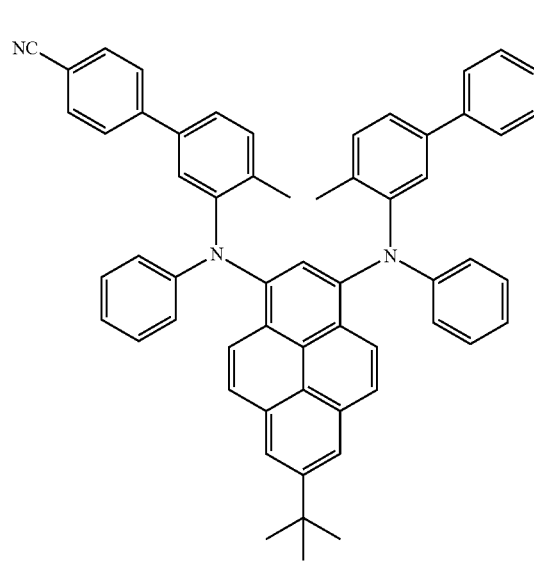
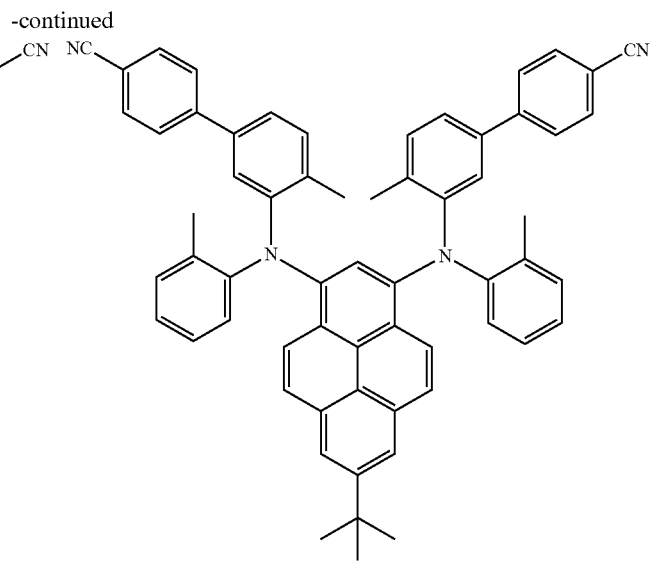
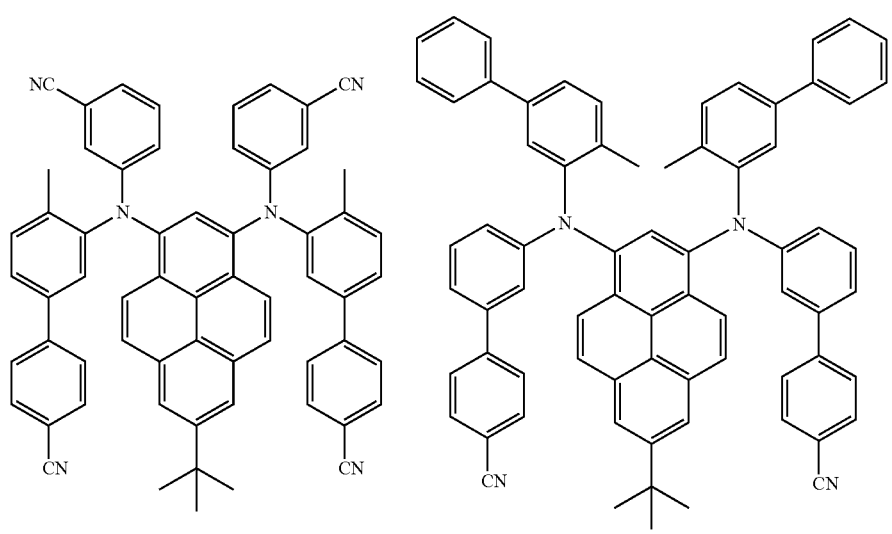
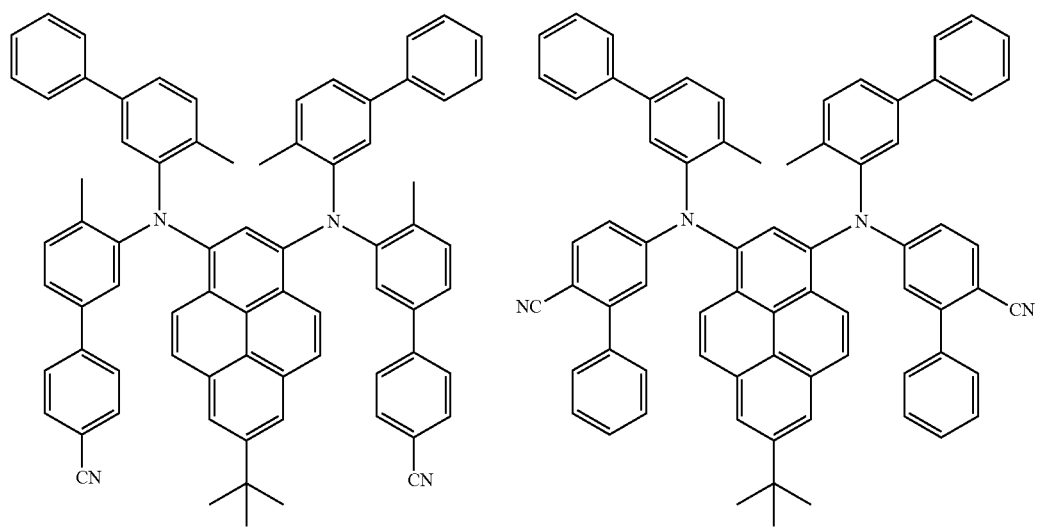

-continued
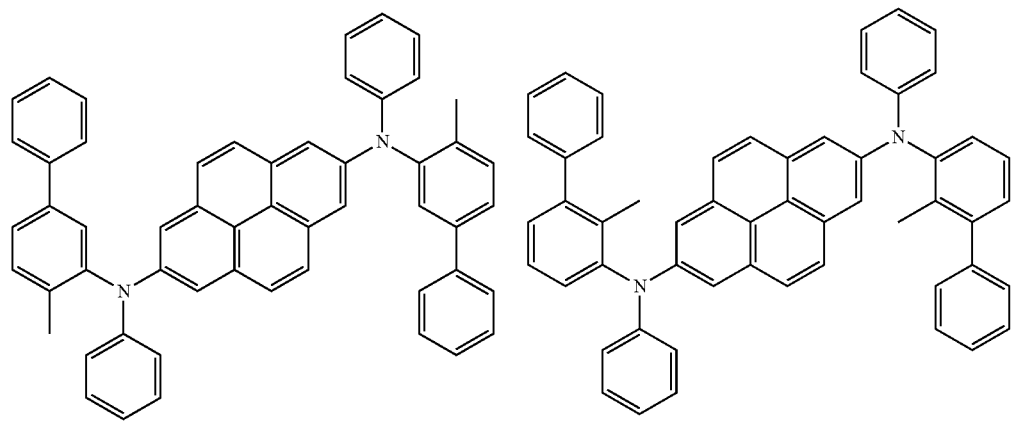
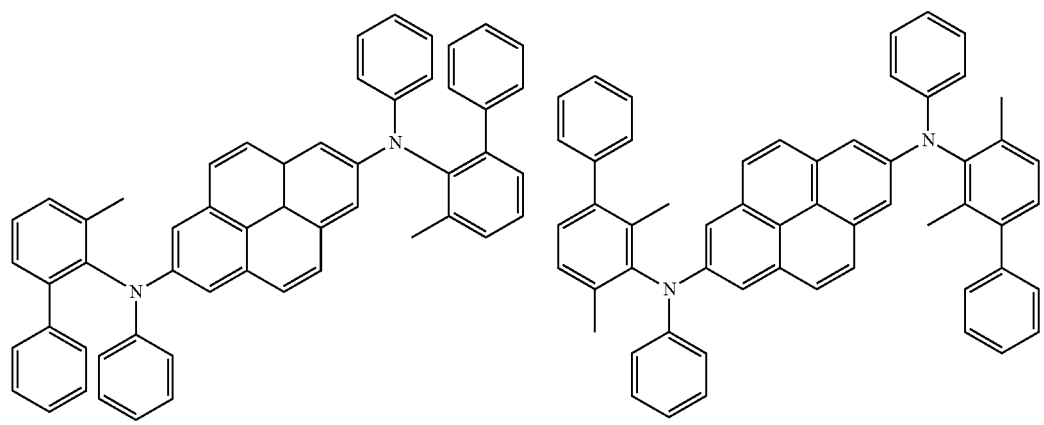
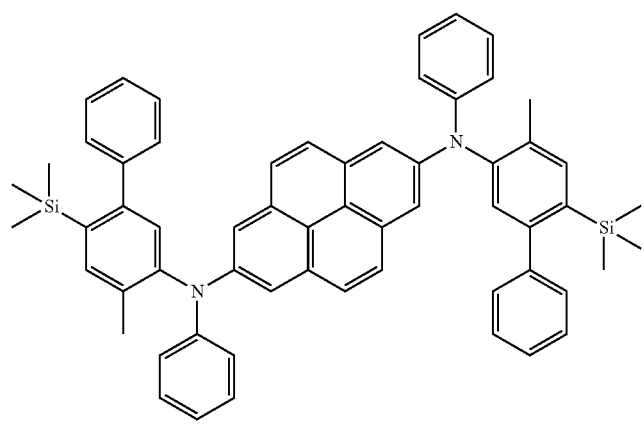
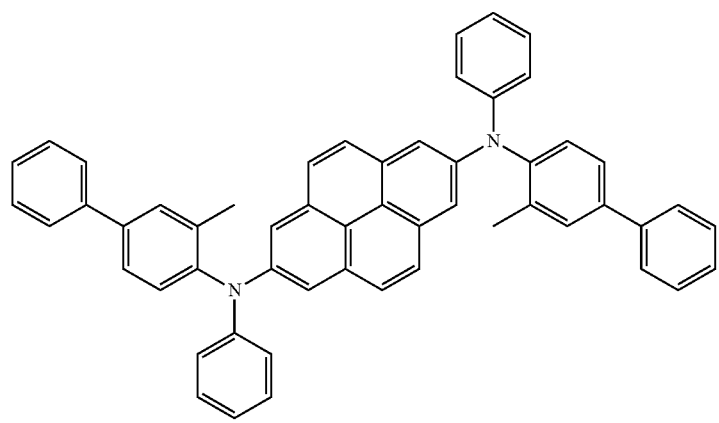

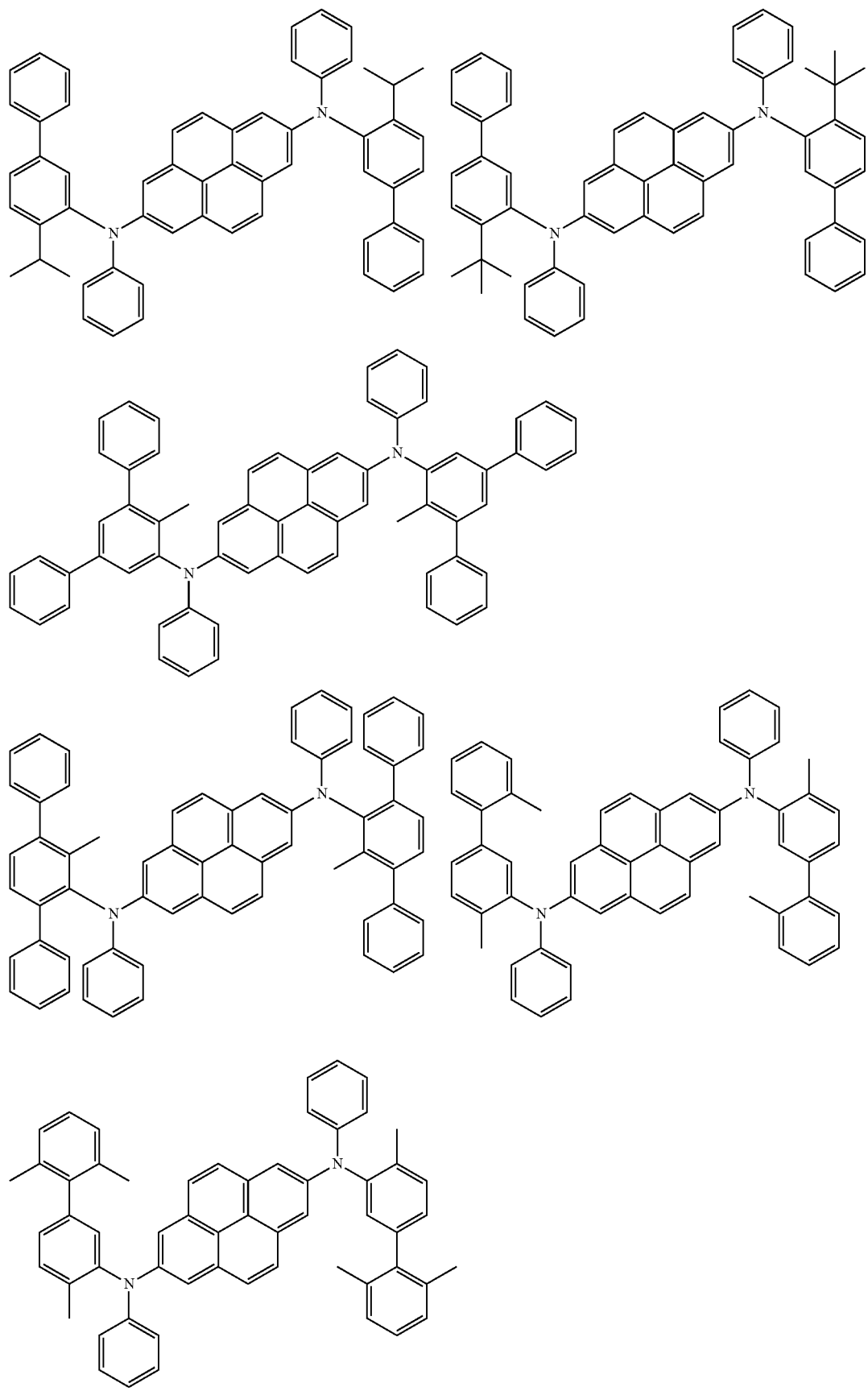

181  182
-continued
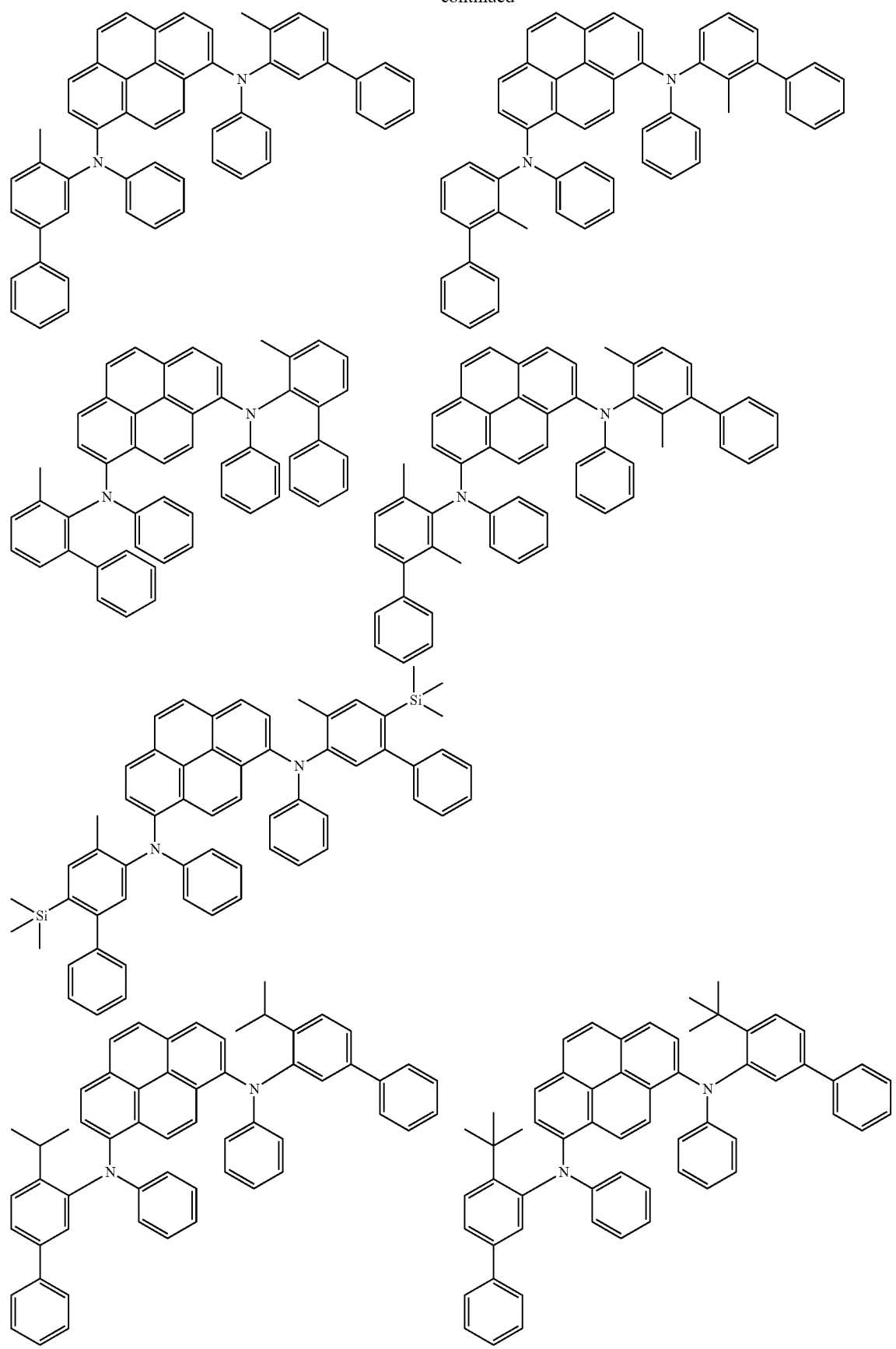

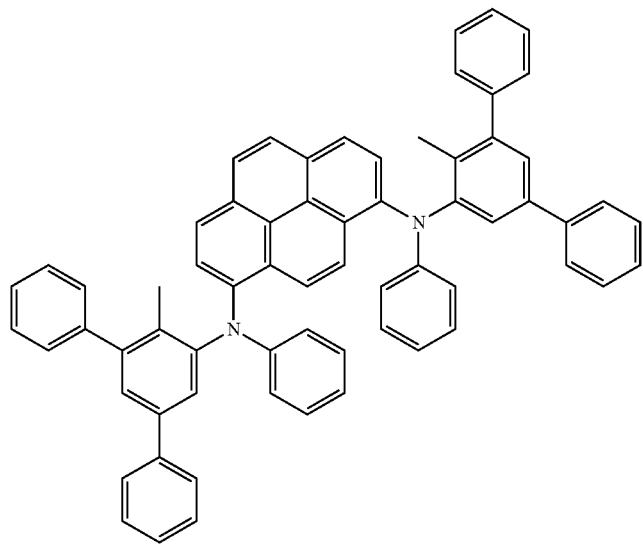
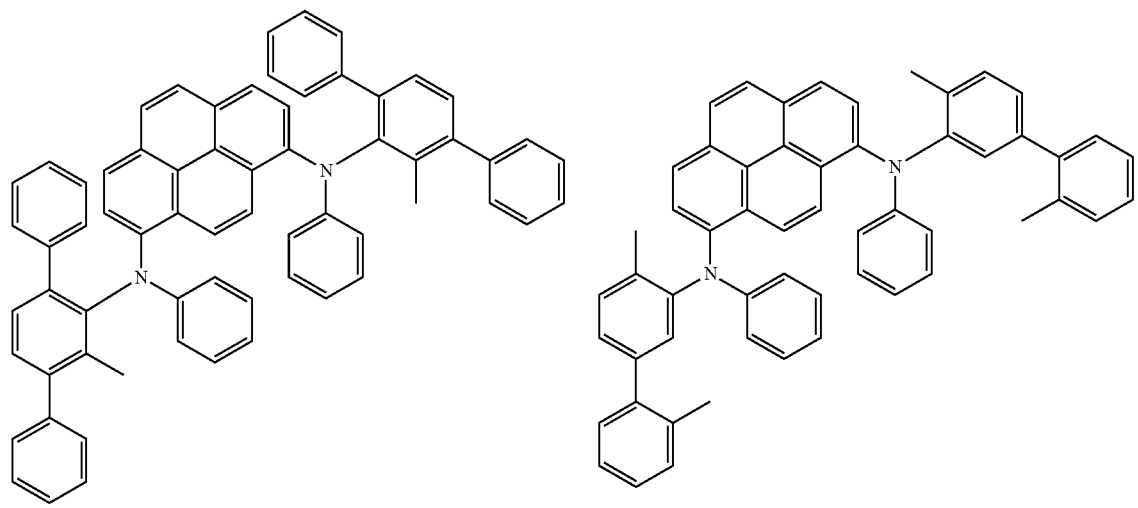
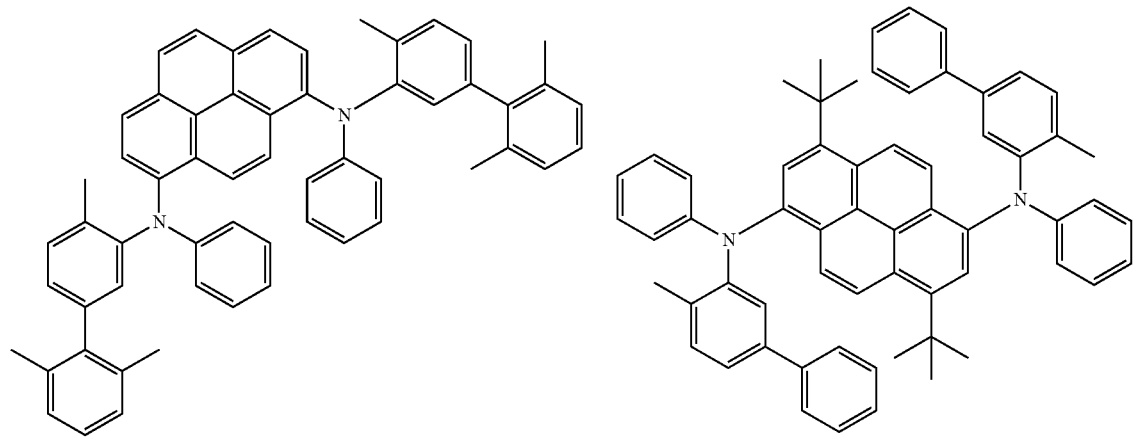

185
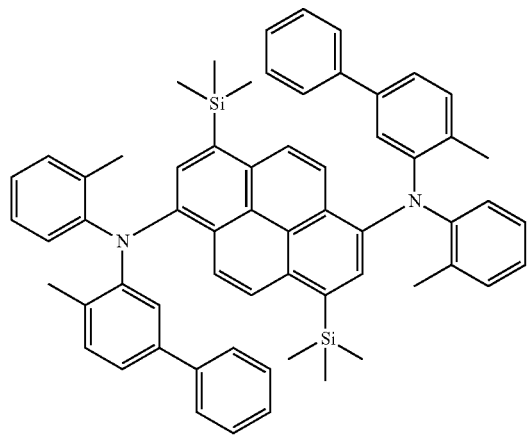
186
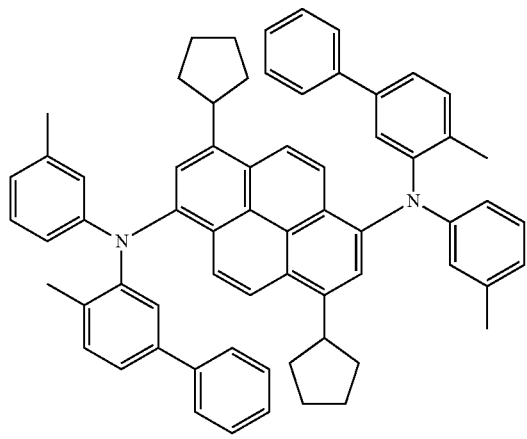
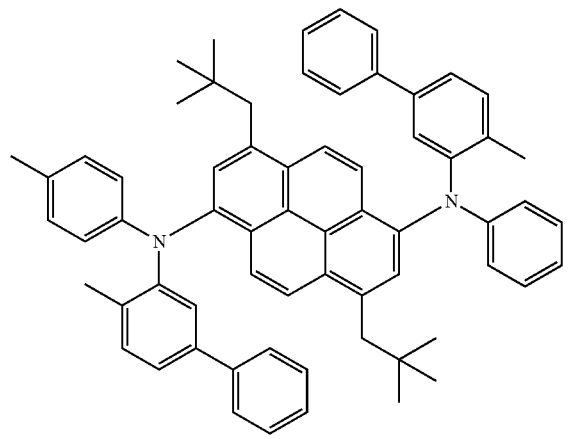
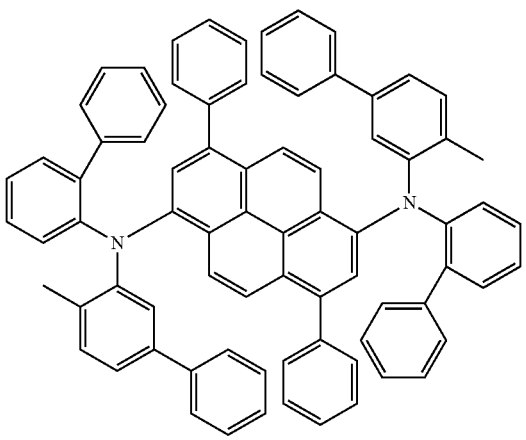
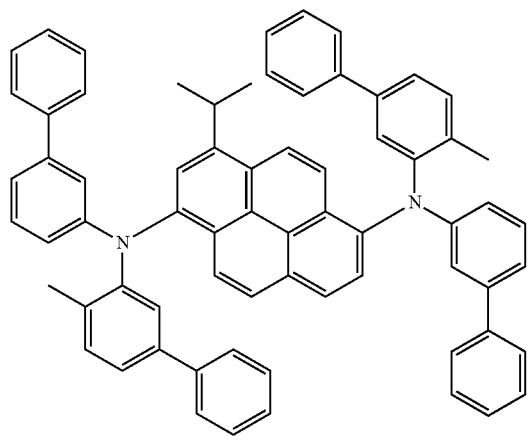
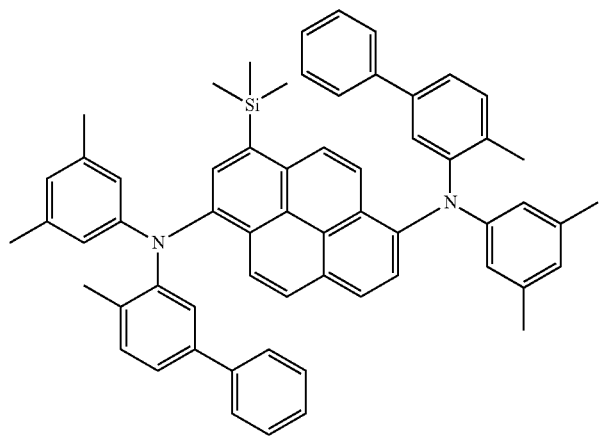

187 188
-continued
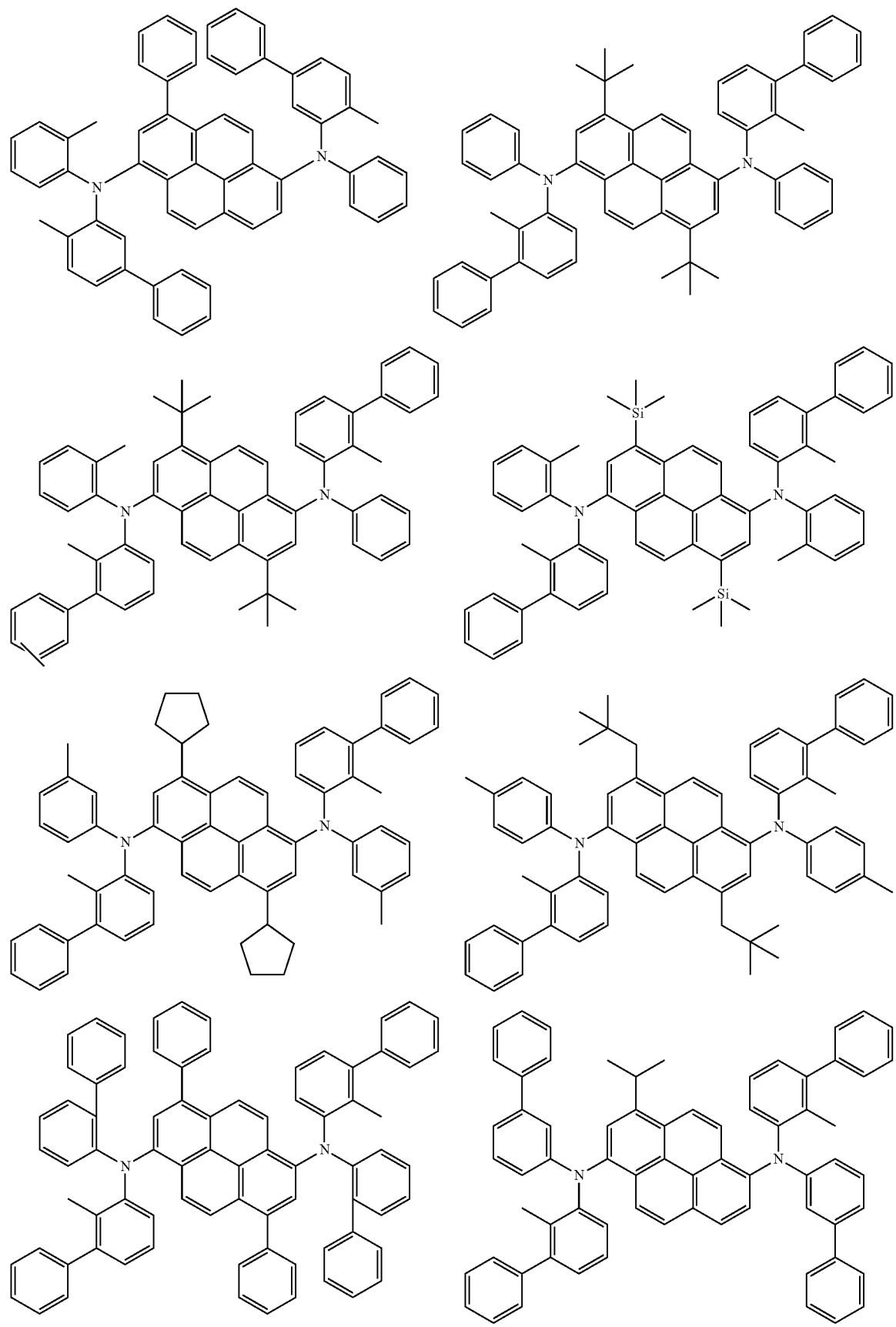

189 190
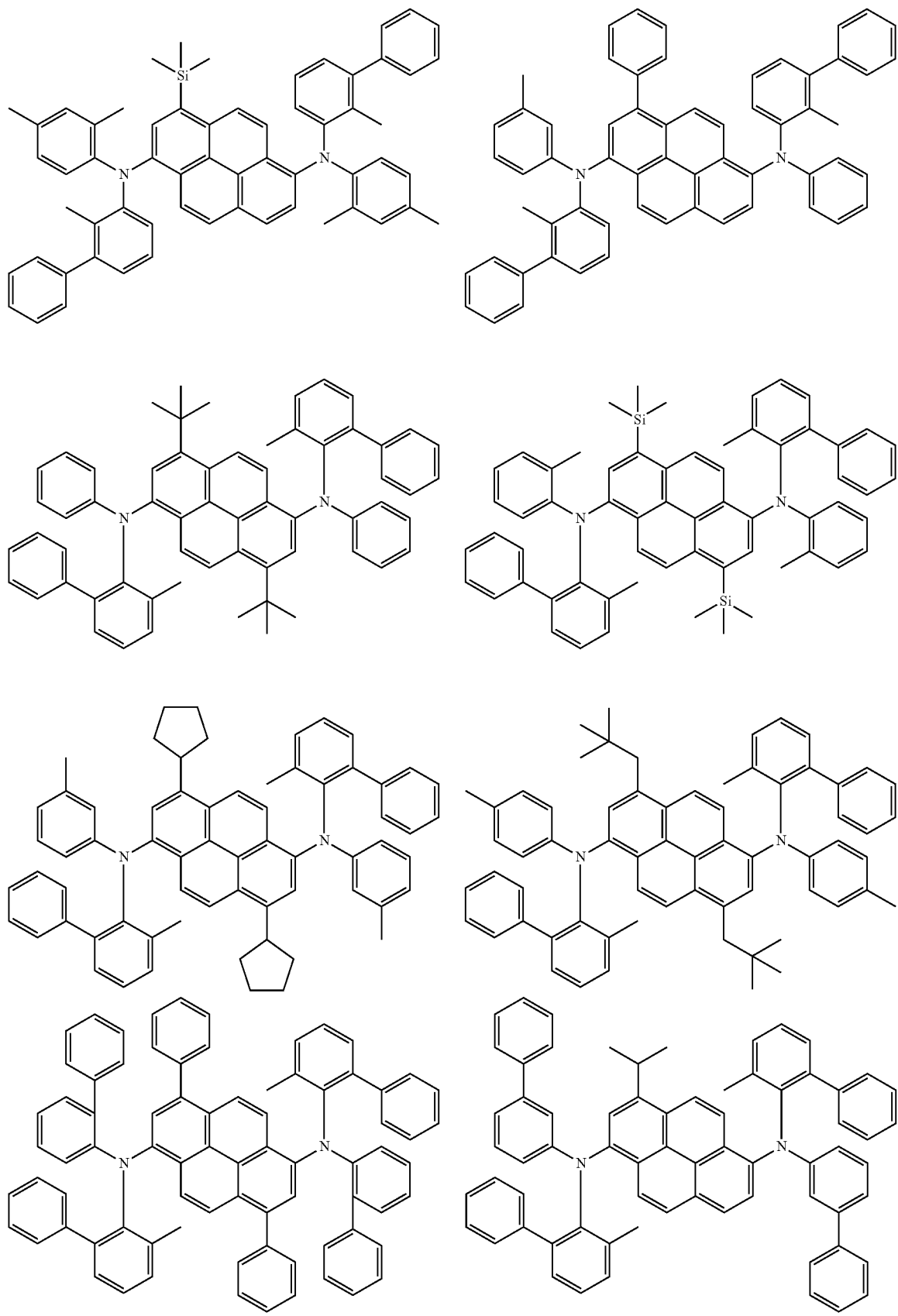
-continued

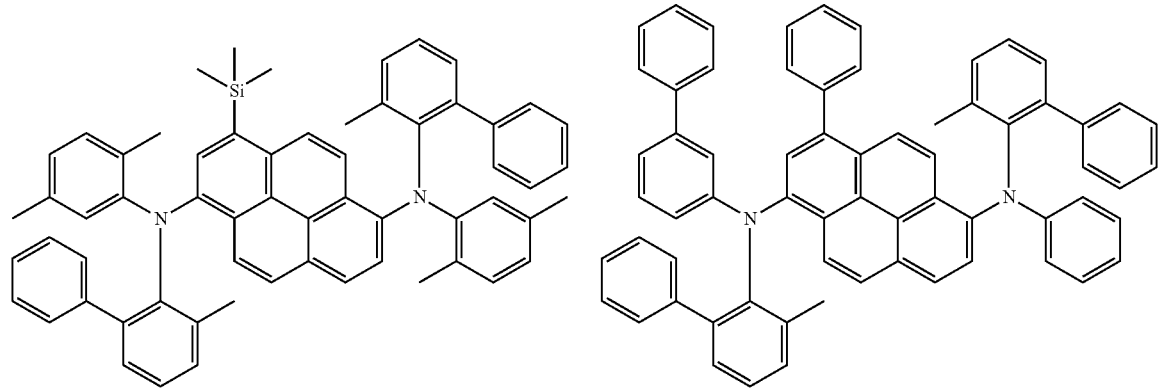
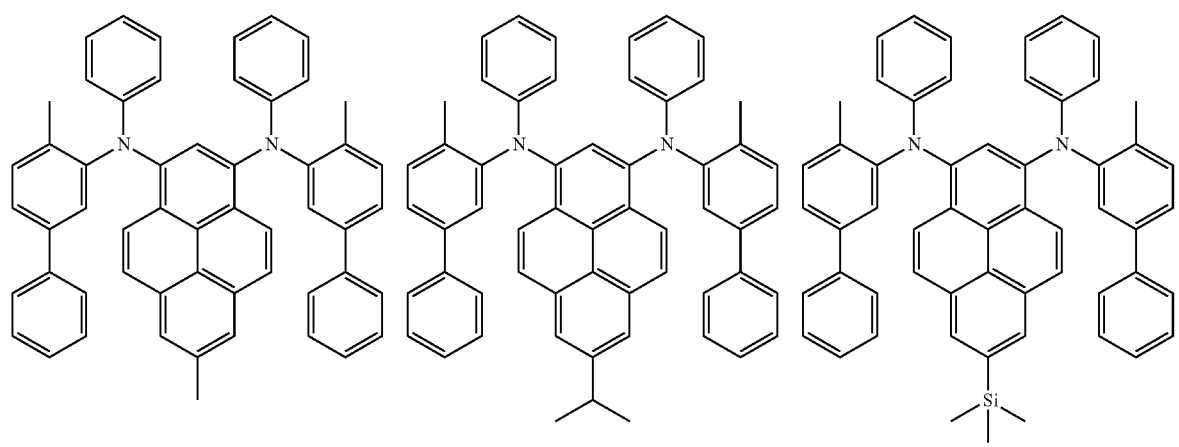
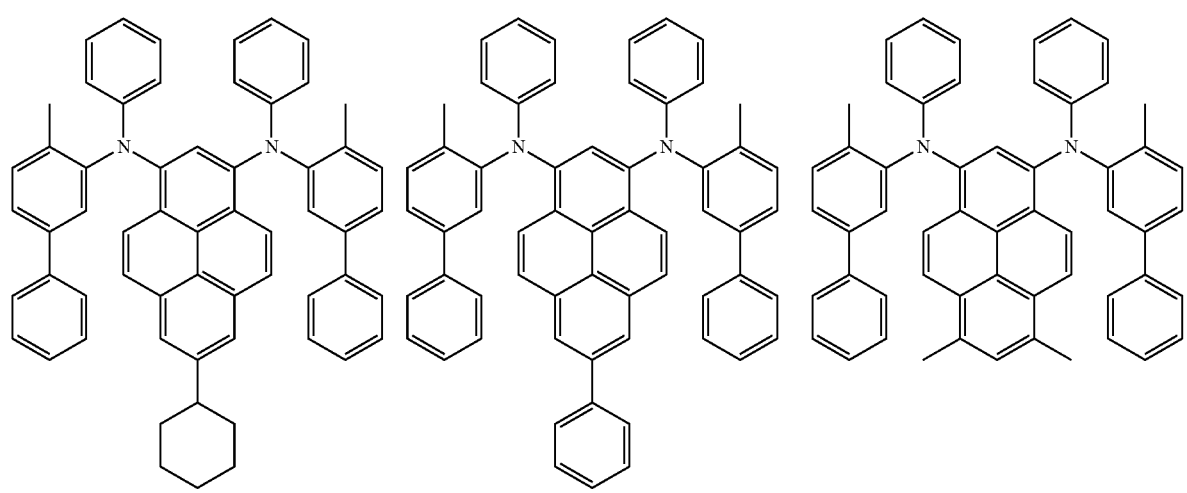

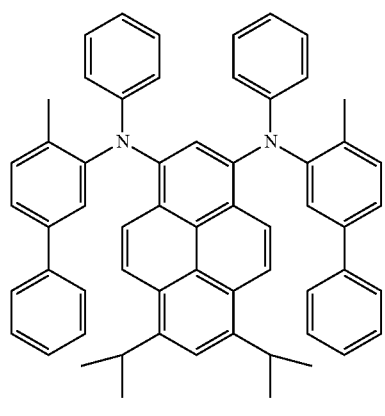
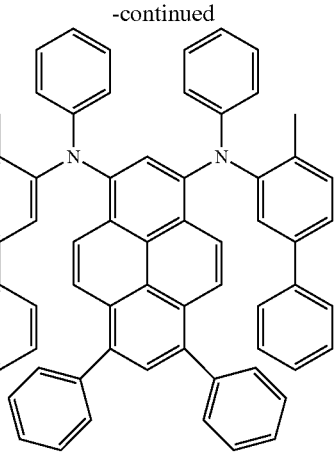
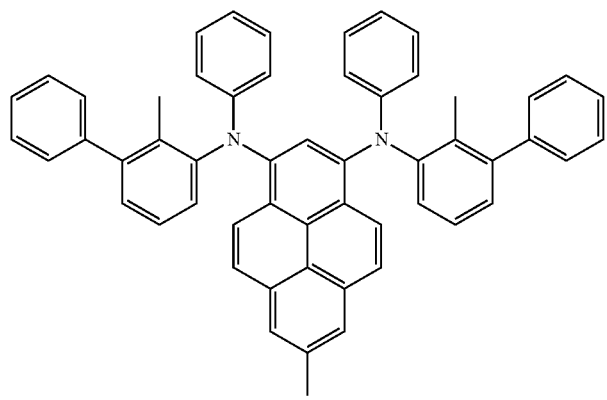
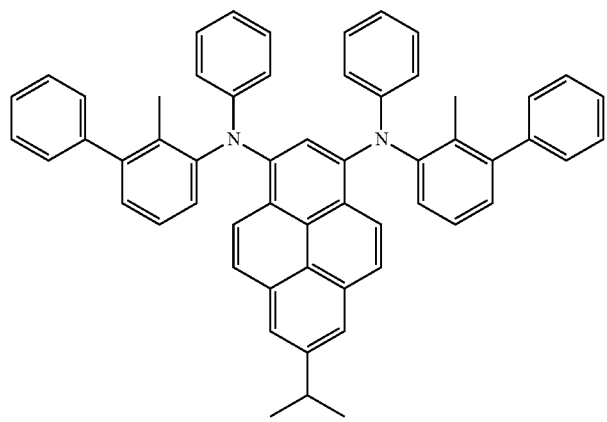
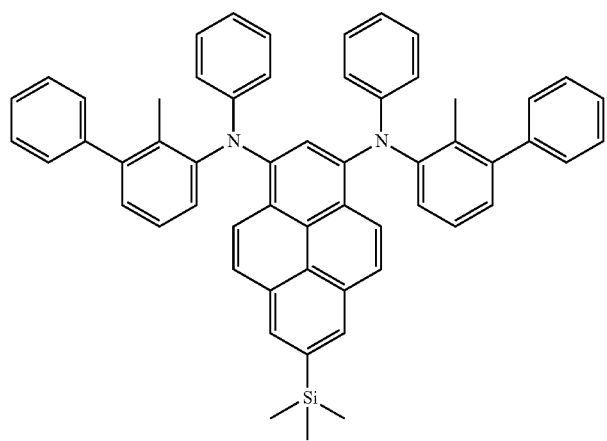

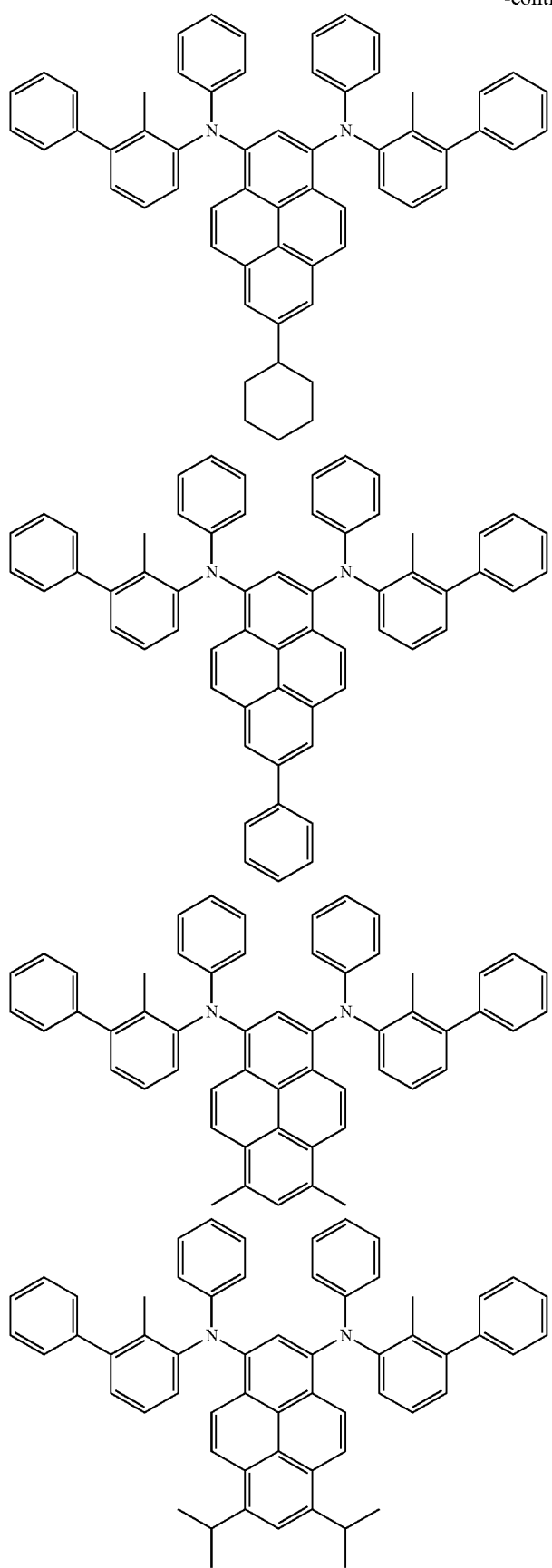

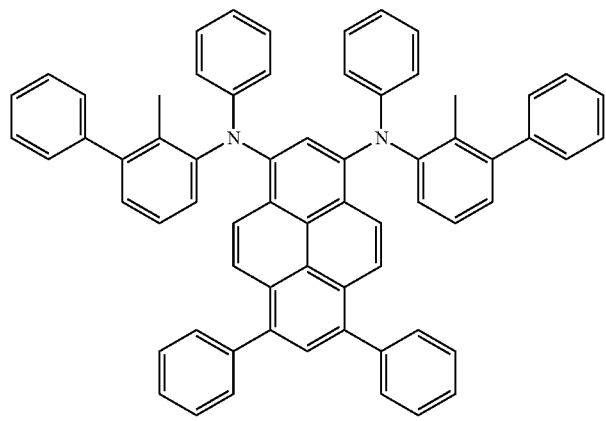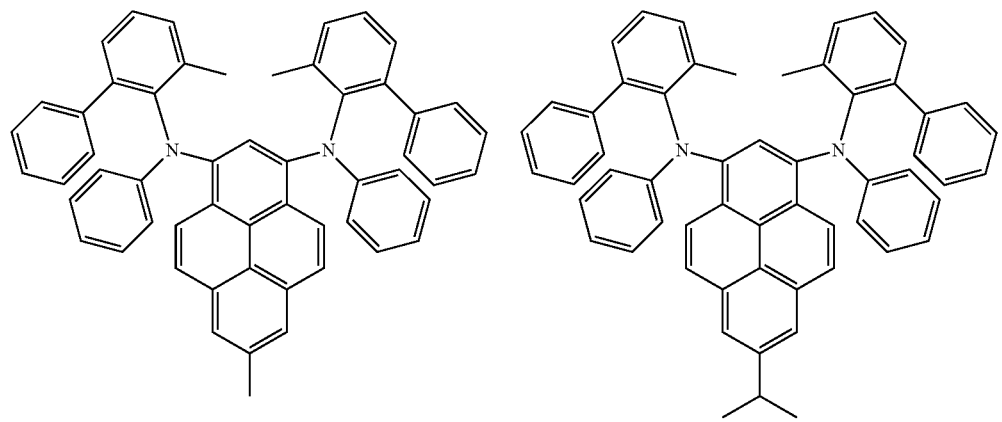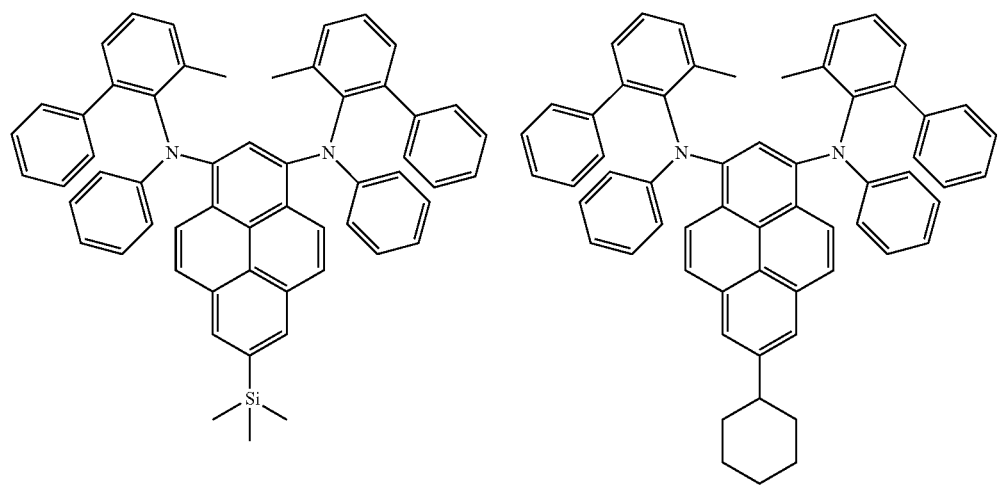

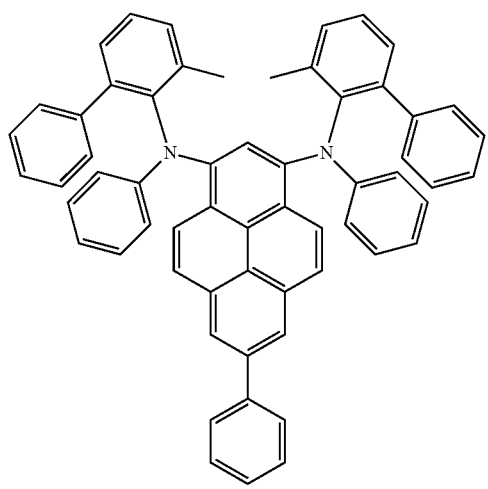
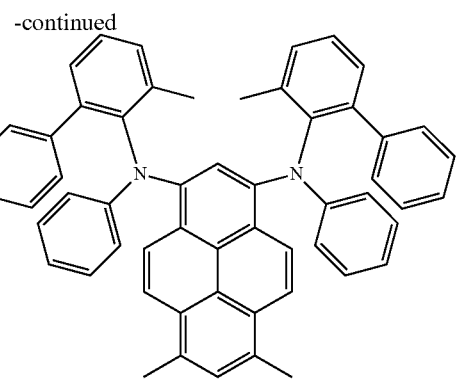
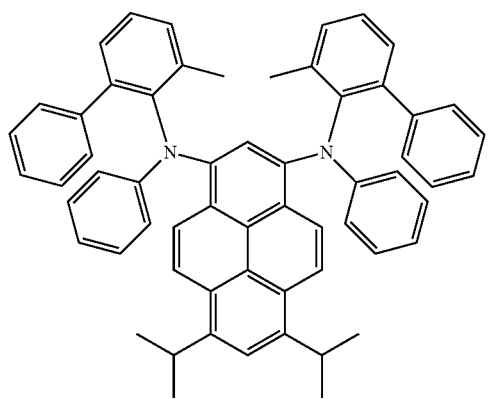
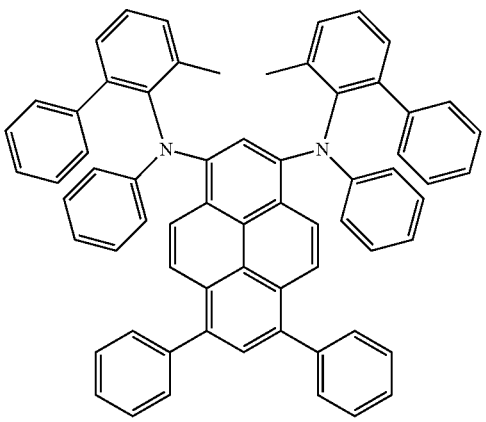

The compound according to one aspect of the invention may be used as a material for an organic electroluminescence (EL) device (preferably an emitting material for an organic EL device, and more preferably a dopant (dopant material)).

An organic EL device according to one aspect of the invention includes a cathode, an anode, and one or more organic thin film layers that are provided between the cathode and the anode, the one or more organic thin film layers including at least an emitting layer, and at least one organic thin film layer included in the one or more organic thin film layers including the compound represented by the formula (1) either alone or as a component of a mixture.

It is preferable that the emitting layer include the compound. The emitting layer may include only the compound, or may include the compound as a host or a dopant.

In the organic EL device according to one aspect of the invention, it is preferable that at least one organic thin film layer included in the one or more organic thin film layers include the compound, and at least one compound among an anthracene derivative represented by the following formula (5) and a pyrene derivative represented by the following formula (6). It is preferable that the emitting layer include the compound as a dopant, and include the anthracene derivative as a host.

The anthracene derivative is a compound represented by the following formula (5).

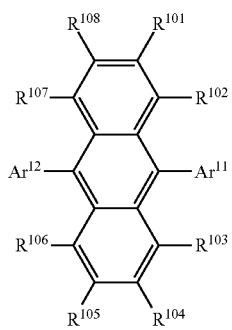

(5)

$Ar^{11}$ and $Ar^{12}$ in the formula (5) are independently a substituted or unsubstituted monocyclic group including 5 to 50 ring atoms, a substituted or unsubstituted fused ring group including 8 to 50 ring atoms, or a group formed by a combination of the monocyclic group and the fused ring group.

$R^{101}$ to $R^{108}$ are independently an atom or a group selected from the group consisting of a hydrogen atom, a substituted or unsubstituted monocyclic group including 5 to 50 (preferably 5 to 30, more preferably 5 to 20, and still more preferably 5 to 12) ring atoms, a substituted or unsubstituted fused ring group including 8 to 50 (preferably 8 to 30, more preferably 8 to 20, and still more preferably 8 to 14) ring atoms, a group formed by a combination of the monocyclic group and the fused ring group, a substituted or unsubstituted alkyl group including 1 to 50 (preferably 1 to 20, more preferably 1 to 10, and still more preferably 1 to 6) carbon atoms, a substituted or unsubstituted cycloalkyl group including 3 to 50 (preferably 3 to 20, more preferably 3 to 10, and still more preferably 5 to 8) ring carbon atoms, a substituted or unsubstituted alkoxy group including 1 to 50 (preferably 1 to 20, more preferably 1 to 10, and still more preferably 1 to 6) carbon atoms, a substituted or unsubstituted aralkyl group including 7 to 50 (preferably 7 to 20, and more preferably 7 to 14) carbon atoms, a substituted or unsubstituted aryloxy group including 6 to 50 (preferably 6 to 20, and more preferably 6 to 12) ring carbon atoms, a substituted or unsubstituted silyl group, a halogen atom, and a cyano group.

It is preferable that all of $R^{101}$ to $R^{108}$ be a hydrogen atom, or either $R^{101}$ or $R^{108}$, either $R^{104}$ or $R^{106}$, both $R^{101}$ and $R^{106}$, or both $R^{108}$ and $R^{104}$ be a group selected from the group consisting of a monocyclic group including 5 to 50 ring atoms (preferably a phenyl group, a biphenylyl group, and a terphenylyl group), a substituted or unsubstituted alkyl group having 1 to 50 carbon atoms (preferably a methyl group, an ethyl group, an n-propyl group, an isopropyl group, an n-butyl group, an isobutyl group, an s-butyl group, and a t-butyl group), and a substituted silyl group (preferably a trimethylsilyl group), and it is more preferable that all of $R^{101}$ to $R^{108}$ be a hydrogen atom.

The term "monocyclic group" used herein in connection with the formula (5) refers to a group that includes only a ring structure that does not have a fused ring structure.

Specific examples of a preferable monocyclic group including 5 to 50 ring atoms include an aromatic group (e.g., phenyl group, biphenylyl group, terphenylyl group, and quaterphenylyl group) and a heterocyclic group (e.g., pyridyl group, pyrazyl group, pyrimidyl group, triazinyl group, furyl group, and thienyl group).

Among these, a phenyl group, a biphenylyl group, and a terphenylyl group are preferable.

The term "fused ring group" used herein in connection with the formula (5) refers to a group in which two or more ring (cyclic) structures are fused.

Specific examples of a preferable fused ring group including 8 to 50 ring atoms include a fused aromatic ring group (e.g., naphthyl group, phenanthryl group, anthryl group, chrysenyl group, benzanthryl group, benzophenanthryl group, triphenylenyl group, benzochrysenyl group, indenyl group, fluorenyl group, benzofluorenyl group, dibenzofluorenyl group, fluoranthenyl group, and benzofluoranthenyl group) and a fused heterocyclic group (e.g., benzofuranyl group, benzothiophenyl group, indolyl group, dibenzofuranyl group, dibenzothiophenyl group, carbazolyl group, quinolyl group, and phenanthrolinyl group).

The fluorenyl group may be substituted with one or two substituents at the position 9. Examples of the substituent include an alkyl group, an aryl group, an alkylsilyl group, an arylsilyl group, an alkoxy group, and the like. Specific examples of such a substituted fluorenyl group include a 9,9-dimethylfluorenyl group, a 9,9-diphenylfluorenyl group, and the like. The term "fluorenyl group" used hereinafter includes such a substituted fluorenyl group unless otherwise specified.

A naphthyl group, a phenanthryl group, an anthryl group, a fluorenyl group (e.g., 9,9-dimethylfluorenyl group), a fluoranthenyl group, a benzanthryl group, a dibenzothiophenyl group, a dibenzofuranyl group, and a carbazolyl group are preferable as the fused ring group.

Specific examples of the alkyl group, the cycloalkyl group, the alkoxy group, the alkyl moiety and the aryl moiety of the aralkyl group, the aryloxy group, the substituted silyl group (alkylsilyl group and arylsilyl group), and the halogen atom mentioned above in connection with the formula (5) include those (group and substituent) mentioned above in connection with the formula (1).

The aralkyl group is represented by —Y—Z. Examples of Y include alkylene groups that correspond to those mentioned above in connection with the alkyl group. Examples of Z include those mentioned above in connection with the aryl group. The number of carbon atoms of the aralkyl group is preferably 7 to 50 (i.e., the number of carbon atoms of the aryl moiety is 6 to 49 (preferably 6 to 30, more preferably 6 to 20, and particularly preferably 6 to 12), and the number of carbon atoms of the alkyl moiety is 1 to 44 (preferably 1 to 30, more preferably 1 to 20, still more preferably 1 to 10, and particularly preferably 1 to 6)). Examples of the aralkyl group include a benzyl group, a phenylethyl group, and a 2-phenylpropan-2-yl group.

A substituent that may substitute $Ar^{11}$, $Ar^{12}$, and $R^1$ to $R^8$ is preferably a monocyclic group, a fused ring group, an alkyl group, a cycloalkyl group, a silyl group, an alkoxy group, a cyano group, or a halogen atom (particularly a fluorine atom), and particularly preferably a monocyclic group or a fused ring group. Specific examples of a preferable substituent include those mentioned above.

Note that a substituent that may substitute $Ar^{11}$ and $Ar^{12}$ is preferably the monocyclic group or the fused ring group mentioned above.

The anthracene derivative represented by the formula (5) is preferably an anthracene derivative among the following anthracene derivatives (A), (B), and (C). The anthracene derivative is selected taking account of the configuration and the desired properties of the organic EL device.

Anthracene Derivative (A)

The anthracene derivative (A) is the anthracene derivative represented by the formula (5) wherein $Ar^{11}$ and $Ar^{12}$ are independently a substituted or unsubstituted fused ring group including 8 to 50 ring atoms. $Ar^{11}$ and $Ar^{12}$ in the anthracene derivative may be either identical or different.

The anthracene derivative (A) is preferably the anthracene derivative represented by the formula (5) wherein $Ar^{11}$ and $Ar^{12}$ are a substituted or unsubstituted fused ring group and differ from each other (including a difference in the position at which the anthracene ring is bonded). Specific examples of a preferable fused ring group include those mentioned above. A naphthyl group, a phenanthryl group, a benzanthryl group, a fluorenyl group (e.g., 9,9-dimethylfluorenyl group), and a dibenzofuranyl group are preferable as the fused ring group.

Anthracene Derivative (B)

The anthracene derivative (B) is the anthracene derivative represented by the formula (5) wherein one of $Ar^{11}$ and $Ar^{12}$ is a substituted or unsubstituted monocyclic group including 5 to 50 ring atoms, and the other of $Ar^{11}$ and $Ar^{12}$ is a substituted or unsubstituted fused ring group including 8 to 50 ring atoms.

Examples of a preferable anthracene derivative (B) include the anthracene derivative represented by the formula (5) wherein $Ar^{12}$ is a naphthyl group, a phenanthryl group, a benzanthryl group, a fluorenyl group (e.g., 9,9-dimethylfluorenyl group), or a dibenzofuranyl group, and $Ar^{11}$ is an unsubstituted phenyl group, or a phenyl group substituted with a monocyclic group or a fused ring group (e.g., phenyl group, biphenyl group, naphthyl group, phenanthryl group, fluorenyl group (e.g., 9,9-dimethylfluorenyl group), or dibenzofuranyl group). Specific examples of a preferable monocyclic group and a preferable fused ring group include those mentioned above.

Further examples of a preferable anthracene derivative (B) include the anthracene derivative represented by the formula (5) wherein $Ar^{12}$ is a substituted or unsubstituted fused ring group including 8 to 50 ring atoms, and $Ar^{11}$ is an unsubstituted phenyl group. In this case, a phenanthryl group, a fluorenyl group (e.g., 9,9-dimethylfluorenyl group), a dibenzofuranyl group, and a benzanthryl group are particularly preferable as the fused ring group.

Anthracene Derivative (C)

The anthracene derivative (C) is the anthracene derivative represented by the formula (5) wherein $Ar^{11}$ and $Ar^{12}$ are independently a substituted or unsubstituted monocyclic group including 5 to 50 ring atoms.

Examples of a preferable anthracene derivative (C) include the anthracene derivative represented by the formula (5) wherein $Ar^{11}$ and $Ar^{12}$ are a substituted or unsubstituted phenyl group. Examples of a more preferable anthracene derivative (C) include the anthracene derivative represented by the formula (5) wherein $Ar^{11}$ is an unsubstituted phenyl group, and $Ar^{12}$ is a phenyl group substituted with a monocyclic group or a fused ring group, and the anthracene derivative represented by the formula (5) wherein $Ar^{11}$ and $Ar^{12}$ are independently a phenyl group substituted with a monocyclic group or a fused ring group.

Specific examples of a preferable monocyclic group and a preferable fused ring group as a substituent include those mentioned above. The monocyclic group used as a substituent is more preferably a phenyl group or a biphenyl group, and the fused ring group used as a substituent is more preferably a naphthyl group, a phenanthryl group, a fluorenyl group (e.g., 9,9-dimethylfluorenyl group), a dibenzofuranyl group, or a benzanthryl group.

Specific examples of the anthracene derivative represented by the formula (5) include the following compounds.

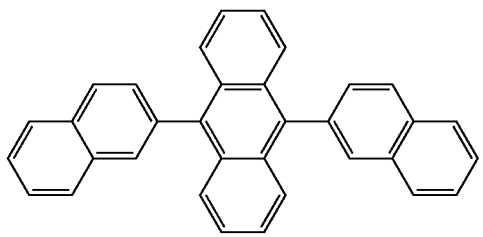
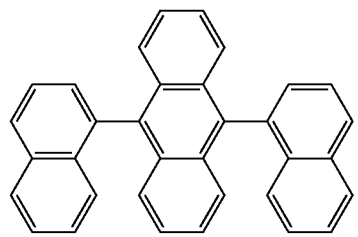
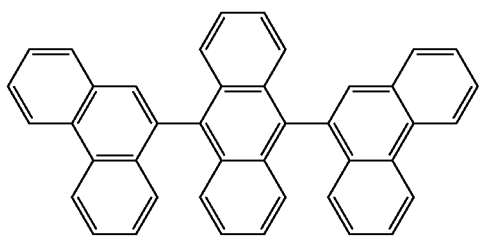
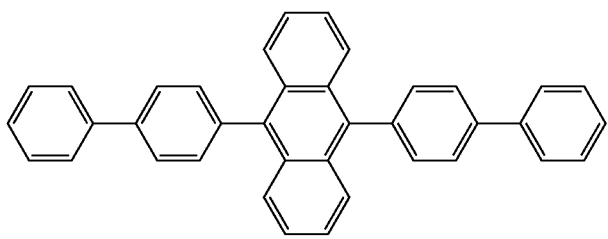
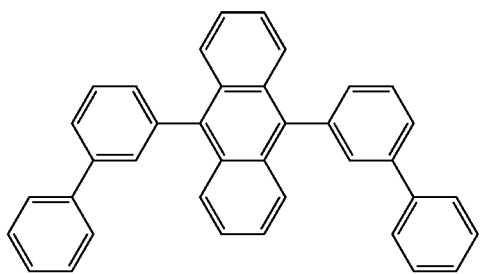
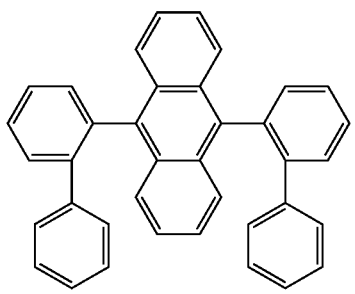
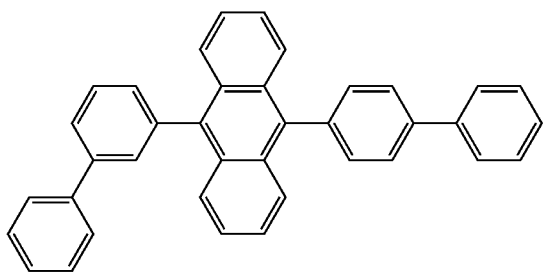

-continued
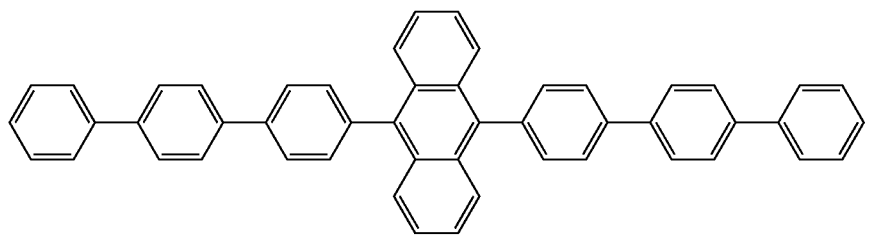
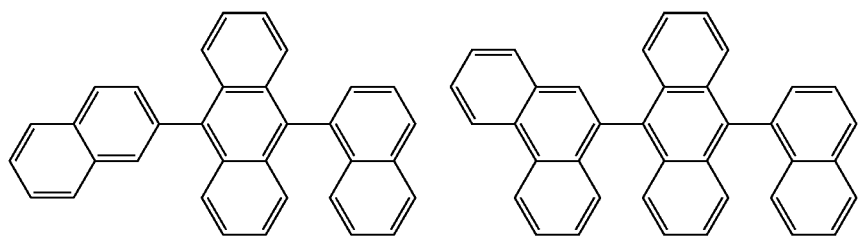
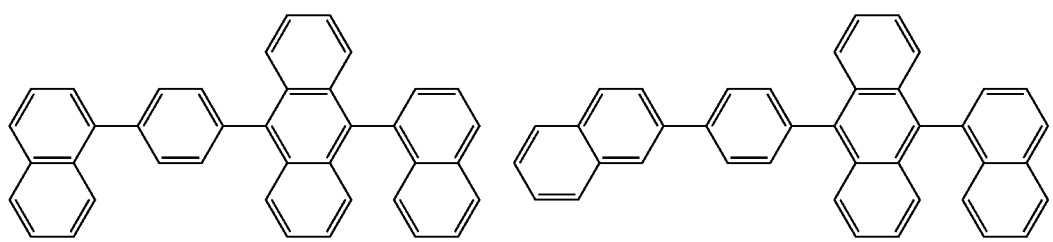
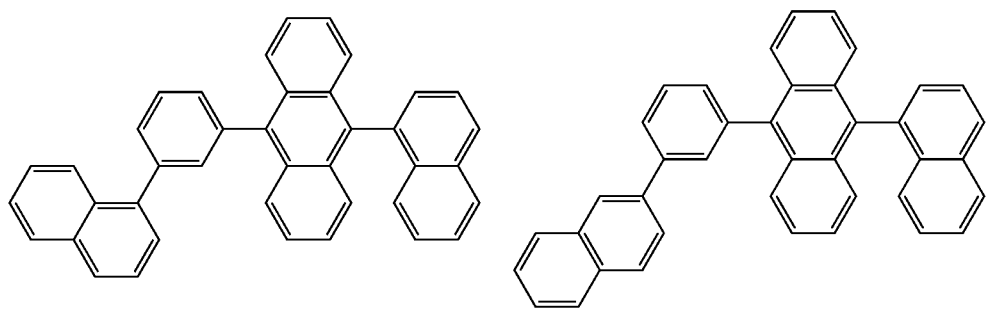
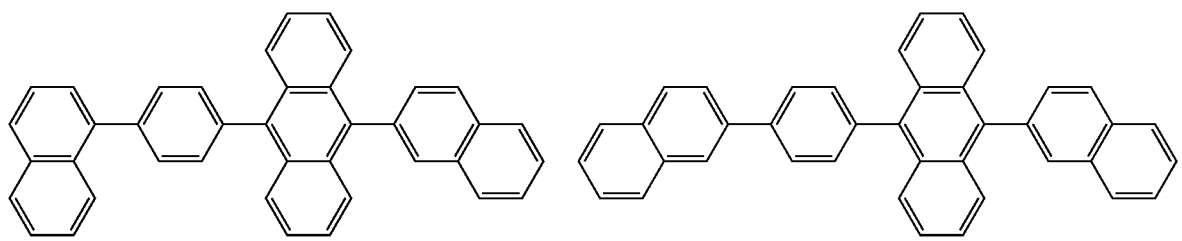
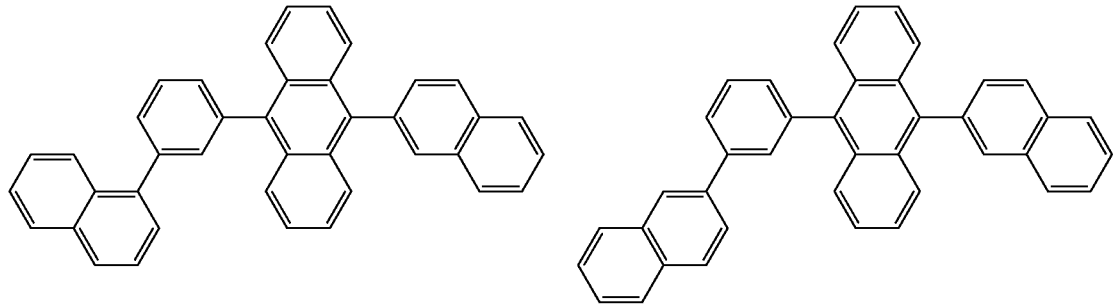

207 208
-continued
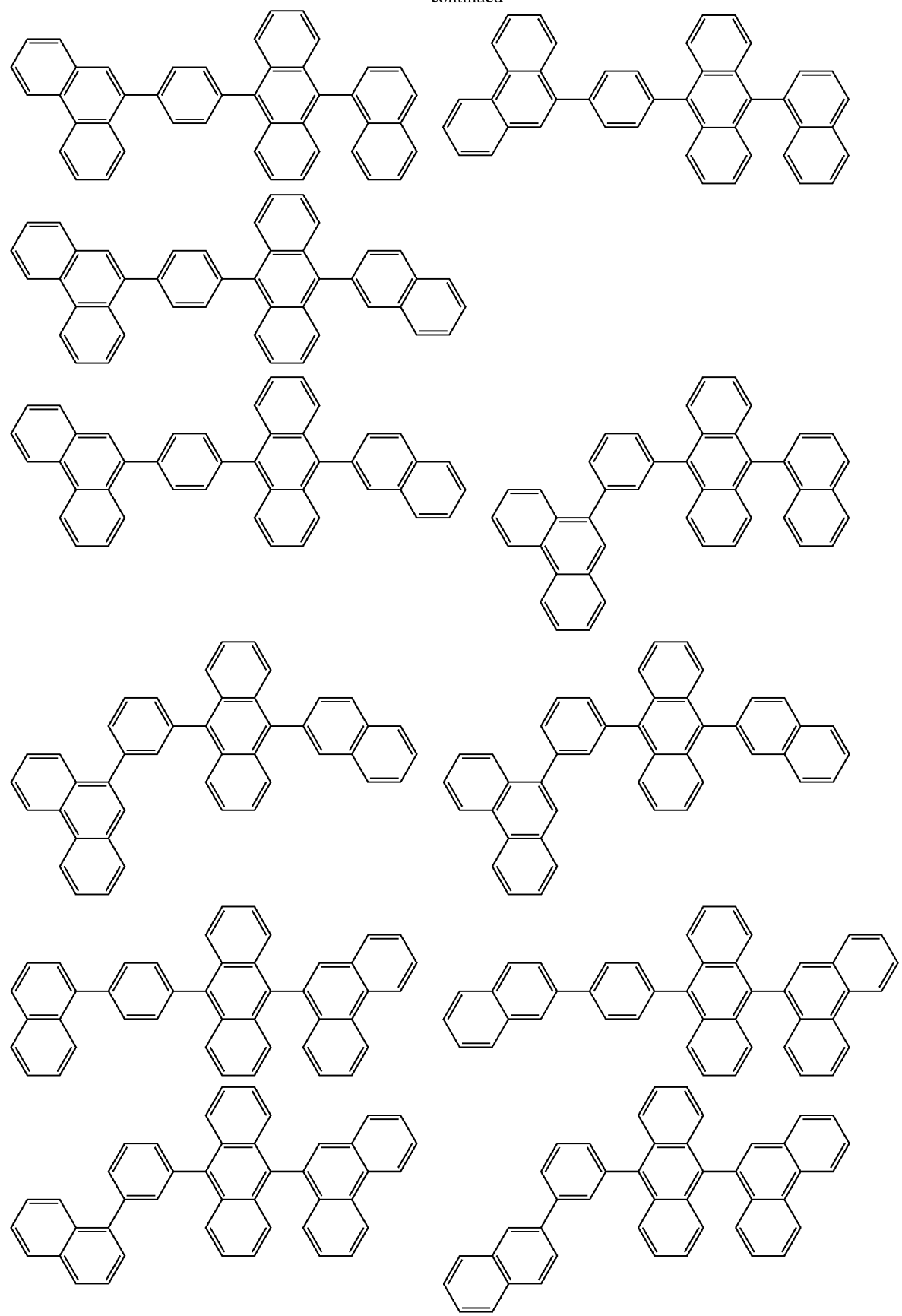

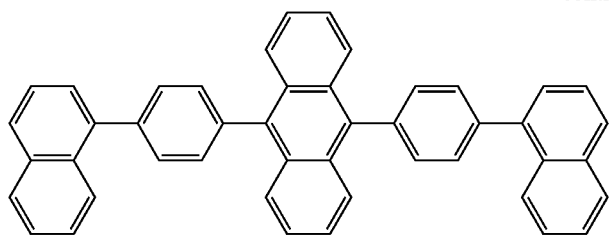
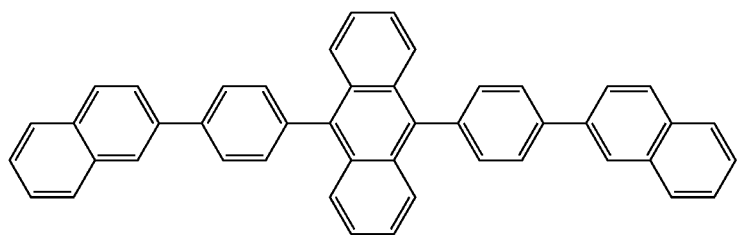
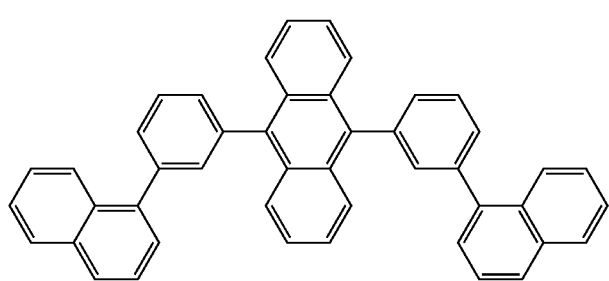
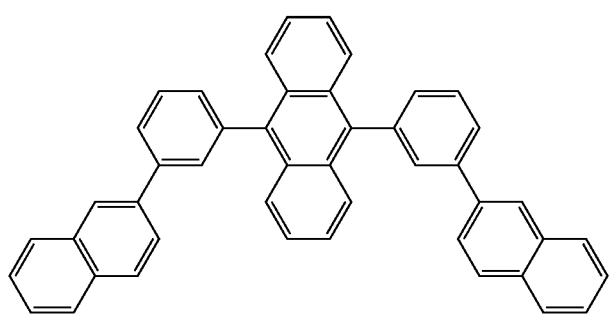
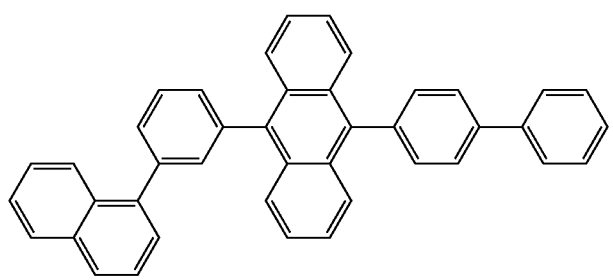
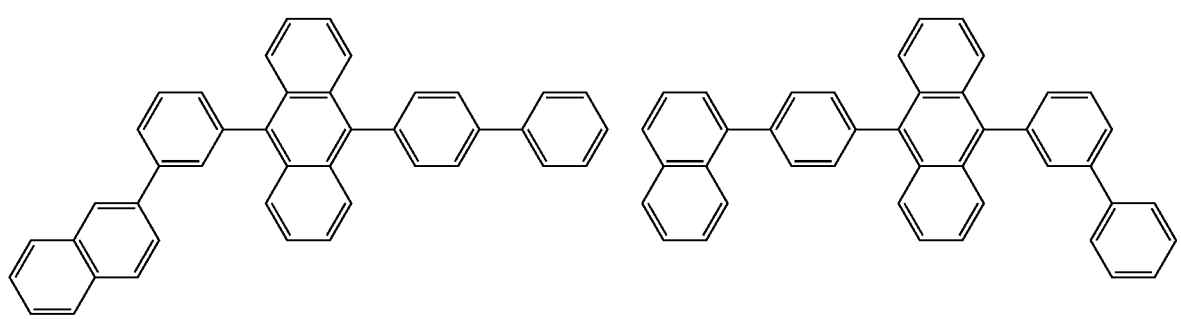

-continued
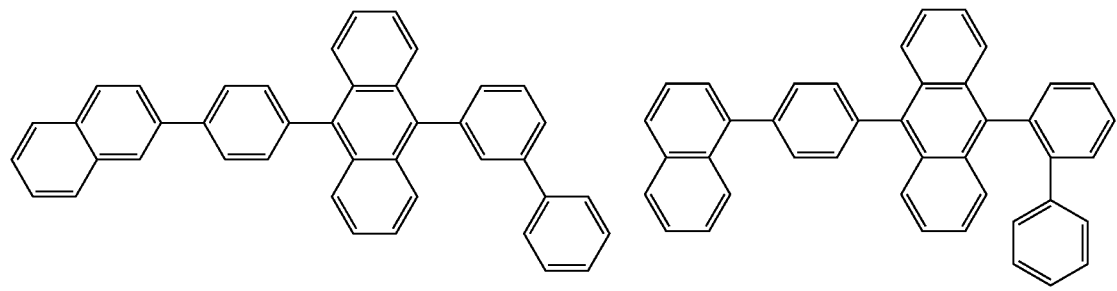
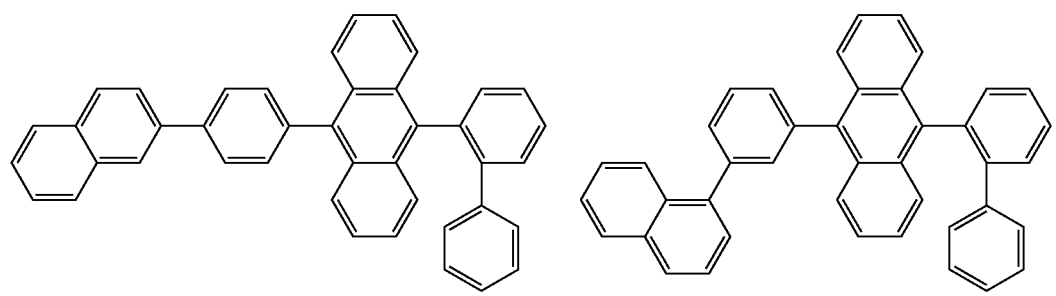
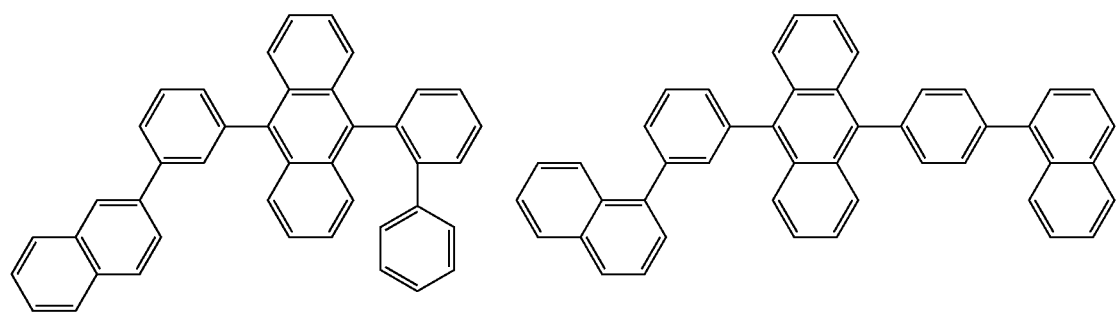
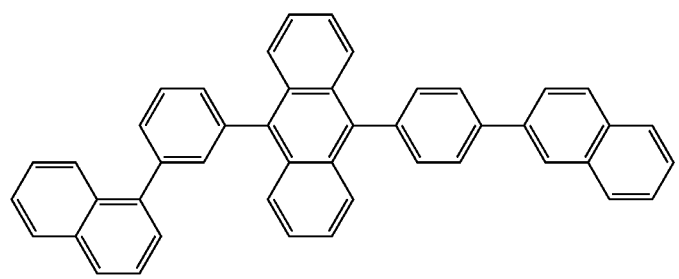
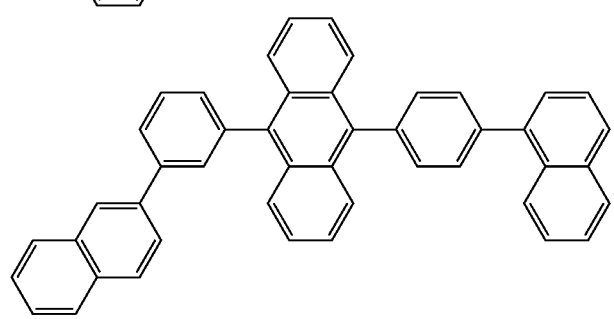

213 214
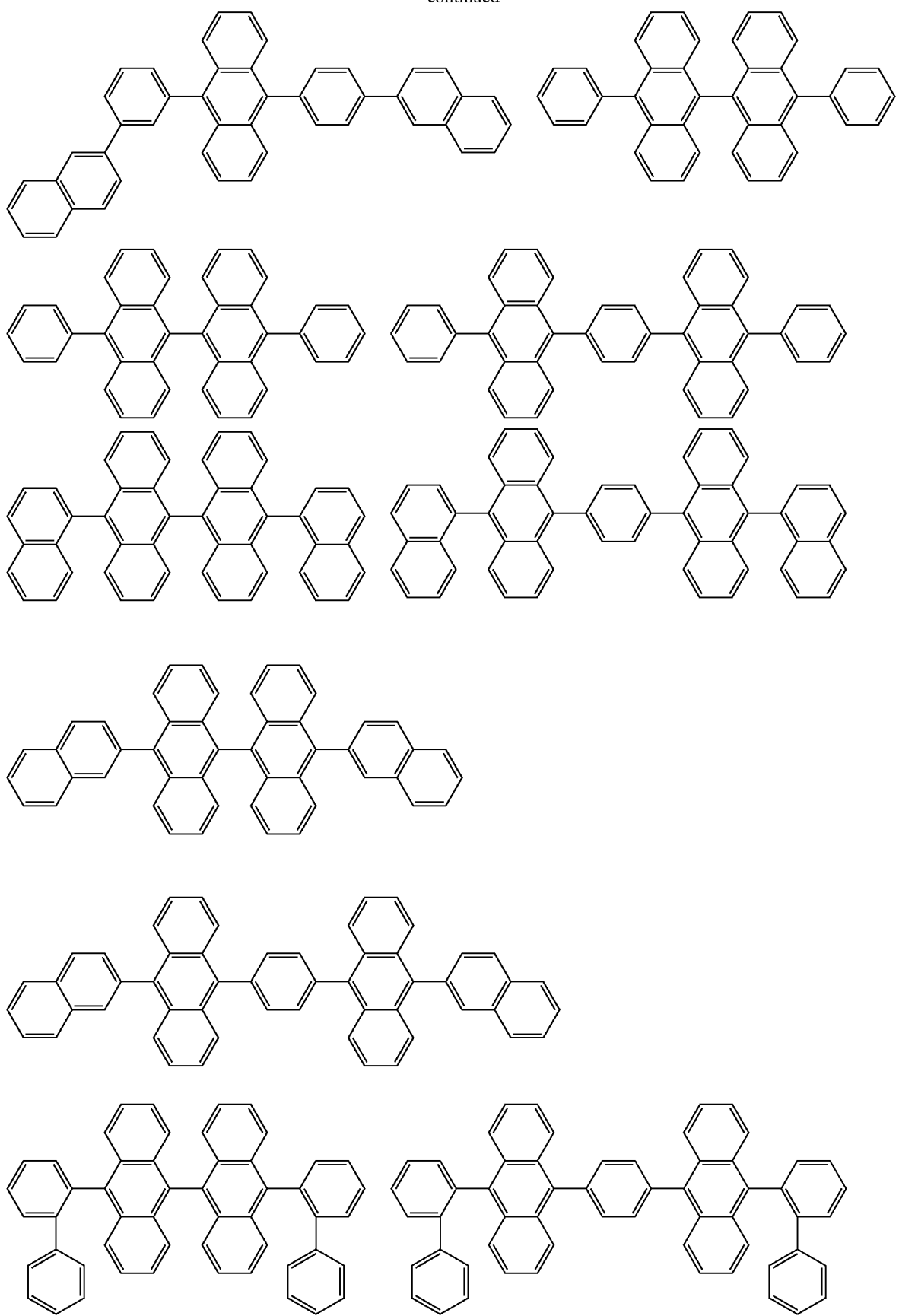

-continued
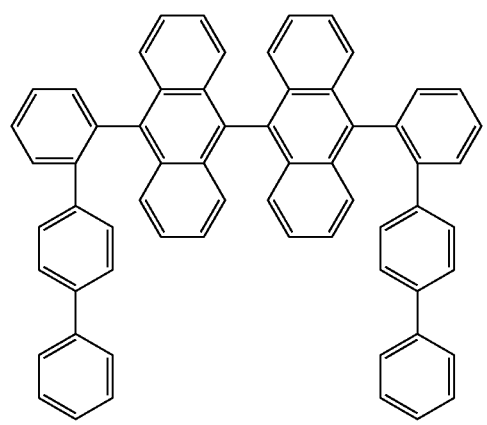
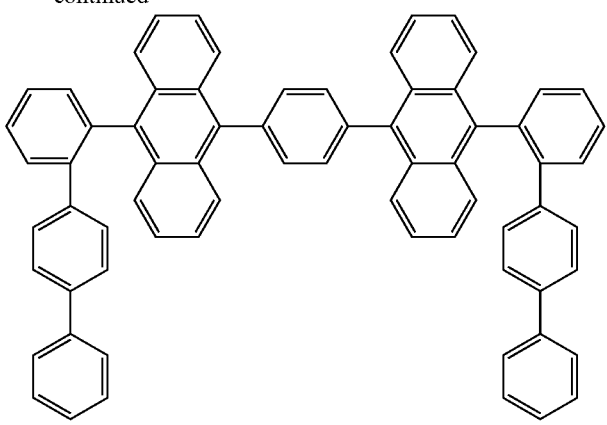
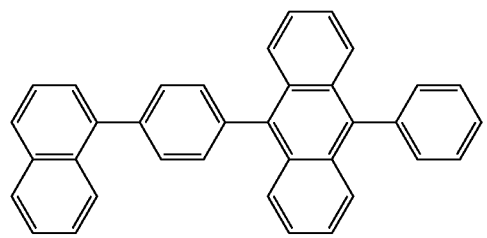
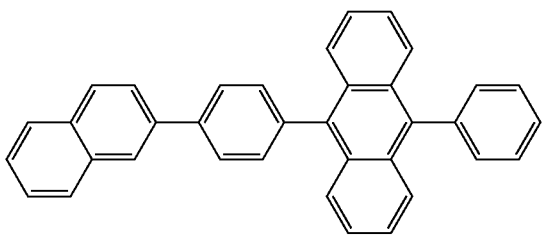
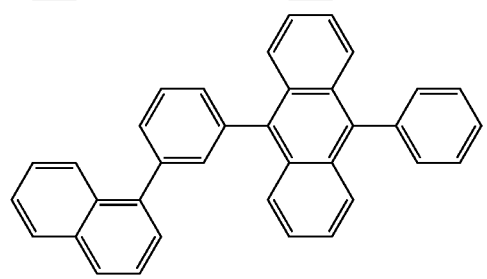
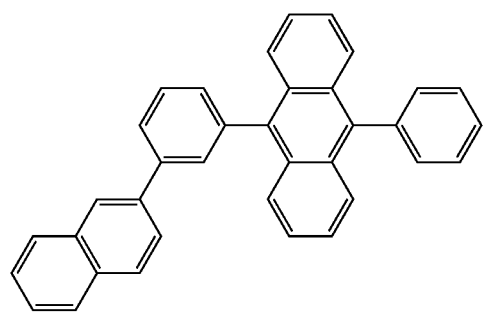
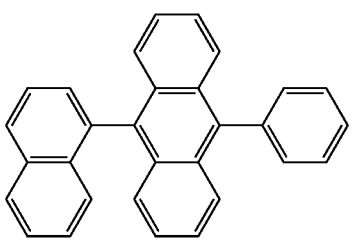
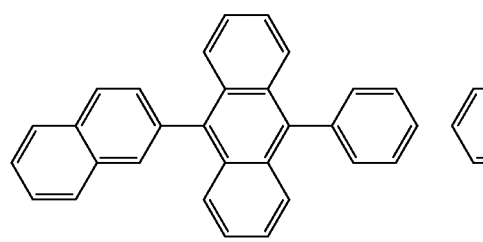
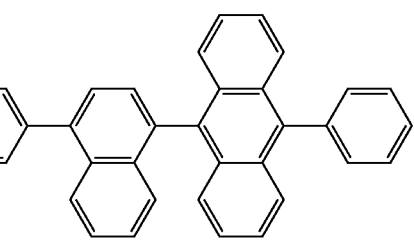
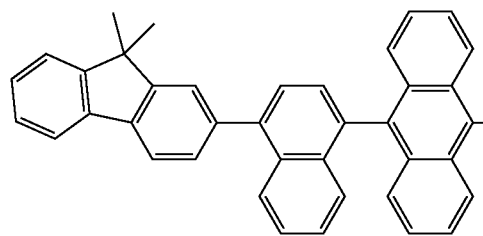
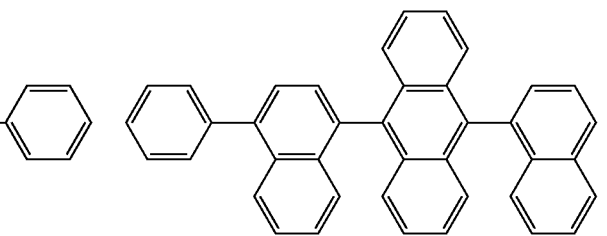

-continued
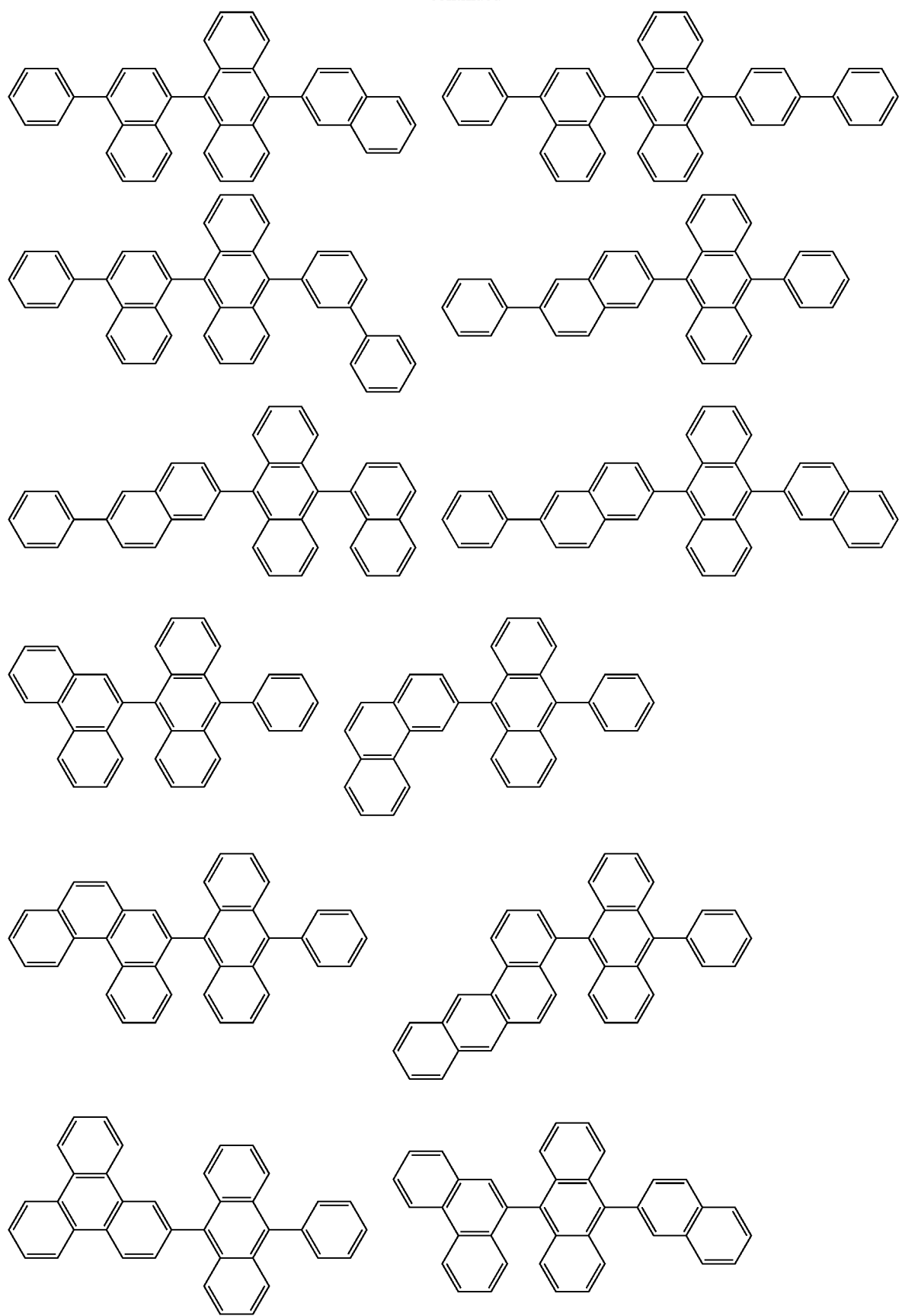

-continued
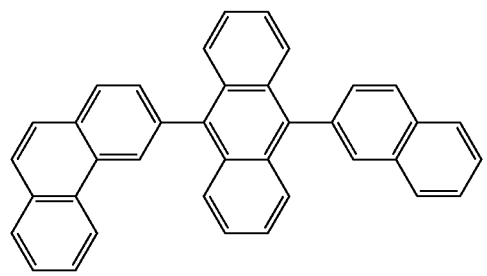
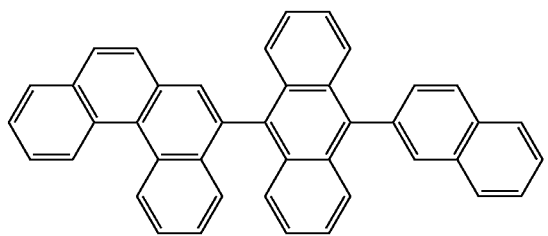
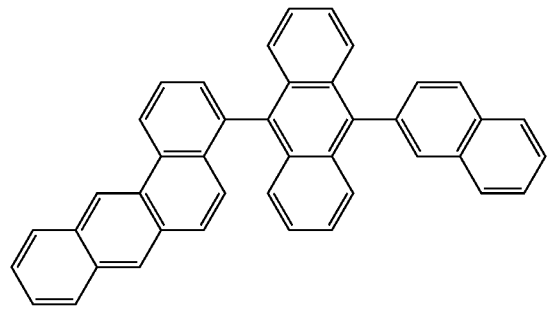
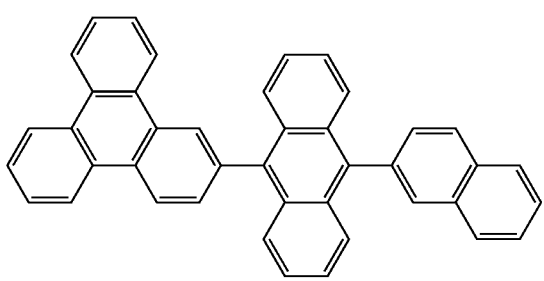
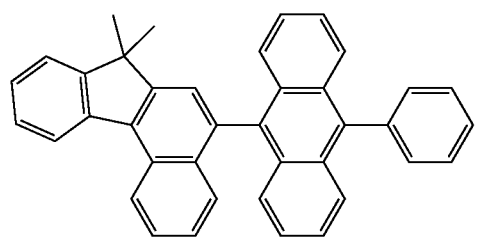
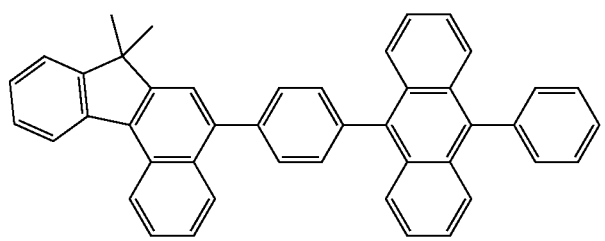
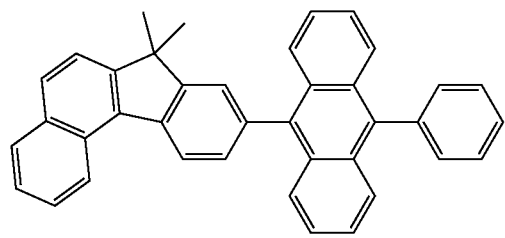
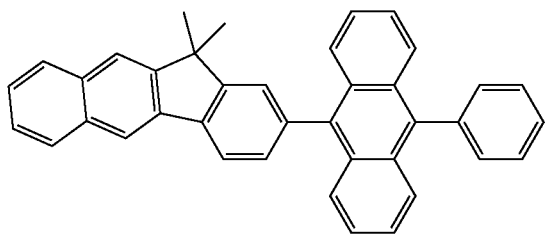
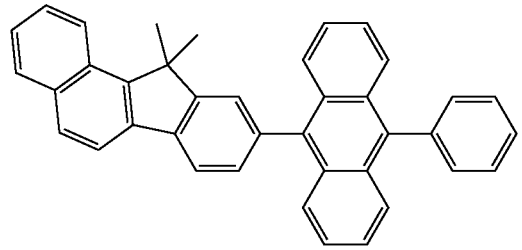
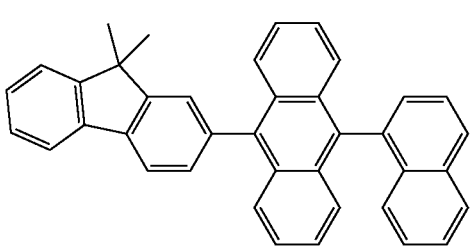
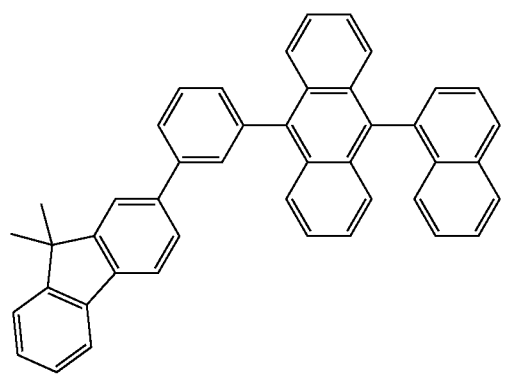
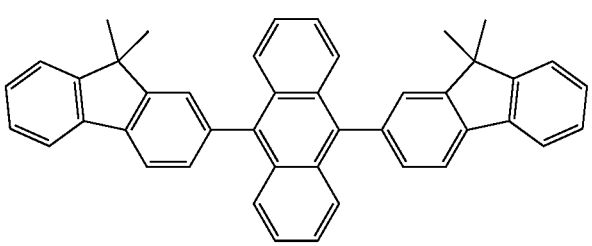

221 222
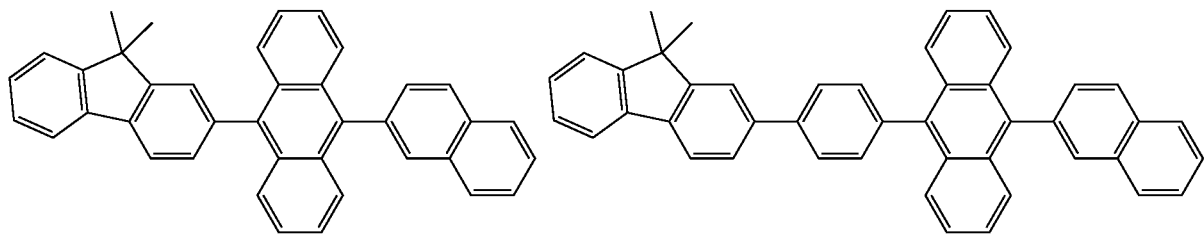
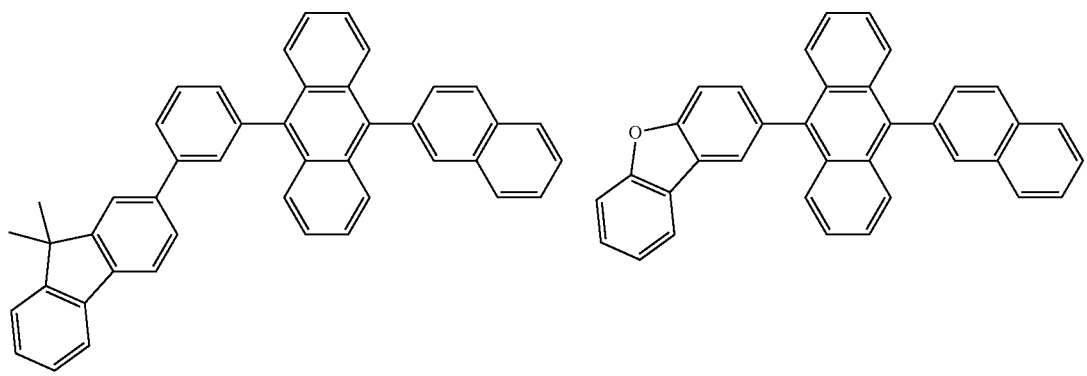
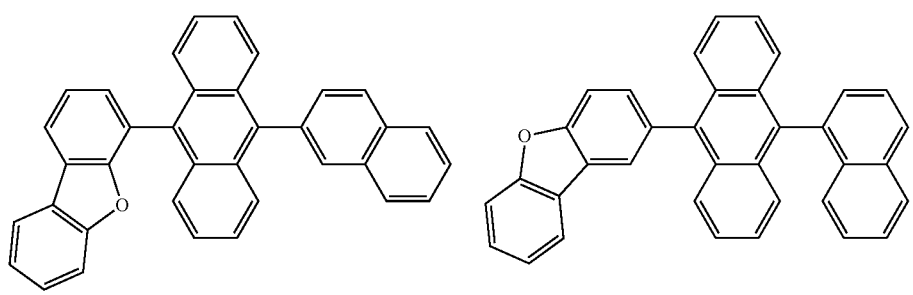
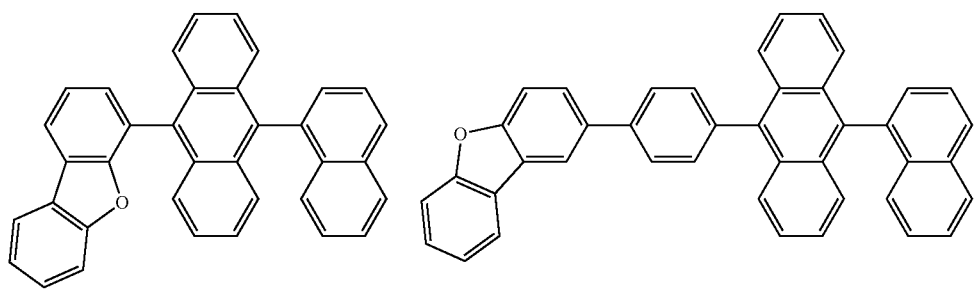
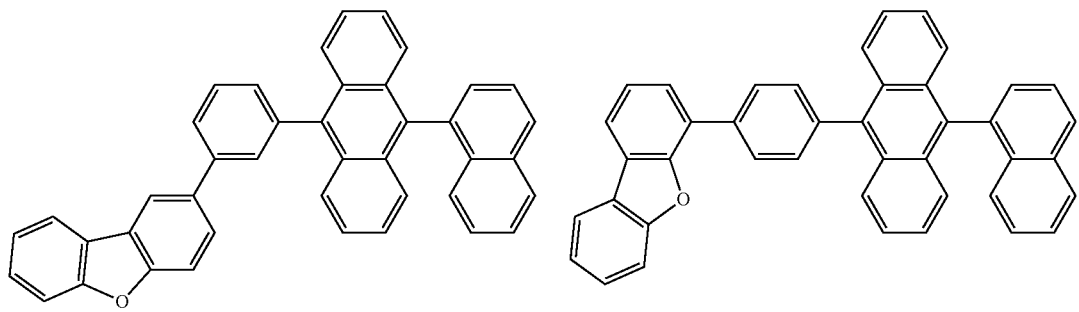

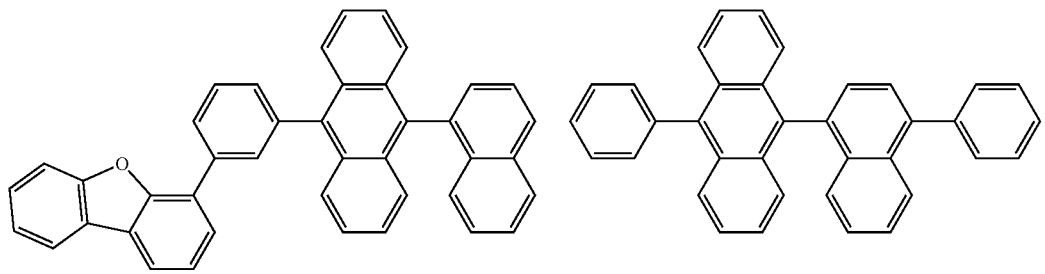
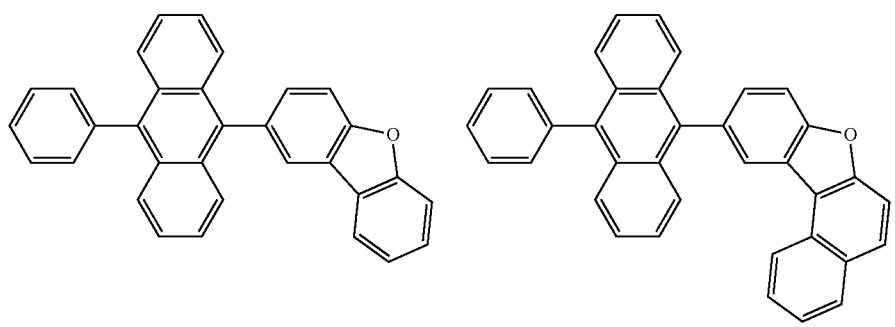
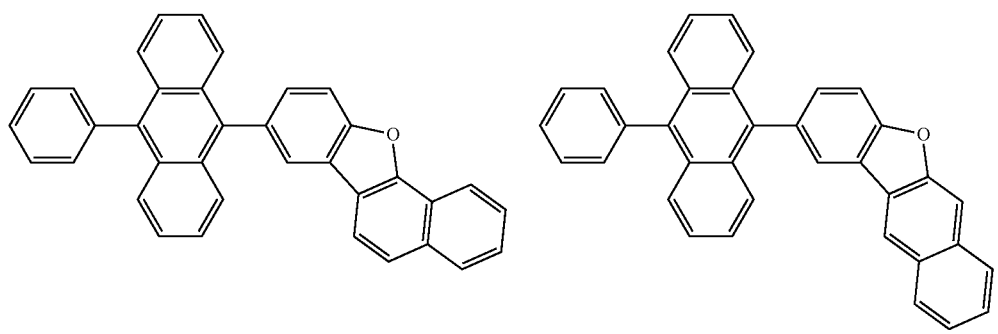
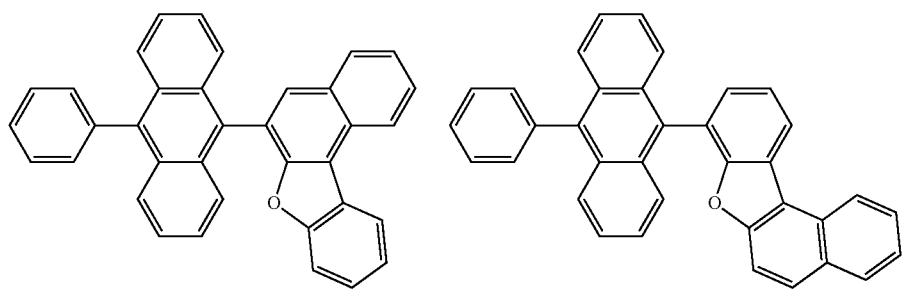
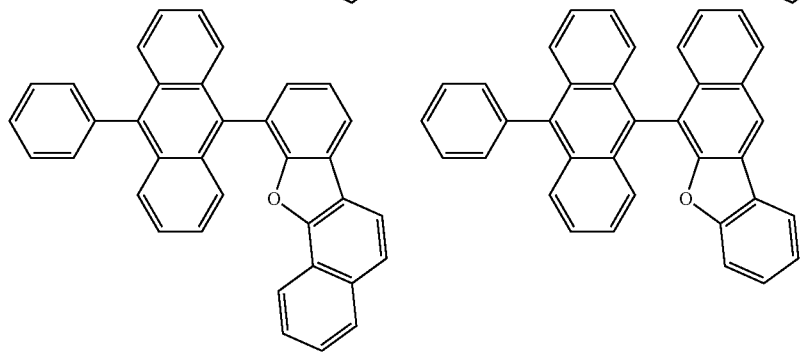

225
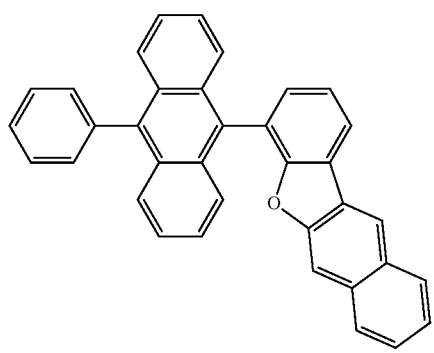
226
-continued
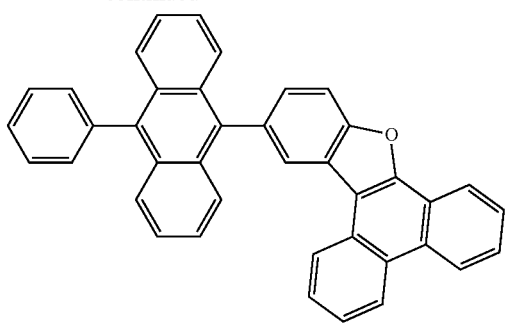
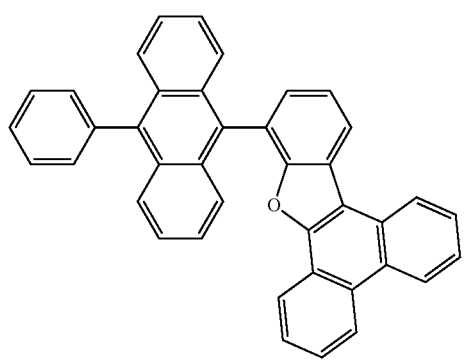
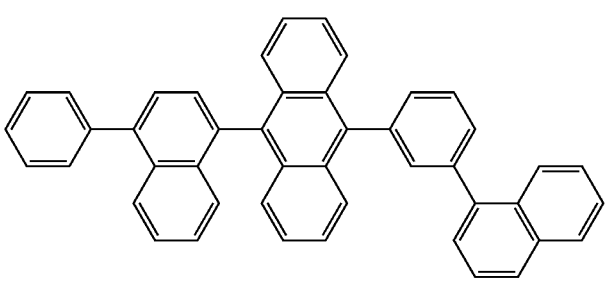
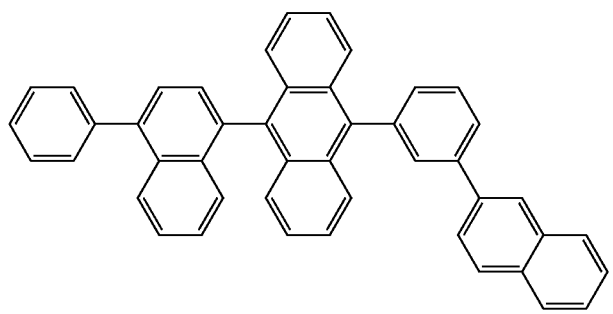
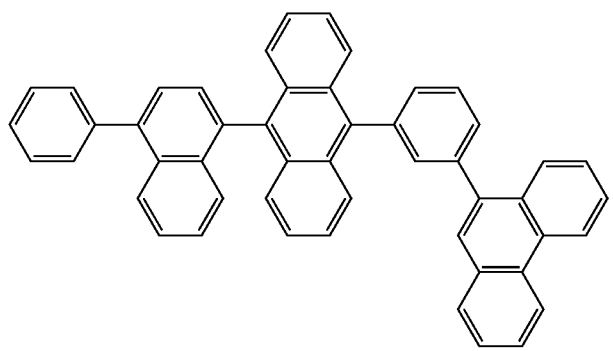
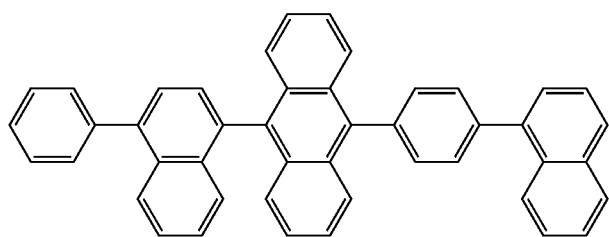

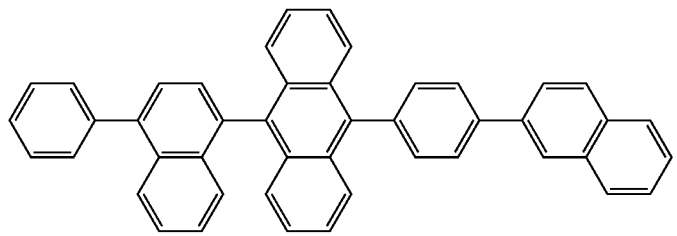
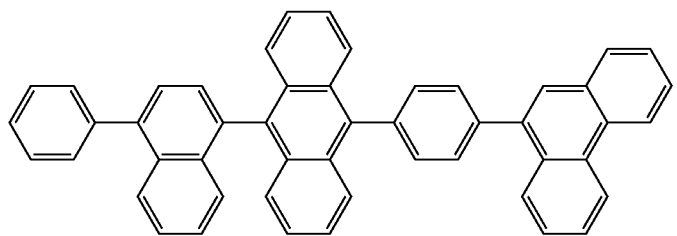
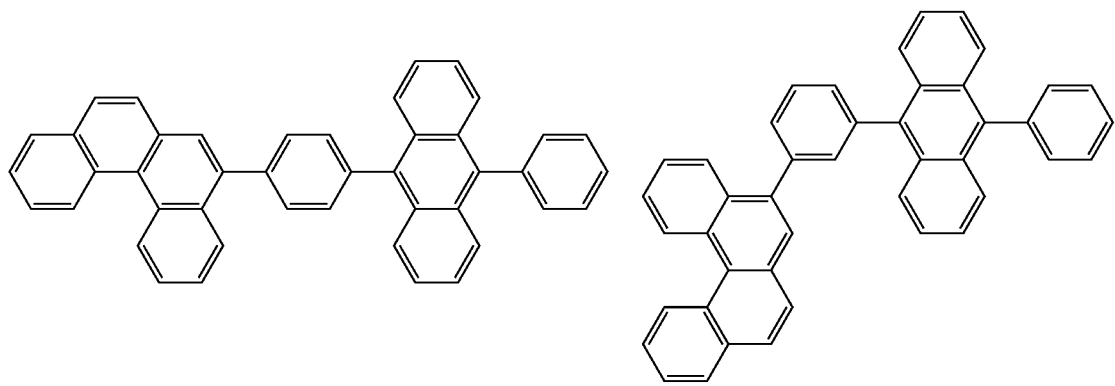
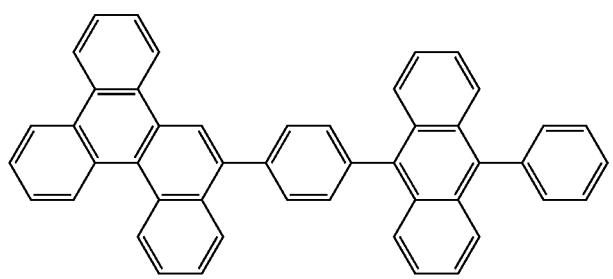
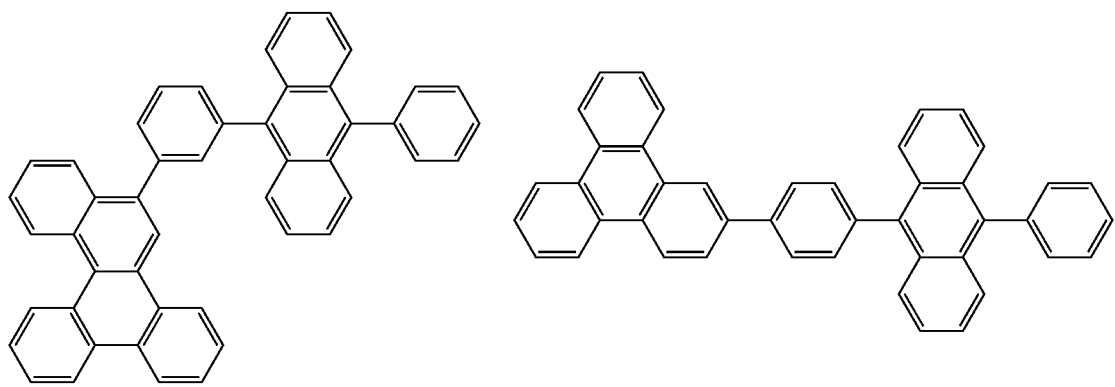

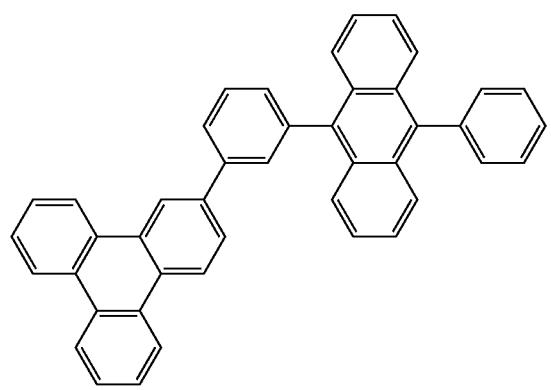

The pyrene derivative is represented by the following formula (6).

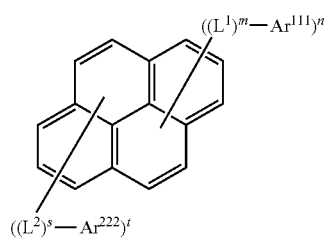

(6)

Ar$^{111}$ and Ar$^{222}$ in the formula (6) are independently a substituted or unsubstituted aryl group including 6 to 30 ring carbon atoms.

L$^1$ and L$^2$ are independently a substituted or unsubstituted divalent arylene group including 6 to 30 ring carbon atoms, or a heterocyclic group.

m is an integer from 0 to 1, n is an integer from 1 to 4, s is an integer from 0 to 1, and t is an integer from 0 to 3.

L$^1$ or Ar$^{111}$ is bonded to one of the positions 1 to 5 of the pyrene ring, and L$^2$ or Ar$^{222}$ is bonded to one of the positions 6 to 10 of the pyrene ring.

L$^1$ and L$^2$ in the formula (6) are preferably a substituted or unsubstituted phenylene group, a substituted or unsubstituted biphenylene group, a substituted or unsubstituted naphthylene group, a substituted or unsubstituted terphenylene group, a substituted or unsubstituted fluorenylene group, or a divalent aryl group formed by a combination of these groups.

Examples of a substituent include those mentioned above in connection with the formula (1). A substituent that may substitute L$^1$ and L$^2$ is preferably an alkyl group including 1 to 20 carbon atoms.

m in the formula (6) is preferably an integer from 0 to 1. n in the formula (6) is preferably an integer from 1 to 2. s in the formula (6) is preferably an integer from 0 to 1. t in the formula (6) is preferably an integer from 0 to 2.

Examples of the aryl group represented by Ar$^{111}$ and Ar$^{222}$ include those mentioned above in connection with the formula (1). Ar$^{111}$ and Ar$^{222}$ are preferably a substituted or unsubstituted aryl group including 6 to 20 ring carbon atoms, and more preferably a substituted or unsubstituted aryl group including 6 to 16 ring carbon atoms. Specific examples of a preferable aryl group include a phenyl group, a naphthyl group, a phenanthryl group, a fluorenyl group, a biphenyl group, an anthryl group, and a pyrenyl group.

When the organic thin film layer includes the compound represented by the formula (1) as a dopant, the content of the compound represented by the formula (1) in the organic thin film layer is preferably 0.1 to 20 mass %, and more preferably 1 to 10 mass %.

The compound represented by the formula (1) and the anthracene derivative or the pyrene derivative may also be used for a hole-injecting layer, a hole-transporting layer, an electron-injecting layer, or an electron-transporting layer in addition to the emitting layer.

When the organic EL device according to one aspect of the invention includes a plurality of organic thin film layers, the organic EL device may have a stacked structure such as an (anode/hole-injecting layer/emitting layer/cathode) stacked structure, an (anode/emitting layer/electron-injecting layer/cathode) stacked structure, an (anode/hole-injecting layer/emitting layer/electron-injecting layer/cathode) stacked structure, or an (anode/hole-injecting layer/hole-transporting layer/emitting layer/electron-injecting layer/cathode) stacked structure.

When the organic EL device includes a plurality of organic thin film layers, a decrease in luminance or lifetime due to quenching can be prevented. An emitting material, a doping material, a hole-injecting material, and an electron-injecting material may optionally be used in combination. The luminance or the luminous efficiency may be improved depending on the doping material. The hole-injecting layer, the emitting layer, and the electron-injecting layer may respectively include two or more layers. When the hole-injecting layer includes two or more layers, a layer into which holes are injected from the electrode is referred to as "hole-injecting layer", and a layer that receives holes from the hole-injecting layer, and transports the holes to the emitting layer is referred to as "hole-transporting layer". Likewise, when the electron-injecting layer includes two or more layers, a layer into which electrons are injected from the electrode is referred to as "electron-injecting layer", and a layer that receives electrons from the electron-injecting layer, and transports the electrons to the emitting layer is referred to as "electron-transporting layer". Each layer is selected taking account of the energy level of the material, the heat resistance of the material, the adhesion of the material to an organic layer or a metal electrode, and the like.

Examples of a material other than the compounds represented by the formulas (5) and (6) that may be used for the emitting layer together with the compound represented by the formula (1) include, but are not limited to, a fused polycyclic aromatic compound such as naphthalene, phenanthrene, rubrene, anthracene, tetracene, pyrene, perylene, chrysene, decacyclene, coronene, tetraphenylcyclopentadiene, pentaphenylcyclopentadiene, fluorene, and spirofluorene, and a derivative thereof, an organic metal complex such as tris(8-quinolinolate)aluminum, a triarylamine derivative, a styrylamine derivative, a stilbene derivative, a coumarin derivative, a pyran derivative, an oxazone derivative, a benzothiazole derivative, a benzoxazole derivative, a benzimidazole derivative, a pyrazine derivative, a cinnamate derivative, a diketopyrrolopyrrole derivative, an acridone derivative, a quinacridone derivative, and the like.

The hole-injecting layer is a layer that includes a substance that has a high hole-injecting capability. Examples of the substance that has a high hole-injecting capability include molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, a polymer compound (e.g., oligomer, dendrimer, and polymer), and the like.

The hole-transporting layer is a layer that includes a substance that has a high hole-transporting capability. An aromatic amine compound, a carbazole derivative, an anthracene derivative, and the like may be used to form the hole-transporting layer. A polymer compound such as poly(N-vinylcarbazole) (PVK) and poly(4-vinyltriphenylamine) (PVTPA) may also be used to form the hole-transporting layer. Note that another substance may also be used as long as the hole-transporting capability of the substance is higher than the electron-transporting capability. The layer that includes a substance that has a high hole-transporting capability may be a single layer, or may have a structure in which two or more layers formed of the substance that has a high hole-transporting capability are stacked.

The electron-transporting layer is a layer that includes a substance that has a high electron-transporting capability. The electron-transporting layer may be formed using 1) a metal complex such as an aluminum complex, a beryllium complex, or a zinc complex, 2) a heteroaromatic compound such as an imidazole derivative, a benzimidazole derivative, an azine derivative, a carbazole derivative, or a phenanthroline derivative, or 3) a polymer compound.

The electron-injecting layer is a layer that includes a substance that has a high electron-injecting capability. The electron-injecting layer may be formed using an alkali metal, an alkaline-earth metal, or a compound thereof (e.g., lithium (Li), lithium fluoride (LiF), cesium fluoride (CsF), calcium fluoride ($CaF_2$), and lithium oxide ($LiO_x$)).

In the organic EL device according to one aspect of the invention, the emitting layer may include at least one of the emitting material, the doping material, the hole-injecting material, the hole-transporting material, and the electron-injecting material in addition to at least one compound represented by the formula (1). A protective layer may be provided on the surface of the organic EL device, or the entire organic EL device may be protected with silicon oil, a resin, or the like so that the resulting organic EL device exhibits improved stability against temperature, humidity, atmosphere, and the like.

The anode is preferably formed on the substrate using a metal, an alloy, or an electrically conductive compound having a large work function (e.g., 4.0 eV or more), or a mixture thereof, for example. Specific examples of such a material include indium tin oxide (ITO), indium tin oxide that includes silicon or silicon oxide, indium zinc oxide, tungsten oxide, indium oxide that includes zinc oxide, graphene, and the like. Gold (Au), platinum (Pt), a nitride of a metal material (e.g., titanium nitride), and the like may also be used.

The cathode is preferably formed using a metal, an alloy, or an electrically conductive compound having a small work function (e.g., 3.8 eV or less), or a mixture thereof, for example. Specific examples of such a cathode material include the elements that belong to Group 1 or 2 in the periodic table (i.e., an alkali metal such as lithium (Li) and cesium (Cs), and an alkaline-earth metal such as magnesium (Mg)) and an alloy thereof (e.g., MgAg and AlLi), a rare-earth metal and an alloy thereof, and the like.

The anode and the cathode may optionally include two or more layers.

It is desirable that at least one side of the organic EL device be sufficiently transparent within the emission wavelength region of the device so that the device efficiently emits light. It is desirable that the substrate also be transparent. A transparent electrode is formed by deposition, sputtering, or the like using the above conductive material so that a given translucency is achieved. It is desirable that the emitting-side electrode have a light transmittance of 10% or more.

A glass substrate, a quartz substrate, a plastic substrate, or the like may be used as the substrate, for example. A flexible substrate may also be used. The term "flexible substrate" used herein refers to a substrate that can be bent (i.e., is flexible). Examples of such a flexible substrate include a plastic substrate formed of a polycarbonate or polyvinyl chloride, and the like.

Each layer of the organic EL device may be formed using a dry film-forming method such as a vacuum deposition method, a sputtering method, a plasma method, or an ion plating method, or a wet film-forming method such as a spin coating method, a dipping method, or a flow coating method. The thickness of each layer is not particularly limited as long as each layer has an appropriate thickness. If the thickness of each layer is too large, a high applied voltage may be required to obtain a constant optical output (i.e., deterioration in efficiency may occur). If the thickness of each layer is too small, pinholes or the like may occur, and sufficient luminance may not be obtained even if an electric field is applied. The thickness of each layer is normally 5 nm to 10 μm, and preferably 10 nm to 0.2 μm.

When using a wet film-forming method, the material for forming each layer is dissolved or dispersed in an appropriate solvent (e.g., ethanol, chloroform, tetrahydrofuran, or dioxane), and a thin film is formed using the solution or the dispersion. The solvent is not particularly limited.

An organic EL material-containing solution that includes the compound represented by the formula (1) (i.e., organic EL material) and a solvent may be used as a solution that is suitable for the wet film-forming method.

It is preferable that the organic EL material include a host material and a dopant material, the dopant material be the compound represented by the formula (1), and the host material be at least one compound selected from the compound represented by the formula (5).

An appropriate resin or an appropriate additive may be added to each organic thin film layer in order to improve the film-forming capability and prevent the occurrence of pinholes, for example.

The organic EL device according to one aspect of the invention may be used as a planar emitting device (e.g., a flat panel display used for a wall TV), a backlight of a copier, a printer, or a liquid crystal display, a light source of an instrument (meter), a signboard, a marker lamp (light), and the like. The compound according to one aspect of the invention may also be used in the fields of an electrophotographic photoreceptor, a photoelectric conversion device, a solar cell, an image sensor, and the like in addition to the field of an organic EL device.

EXAMPLES

The invention is further described below by way of examples. Note that the invention is not limited to the following examples.

Example 1

Synthesis of Compound 1

A compound 1 was synthesized according to the following scheme.

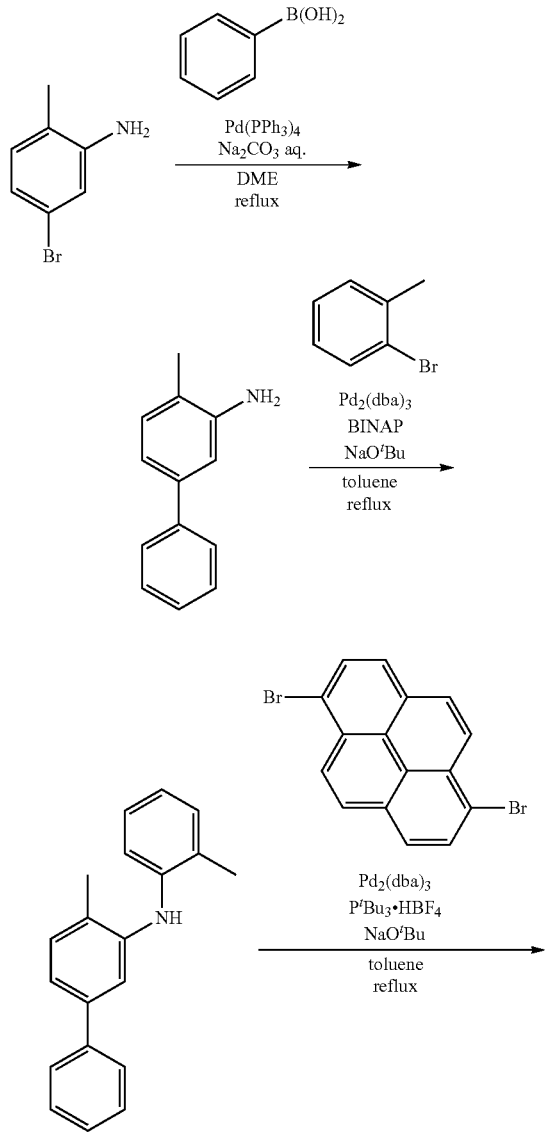

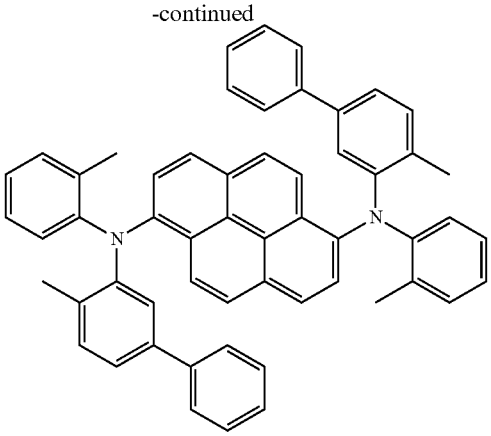

Compound 1

(1-1) Synthesis of 2-methyl-5-phenylaniline

A mixture of 5-bromo-2-methylaniline (10.0 g), phenylboronic acid (8.52 g), tetrakis(triphenylphosphine)palladium (0) (1.86 g), a 2 M sodium carbonate aqueous solution (80.6 mL), and 1,2-dimethoxyethane (DME) (135 mL) was refluxed for 5 hours in an argon atmosphere. The resulting reaction mixture was cooled to room temperature, and extracted with dichloromethane. The organic layer was washed with water, and dried over anhydrous magnesium sulfate, and the solvent was evaporated under reduced pressure. The resulting crude 2-methyl-5-phenylaniline was used directly for the subsequent step.

(1-2) Synthesis of 2-methyl-N-(o-tolyl)-5-phenylaniline

A mixture of crude 2-methyl-5-phenylaniline obtained by the step (1-1), 2-bromotoluene (7.35 g), tris(dibenzylideneacetone)dipalladium(0) (0.98 g), 2,2'-bis(diphenylphosphino)-1,1'-binaphthyl (BINAP) (1.67 g), sodium t-butoxide (7.75 g), and toluene (270 g) was refluxed for 5 hours in an argon atmosphere. The resulting reaction mixture was cooled to room temperature. After the addition of water, the mixture was extracted with toluene. The organic layer was washed with a saturated sodium chloride solution, and dried over anhydrous magnesium sulfate, and the solvent was evaporated under reduced pressure. The residue was purified by silica gel column chromatography to obtain 2-methyl-N-(o-tolyl)-5-phenylaniline (10.17 g). The yield achieved by the steps (1-1) and (1-2) was 69%.

(1-3) Synthesis of Compound 1

A mixture of 1,6-dibromopyrene (5.82 g), 2-methyl-N-(o-tolyl)-5-phenylaniline (10.17 g) obtained by the step (1-2), tris(dibenzylideneacetone)dipalladium(0) (0.89 g), tri-t-butylphosphine tetrafluoroborate (0.56 g), sodium t-butoxide (6.22 g), and toluene (162 mL) was refluxed for 7 hours in an argon atmosphere. The resulting reaction mixture was cooled to room temperature. After the addition of water, the mixture was extracted with toluene. The organic layer was washed with a saturated sodium chloride solution, and dried over anhydrous magnesium sulfate, and the solvent was evaporated under reduced pressure. The residue was purified by silica gel column chromatography and recrystallization to obtain a compound 1 (0.29 g). The yield was 3%. It was confirmed by mass spectrum analysis that the compound 1 was obtained. The compound 1 had a molecular weight of 744.35 (m/e=744).

Example 2

Synthesis of Compound 2

A compound 2 was synthesized according to the following scheme.

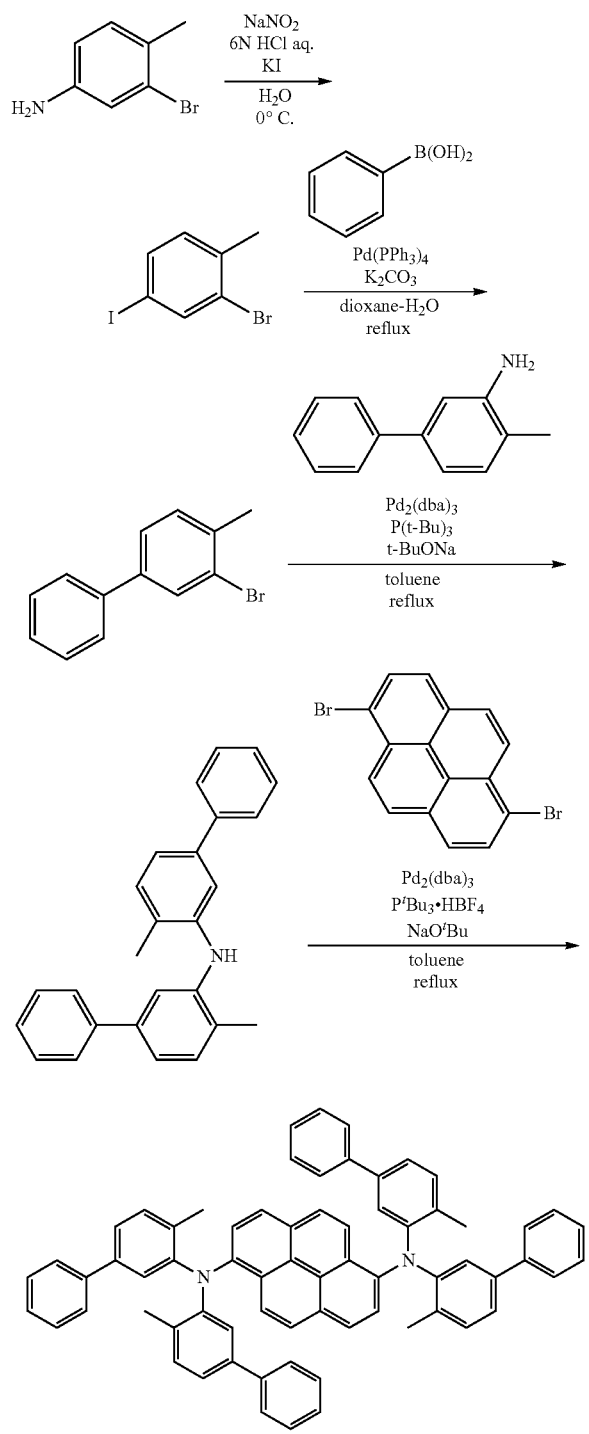

Compound 2

(2-1) Synthesis of 2-bromo-4-iodotoluene

A mixture of 3-bromo-4-methylaniline (18.6 g) and 6 M hydrochloric acid (80 mL) was cooled to −5° C. in an argon atmosphere. After the dropwise addition of an aqueous solution (15 mL) of sodium nitrite (7.35 g) while maintaining the mixture at 0° C. or less, the resulting mixture was stirred at −8° C. for 45 minutes. Potassium iodide (33.2 g) was added to the mixture over 3 hours while maintaining the mixture at 00° C. or less. The resulting reaction mixture was returned to room temperature. After the addition of a 10% sodium hydrogen sulfite aqueous solution (50 mL), the mixture was extracted with diethyl ether. The organic layer was washed with a 10% sodium hydrogen sulfite aqueous solution, and dried over anhydrous magnesium sulfate, and the solvent was evaporated under reduced pressure. The residue was purified by silica gel column chromatography to obtain 2-bromo-4-iodotoluene (14.5 g). The yield was 49%.

(2-2) Synthesis of 2-bromo-1-methyl-4-phenylbenzene

A mixture of 2-bromo-4-iodotoluene (14.5 g) obtained by the step (2-1), phenylboronic acid (6.35 g), tetrakis(triphenylphosphine)palladium (0) (1.69 g), potassium carbonate (20.2 g), 1,4-dioxane (117 mL), and water (13 mL) was refluxed for 3 hours in an argon atmosphere. The resulting reaction mixture was returned to room temperature, and extracted with dichloromethane. The organic layer was washed with a saturated sodium chloride solution, and the solvent was evaporated under reduced pressure. The residue was purified by silica gel column chromatography to obtain 2-bromo-1-methyl-4-phenylbenzene (8.6 g). The yield was 71%.

(2-3) Synthesis of N,N-bis(2-methyl-5-phenylphenyl)amine

A mixture of crude 2-methyl-5-phenylaniline produced from 6.59 g of 5-bromo-2-methylaniline in the same manner as in the step (1-1) of Example 1, 2-bromo-1-methyl-4-phenylbenzene (7.0 g) obtained by the step (2-2), tris(dibenzylideneacetone)dipalladium(0) (0.65 g), BINAP (1.1 g), sodium t-butoxide (5.1 g), and toluene (100 mL) was refluxed for 4.5 hours in an argon atmosphere. The resulting reaction mixture was cooled to room temperature, and filtered through celite, and the solvent was evaporated under reduced pressure. The residue was purified by silica gel column chromatography to obtain N,N-bis(2-methyl-5-phenylphenyl)amine (6.03 g). The yield was 61%.

(2-4) Synthesis of Compound 2

A mixture of 1,6-dibromopyrene (5.09 g), N,N-bis(2-methyl-5-phenylphenyl)amine (11.87 g) obtained by the step (2-3), tris(dibenzylideneacetone)dipalladium(0) (0.78 g), tri-t-butylphosphine tetrafluoroborate (0.82 g), sodium t-butoxide (4.08 g), and toluene (150 mL) was refluxed for 6.5 hours in an argon atmosphere. After the addition of tris(dibenzylideneacetone)dipalladium(0) (0.16 g) and tri-t-butylphosphine tetrafluoroborate (0.16 g) to the resulting reaction mixture, the resulting mixture was refluxed for 5 hours. The resulting reaction mixture was returned to room temperature. After the addition of water, a solid produced in the system was filtered off, washed with water and methanol, and purified by silica gel column chromatography and recrystallization to obtain a compound 2 (2.18 g). The yield was 17%. It was confirmed by mass spectrum analysis that the compound 2 was obtained. The compound 2 had a molecular weight of 896.41 (m/e=896).

Example 3

Synthesis of Compound 3

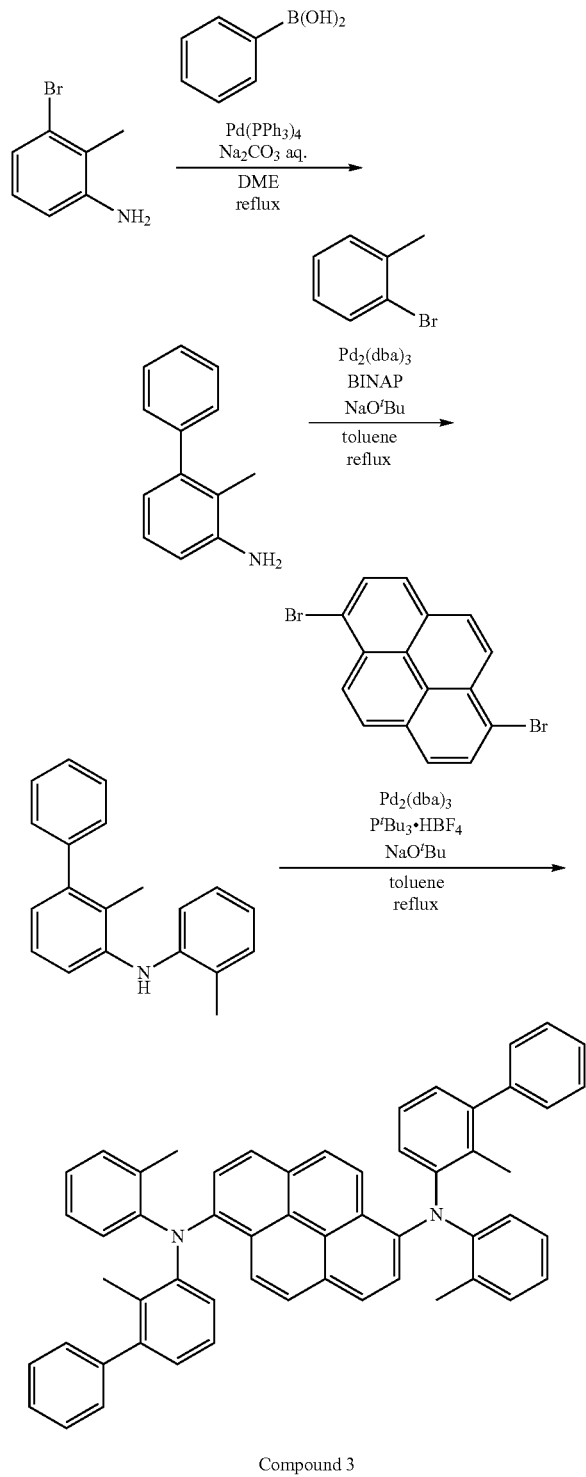

Compound 3

A compound 3 was obtained in the same manner as in Example 1, except that 3-bromo-2-methylaniline was used instead of 5-bromo-2-methylaniline. It was confirmed by mass spectrum analysis that the compound 3 was obtained. The compound 3 had a molecular weight of 744.35 (m/e=744).

Example 4

Synthesis of Compound 4

A compound 4 was synthesized according to the following scheme.

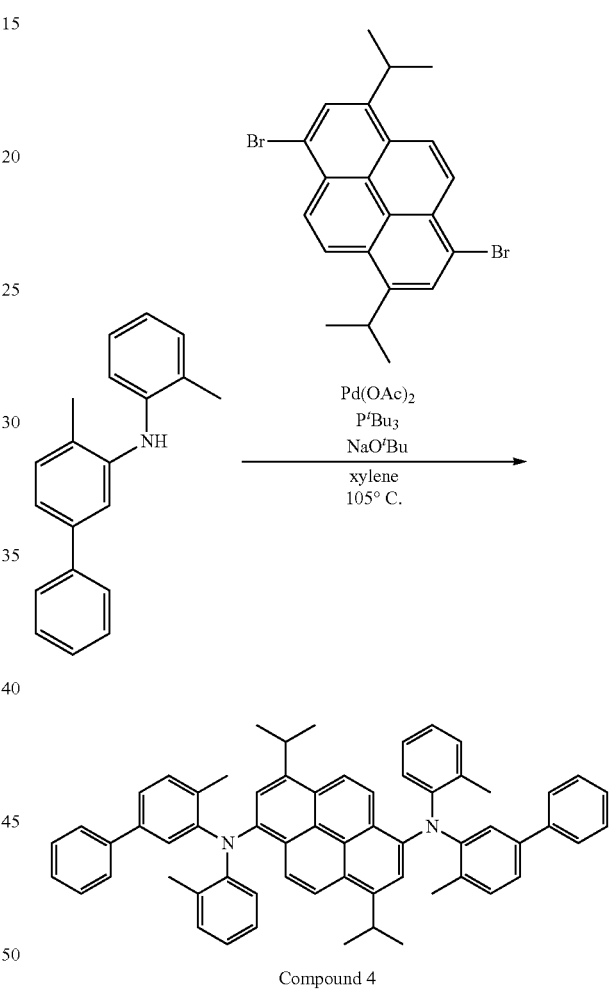

Compound 4

A mixture of 1,6-dibromo-3,8-diisopropylpyrene (18.4 g), 2-methyl-N-(o-tolyl)-5-phenylaniline (10.17 g) obtained by the step (1-2), palladium(II) acetate (0.37 g), tri-t-butylphosphine (0.67 g), sodium t-butoxide (9.6 g), and xylene (430 mL) was stirred at 105° C. for 21.5 hours in an argon atmosphere. The resulting reaction mixture was cooled to room temperature. After the addition of methanol, the resulting mixture was stirred for 3 hours. A solid that precipitated was filtered off, and purified by silica gel column chromatography and recrystallization to obtain a compound 4 (13.4 g). The yield was 37%. It was confirmed by mass spectrum analysis that the compound 4 was obtained. The compound 4 had a molecular weight of 828.44 (m/e=828).

Example 5

Synthesis of Compound 5

A compound 5 was synthesized according to the following scheme.

Example 6

Synthesis of Compound 6

A compound 6 was synthesized according to the following scheme.

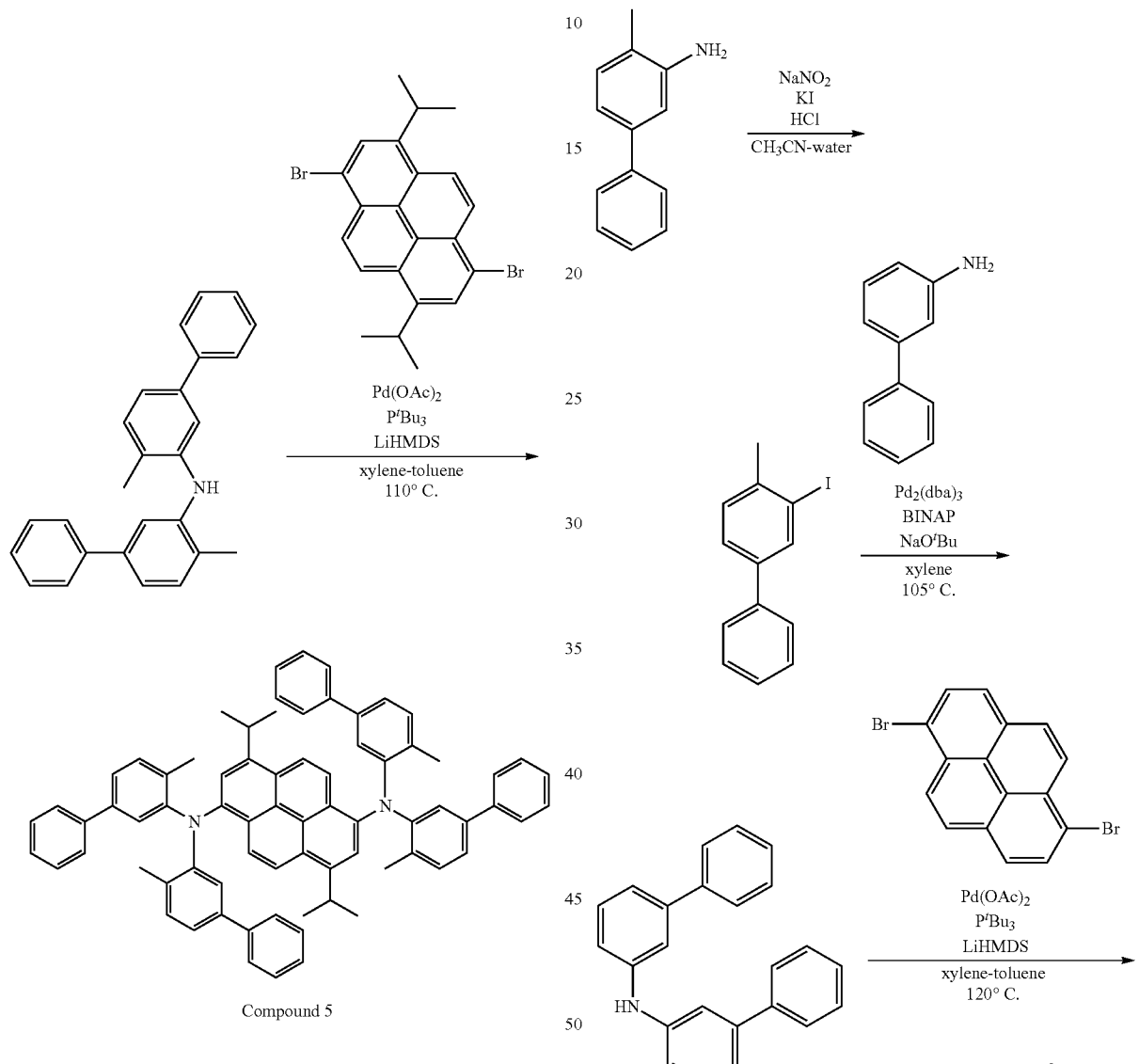

Compound 5

A mixture of 1,6-dibromo-3,8-diisopropylpyrene (14 g), N,N-bis(2-methyl-5-phenylphenyl)amine (24.2 g) obtained by the step (2-3), palladium(II) acetate (0.28 g), tri-t-butyl-phosphine (0.51 g), a toluene solution (1 M, 75.6 mL) of LiHMDS, and xylene (280 mL) was stirred at 110° C. for 13 hours in an argon atmosphere. The resulting reaction mixture was cooled to room temperature. After the addition of methanol, the resulting mixture was stirred for 0.5 hours. A solid that precipitated was filtered off, and purified by silica gel column chromatography and recrystallization to obtain a compound 5 (16.6 g). The yield was 53%. It was confirmed by mass spectrum analysis that the compound 5 was obtained. The compound 5 had a molecular weight of 980.51 (m/e=980).

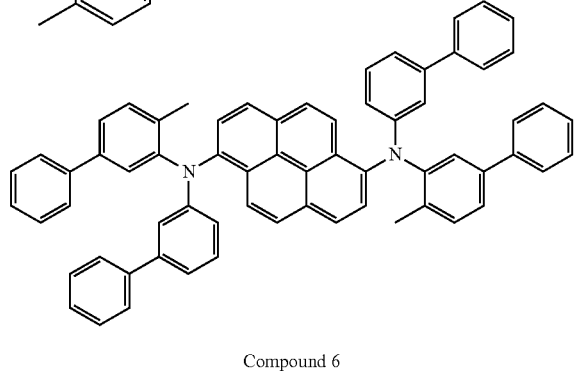

Compound 6

241

(6-1) Synthesis of 3-iodo-4-methylbiphenyl

Concentrated hydrochloric acid (169 mL) was added dropwise to 2-methyl-N-(o-tolyl)-5-phenylaniline (62.6 g), acetonitrile (130 mL), and ice water (200 g) at 0° C. or less, and the mixture was stirred for 30 minutes. An aqueous solution (250 mL) of sodium nitrite (28.4 g) was added dropwise to the resulting reaction mixture at −5° C., and the resulting mixture was stirred at −5° C. for 1 hour. After the addition of an aqueous solution (200 mL) of potassium iodide (142 g) to the resulting reaction mixture at −2° C., the resulting mixture was stirred at room temperature overnight. After the addition of chloroform and a sodium thiosulfate aqueous solution to the resulting reaction mixture, the resulting mixture was stirred. After separating the resulting reaction mixture, the chloroform layer was washed with water, and the solvent was evaporated under reduced pressure. The residue was purified by silica gel column chromatography to obtain 3-iodo-4-methylbiphenyl (73.4 g). The yield was 73%.

(6-2) Synthesis of 2-methyl-5-phenyl-N-(3-biphenyl)aniline

A mixture of 3-iodo-4-methylbiphenyl (38 g) synthesized by the step (6-1), 3-aminobiphenyl (43.7 g), tris(dibenzylideneacetone)dipalladium(0) (4.57 g), 2,2'-bis(diphenylphosphino)-1,1'-binaphthyl (BINAP) (2.41 g), sodium t-butoxide (27.3 g), and xylene (820 mL) was stirred at 105° C. for 9 hours in an argon atmosphere. The resulting reaction mixture was cooled to room temperature, and the solvent was evaporated under reduced pressure. The residue was purified by silica gel column chromatography to obtain 2-methyl-5-phenyl-N-(3-biphenyl)aniline (23 g). The yield was 53%.

(6-3) Synthesis of Compound 6

A mixture of 1,6-dibromopyrene (10 g), 2-methyl-5-phenyl-N-(3-biphenyl)aniline (20.5 g) obtained by the step (6-2), palladium(II) acetate (0.25 g), tri-t-butylphosphine (0.45 g), a toluene solution (1 M, 67 mL) of LiHMDS, and xylene (300 mL) was stirred at 120° C. for 18 hours in an argon atmosphere. The resulting reaction mixture was cooled to room temperature, concentrated, and purified by silica gel column chromatography and recrystallization to obtain a compound 6 (17.9 g). The yield was 74%. It was confirmed by mass spectrum analysis that the compound 6 was obtained. The compound 6 had a molecular weight of 868.38 (m/e=868).

Example 7

Synthesis of Compound 7

A compound 7 was synthesized according to the following scheme.

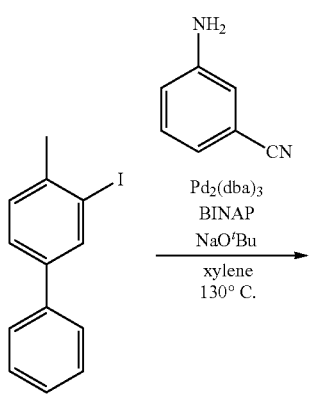

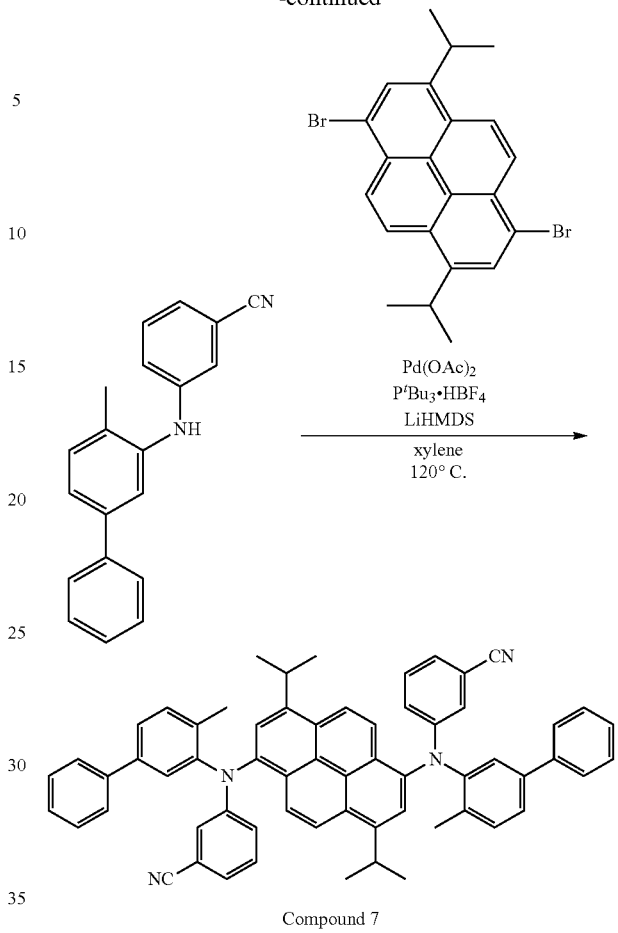

Compound 7

(7-1) Synthesis of 3-(2-methyl-5-phenylanilino)benzonitrile

A mixture of 3-aminobenzonitrile (2.41 g), 3-iodo-4-methylbiphenyl (5.0 g), tris(dibenzylideneacetone)dipalladium(0) (0.23 g), 2,2'-bis(diphenylphosphino)-1,1'-binaphthyl (BINAP) (0.32 g), sodium t-butoxide (2.45 g), and xylene (57 mL) was stirred at 110° C. for 1 hour, and then stirred at 130° C. for 2 hours in an argon atmosphere. After the addition of tris(dibenzylideneacetone)dipalladium(0) (0.23 g) and 2,2'-bis(diphenylphosphino)-1,1'-binaphthyl (BINAP) (0.32 g), the resulting mixture was stirred for 14 hours. The resulting reaction mixture was cooled to room temperature, and the solvent was evaporated under reduced pressure. The residue was purified by silica gel column chromatography to obtain 3-(2-methyl-5-phenylanilino)benzonitrile (2.32 g). The yield was 48%.

(7-2) Synthesis of Compound 7

A mixture of 1,6-dibromo-3,8-diisopropylpyrene (1.65 g), 3-(2-methyl-5-phenylanilino)benzonitrile (2.32 g) obtained by the step (7-1), palladium(II) acetate (0.033 g), tri-t-butylphosphine tetrafluoroborate (0.086 g), a toluene solution (1 M, 8.9 mL) of LiHMDS, and xylene (74 mL) was stirred at 120° C. overnight in an argon atmosphere. The resulting reaction mixture was cooled to room temperature, concentrated, and purified by silica gel column chromatography and recrystallization to obtain a compound 7 (1.9 g). The yield was 60%. It was confirmed by mass spectrum analysis that the compound 7 was obtained. The compound 7 had a molecular weight of 850.40 (m/e=850).

Example 8

Synthesis of Compound 8

A compound 8 was synthesized according to the following scheme.

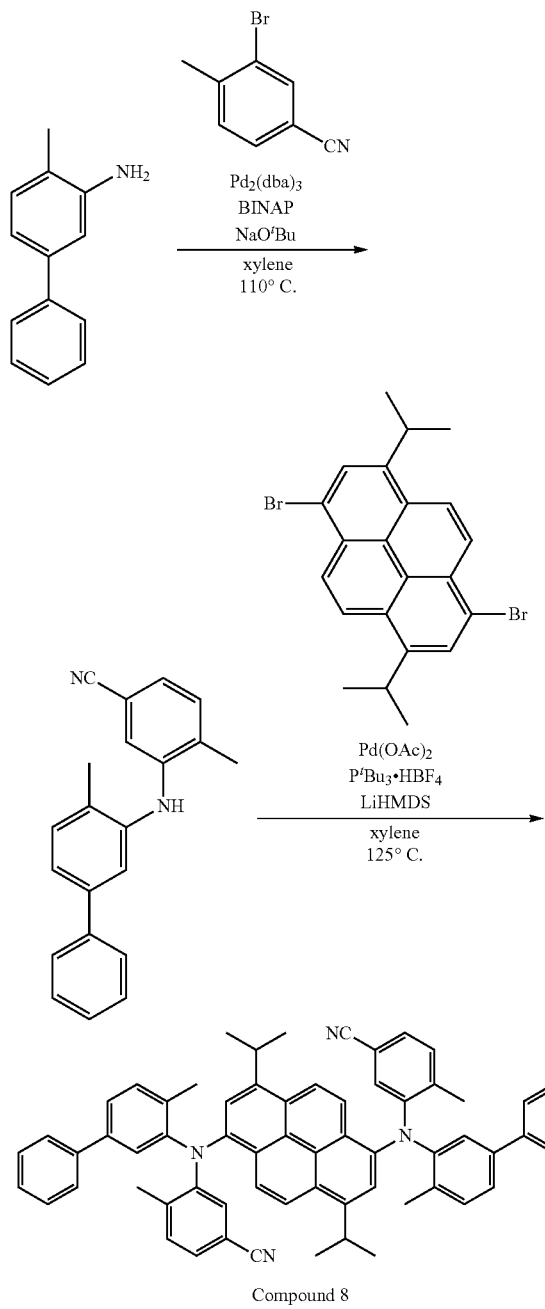

Compound 8

(8-1) Synthesis of 4-methyl-3-(2-methyl-5-phenylanilino)benzonitrile

A mixture of 3-bromo-4-methylbenzonitrile (5.88 g), 2-methyl-N-(o-tolyl)-5-phenylaniline (5.0 g), tris(dibenzylideneacetone)dipalladium(0) (0.50 g), 2,2'-bis(diphenylphosphino)-1,1'-binaphthyl (BINAP) (0.68 g), sodium t-butoxide (3.93 g), and xylene (91 mL) was stirred at 110° C. for 3.5 hours in an argon atmosphere. The resulting reaction mixture was cooled to room temperature, and the solvent was evaporated under reduced pressure. The residue was purified by silica gel column chromatography to obtain 4-methyl-3-(2-methyl-5-phenylanilino)benzonitrile (5.25 g). The yield was 63%.

(8-2) Synthesis of Compound 8

A mixture of 1,6-dibromo-3,8-diisopropylpyrene (5.0 g), 4-methyl-3-(2-methyl-5-phenylanilino)benzonitrile (7.39 g) obtained by the step (8-1), palladium(II) acetate (0.10 g), tri-t-butylphosphine tetrafluoroborate (0.26 g), a toluene solution (1 M, 27 mL) of LiHMDS, and xylene (225 mL) was stirred at 125° C. for 6 hours in an argon atmosphere. The resulting reaction mixture was cooled to room temperature, and purified by silica gel column chromatography and recrystallization to obtain a compound 8 (4.26 g). The yield was 43%. It was confirmed by mass spectrum analysis that the compound 8 was obtained. The compound 8 had a molecular weight of 878.43 (m/e=878).

Example 9

Synthesis of Compound 9

A compound 9 was synthesized according to the following scheme.

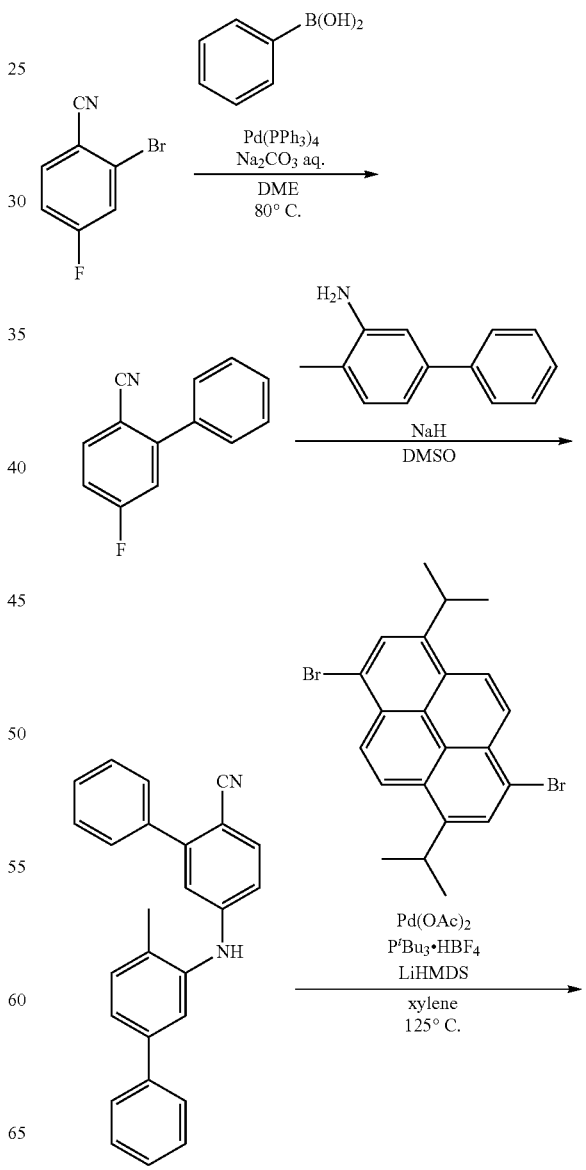

245

-continued

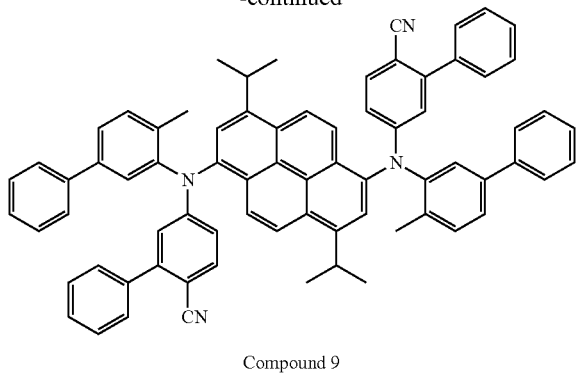

Compound 9

(9-1) Synthesis of 4-fluoro-2-phenylbenzonitrile

A mixture of 2-bromo-4-fluorobenzonitrile (25.0 g), phenylboronic acid (18.32 g), tetrakis(triphenylphosphine)palladium (0) (2.89 g), a 2 M sodium carbonate aqueous solution (125 mL), and 1,2-dimethoxyethane (DME) (250 mL) was stirred at 80° C. for 3 hours in an argon atmosphere. The resulting reaction mixture was cooled to room temperature, and extracted with ethyl acetate. The organic layer was washed with water and a saturated sodium chloride solution, and dried over anhydrous magnesium sulfate, and the solvent was evaporated under reduced pressure. The residue was purified by silica gel column chromatography to obtain 4-fluoro-2-phenylbenzonitrile (22.1 g). The yield was 90%.

(9-2) Synthesis of 4-(2-methyl-5-phenylanilino)-2-phenylbenzonitrile

Sodium hydride (2.2 g) was added to a DMSO (32 mL) solution of 2-methyl-N-(o-tolyl)-5-phenylaniline (9.16 g), and the mixture was stirred at room temperature for 1 hour. A DMSO (31 mL) solution of 4-fluoro-2-phenylbenzonitrile (4.93 g) synthesized in the step (9-1) was added dropwise to the resulting reaction mixture over 1 hour with water cooling, and the mixture was stirred for 6 hours. The resulting reaction mixture was diluted with toluene (150 mL). The dilution was added to a hydrochloric acid-ice mixture (100 mL), and the resulting mixture was stirred for 1 hour. After separating the resulting mixture, the toluene layer was washed with hydrochloric acid and a saturated sodium chloride solution, and dried over anhydrous magnesium sulfate, and the solvent was evaporated under reduced pressure. The residue was purified by silica gel column chromatography to obtain 4-(2-methyl-5-phenylanilino)-2-phenylbenzonitrile (2.73 g). The yield was 30%.

(9-3) Synthesis of Compound 9

A mixture of 1,6-dibromo-3,8-diisopropylpyrene (3.5 g), 4-(2-methyl-5-phenylanilino)-2-phenylbenzonitrile (5.68 g) obtained by the step (9-2), palladium(II) acetate (0.07 g), tri-t-butylphosphine tetrafluoroborate (0.18 g), a toluene solution (1 M, 18.9 mL) of LiHMDS, and xylene (158 mL) was stirred at 125° C. for 6 hours in an argon atmosphere. The resulting reaction mixture was cooled to room temperature. After the addition of water, the mixture was stirred, and a solid produced was filtered off. The solid was purified by silica gel column chromatography and recrystallization to obtain a compound 9 (4.8 g). The yield was 60%. It was confirmed by mass spectrum analysis that the compound 9 was obtained. The compound 9 had a molecular weight of 1,002.47 (m/e=1,002).

246

Example 10

Fabrication of Organic EL Device

A glass substrate provided with an ITO transparent electrode (anode) (25 mm×75 mm×1.1 mm (thickness)) (manufactured by Geomatics) was subjected to ultrasonic cleaning for 5 minutes in isopropyl alcohol, and subjected to UV ozone cleaning for 30 minutes.

The glass substrate was then mounted on the substrate holder of a vacuum deposition device, and a compound HI-1 was deposited on the side of the glass substrate on which the linear transparent electrode was formed so as to cover the transparent electrode to form an HI-1 film having a thickness of 10 nm. The HI-1 film functions as a hole-injecting layer.

A compound HT-1 was deposited on the HI-1 film to form an HT-1 film having a thickness of 80 nm on the HI-1 film. The HT-1 film functions as a first hole-transporting layer.

A compound HT-2 was deposited on the HT-1 film to form an HT-2 film having a thickness of 10 nm on the HT-1 film. The HT-2 film functions as a second hole-transporting layer.

A compound BH-1 (host material) and the compound 1 (dopant material) were codeposited on the HT-2 film so that the ratio (weight ratio) of the compound 1 was 4% to form an emitting layer having a thickness of 25 nm.

A compound ET-1 was deposited on the emitting layer to form an electron-transporting layer having a thickness of 25 nm. A compound ET-2 (electron-injecting material) was deposited on the electron-transporting layer to form an electron-injecting layer having a thickness of 10 nm. LiF was deposited on the electron-injecting layer to form an LiF film having a thickness of 1 nm. Al was deposited on the LiF film to form a metal cathode having a thickness of 80 nm.

An organic EL device was thus fabricated. The compounds used to fabricate the organic EL device are shown below.

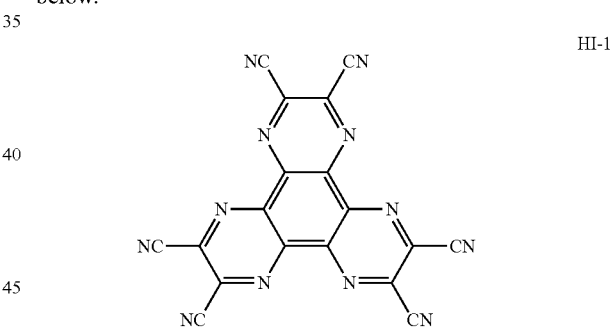

HI-1

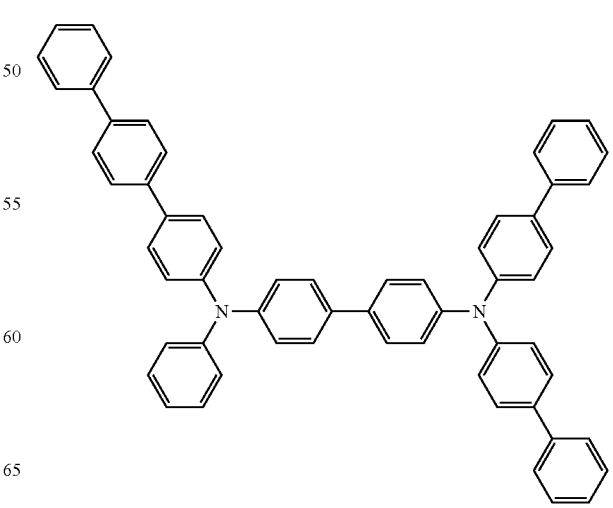

HT-1

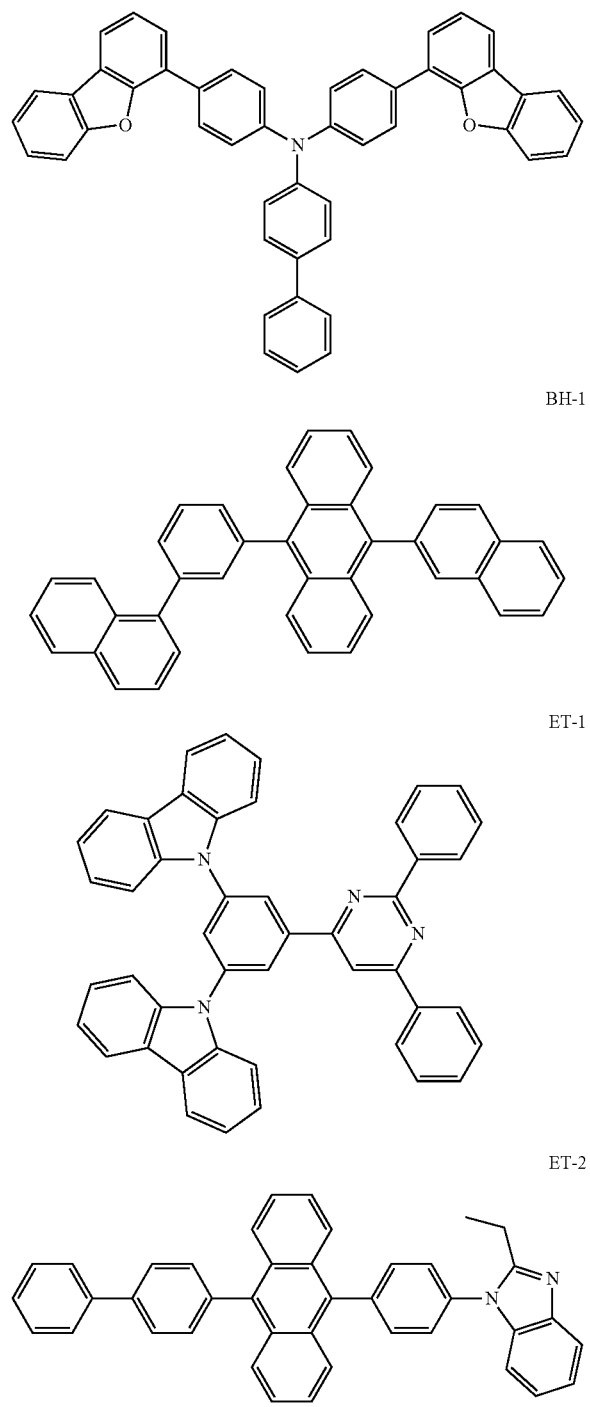

HT-2

BH-1

ET-1

ET-2

Evaluation of Organic EL Device

The organic EL device was evaluated as described below. Specifically, a voltage was applied to the organic EL device so that the current density was 10 mA/cm², and the EL emission spectrum was measured using a spectroradiometer ("CS-1000" manufactured by Konica Minolta, Inc.). The external quantum efficiency (EQE) (%) and the emission peak wavelength were calculated from the resulting spectral radiance spectrum. The results are shown in Table 1.

Examples 11 to 17 and Comparative Examples 1 to 6

An organic EL device was fabricated and evaluated in the same manner as in Example 10, except that the compound listed in Table 1 was used instead of the compound 1. The results are shown in Table 1.

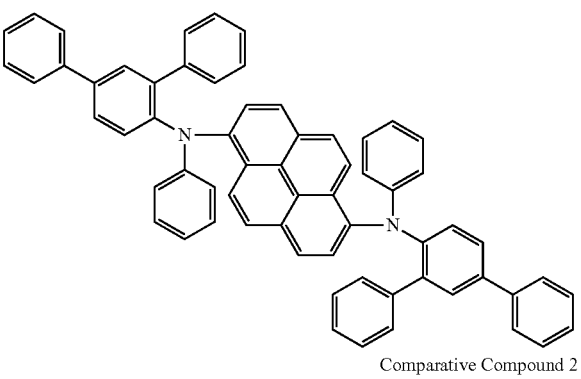

Comparative Compound 1

Comparative Compound 2

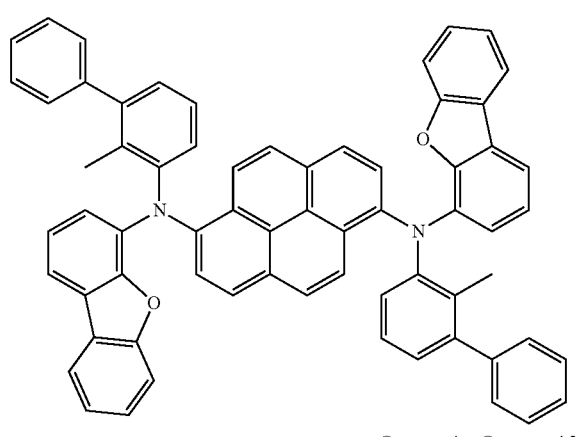

Comparative Compound 3

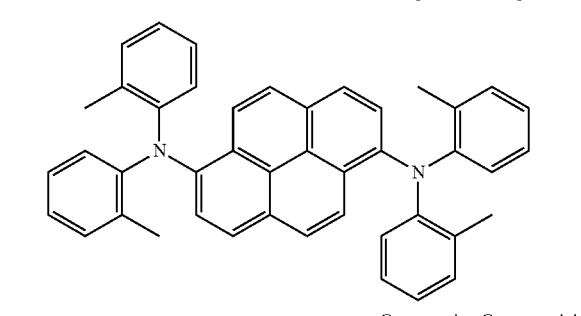

Comparative Compound 4

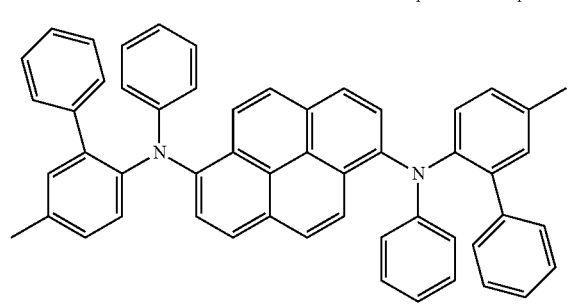

-continued

Comparative Compound 5

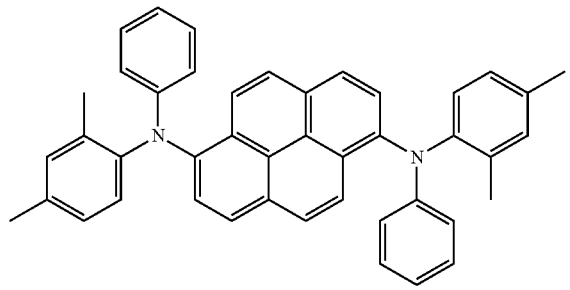

Comparative Compound 6

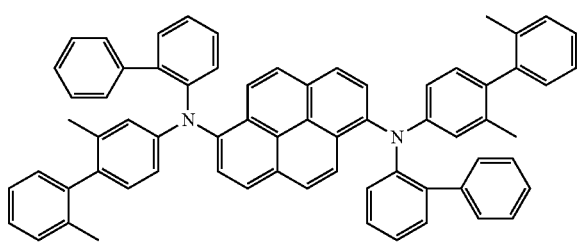

TABLE 1

| | Dopant material | EQE (%) | Emission peak wavelength (nm) |
|---|---|---|---|
| Example 10 | Compound 1 | 10.1 | 458 |
| Example 11 | Compound 2 | 10.5 | 459 |
| Example 12 | Compound 3 | 10.0 | 459 |
| Example 13 | Compound 4 | 10.2 | 461 |
| Example 14 | Compound 5 | 10.5 | 461 |
| Example 15 | Compound 6 | 10.2 | 461 |
| Example 16 | Compound 7 | 10.1 | 458 |
| Example 17 | Compound 8 | 10.0 | 454 |
| Comparative Example 1 | Comparative compound 1 | 9.4 | 469 |
| Comparative Example 2 | Comparative compound 2 | 9.3 | 457 |
| Comparative Example 3 | Comparative compound 3 | 9.6 | 458 |
| Comparative Example 4 | Comparative compound 4 | 9.4 | 467 |
| Comparative Example 5 | Comparative compound 5 | 9.2 | 466 |
| Comparative Example 6 | Comparative compound 6 | 9.3 | 471 |

Example 18

Fabrication of Organic EL Device

A glass substrate provided with an ITO transparent electrode (anode) (25 mm×75 mm×1.1 mm (thickness)) (manufactured by Geomatics) was subjected to ultrasonic cleaning for 5 minutes in isopropyl alcohol, and subjected to UV ozone cleaning for 30 minutes.

The glass substrate was then mounted on the substrate holder of a vacuum deposition device, and a compound HI-1 was deposited on the side of the glass substrate on which the linear transparent electrode was formed so as to cover the transparent electrode to form an HI-1 film having a thickness of 5 nm. The HI-1 film functions as a hole-injecting layer.

A compound HT-1 was deposited on the HI-1 film to form an HT-1 film having a thickness of 90 nm on the HI-1 film. The HT-1 film functions as a first hole-transporting layer.

A compound HT-2 was deposited on the HT-1 film to form an HT-2 film having a thickness of 5 nm on the HT-1 film. The HT-2 film functions as a second hole-transporting layer.

A compound BH-2 (host material) and the compound 1 (dopant material) were co-deposited on the HT-2 film so that the ratio (weight ratio) of the compound 1 was 4% to form an emitting layer having a thickness of 25 nm.

A compound ET-3 was deposited on the emitting layer to form an electron-transporting layer having a thickness of 5 nm. A compound ET-2 and a compound ET-4 were deposited on the electron-transporting layer in a weight ratio of 1:1 to form an electron-injecting layer having a thickness of 25 nm. A compound ET-4 was deposited on the electron-injecting layer to form an ET-4 film having a thickness of 1 nm. Al metal was deposited on the ET-4 film to form a metal cathode having a thickness of 80 nm.

An organic EL device was thus fabricated. The compounds used to fabricate the organic EL device are shown below.

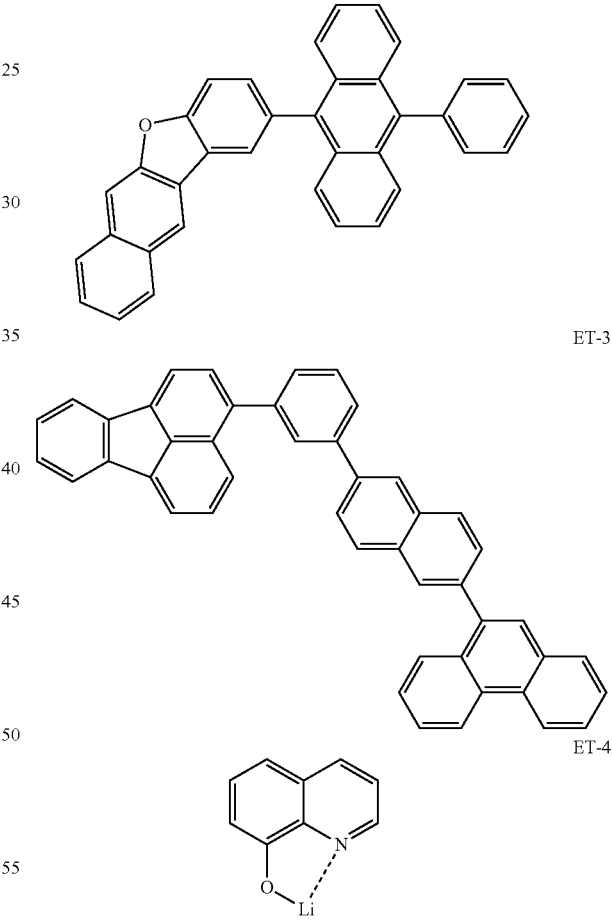

Evaluation of Organic EL Device

The organic EL device was evaluated as described below. Specifically, a voltage was applied to the organic EL device so that the current density was 10 mA/cm$^2$, and the EL emission spectrum was measured using a spectroradiometer ("CS-1000" manufactured by Konica Minolta, Inc.). The external quantum efficiency (EQE) (%) and the emission peak wavelength were calculated from the resulting spectral radiance spectrum. The results are shown in Table 2.

Examples 19 to 27 and Comparative Examples 7 and 8

An organic EL device was fabricated and evaluated in the same manner as in Example 18, except that the compounds listed in Table 2 were used instead of compound 1 and compound BH-2. The compound used to fabricate the organic EL device is shown below. The results are shown in Table 2.

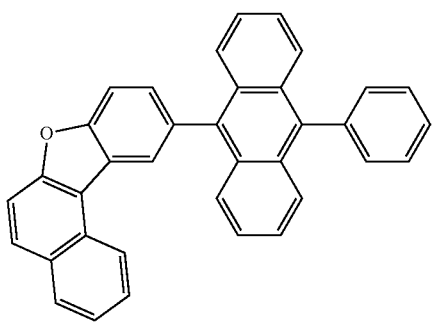

BH-3

TABLE 2

|  | Dopant material | Host material | EQE (%) | Emission peak wavelength (nm) |
|---|---|---|---|---|
| Example 18 | Compound 1 | BH-2 | 10.0 | 459 |
| Example 19 | Compound 2 | BH-2 | 10.4 | 459 |
| Example 20 | Compound 4 | BH-2 | 9.9 | 461 |
| Example 21 | Compound 5 | BH-2 | 10.5 | 462 |
| Example 22 | Compound 6 | BH-2 | 10.1 | 463 |
| Example 23 | Compound 1 | BH-3 | 9.9 | 459 |
| Example 24 | Compound 2 | BH-3 | 10.2 | 459 |
| Example 25 | Compound 4 | BH-3 | 10.0 | 461 |
| Example 26 | Compound 5 | BH-3 | 10.4 | 461 |
| Example 27 | Compound 6 | BH-3 | 10.0 | 462 |
| Comparative Example 7 | Comparative compound 1 | BH-2 | 9.4 | 469 |
| Comparative Example 8 | Comparative compound 1 | BH-3 | 9.2 | 469 |

As is clear from Tables 1 and 2, the organic EL device fabricated using the compound according to one aspect of the invention exhibited excellent efficiency.

The compound according to one aspect of the invention achieves high efficiency due to the presence of an alkyl group situated at the ortho position and one or more aryl groups that are bonded to at least one of the side-chain substituents (phenyl groups) of the diaminopyrene structure. It is considered that energy loss when the energy obtained from the host material is converted into light can be reduced when an alkyl group is situated at the ortho position of the phenyl group. It is considered that interaction with the host material included in the emitting layer is optimized, and smooth energy transfer and emission occur due to one or more aryl groups, so that the luminous efficiency is improved.

It is clear from a comparison with the comparative compounds 1, 4, and 6 that the presence of an alkyl group situated at the ortho position contributes to an improvement in luminous efficiency. It is clear from a comparison with the comparative compounds 3 and 5 that the presence of an aryl group contributes to an emission effect. It is considered that the compound according to one aspect of the invention reduces inactivation due to vibrations of the side-chain substituent as compared with the comparative compound 2 in which a fused-ring substituent is present (bonded directly) in addition to the center pyrene ring. It is considered that higher efficiency was thus obtained.

Although only some exemplary embodiments and/or examples of the invention have been described in detail above, those skilled in the art will readily appreciate that many modifications are possible in the exemplary embodiments and/or examples without materially departing from the novel teachings and advantages of the invention. Accordingly, all such modifications are intended to be included within the scope of the invention.

The specification of the Japanese patent application to which the present application claims priority under the Paris Convention is incorporated herein by reference in its entirety.

The invention claimed is:

1. A compound of a formula (1),

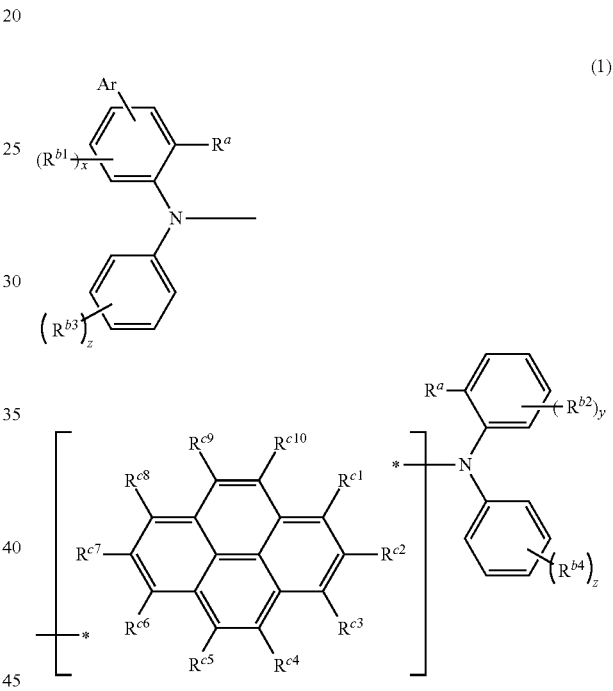

(1)

wherein Ar is a substituted or unsubstituted phenyl group, a substituted or unsubstituted naphthyl group, a substituted or unsubstituted anthryl group, a substituted or unsubstituted phenanthryl group, a substituted or unsubstituted naphthacenyl group, a substituted or unsubstituted pyrenyl group, a substituted or unsubstituted chrysenyl group, a substituted or unsubstituted benzo[c]phenanthryl group, a substituted or unsubstituted benzo[g]chrysenyl group, a substituted or unsubstituted triphenylenyl group, a substituted or unsubstituted benzofluorenyl group, a substituted or unsubstituted dibenzofluorenyl group, a substituted or unsubstituted biphenylyl group, a substituted or unsubstituted o-terphenyl group, a substituted or unsubstituted m-terphenyl group, a substituted or unsubstituted p-terphenyl group, a substituted or unsubstituted fluoranthenyl group, $R^a$ are independently a substituted or unsubstituted alkyl group including 1 to 15 carbon atoms, or a substituted or unsubstituted cycloalkyl group including 3 to 15 carbon atoms, $R^{b1}$ to $R^{b4}$ are independently a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 ring atoms, $R^{c1}$ to $R^{c10}$ are independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, a substituted or unsubstituted heteroaryl group including 3 to 30 ring atoms, or a single bond that is bonded to either nitrogen atom,

* is a bonding position at which any of $R^{c1}$ to $R^{c10}$ is bonded to either nitrogen atom, x is an integer from 0 to 3, y is an integer from 0 to 4, z are independently an integer from 0 to 5, a plurality of $R^{b1}$ are either identical or different when x is an integer equal to or larger than 2, a plurality of $R^{b2}$ are either identical or different when y is an integer equal to or larger than 2, and a plurality of $R^{b3}$ or $R^{b4}$ are either identical or different when z is an integer equal to or larger than 2, when $R^a$ is substituted with a substituent, the substituent is an alkyl group including 1 to 10 carbon atoms, a cycloalkyl group including 3 to 10 ring carbon atoms, an alkylsilyl group including 3 to 30 carbon atoms, an arylsilyl group including 6 to 60 carbon atoms, an alkoxy group including 1 to 10 carbon atoms, aryloxy group including 6 to 20 ring carbon atoms, an alkylthio group including 1 to 10 carbon atoms, an arylthio group including 6 to 20 ring carbon atoms, an arylamino group including 12 to 30 ring carbon atoms, an aryl group including 6 to 20 ring carbon atoms, or a heteroaryl group including 5 to 20 ring atoms.

2. The compound according to claim 1, the compound being of a formula (2),

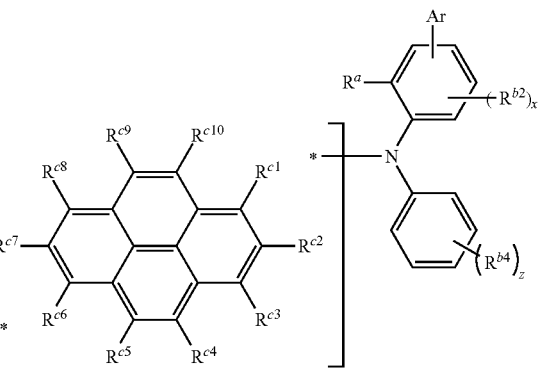

(2)

wherein Ar, $R^a$, $R^{b1}$ to $R^{b4}$, $R^{c1}$ to $R^{c10}$, x, z, and * are the same as defined for the formula (1).

3. The compound according to claim 1, wherein $R^{c1}$ to $R^{c10}$ are independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted aryl group including 6 to 30 ring carbon atoms, a substituted or unsubstituted heteroaryl group including 3 to 30 ring atoms, or a single bond that is bonded to either nitrogen atom.

4. The compound according to claim 1, the compound being of a formula (3),

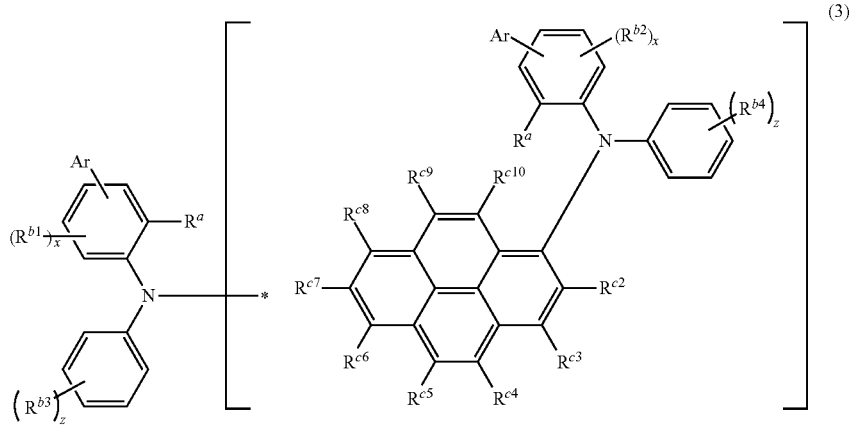

wherein Ar, $R^a$, $R^{b1}$ to $R^{b4}$, $R^{c2}$ to $R^{c10}$, x, z, and * are the same as defined for the formula (1).

5. The compound according claim 1, the compound being of a formula (4),

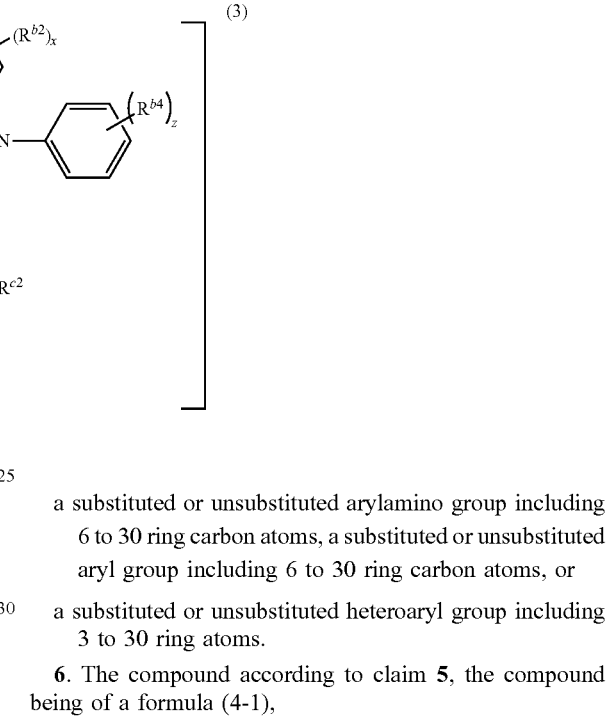

wherein Ar, $R^a$, $R^{b1}$ to $R^{b4}$, x, and z are the same as defined for the formula (1), and $R^{c2}$ to $R^{c5}$ and $R^{c7}$ to $R^{c10}$ are independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 ring atoms.

6. The compound according to claim 5, the compound being of a formula (4-1),

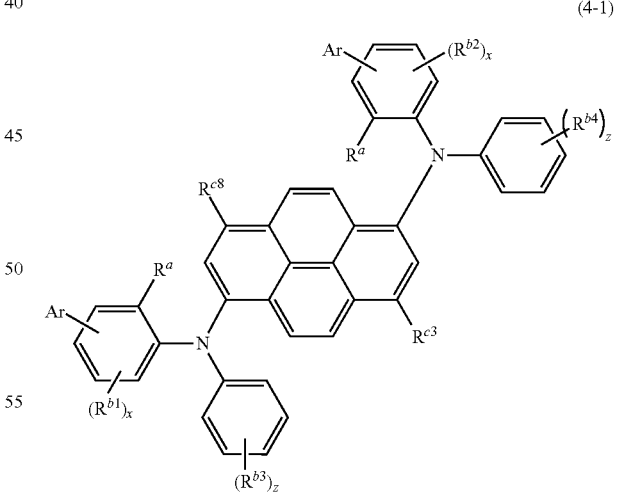

wherein Ar, $R^a$, $R^{b1}$ to $R^{b4}$, $R^{c3}$, $R^{c8}$, x, and z are the same as defined for the formula (4).

7. The compound according to claim 6, wherein $R^{c3}$ and $R^{c8}$ are independently a hydrogen atom, an alkyl group including 1 to 6 carbon atoms, or a cycloalkyl group including 1 to 6 carbon atoms.

8. The compound according to claim 1, the compound being of a formula (5),

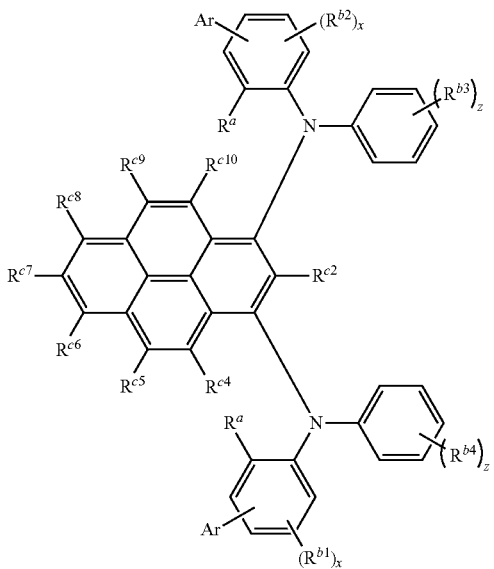

(5)

wherein Ar, $R^a$, $R^{b1}$ to $R^{b4}$, x, and z are the same as defined for the formula (1), and $R^{c2}$ and $R^{c4}$ to $R^{c10}$ are independently a hydrogen atom, a halogen atom, a cyano group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 ring atoms.

9. The compound according to claim 8, the compound being of a formula (5-1),

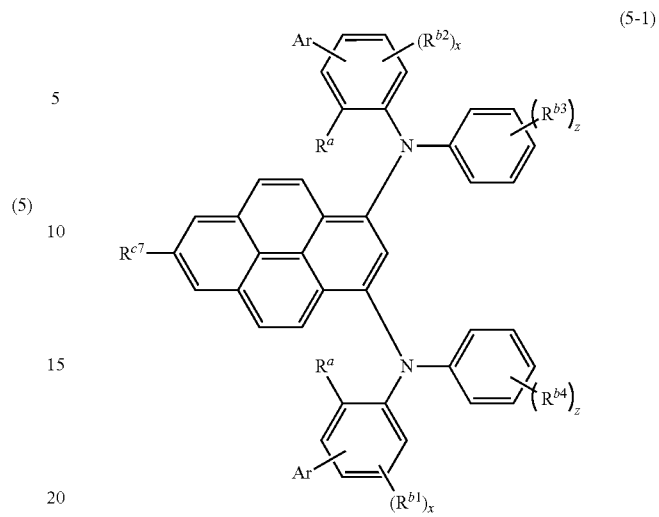

(5-1)

wherein Ar, $R^a$, $R^{b1}$ to $R^{b4}$, $R^{c7}$, x, and z are the same as defined for the formula (5).

10. The compound according to claim 9, wherein $R^{c7}$ is a substituted or unsubstituted alkyl group including 1 to 15 carbon atoms, or a substituted or unsubstituted cycloalkyl group including 3 to 15 carbon atoms.

11. The compound according to claim 1, wherein the benzene ring-containing group to which $R^{b1}$ is bonded has a structure in which $R^{b1}$ and Ar are not bonded at the para position with respect to the bonding position at which the N atom is bonded, and the benzene ring-containing group to which $R^{b2}$ is bonded has a structure in which $R^{b2}$ is not bonded at the para position with respect to the bonding position at which the N atom is bonded.

12. The compound according to claim 1, wherein the benzene ring-containing group to which $R^{b1}$ is bonded is represented by a formula (10), and the benzene ring-containing group to which $R^{b2}$ is bonded is represented by a formula (11),

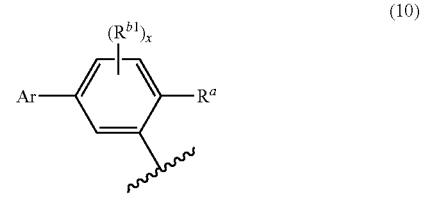

(10)

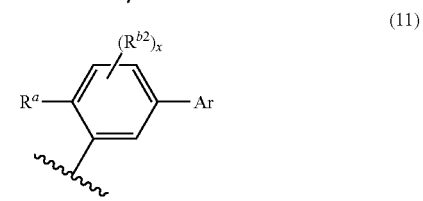

(11)

wherein Ar, $R^a$, $R^{b1}$, $R^{b2}$, and x are the same as defined for the formula (1).

13. The compound according to claim 1, wherein the benzene ring-containing group to which $R^{b3}$ is bonded is represented by a formula (12), and the benzene ring-containing group to which $R^{b4}$ is bonded is represented by a formula (13),

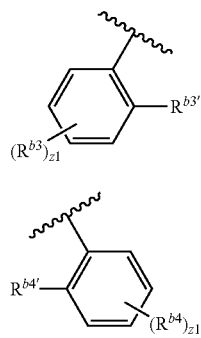

(12)

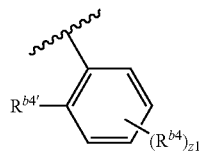

(13)

wherein $R^{b3}$ and $R^{b4}$ are the same as defined for the formula (1), $R^{b3'}$ and $R^{b4'}$ are independently a substituted or unsubstituted alkyl group including 1 to 15 carbon atoms, or a substituted or unsubstituted cycloalkyl group including 3 to 15 carbon atoms, and z1 are independently an integer from 0 to 4.

14. The compound according to claim 1, wherein $R^{b1}$ to $R^{b4}$ are independently a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, a substituted or unsubstituted alkoxy group including 1 to 15 carbon atoms, a substituted or unsubstituted aryloxy group including 6 to 30 ring carbon atoms, a substituted or unsubstituted alkylthio group including 1 to 15 carbon atoms, a substituted or unsubstituted arylthio group including 6 to 30 ring carbon atoms, a substituted or unsubstituted arylamino group including 6 to 30 ring carbon atoms, a substituted or unsubstituted aryl group including 6 to 30 ring carbon atoms, or a substituted or unsubstituted heteroaryl group including 3 to 30 ring atoms.

15. The compound according to claim 1, wherein $R^{b1}$ to $R^{b4}$ are independently a cyano group, an unsubstituted phenyl group, a substituted or unsubstituted alkyl group including 1 to 15 carbon atoms, a substituted or unsubstituted cycloalkyl group including 3 to 15 carbon atoms, a substituted or unsubstituted alkylsilyl group including 1 to 45 carbon atoms, a substituted or unsubstituted arylsilyl group including 6 to 50 carbon atoms, or a substituted or unsubstituted aryl group including 6 to 30 ring carbon atoms.

16. The compound according to claim 1, wherein $R^a$ are independently a substituted or unsubstituted alkyl group including 1 to 6 carbon atoms.

17. The compound according to claim 1, the compound being a material for an organic electroluminescence device.

18. The compound according to claim 1, the compound being an emitting material for an organic electroluminescence device.

19. The compound according to claim 1, the compound being a doping material for an organic electroluminescence device.

20. An organic electroluminescence device comprising a cathode, an anode, and one or more organic thin film layers that are provided between the cathode and the anode, the one or more organic thin film layers comprising at least an emitting layer, and at least one organic thin film layer included in the one or more organic thin film layers comprising the compound according to claim 1 either alone or as a component of a mixture.

21. The organic electroluminescence device according to claim 20, wherein the at least one organic thin film layer is the emitting layer.

22. The organic electroluminescence device according to claim 20, wherein the compound is a dopant material.

23. An electronic apparatus comprising the organic electroluminescence device according to claim 20.

24. The compound according to claim 1, wherein $R^a$ are independently an unsubstituted alkyl group including 1 to 15 carbon atoms, or an unsubstituted cycloalkyl group including 3 to 15 carbon atoms.

25. The compound according to claim 1, wherein $R^{b1}$ to $R^{b4}$ are independently an unsubstituted phenyl group, or an unsubstituted alkyl group including 1 to 15 carbon atoms.

* * * * *

UNITED STATES PATENT AND TRADEMARK OFFICE
CERTIFICATE OF CORRECTION

PATENT NO. : 9,902,687 B2
APPLICATION NO. : 14/908929
DATED : February 27, 2018
INVENTOR(S) : Ito et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 49 days.

Signed and Sealed this
Nineteenth Day of February, 2019

Andrei Iancu
*Director of the United States Patent and Trademark Office*